(12) United States Patent
Brenneman et al.

(10) Patent No.: US 8,906,904 B2
(45) Date of Patent: Dec. 9, 2014

(54) ALKOXY PYRAZOLES AS SOLUBLE GUANYLATE CYCLASE ACTIVATORS

(71) Applicants: Jehrod Burnett Brenneman, Southbury, CT (US); John Ginn, New Milford, CT (US); Michael D. Lowe, White Plains, NY (US); Christopher Ronald Sarko, New Milford, CT (US); Edward S. Tasber, Binghampton, NY (US); Zhonghua Zhang, Ridgefield, CT (US)

(72) Inventors: Jehrod Burnett Brenneman, Southbury, CT (US); John Ginn, New Milford, CT (US); Michael D. Lowe, White Plains, NY (US); Christopher Ronald Sarko, New Milford, CT (US); Edward S. Tasber, Binghampton, NY (US); Zhonghua Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/016,452

(22) Filed: Sep. 3, 2013

(65) Prior Publication Data
US 2014/0073629 A1    Mar. 13, 2014

Related U.S. Application Data

(60) Provisional application No. 61/697,899, filed on Sep. 7, 2012.

(51) Int. Cl.
    *C07D 401/14*    (2006.01)
    *C07D 405/14*    (2006.01)
    *C07D 498/04*    (2006.01)

(52) U.S. Cl.
    USPC ............ 514/211.09; 514/229.2; 514/307; 514/213.01; 514/278; 514/341; 514/217.01; 544/67; 546/148; 546/15; 546/276; 540/593; 540/552; 540/594

(58) Field of Classification Search
    CPC ... C07D 401/14; C07D 498/04; C07D 405/14
    USPC ............ 514/211.09, 229.2, 307, 213.01, 278, 514/341, 217.01; 544/67; 546/148, 15, 276; 540/593, 552, 594
    See application file for complete search history.

(56) References Cited

U.S. PATENT DOCUMENTS

| 8,569,339 B2 | 10/2013 | Brenneman et al. |
| 2009/0209556 A1 | 8/2009 | Bittner et al. |
| 2010/0016305 A1 | 1/2010 | Krahn et al. |
| 2010/0216764 A1 | 8/2010 | Kim et al. |
| 2013/0065918 A1 | 3/2013 | Brenneman et al. |
| 2013/0203729 A1 | 8/2013 | Bosanac et al. |

FOREIGN PATENT DOCUMENTS

| WO | 2002026712 A2 | 4/2002 |
| WO | 2008021339 A2 | 2/2008 |
| WO | 2008138483 A1 | 11/2008 |
| WO | 2009032249 A1 | 3/2009 |
| WO | 2009068652 A1 | 6/2009 |
| WO | 2009071504 A1 | 6/2009 |
| WO | 2010015652 A2 | 2/2010 |
| WO | 2010015653 A1 | 2/2010 |
| WO | 2010065275 A1 | 6/2010 |
| WO | 2010099054 A2 | 9/2010 |
| WO | 2012058132 A1 | 5/2012 |
| WO | 2012122340 A1 | 9/2012 |
| WO | 2013025425 A1 | 2/2013 |

OTHER PUBLICATIONS

U.S. Appl. No. 61/697,899, filed Sep. 7, 2012.
Schindler, Ursula., "Biochemistry and Pharmacology of Novel Anthranilic Acid Derivates Activating Heme-Oxidized Soluble Guanylyl Cyclase" Molecular Pharmacology (2006) vol. 69', No. 4 pp. 1260-1268.
Stasch, Johannes-Peter, et al., "NO- and HAEM-Independent Activation of Soluble Guanylyl Cyclase: Molecular Basis and Cardiovascular Implications of a New Pharmacological Principle" British Journal of Pharmacology (2002) vol. 136 pp. 773-783.
Evgenov, Oleg, V. et al., "NO-Independent Stimulators and Activators of Soluble Guanylate Cyclase: Discovery and Therapeutic Potential" Nature Reviews / Drug Discovery (2006) vol. 5 pp. 755-768.
Notice of Allowance mailed May 23, 2014 for U.S. Appl. No. 13/570,432, filed Aug. 9, 2012, Inventor: Todd Bosanac.
Issue Fee Payment for U.S. Appl. No. 13/570,432, filed Jun. 6, 2014, Inventor: Todd Bosanac.

*Primary Examiner* — Kahsay Habte
(74) *Attorney, Agent, or Firm* — Michael P. Morris; Edward S. Lazer

(57) ABSTRACT

The present invention relates to compounds of formula (I):

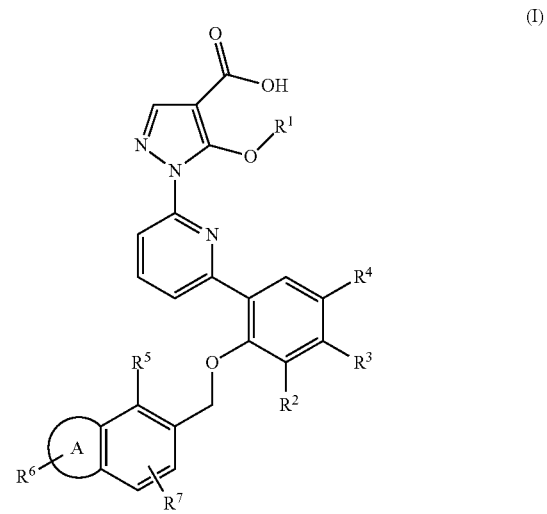

and pharmaceutically acceptable salts thereof, wherein $R^1$, $R^2$, $R^3$, $R^4$, $R^5$, $R^6$ and $R^7$ are as defined herein. The invention also relates to pharmaceutical compositions comprising these compounds, methods of using these compounds in the treatment of various diseases and disorders, processes for preparing these compounds and intermediates useful in these processes.

35 Claims, No Drawings

ALKOXY PYRAZOLES AS SOLUBLE GUANYLATE CYCLASE ACTIVATORS

FIELD OF THE INVENTION

This invention relates to heterocyclic compounds which are useful as activators of soluble guanylate cyclase and are thus useful for treating a variety of diseases that are mediated or sustained by decreased or diminished soluble guanylate cyclase activity, including cardiovascular diseases, renal disease, diabetes, fibrotic disorders, urologic disorders, neurological disorders and inflammatory disorders. This invention also relates to pharmaceutical compositions comprising these compounds, methods of using these compounds in the treatment of various diseases and disorders, processes for preparing these compounds and intermediates useful in these processes.

BACKGROUND

Soluble guanylate cyclase (sGC) is a receptor for nitric oxide (NO) which is found in the cytoplasm of many cell types. In humans, functional sGC is a heterodimer composed of either an alpha 1 or alpha 2 subunit combined with the beta 1 subunit which has a heme prosthetic group. Under non-pathophysiological conditions, NO binding to the heme of sGC activates the enzyme to catalyze the conversion of guanosine-5'-triphosphate (GTP) to cyclic guanosine monophosphate (cGMP). cGMP is a second messenger which exerts effects by modulating cGMP dependent protein kinase (PKG) isoforms, phosphodiesterases, and cGMP gated ion channels. In doing so, sGC has been demonstrated to modulate numerous pathways associated with diseases including arterial hypertension, pulmonary hypertension, atherosclerosis, heart failure, liver cirrhosis, renal fibrosis, and erectile dysfunction (O. Evgenov et al., Nature Reviews, 2006, 5, 755-768 and Y. Wang-Rosenke et al., Curr. Med. Chem., 2008, 15, 1396-1406).

Under normal conditions, the iron in sGC exists in the ferrous state which is capable of binding to NO and carbon monoxide (CO). However, under conditions of oxidative stress which can occur in various diseases, published reports indicate that the heme iron becomes oxidized to the ferric state which is incapable of being activated by NO or CO. The inability of NO to signal through sGC with an oxidized heme iron has been hypothesized to contribute to disease processes. Recently, two novel classes of compounds have been described which potentiate sGC activity in a heme dependent (sGC stimulators) and heme independent (sGC activators) manner. The activity of sGC stimulators synergizes with NO to increase cGMP production while sGC activators are only additive with NO to augment cGMP levels (O. Evgenov et al., Nature Reviews, 2006, 5, 755-768). Both stimulators and activators of sGC have demonstrated benefit in animal models of disease. Activators of sGC provide the advantage of being able to preferentially target the diseased, non-functional form of the enzyme. sGC activators include BAY 58-2667 (cinaciguat) (J-P Stasch et al., Brit J. Pharmacol., 2002, 136, 773-783) and HMR-1766 (ataciguat) (U. Schindler et al., 2006, Mol. Pharmacol., 69, 1260-1268).

NO has an important role in maintaining normal cellular and tissue function. However, adequate signaling in the NO pathway can be disrupted at a number of steps. NO signaling can be impaired by reduced levels of nitric oxide synthase (NOS) enzymes, NOS activity, NO bioavailability, sGC levels, and sGC activity. sGC activators have the potential to bypass the functional impediment produced by all of these impairments. Since sGC activation occurs downstream of NO synthesis or NO availability, these deficiencies will not impact the activity of sGC activators. As described above, the activity of sGC in which function is disrupted by heme iron oxidation will be corrected by sGC activators. Thus, sGC activators have the potential to provide benefit in many diseases caused by defective signaling in the NO pathway.

Activation of sGC has the potential to provide therapeutic benefit for atherosclerosis and arteriosclerosis. Cinaciguat treatment has been demonstrated to prevent neointimal hyperplasia after endothelial denudation by wire injury of the carotid artery in rats (K. Hirschberg et al., Cardiovasc. Res., 2010, 87, Suppl. 1, S100, Abstract 343). Ataciguat inhibited atherosclerotic plaque formation in ApoE−/− mice feed a high fat diet (M. van Eickels, BMC Pharmacology, 2007, 7, Suppl. 1, S4). Decreased NO production in endothelial nitric oxide synthase (eNOS) deficient mice increased vascular inflammation and insulin resistance in response to nutrient excess. In the same study, the phosphodiesterase 5 (PDE5) inhibitor sildenafil reduced vascular inflammation and insulin resistance in mice fed a high-fat diet (N. Rizzo et al., Arterioscler. Thromb. Vasc. Biol., 2010, 30, 758-765). Lastly, after balloon-injury of rat carotid arteries in vivo, a sGC stimulator (YC-1) inhibited neotima formation (C. Wu, J. Pharmacol. Sci., 2004, 94, 252-260

The complications of diabetes may be reduced by sGC activation. Glucose induced suppression of glucagon release is lost in pancreatic islets that lack PKG, thus suggesting a role of sGC mediated cGMP production in glucose regulation (V. Leiss et al., BMC Pharmacology, 2009, 9, Suppl. 1, P40).

It is well established clinically that elevation of cGMP by treatment with PDE5 inhibitors is efficacious for the treatment of erectile dysfunction (ED). However, 30% of ED patients are resistant to PDE5 inhibitor treatment (S. Gur et al., Curr. Pharm. Des., 2010, 16, 1619-1633). The sGC stimulator BAY-41-2272 is able to relax corpus cavernosum muscle in a sGC dependent manner, thus suggesting that increased sGC activity could provide benefit in ED patients (C. Teixeira et al., J. Pharmacol. & Exp. Ther., 2007, 322, 1093-1102). Furthermore, sGC stimulators and sGC activators used individually or either in combination with PDE5 inhibitor was able to treat ED in animal models (WO 10/081,647).

There is evidence that sGC activation may be useful in preventing tissue fibrosis, including that of the lung, liver, and kidney. The processes of epithelial to mesenchyal transition (EMT) and fibroblast to myofibroblast conversion are believed to contribute to tissue fibrosis. When either cinaciguat or BAY 41-2272 was combined with sildenafil, lung fibroblast to myofibroblast conversion was inhibited (T. Dunkern et al., Eur. J. Pharm., 2007, 572, 12-22). NO is capable of inhibiting EMT of alveolar epithelial cells (S. Vyas-Read et al., Am. J. Physiol. Lung Cell Mol. Physiol., 2007, 293, 1212-1221), suggesting that sGC activation is involved in this process. NO has also been shown to inhibit glomerular TGF beta signaling (E. Dreieicher et al., J. Am. Soc. Nephrol., 2009, 20, 1963-1974) which indicates that sGC activation may be able to inhibit glomerular sclerosis. In a pig serum model and carbon tetrachloride model of liver fibrosis, an sGC activator (BAY 60-2260) was effective at inhibiting fibrosis (A. Knorr et al., Arzneimittel-Forschung, 2008, 58, 71-80).

Clinical studies have demonstrated efficacy using the sGC activator cinaciguat for the treatment of acute decompensated heart failure (H. Lapp et al., Circulation, 2009, 119, 2781-2788). This is consistent with results from a canine tachypacing-induced heart failure model in which acute intravenous infusion of cinaciguat was able to produce cardiac unloading (G. Boerrigter et al., Hypertension, 2007, 49, 1128-1133). In a rat myocardial infarction induced chronic heart failure model, HMR 1766 improved cardiac function and reduced cardiac fibrosis which was further potentiated by ramipril (F. Daniela, Circulation, 2009, 120, Suppl. 2, S852-S853).

Activators of sGC can be used to treat hypertension. This has been clearly demonstrated in clinical studies in which the dose of cinaciguat is titrated based on the magnitude of blood pressure reduction achieved (H. Lapp et al., Circulation, 2009, 119, 2781-2788). Preclinical studies using cinaciguat had previously shown the ability of sGC activation to reduce blood pressure (J.-P. Stasch et al., 2006, J. Clin. Invest., 116, 2552-2561). Similar findings have been reported using the sGC activator HMR 1766 as well (U. Schindler et al., 2006, Mol. Pharmacol., 69, 1260-1268).

The activation of sGC has the potential to reduce inflammation by effects on the endothelium. BAY 41-2272 and a NO donor inhibited leukocyte rolling and adhesion in eNOS deficient mice. This was demonstrated to be mediated by down-regulation of expression of the adhesion molecule P-selectin (A. Ahluwalla et al., Proc. Natl. Acad. Sci. USA, 2004, 101, 1386-1391). Inhibitors of NOS and sGC were shown to increase endotoxin (LPS) induced ICAM expression on mesenteric microcirculation vessels. This was reduced by an NO donor in a cGMP dependent manner. Treatment of mice with NOS or sGC inhibitors increased neutrophil migration, rolling, and adhesion induced by LPS or carrageenen (D. Dal Secco, Nitric Oxide, 2006, 15, 77-86). Activation of sGC has been shown to produce protection from ischemia-reperfusion injury using BAY 58-2667 in both in vivo and in an isolated heart model (T. Krieg et al., Eur. Heart J., 2009, 30, 1607-6013). Similar results were obtained using the same compound in a canine model of cardioplegic arrest and extracorporeal circulation (T. Radovits et al., Eur J. Cardiothorac. Surg., 2010).

Some studies have indicated the potential of sGC activation to have antinociceptive effects. In streptozotocin-induced diabetes models of nociception in mice (writhing assay) and rats (paw hyperalgesia), elevation of cGMP levels by administration of sildenafil blocked the pain response, which in turn was abrogated by a NOS or sGC inhibitor (C. Patil et al., Pharm., 2004, 72, 190-195). The sGC inhibitor 1H-1,2,4.-oxadiazolo-4,2-a.quinoxalin-1-one (ODQ) has been demonstrated to block the antinociceptive effects of various agents including meloxicam and diphenyl diselenide in a formalin induced pain model (P. Aguirre-Banuelos et al., Eur. J. Pharmacol., 2000, 395, 9-13 and L. Savegnago et al., J. Pharmacy Pharmacol., 2008, 60, 1679-1686) and xylazine in a paw pressure model (T. Romero et al., Eur. J. Pharmacol., 2009, 613, 64-67). Furthermore, ataciguat was antinociceptive in the carrageenan model of inflammatory triggered thermal hyperalgesia and the spared nerve injury model of neuropathic pain in mice (WO 09/043,495).

Inhibition of PDE9, a phosphodiesterase specific for cGMP expressed in the brain, has been shown to improve long-term potentiation (F. van der Staay et al., Neuropharmacol. 2008, 55, 908-918). In the central nervous system, sGC is the primary enzyme which catalyzes the formation of cGMP (K. Domek-Lopacinska et al., Mol. Neurobiol., 2010, 41, 129-137). Thus, sGC activation may be beneficial in treating Alzheimer's and Parkinson's disease. In a phase II clinical study, the sGC stimulator riociguat, was efficacious in treating chronic thromboembolic pulmonary hypertension and pulmonary arterial hypertension (H. Ghofrani et al., Eur. Respir. J., 2010, 36, 792-799). These findings extend the preclinical studies in which BAY 41-2272 and cinaciguat reduced pulmonary hypertension in mouse (R. Dumitrascu et al., Circulation, 2006, 113, 286-295) and lamb (O. Evgenov et al., 2007, Am. J. Respir. Crit. Care Med., 176, 1138-1145) models. Similar results were obtained using HMR 1766 in a mouse model of pulmonary hypertension (N. Weissmann et al., 2009, Am. J. Physiol. Lung Cell. Mol. Physiol., 297, L658-665).

Activation of sGC has the potential to treat chronic kidney disease. Both BAY 58-2667 and HMR 1766 improved renal function and structure in a rat subtotal nephrectomy model of kidney disease (P. Kalk et al., 2006, Brit. J. Pharmacol., 148, 853-859 and K. Benz et al., 2007, Kidney Blood Press. Res., 30, 224-233). Improved kidney function and survival was provided by BAY 58-2667 treatment in hypertensive renin transgenic rats (TG(mRen2)27 rats) treated with a NOS inhibitor (J.-P. Stasch et al., 2006, J. Clin. Invest., 116, 2552-2561). BAY 41-2272 treatment preserved kidney function and structure in a chronic model of kidney disease in rats induced by uninephrectomy and anti-thy1 antibody treatment (Y. Wang et al., 2005, Kidney Intl., 68, 47-61). Diseases caused by excessive blood clotting may be treated with sGC activators. Activation of sGC using BAY 58-2667 was capable of inhibiting platelet aggregation induced by various stimuli ex vivo. Additionally, this compound inhibited thrombus formation in vivo in mice and prolonged bleeding time (J.-P. Stasch et al., 2002, Brit. J. Pharmacol., 136, 773-783). In another study using HMR 1766, in vivo platelet activation was inhibited in streptozotocin treated rats (A. Schafer et al., 2006, Arterioscler. Thromb. Vasc. Biol., 2006, 26, 2813-2818).

sGC activation may also be beneficial in the treatment of urologic disorders (WO/08138483). This is supported by clinical studies using the PDE5 inhibitor vardenafil (C. Stief et al., 2008, Eur. Urol., 53, 1236-1244). The soluble guanylate cyclase stimulator BAY 41-8543 was able to inhibit prostatic, urethra, and bladder smooth muscle cell proliferation using patient samples (B. Fibbi et al., 2010, J. Sex. Med., 7, 59-69), thus providing further evidence supporting the utility of treating urologic disorders with sGC activators.

The above studies provide evidence for the use of sGC activators to treat cardiovascular diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. Additionally, sGC activators have the potential to treat renal disease, diabetes, fibrotic disorders including those of the liver, kidney and lungs, urologic disorders including overactive bladder, benign pro static hyperplasia, and erectile dysfunction, and neurological disorders including Alzheimer's disease, Parkinson's disease, as well as neuropathic pain. Treatment with sGC activators may also provide benefits in inflammatory disorders such as psoriasis, multiple sclerosis, arthritis, asthma, and chronic obstructive pulmonary disease.

BRIEF SUMMARY OF THE INVENTION

The present invention provides novel compounds which activate or potentiate sGC and are thus useful for treating a variety of diseases and disorders that can be alleviated by sGC activation or potentiation including cardiovascular, inflammatory and renal diseases. This invention also relates to pharmaceutical compositions comprising these compounds, methods of using these compounds in the treatment of various diseases and disorders, processes for preparing these compounds and intermediates useful in these processes.

In a further aspect, the present invention provides activators of soluble guanylate cyclase having solubility properties consistent with acceptable pharmacokinetic properties. As is known in the art, poorly soluble compounds may suffer from poor human exposure. The compounds of the present invention would be expected to have exposure properties consistent with being a suitable drug.

In a further aspect, the present invention provides compounds with metabolic stability properties consistent with acceptable pharmacokinetic properties. As is known in the art, compounds having poor metabolic stability may not readily achieve desirable therapeutic levels. The compounds of the present invention would be expected to have metabolic stability properties consistent with being a suitable drug.

DETAILED DESCRIPTION OF THE INVENTION

In an embodiment, there are provided compounds of the formula I

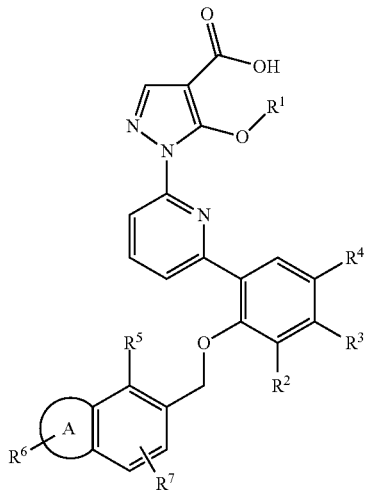

I wherein:
A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;
$R^1$ is $C_{1-4}$ alkyl optionally substituted with a methoxy group;
$R^2$ is selected from H, F, Cl, $C_{1-3}$alkyl, —CN, —OMe and —$CF_3$;
$R^3$ is selected from H and —$CH_3$;
$R^4$ is selected from H, F, —$CH_3$ and —OMe;
$R^5$ is selected from H, Cl, —$CH_3$, —$CH_2CH_3$, —$CF_3$, F, and —OMe;
$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl —$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}O(CH_2)_{2-3}OH$, and —$SO_2CH_3$;
$R^7$ is selected from H, —$CH_3$, —$CH_2CH_3$, —$CF_3$, F, and —CN;
n is 0, 1 or 2
or a salt thereof.

In another embodiment, there are provided compounds as described in the embodiment above, wherein:
A is a 5-7 membered saturated heterocyclyl group containing one nitrogen, wherein one carbon of said heterocyclyl group is optionally substituted with one or two $C_{1-3}$alkyl groups;
$R^1$ is $C_{1-3}$alkyl;
$R^2$ is selected from H, F, Cl, $C_{1-3}$alkyl, —CN, —OMe and —$CF_3$;
$R^3$ is selected from H and —$CH_3$;
$R^4$ is selected from H and F;
$R^5$ is selected from H, Cl and —$CH_3$;
$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl and —$(CH_2)_n$ heteroaryl, wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH and —$SO_2CH_3$;
$R^7$ is H;
and
n is 0, 1 or 2;
or a salt thereof.

In another embodiment, there are provided compounds as described in any of the embodiments above, wherein:
$R^1$ is methyl, ethyl or isopropyl; and
the group

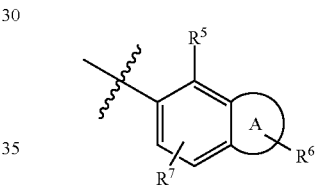

is selected from:

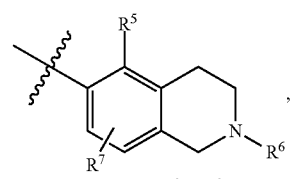

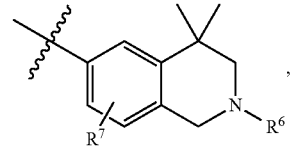

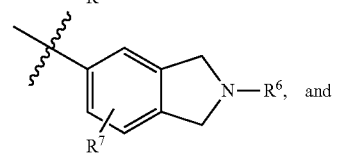

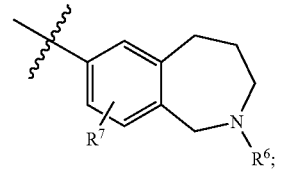

or a salt thereof.

In another embodiment there are provided compounds as described in any of the embodiments above, wherein:

$R^2$ is selected from —$CH_3$, F, Cl, and —$CF_3$; and $R^6$ is selected from H, $C_{1-6}$alkyl, —$(CH_2)_nC_{3-6}$cycloalkyl, —$C(O)C_{1-6}$alkyl and —$(CH_2)_n$ heterocyclyl, wherein said $C_{1-6}$alkyl, —$(CH_2)_n$ cycloalkyl and —$(CH_2)_n$ heterocyclyl are optionally substituted with one to four groups independently selected from $C_{1-3}$alkyl, halogen, $C_{1-3}$alkoxy, —$CF_3$, —OH and —$SO_2CH_3$;

or a salt thereof.

In another embodiment there are provided compounds as described in any of the embodiments above, wherein each heterocyclyl referred to in $R^6$ is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl, 1-oxaspiro[4.5]decanyl and pyrrolidin-2-one;

each heteroaryl referred to in $R^6$ is selected from imidazolyl, isoxazolyl, pyrazinyl, pyrazolyl, pyridinyl, pyrimidinyl, thiazolyl and 4,5,6,7-tetrahydrobenzothiazolyl;

and each aryl referred to in $R^6$ is phenyl;

or a salt thereof.

In another embodiment there are provided compounds as described in any of the embodiments above, wherein:

$R^6$ is —$(CH_2)_n$ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a salt thereof.

In another embodiment there are provided compounds as described in any of the embodiments above, wherein:

$R^2$ is —$CH_3$;

$R^3$ is H;

$R^4$ is H or —$CH_3$;

$R^5$ is H, or —$CH_3$;

$R^7$ is in the position para to $R^5$ and is H, —$CH_3$ or —$CH_2CH_3$;

or a salt thereof.

In another embodiment there are provided compounds as described in any of the embodiments above, wherein:

the group

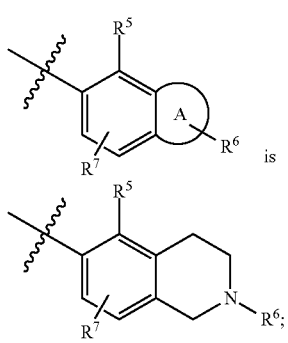

or a salt thereof.

In another embodiment there are provided compounds as described in any of the embodiments above, wherein:

$R^3$ is H; and $R^4$ is H;

or a salt thereof.

Table 1 shows representative compounds of the invention which can be made by the general synthetic schemes, the examples, and known methods in the art.

TABLE 1

| Cpd No. | Structure |
|---|---|
| 1 | |
| 2 | |

TABLE 1-continued

| Cpd No. | Structure |
|---|---|
| 3 | (structure) |
| 4 | (structure) |
| 5 | (structure) |
| 6 | (structure) |
| 7 | (structure) |
| 8 | (structure) |

TABLE 1-continued
| Cpd No. | Structure |
|---|---|
| 9 | 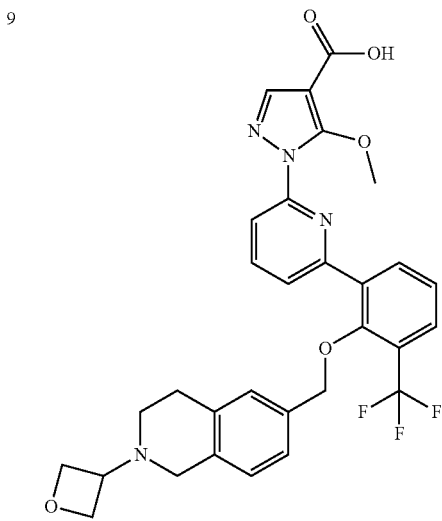 |
| 10 | 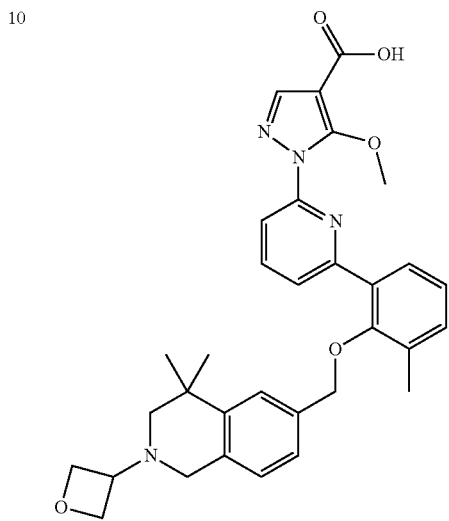 |
| 11 | 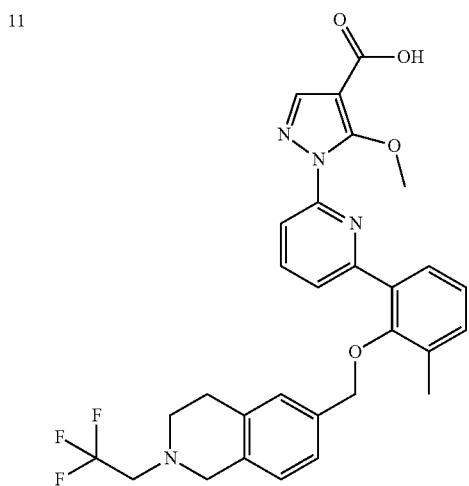 |
| 12 | 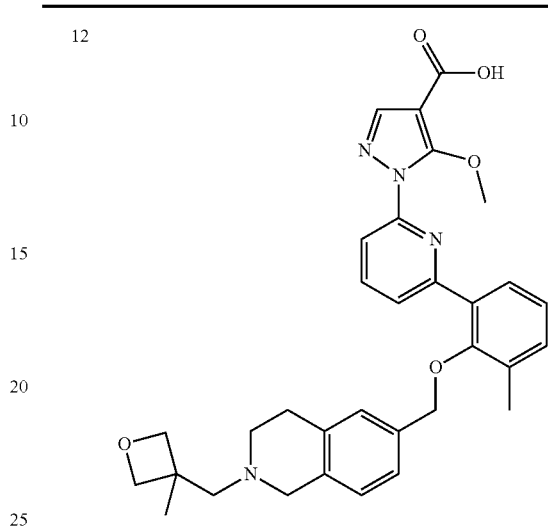 |
| 13 | 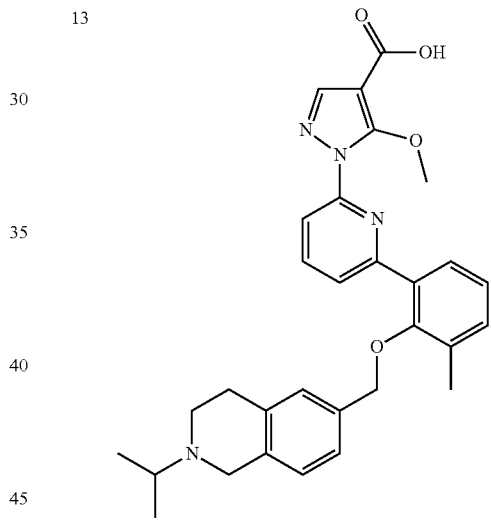 |
| 14 | 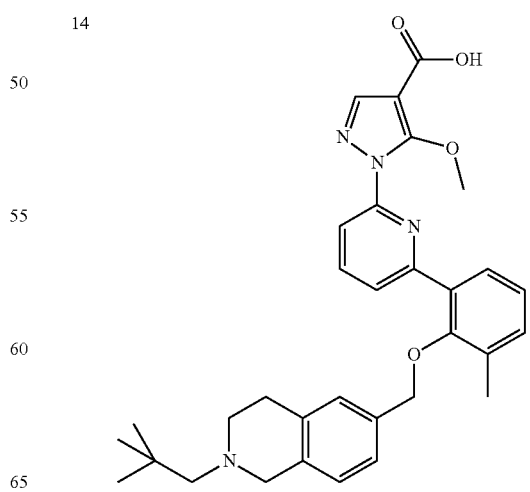 |

TABLE 1-continued
| Cpd No. | Structure |
|---|---|
| 15 | 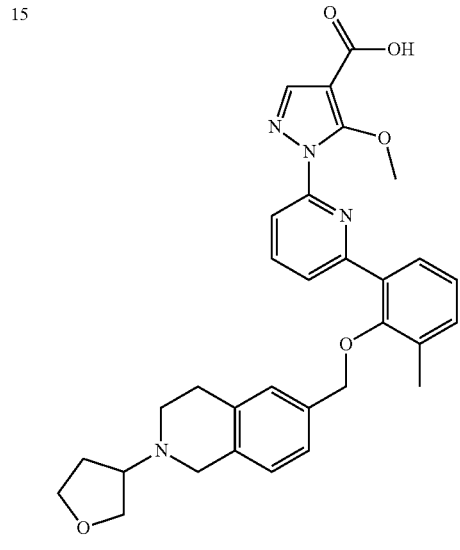 |
| 16 | 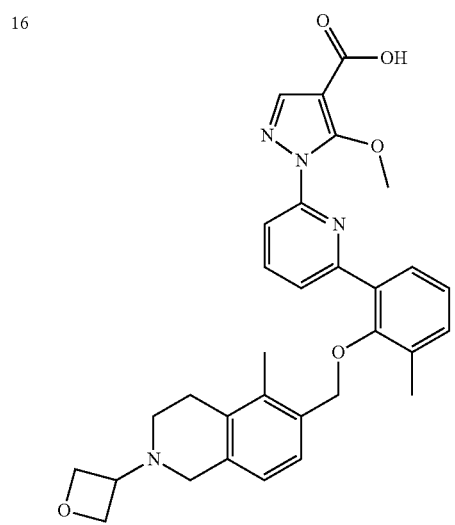 |
| 17 | 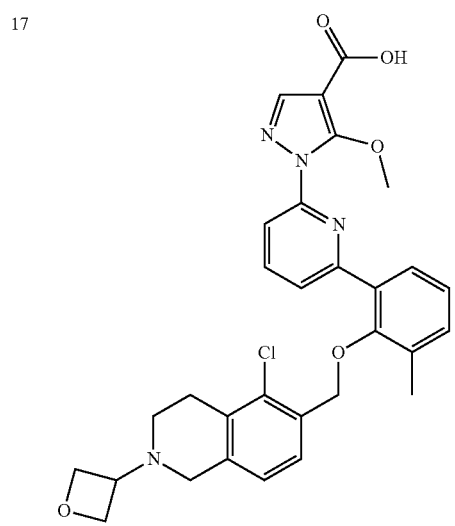 |
| 18 | 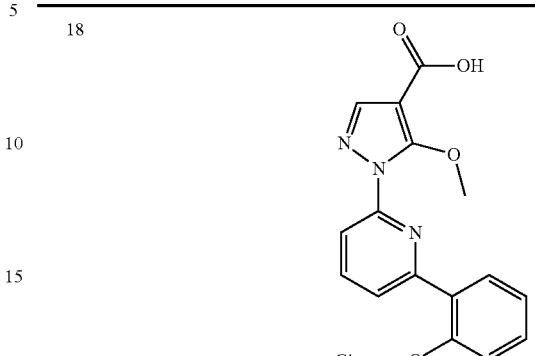 |
| 19 | 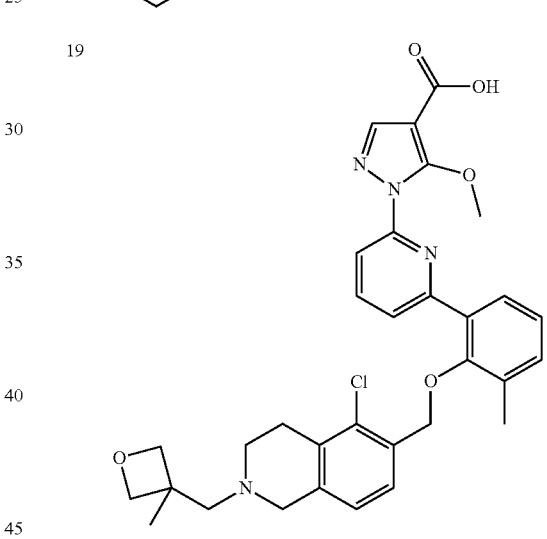 |
| 20 | 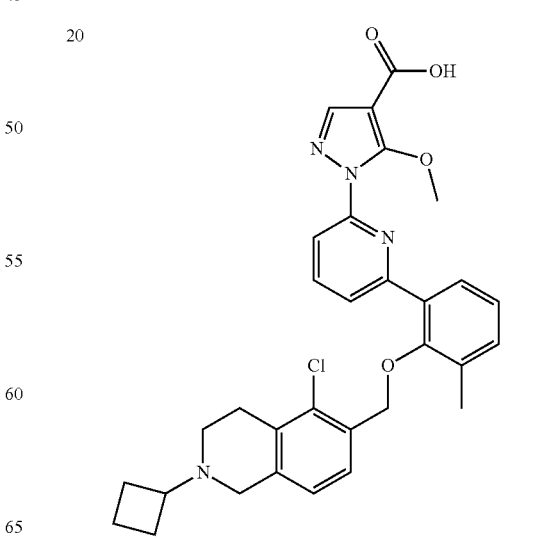 |

TABLE 1-continued

| Cpd No. | Structure |
|---|---|
| 21 | *(structure)* |
| 22 | *(structure)* |
| 23 | *(structure)* |
| 24 | *(structure)* |
| 25 | *(structure)* |
| 26 | *(structure)* |

TABLE 1-continued

| Cpd No. | Structure |
|---|---|
| 27 | 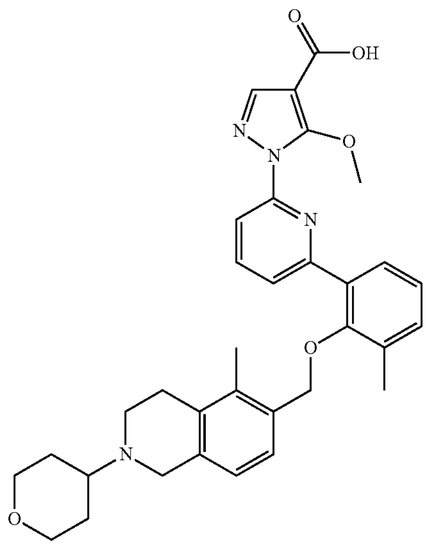 [SMILES: COc1c(C(=O)O)cnn1-c1cccc(-c2cccc(C)c2OCc2ccc3c(c2C)CCN(C2CCOCC2)C3)n1] |
| 28 | 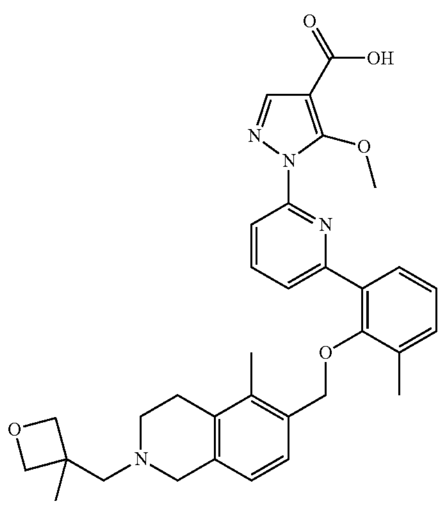 [SMILES: COc1c(C(=O)O)cnn1-c1cccc(-c2cccc(C)c2OCc2ccc3c(c2C)CCN(CC2(C)COC2)C3)n1] |
| 29 | 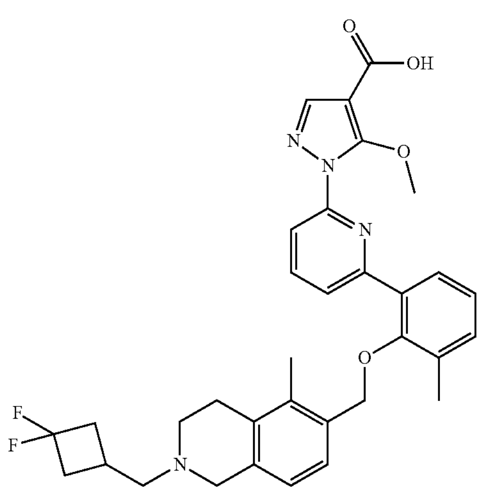 [SMILES: COc1c(C(=O)O)cnn1-c1cccc(-c2cccc(C)c2OCc2ccc3c(c2C)CCN(CC2CC(F)(F)C2)C3)n1] |
| 30 | |
| 31 | |
| 32 | |

TABLE 1-continued
| Cpd No. | Structure |
|---|---|
| 33 | 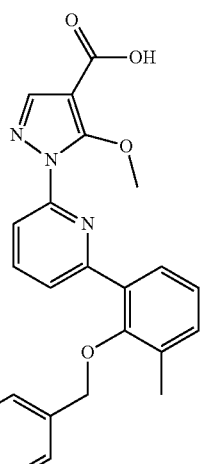 |
| 34 | 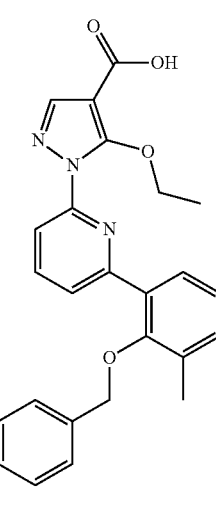 |
| 35 | 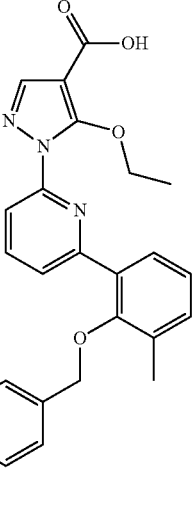 |
TABLE 1-continued
| Cpd No. | Structure |
|---|---|
| 36 | 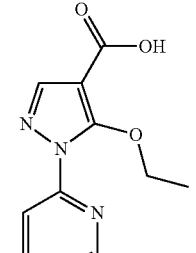 |
| 37 | 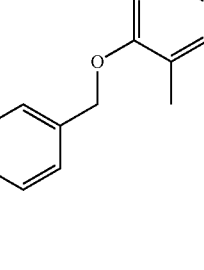 |

TABLE 1-continued
| Cpd No. | Structure |
|---|---|
| 38 | 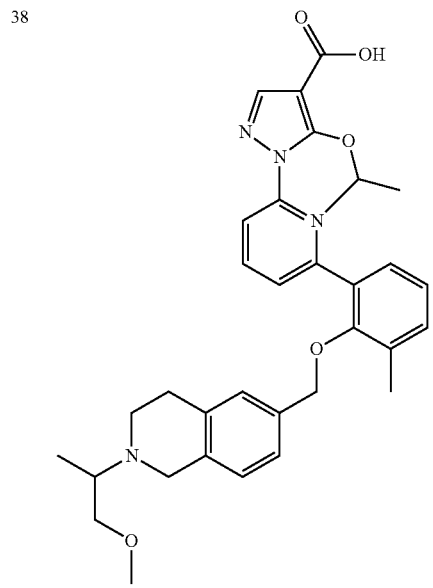 |
| 39 | 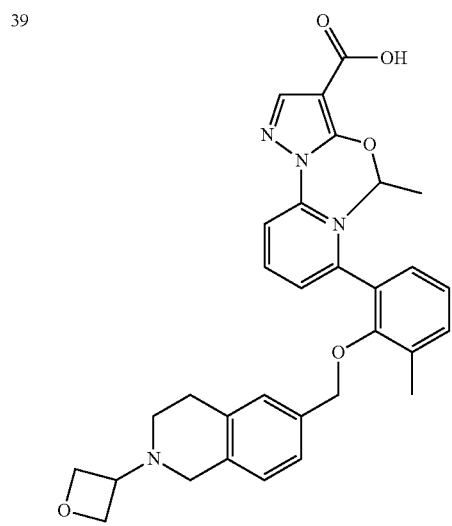 |
| 40 | 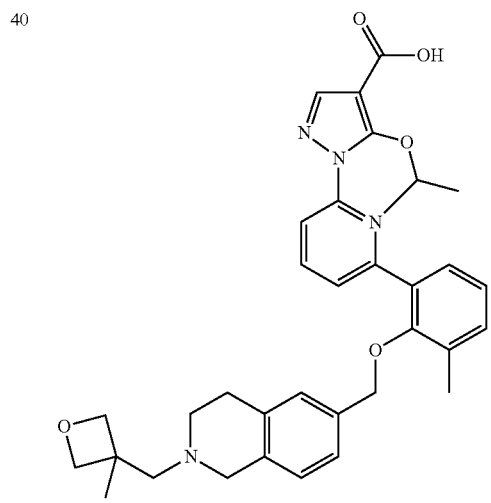 |
TABLE 1-continued
| Cpd No. | Structure |
|---|---|
| 41 | 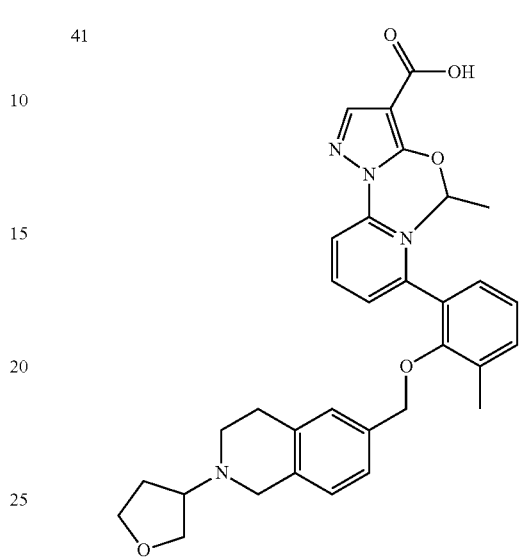 |
| 42 | 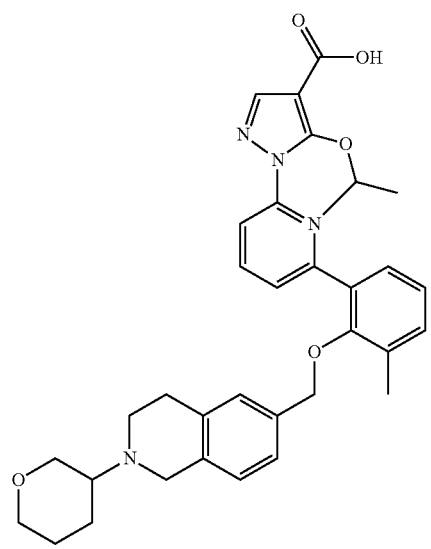 |

TABLE 1-continued
| Cpd No. | Structure |
|---|---|
| 43 | 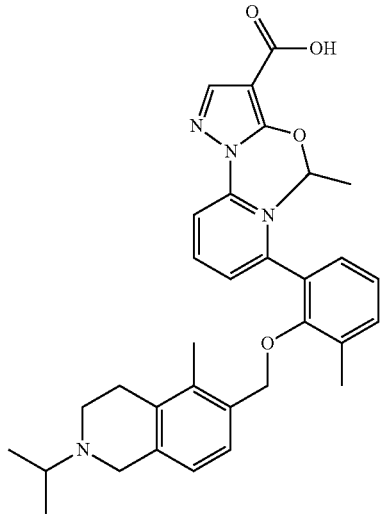 |
| 44 | 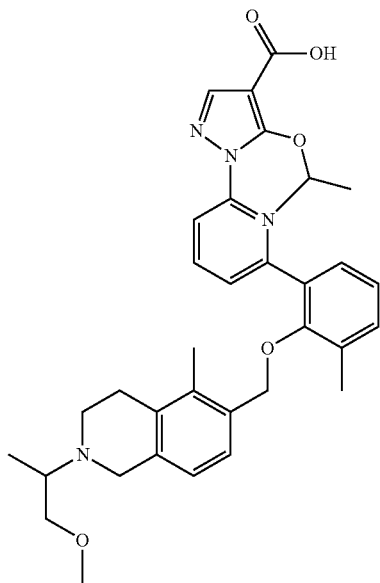 |
| 45 | 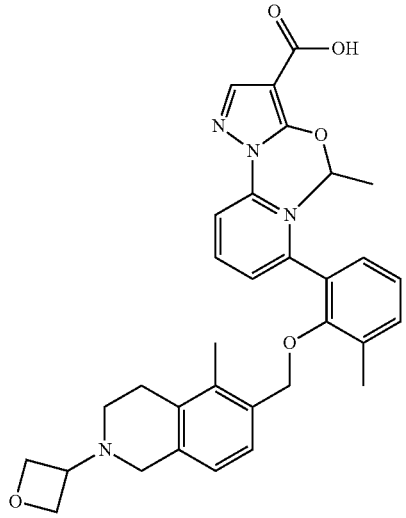 |
| 46 | 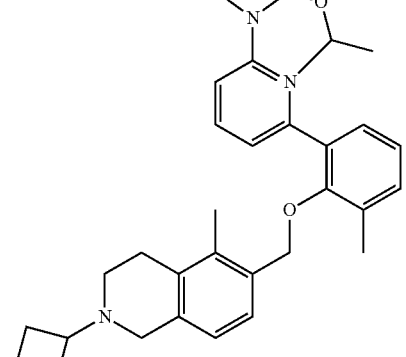 |
| 47 | 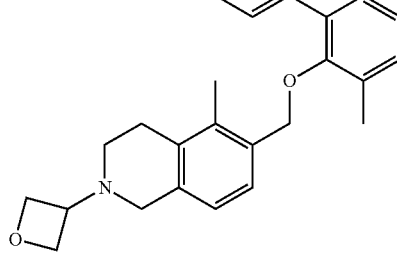 |

TABLE 1-continued
| Cpd No. | Structure |
|---|---|
| 48 | 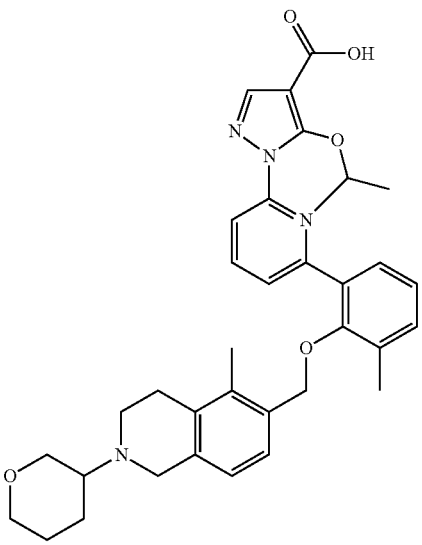 |
| 49 | 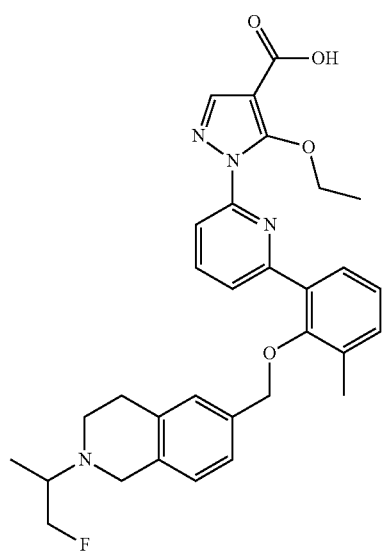 [SMILES: CCOc1c(C(=O)O)cnn1-c1cccc(-c2cccc(C)c2OCc2ccc3c(c2)CCN(C(C)CF)C3)n1] |
| 50 | 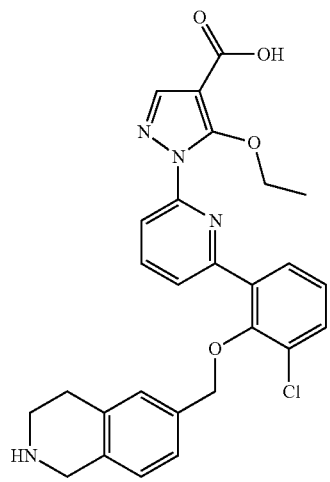 [SMILES: CCOc1c(C(=O)O)cnn1-c1cccc(-c2cccc(Cl)c2OCc2ccc3c(c2)CCNC3)n1] |
| 51 | 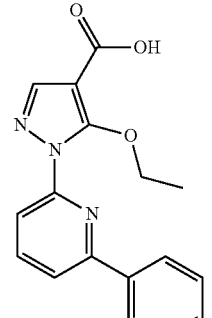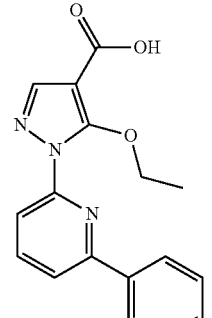 |
| 52 | 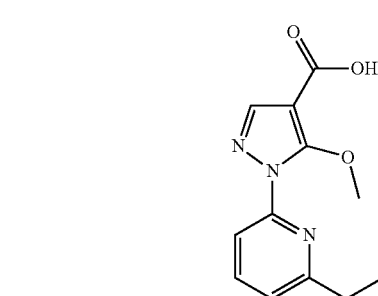 |
| 53 | 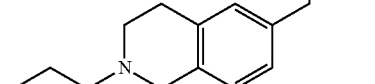 |

TABLE 1-continued
| Cpd No. | Structure |
|---|---|
| 54 | 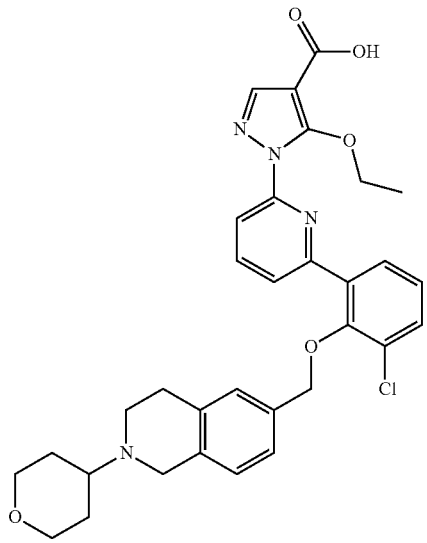 [SMILES: CCOc1c(C(=O)O)cnn1-c1cccc(-c2cccc(Cl)c2OCc2ccc3c(c2)CCN(C2CCOCC2)C3)n1] |
| 55 | 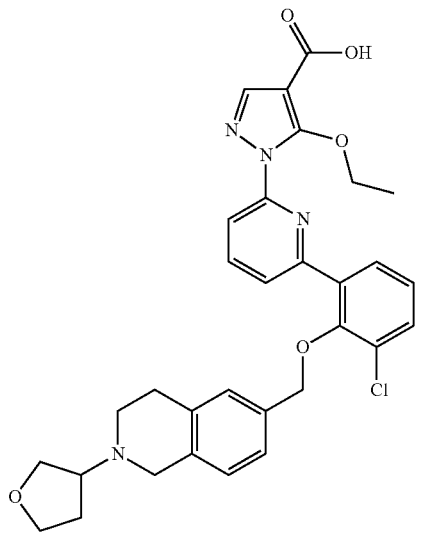 [SMILES: CCOc1c(C(=O)O)cnn1-c1cccc(-c2cccc(Cl)c2OCc2ccc3c(c2)CCN(C2CCOC2)C3)n1] |
| 56 | 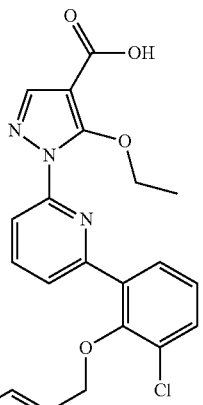 |
| 57 | 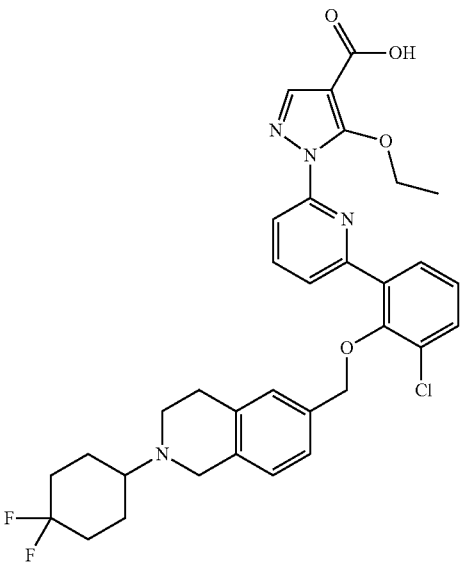 [SMILES: CCOc1c(C(=O)O)cnn1-c1cccc(-c2cccc(Cl)c2OCc2ccc3c(c2)CCN(C2CCC(F)(F)CC2)C3)n1] |

TABLE 1-continued
| Cpd No. | Structure |
|---|---|
| 58 | 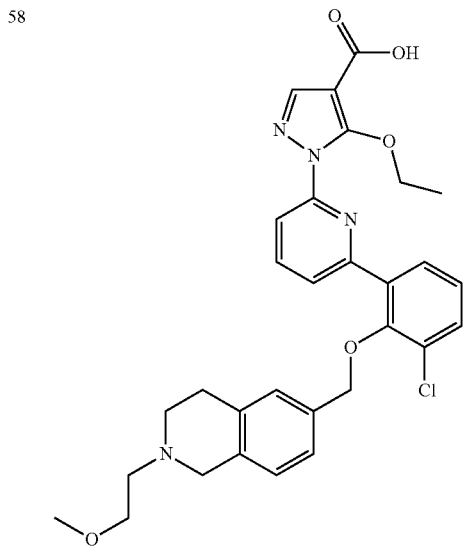 |
| 59 | 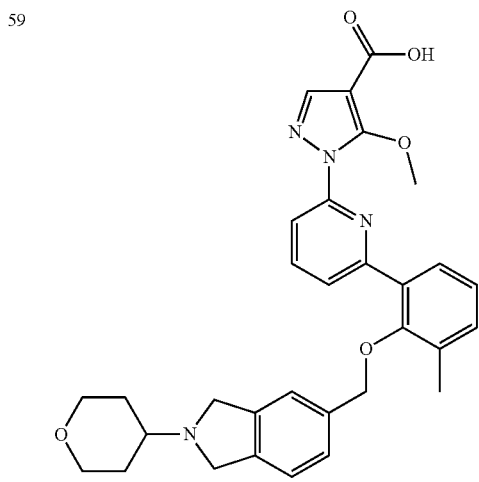 |
| 60 | 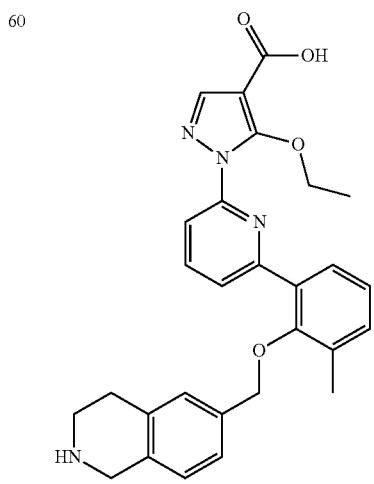 |
TABLE 1-continued
| Cpd No. | Structure |
|---|---|
| 61 | 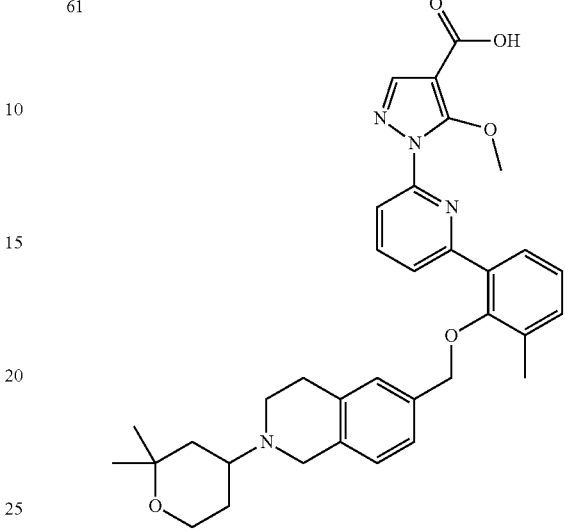 |
| 62 | 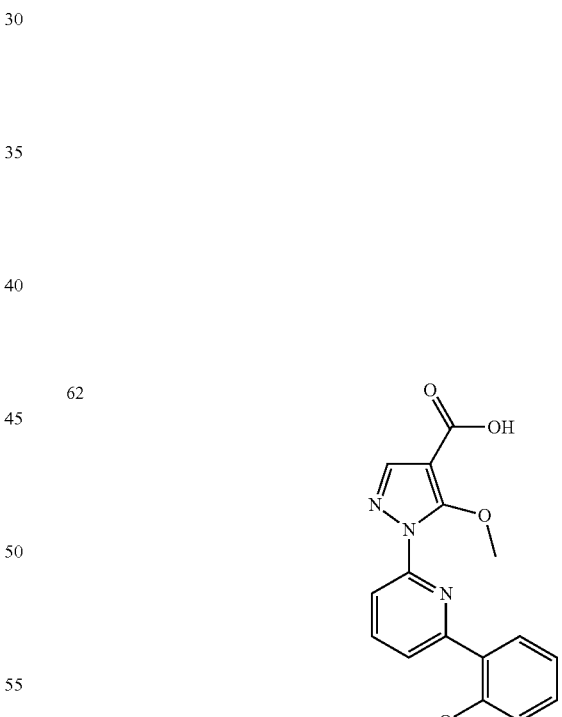 |

TABLE 1-continued
| Cpd No. | Structure |
|---|---|
| 63 | 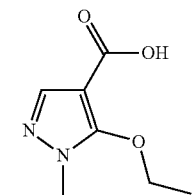 |
| 64 | 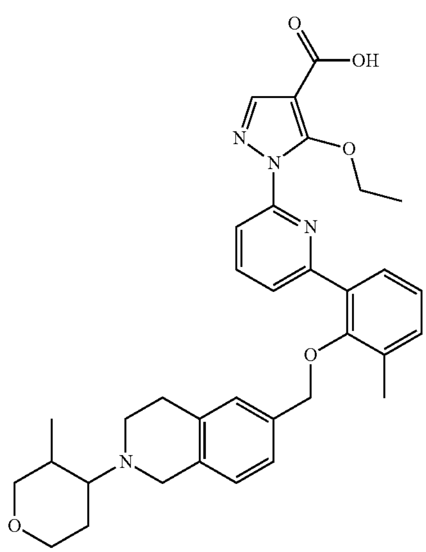 [SMILES: CCOc1c(C(=O)O)cnn1-c1cccc(-c2cccc(C)c2OCc2ccc3c(c2)CCN(C2CCOCC2C)C3)n1] |
| 65 | 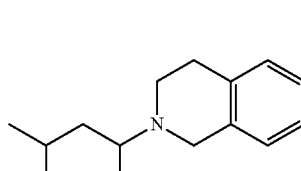 |
| 66 | |

TABLE 1-continued
| Cpd No. | Structure |
|---|---|
| 67 | 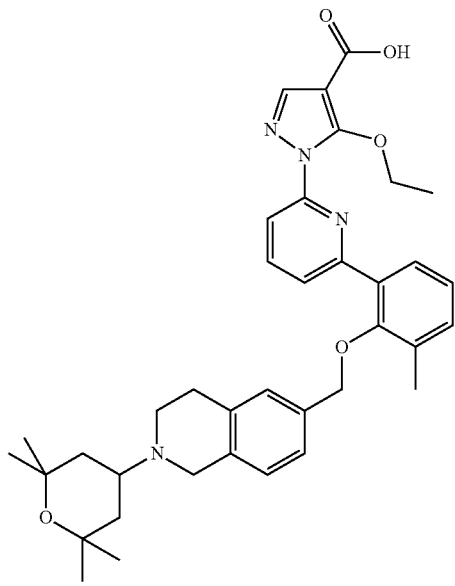 |
| 68 | 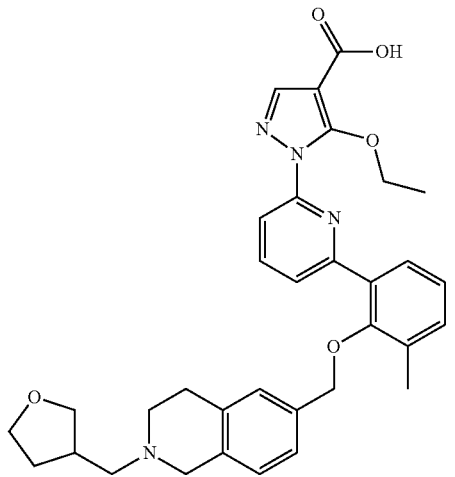 [SMILES: CCOc1c(C(=O)O)cnn1-c1cccc(-c2cccc(C)c2OCc2ccc3c(c2)CCN(CC2CCOC2)C3)n1] |
| 69 | 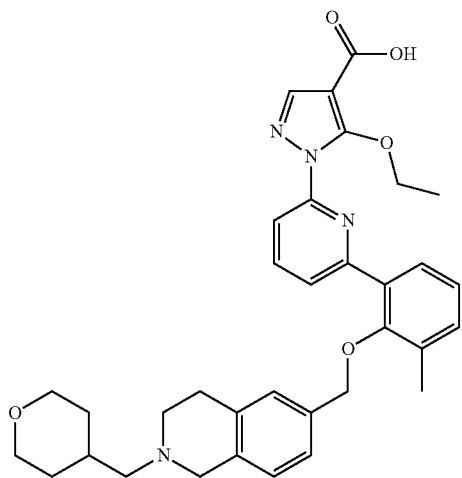 [SMILES: CCOc1c(C(=O)O)cnn1-c1cccc(-c2cccc(C)c2OCc2ccc3c(c2)CCN(CC2CCOCC2)C3)n1] |
| 70 | 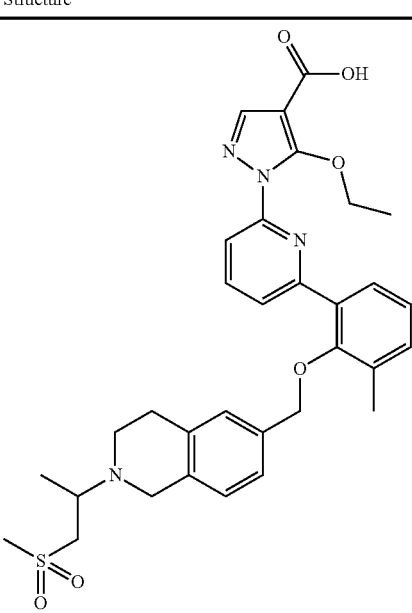 |
| 71 | 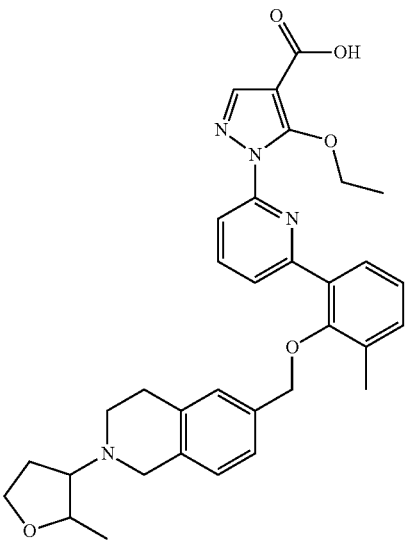 [SMILES: CCOc1c(C(=O)O)cnn1-c1cccc(-c2cccc(C)c2OCc2ccc3c(c2)CCN(C2CCOC2C)C3)n1] |
| 72 | 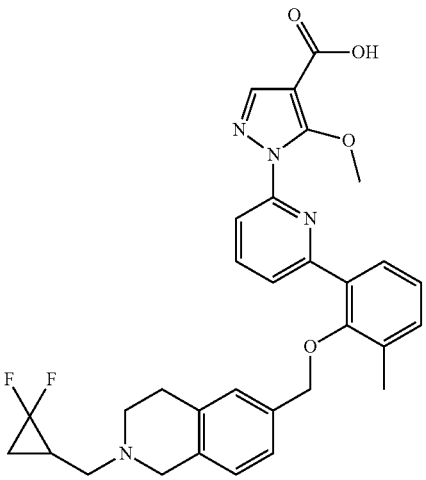 [SMILES: COc1c(C(=O)O)cnn1-c1cccc(-c2cccc(C)c2OCc2ccc3c(c2)CCN(CC2CC2(F)F)C3)n1] |

TABLE 1-continued
| Cpd No. | Structure |
|---|---|
| 73 | 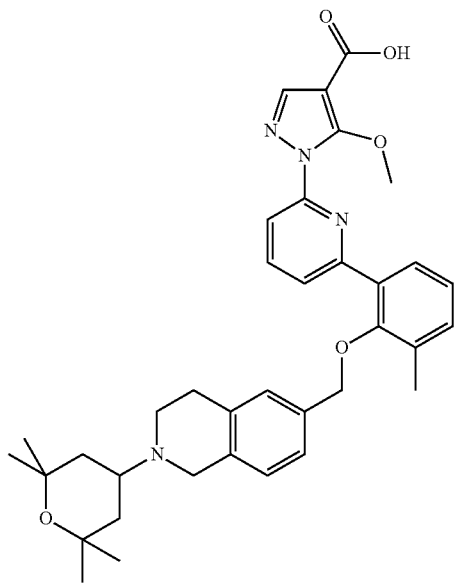 [SMILES: COc1c(C(=O)O)cnn1-c1cccc(-c2cccc(C)c2OCc2ccc3c(c2)CCN(C2CC(C)(C)OC(C)(C)C2)C3)n1] |
| 74 | 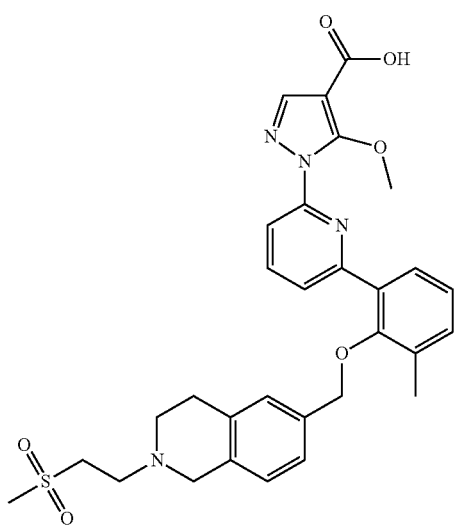 [SMILES: COc1c(C(=O)O)cnn1-c1cccc(-c2cccc(C)c2OCc2ccc3c(c2)CCN(CCS(C)(=O)=O)C3)n1] |
| 75 | 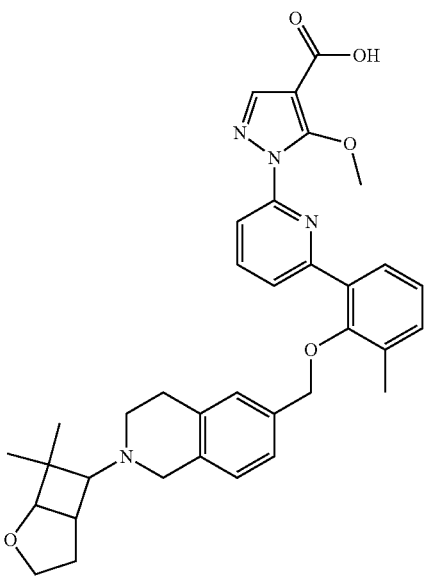 [SMILES: COc1c(C(=O)O)cnn1-c1cccc(-c2cccc(C)c2OCc2ccc3c(c2)CCN(C2C4CCOC4C2(C)C)C3)n1] |
| 76 | 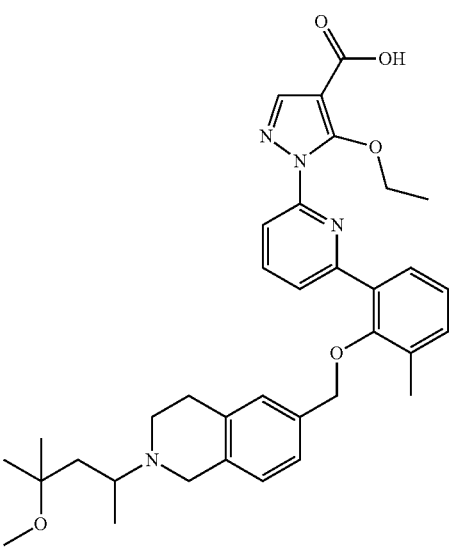 [SMILES: CCOc1c(C(=O)O)cnn1-c1cccc(-c2cccc(C)c2OCc2ccc3c(c2)CCN(C(C)CC(C)(C)OC)C3)n1] |

TABLE 1-continued
| Cpd No. | Structure |
|---|---|
| 77 | 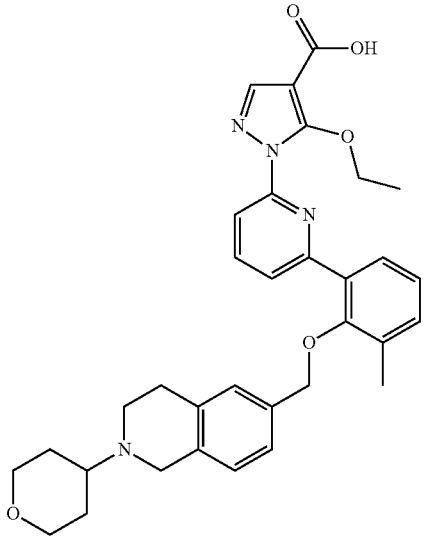 [SMILES: CCOc1c(C(=O)O)cnn1-c1cccc(-c2cccc(C)c2OCc2ccc3c(c2)CCN(C2CCOCC2)C3)n1] |
| 78 | 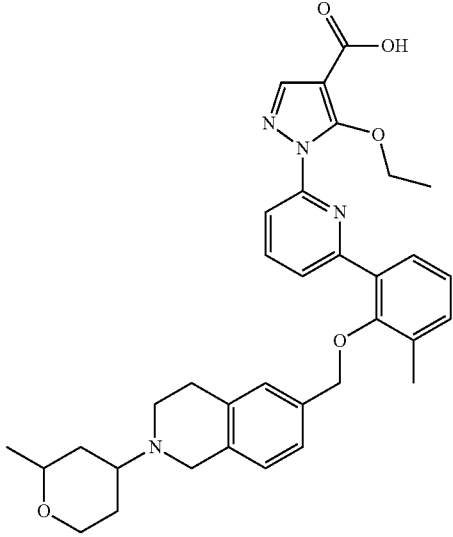 [SMILES: CCOc1c(C(=O)O)cnn1-c1cccc(-c2cccc(C)c2OCc2ccc3c(c2)CCN(C2CCOC(C)C2)C3)n1] |
| 79 | 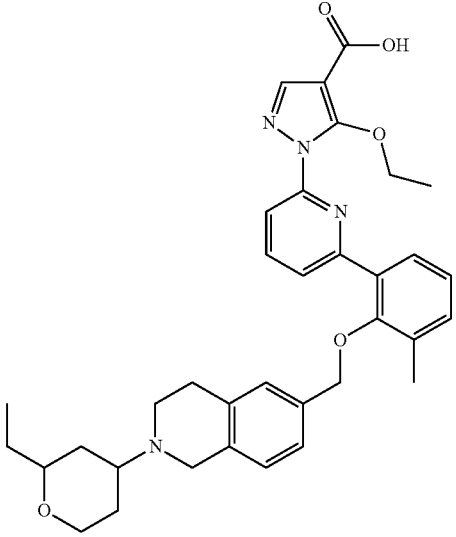 [SMILES: CCOc1c(C(=O)O)cnn1-c1cccc(-c2cccc(C)c2OCc2ccc3c(c2)CCN(C2CCOC(CC)C2)C3)n1] |
| 80 | 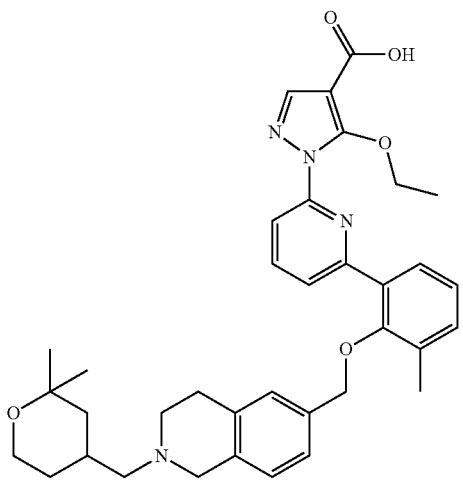 [SMILES: CCOc1c(C(=O)O)cnn1-c1cccc(-c2cccc(C)c2OCc2ccc3c(c2)CCN(CC2CCOC(C)(C)C2)C3)n1] |
| 81 | 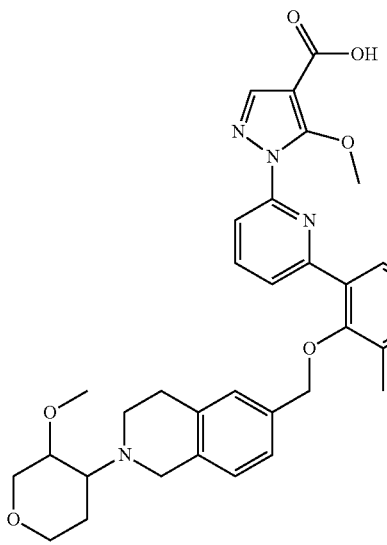 |

TABLE 1-continued
| Cpd No. | Structure |
|---|---|
| 82 | 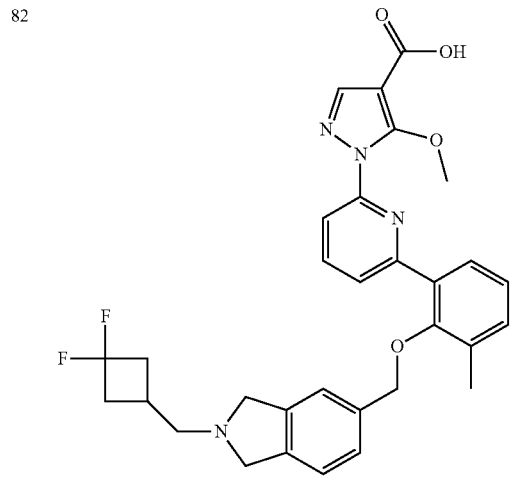 |
| 83 | 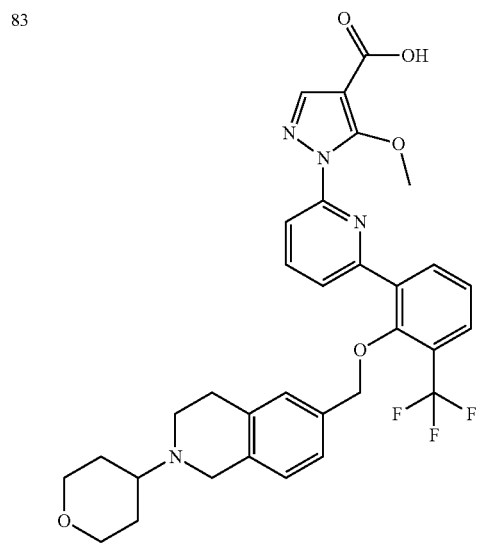 |
| 84 | 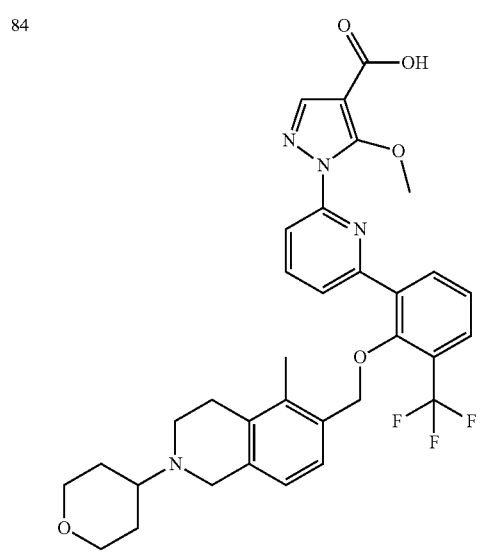 |
| 85 | 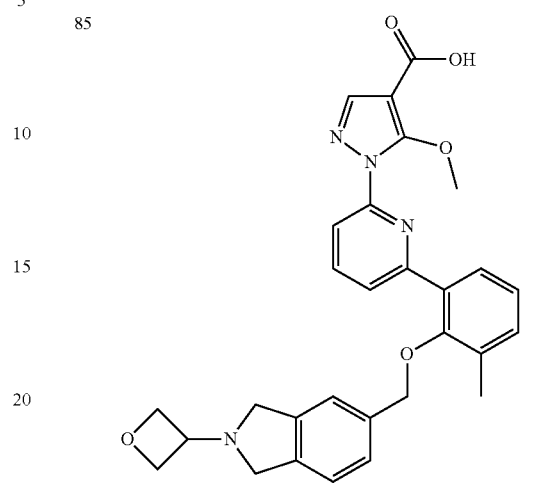 |
| 86 | 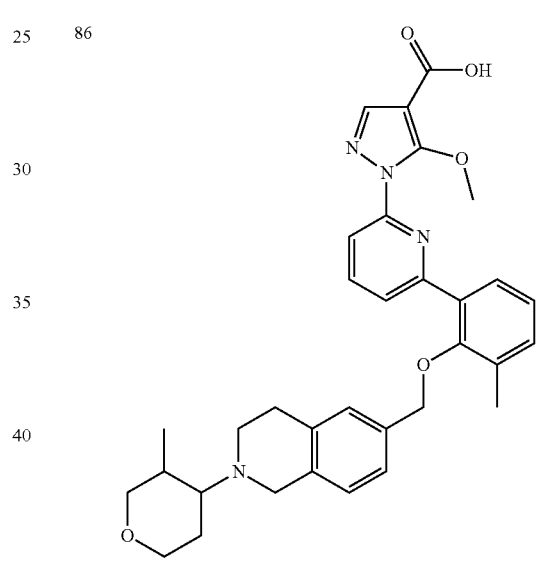 |
| 87 | 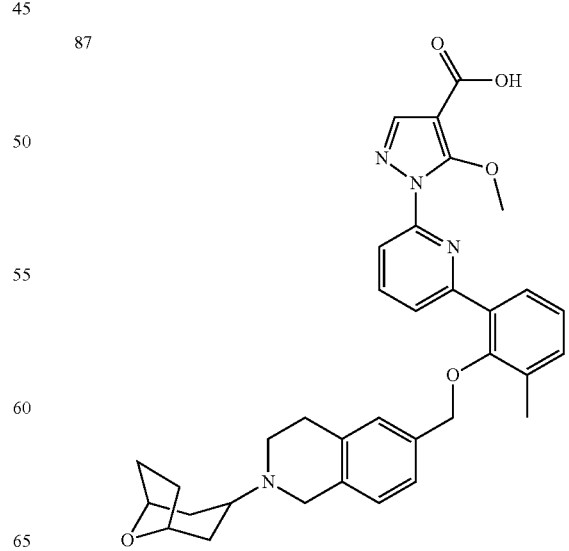 |

TABLE 1-continued

| Cpd No. | Structure |
|---|---|
| 88 | 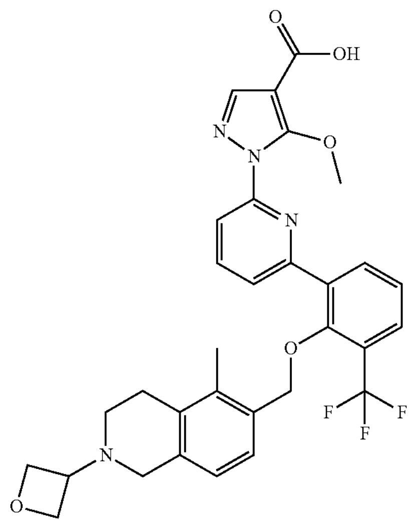 [SMILES: COc1c(C(=O)O)cnn1-c1cccc(-c2cccc(C(F)(F)F)c2OCc2ccc3c(c2C)CCN(C2COC2)C3)n1] |
| 89 | 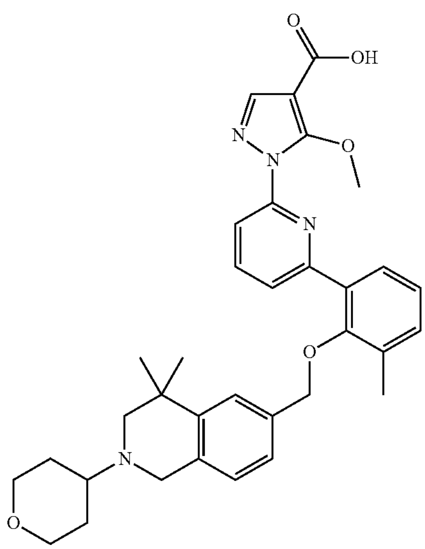 [SMILES: COc1c(C(=O)O)cnn1-c1cccc(-c2cccc(C)c2OCc2ccc3c(c2)C(C)(C)CN(C2CCOCC2)C3)n1] |
| 90 | 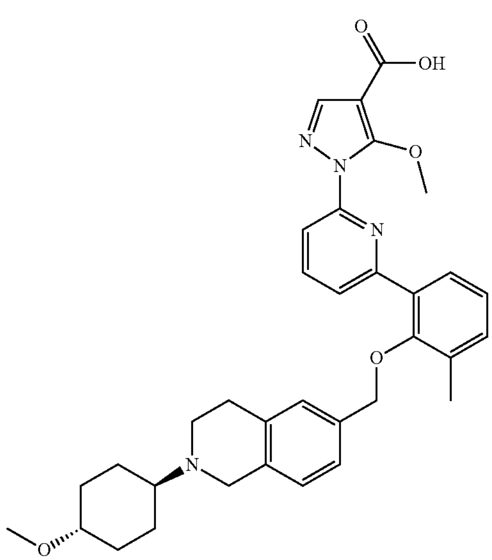 [SMILES: COc1c(C(=O)O)cnn1-c1cccc(-c2cccc(C)c2OCc2ccc3c(c2)CCN([C@H]2CC[C@H](OC)CC2)C3)n1] |
| 91 | |
| 92 | |
| 93 | |

TABLE 1-continued

| Cpd No. | Structure |
|---|---|
| 94 | 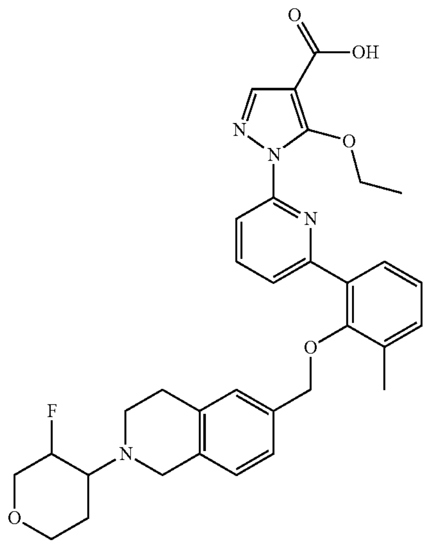 |
| 95 | 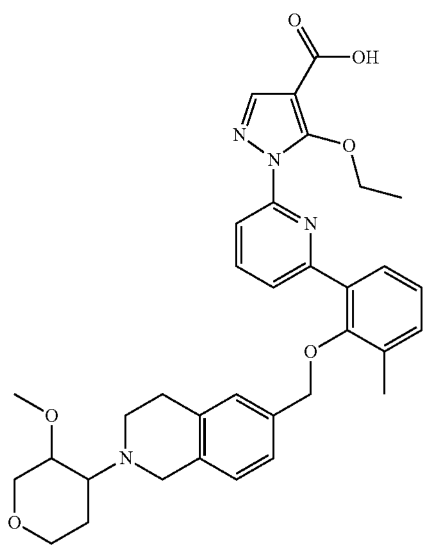 [SMILES: CCOc1c(C(=O)O)cnn1-c1cccc(-c2cccc(C)c2OCc2ccc3c(c2)CCN(C2CCOCC2OC)C3)n1] |
| 96 | 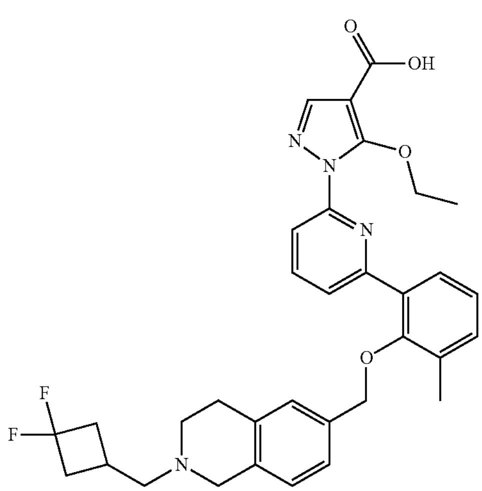 [SMILES: CCOc1c(C(=O)O)cnn1-c1cccc(-c2cccc(C)c2OCc2ccc3c(c2)CCN(CC2CC(F)(F)C2)C3)n1] |
| 97 | |
| 98 | |
| 99 | |

TABLE 1-continued
| Cpd No. | Structure |
|---|---|
| 100 | 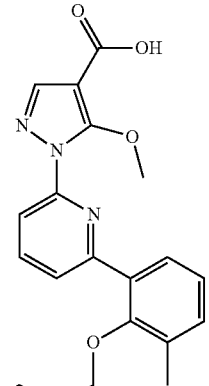 |
| 101 | 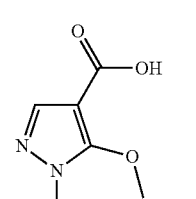 |
| 102 | 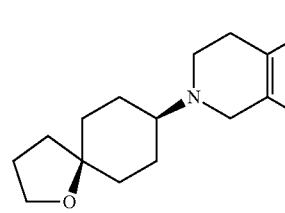 |
| 103 |  |

TABLE 1-continued
| Cpd No. | Structure |
|---|---|
| 104 | 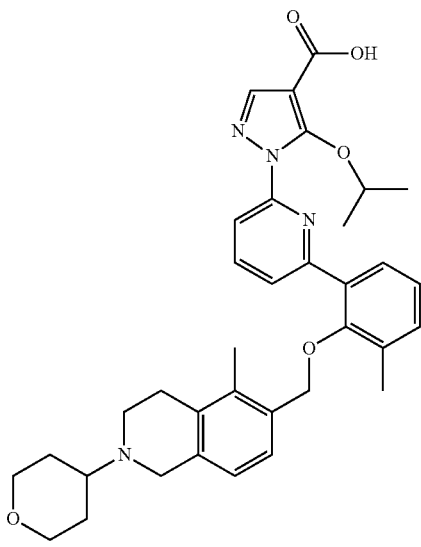 [SMILES: Cc1cccc(-c2cccc(-n3ncc(C(=O)O)c3OC(C)C)n2)c1OCc1ccc2c(c1C)CCN(C1CCOCC1)C2] |
| 105 | 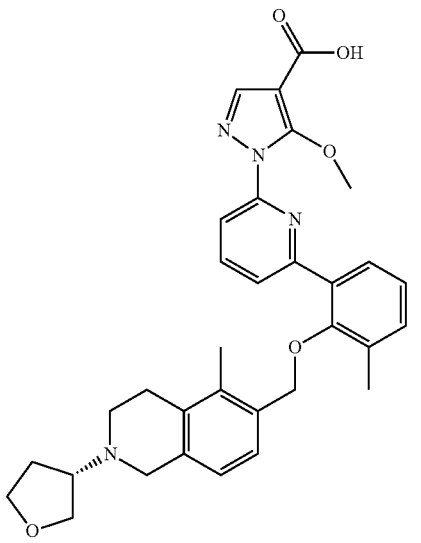 [SMILES: COc1c(C(=O)O)cnn1-c1cccc(-c2cccc(C)c2OCc2ccc3c(c2C)CCN([C@H]2CCOC2)C3)n1] |оставления
TABLE 1-continued
| Cpd No. | Structure |
|---|---|
| 106 | 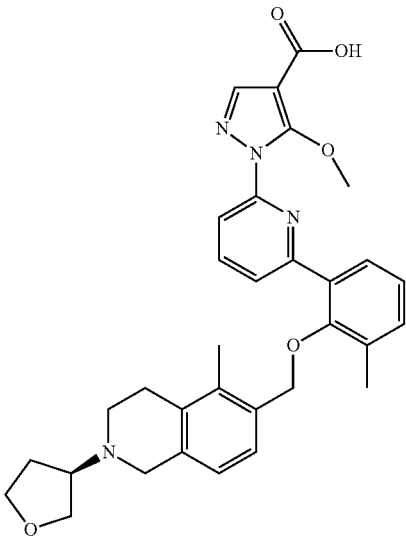 |
| 107 | 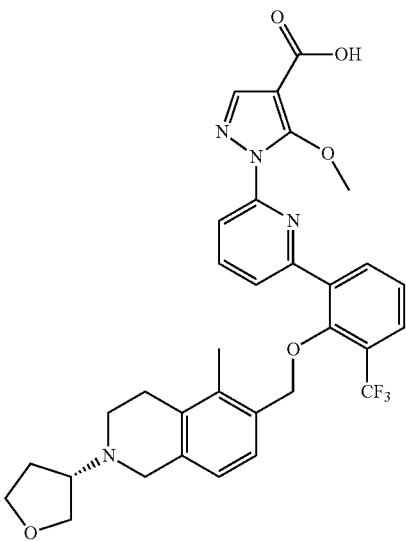 [SMILES: COc1c(C(=O)O)cnn1-c1cccc(-c2cccc(C(F)(F)F)c2OCc2ccc3c(c2C)CCN([C@H]2CCOC2)C3)n1] |

TABLE 1-continued

| Cpd No. | Structure |
|---|---|
| 108 | 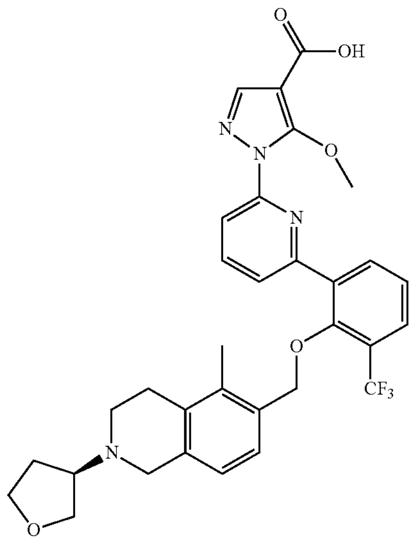 |
| 109 | 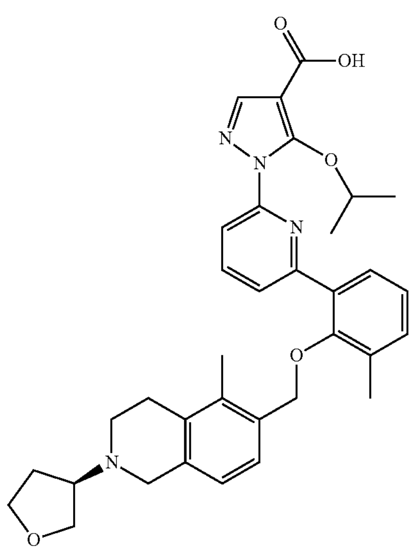 [SMILES: Cc1cccc(-c2cccc(-n3ncc(C(=O)O)c3OC(C)C)n2)c1OCc1ccc2c(c1C)CCN([C@@H]1CCOC1)C2] |
| 110 | |
| 111 | |

TABLE 1-continued
| Cpd No. | Structure |
|---|---|
| 112 | |
| 113 | 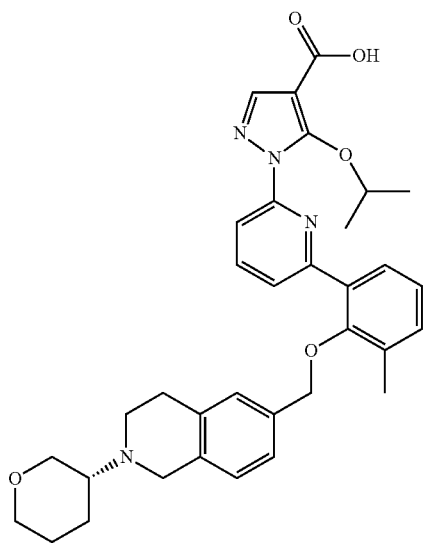 [SMILES: Cc1cccc(-c2cccc(-n3ncc(C(=O)O)c3OC(C)C)n2)c1OCc1ccc2c(c1)CCN([C@@H]1CCCOC1)C2] |["
| 114 | 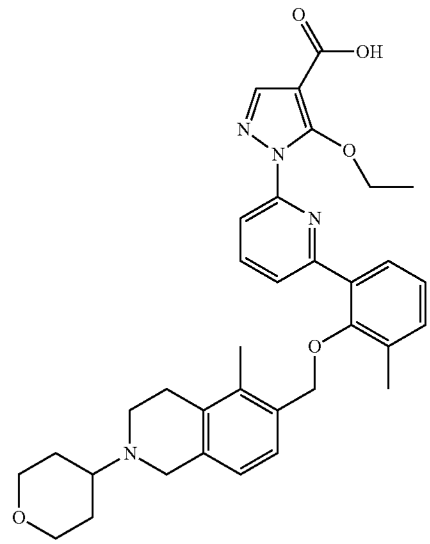 [SMILES: CCOc1c(C(=O)O)cnn1-c1cccc(-c2cccc(C)c2OCc2ccc3c(c2C)CCN(C2CCOCC2)C3)n1] |
| 115 | 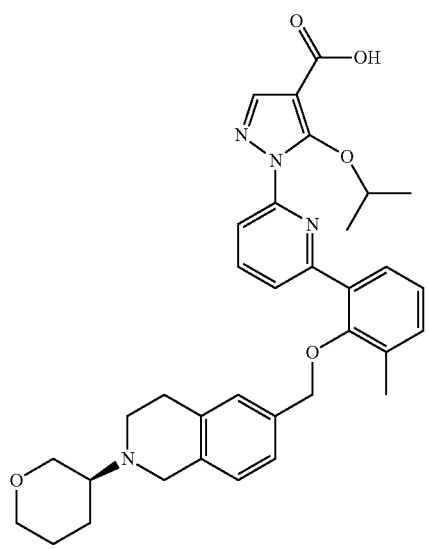 [SMILES: Cc1cccc(-c2cccc(-n3ncc(C(=O)O)c3OC(C)C)n2)c1OCc1ccc2c(c1)CCN([C@H]1CCCOC1)C2] |

TABLE 1-continued

| Cpd No. | Structure |
|---|---|
| 116 | 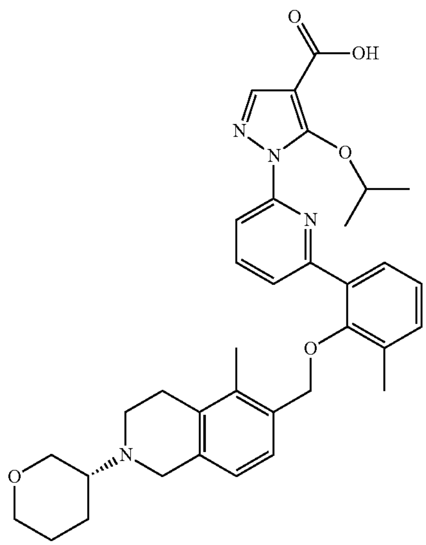 [SMILES: Cc1cccc(-c2cccc(-n3ncc(C(=O)O)c3OC(C)C)n2)c1OCc1ccc2c(c1C)CCN([C@@H]1CCCOC1)C2] |
| 117 | 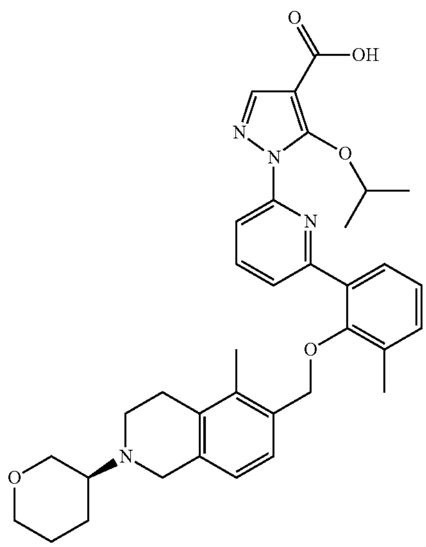 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 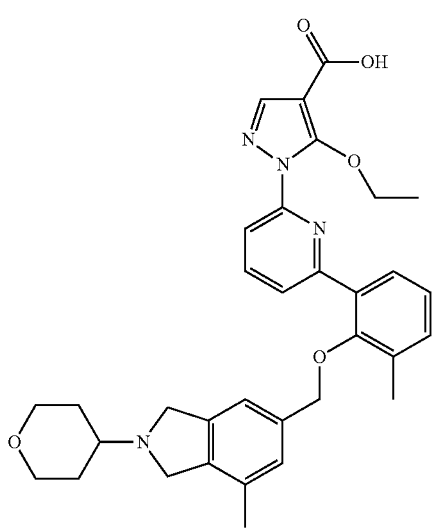 [SMILES: CCOc1c(C(=O)O)cnn1-c1cccc(-c2cccc(C)c2OCc2cc(C)c3c(c2)CN(C2CCOCC2)C3)n1] |
| 119 | |
| 120 | |
| 121 | |

TABLE 1-continued
| Cpd No. | Structure |
|---|---|
| 122 | 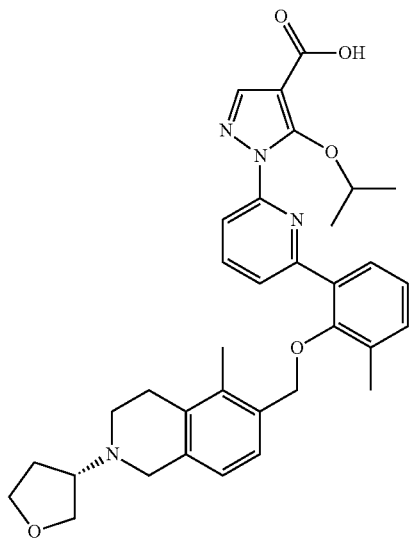 |
| 123 | 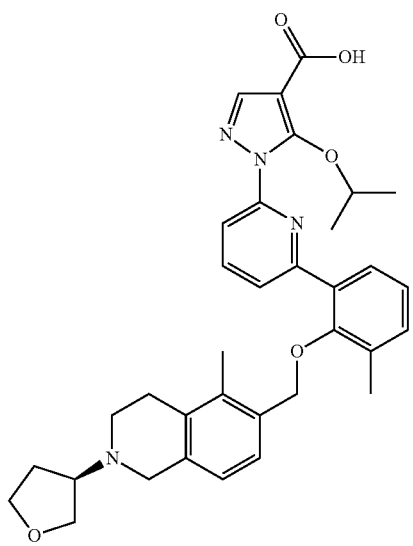 [SMILES: Cc1cccc(-c2cccc(-n3ncc(C(=O)O)c3OC(C)C)n2)c1OCc1ccc2c(c1C)CCN([C@@H]1CCOC1)C2] |
| 124 | 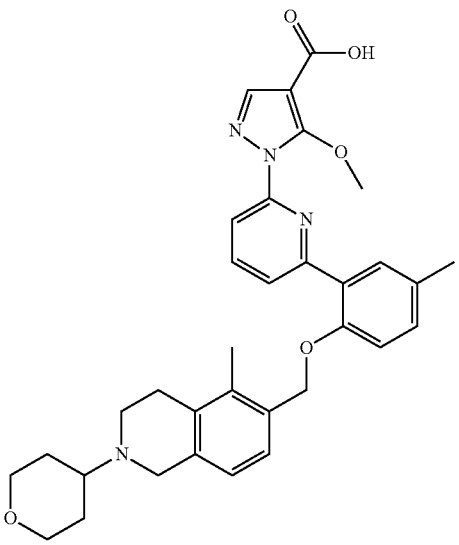 [SMILES: COc1c(C(=O)O)cnn1-c1cccc(-c2cc(C)ccc2OCc2ccc3c(c2C)CCN(C2CCOCC2)C3)n1] |
| 125 | 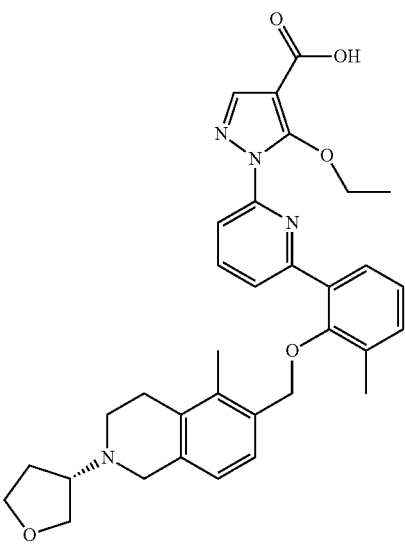 |

TABLE 1-continued
| Cpd No. | Structure |
|---|---|
| 126 | 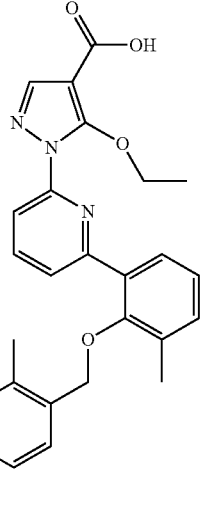 |
| 127 | 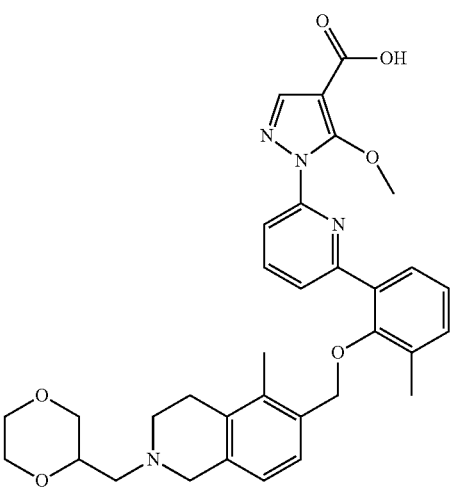 [SMILES: COc1c(C(=O)O)cnn1-c1cccc(-c2cccc(C)c2OCc2ccc3c(c2C)CCN(CC2COCCO2)C3)n1] |
| 128 | 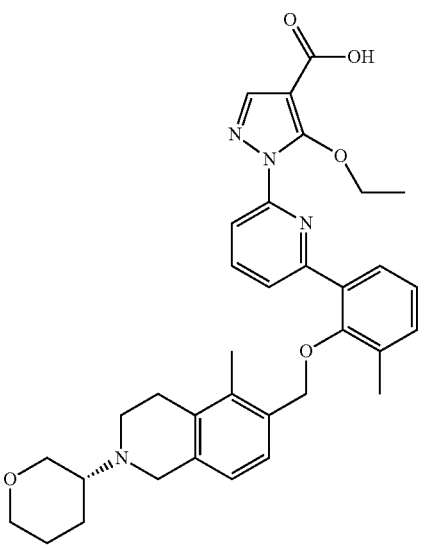 [SMILES: CCOc1c(C(=O)O)cnn1-c1cccc(-c2cccc(C)c2OCc2ccc3c(c2C)CCN([C@@H]2CCCOC2)C3)n1] |
TABLE 1-continued
| Cpd No. | Structure |
|---|---|
| 129 | 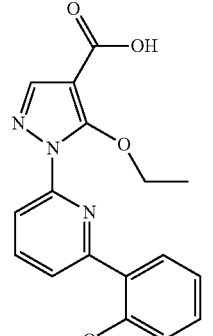 |
| 130 | 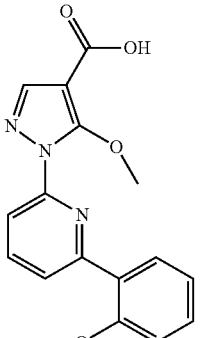 |

TABLE 1-continued
| Cpd No. | Structure |
|---|---|
| 131 | 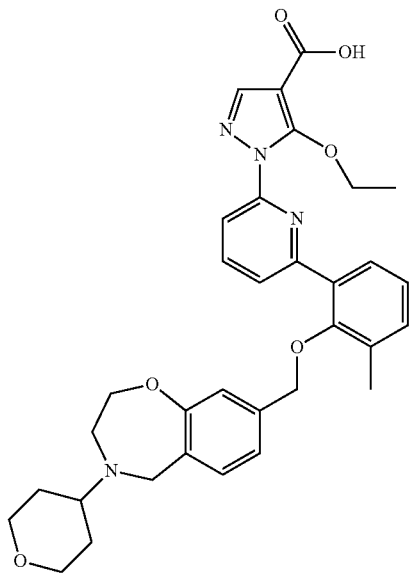 [SMILES: CCOc1c(C(=O)O)cnn1-c1cccc(-c2cccc(C)c2OCc2ccc3c(c2)OCCN(C2CCOCC2)C3)n1] |
| 132 | 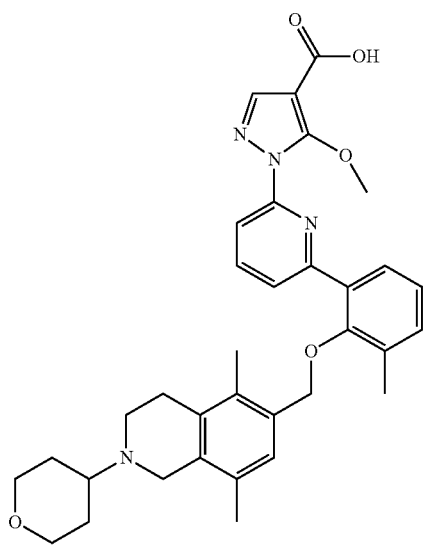 [SMILES: COc1c(C(=O)O)cnn1-c1cccc(-c2cccc(C)c2OCc2cc(C)c3c(c2C)CCN(C2CCOCC2)C3)n1] |
| 133 | 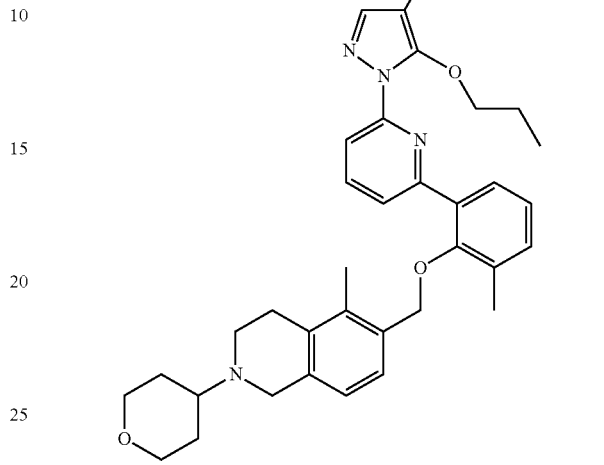 |
| 134 | 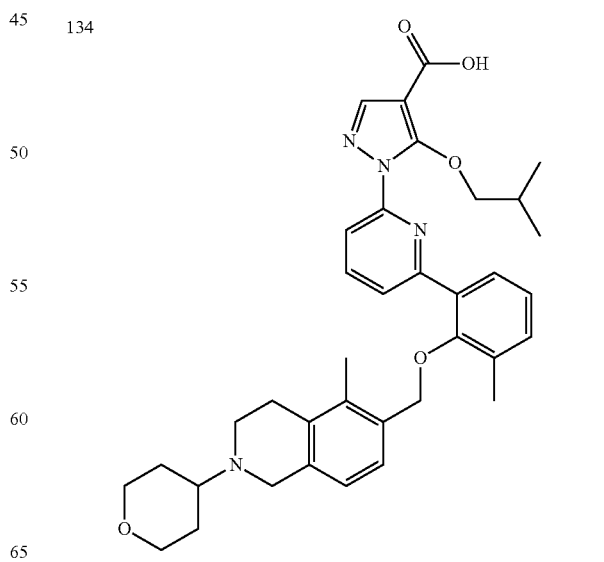 |

TABLE 1-continued
| Cpd No. | Structure |
|---|---|
| 135 | 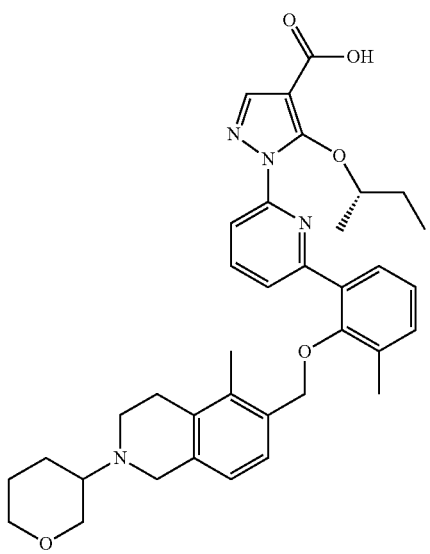 [SMILES: CC[C@H](C)Oc1c(C(=O)O)cnn1-c1cccc(-c2cccc(C)c2OCc2ccc3c(c2C)CCN(C2CCCOC2)C3)n1] |
| 136 | 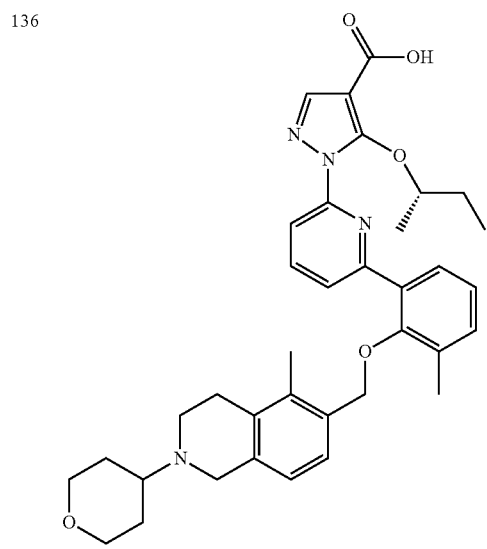 |
| 137 | 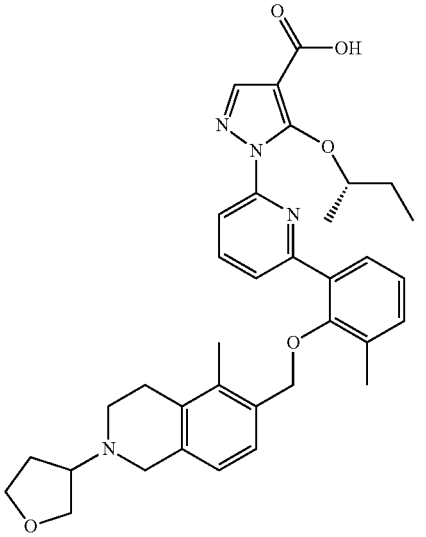 [SMILES: CC[C@H](C)Oc1c(C(=O)O)cnn1-c1cccc(-c2cccc(C)c2OCc2ccc3c(c2C)CCN(C2CCOC2)C3)n1] |
| 138 | 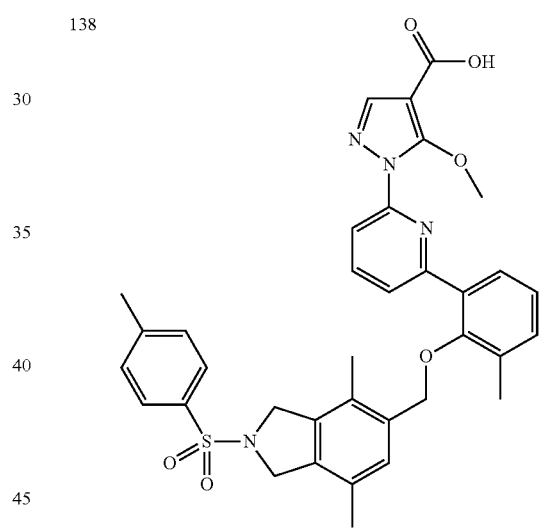 |
| 139 | 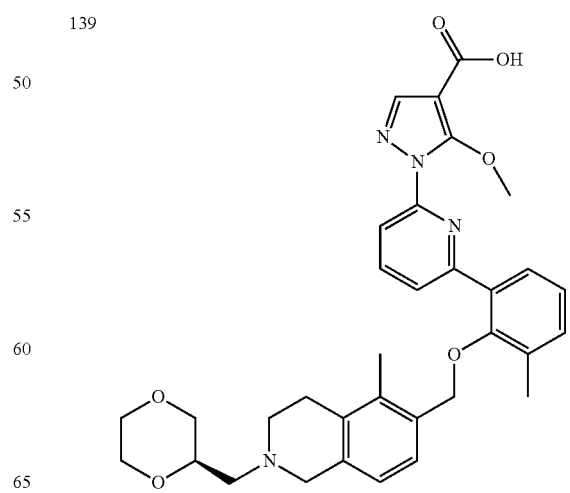 |

TABLE 1-continued
| Cpd No. | Structure |
|---|---|
| 140 | 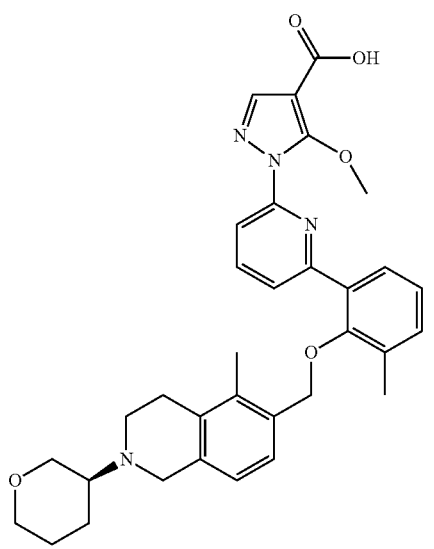 [SMILES: COc1c(C(=O)O)cnn1-c1cccc(-c2cccc(C)c2OCc2ccc3c(c2C)CCN([C@H]2CCCOC2)C3)n1] |
| 141 | 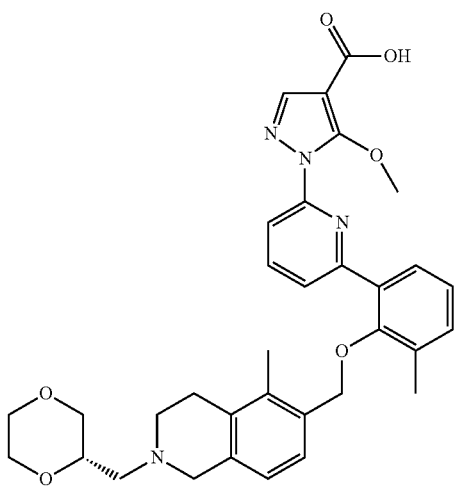 [SMILES: COc1c(C(=O)O)cnn1-c1cccc(-c2cccc(C)c2OCc2ccc3c(c2C)CCN(C[C@H]2COCCO2)C3)n1] |
| 142 | |
TABLE 1-continued
| Cpd No. | Structure |
|---|---|
| 143 | 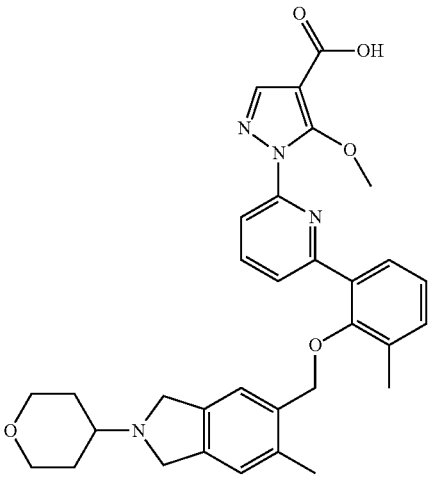 [SMILES: COc1c(C(=O)O)cnn1-c1cccc(-c2cccc(C)c2OCc2cc3c(cc2C)CN(C2CCOCC2)C3)n1] |
| 144 | 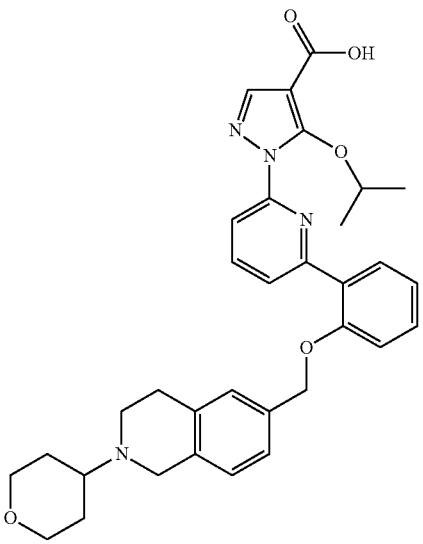 [SMILES: CC(C)Oc1c(C(=O)O)cnn1-c1cccc(-c2ccccc2OCc2ccc3c(c2)CCN(C2CCOCC2)C3)n1] |
| 145 | |

TABLE 1-continued

| Cpd No. | Structure |
|---|---|
| 146 | 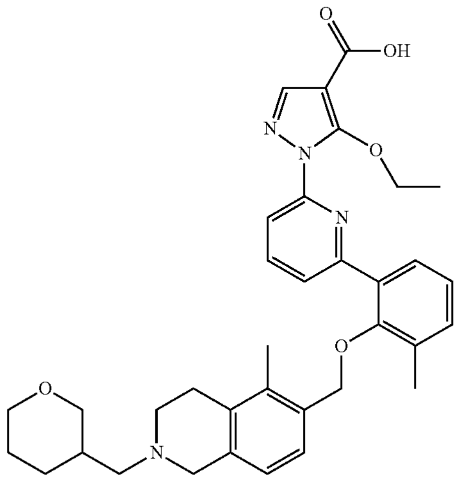 |
| 147 | 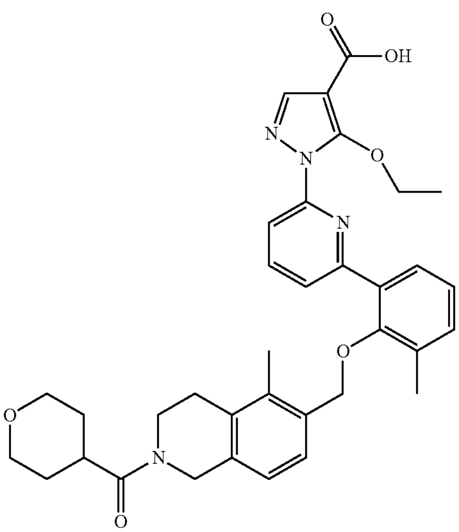 [SMILES: CCOc1c(C(=O)O)cnn1-c1cccc(-c2cccc(C)c2OCc2ccc3c(c2C)CCN(C(=O)C2CCOCC2)C3)n1] |
| 148 | 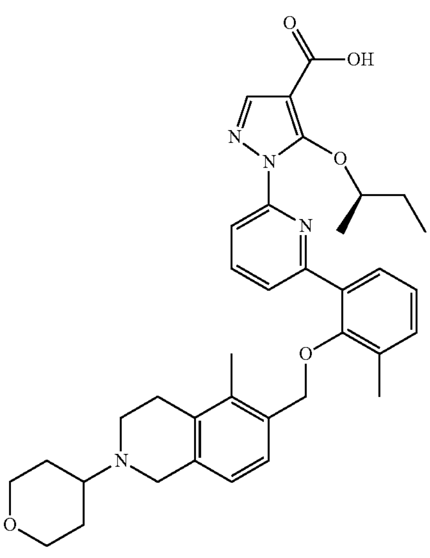 [SMILES: CC[C@@H](C)Oc1c(C(=O)O)cnn1-c1cccc(-c2cccc(C)c2OCc2ccc3c(c2C)CCN(C2CCOCC2)C3)n1] |
| 149 | |
| 150 | |

TABLE 1-continued
| Cpd No. | Structure |
|---|---|
| 151 | 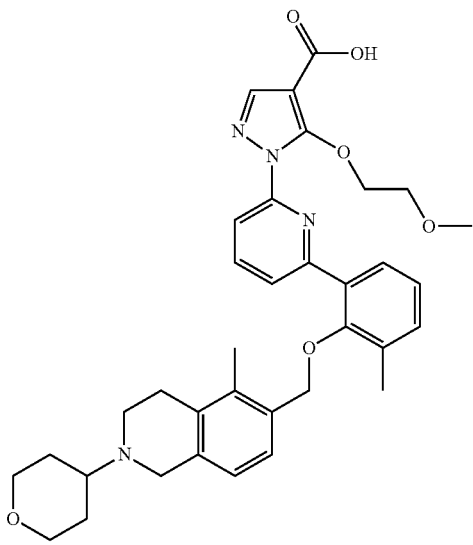 [SMILES: COCCOc1c(C(=O)O)cnn1-c1cccc(-c2cccc(C)c2OCc2ccc3c(c2C)CCN(C2CCOCC2)C3)n1] |
| 152 | 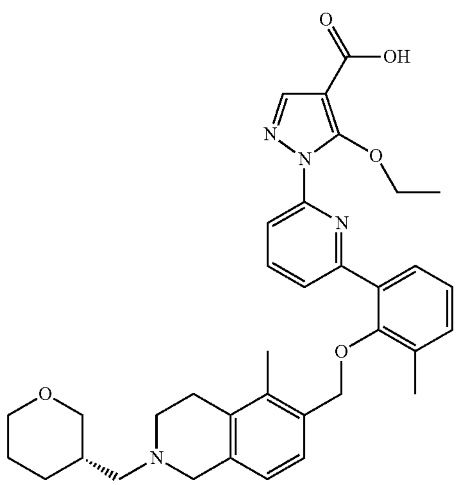 [SMILES: CCOc1c(C(=O)O)cnn1-c1cccc(-c2cccc(C)c2OCc2ccc3c(c2C)CCN(C[C@@H]2CCCOC2)C3)n1] |
| 153 | 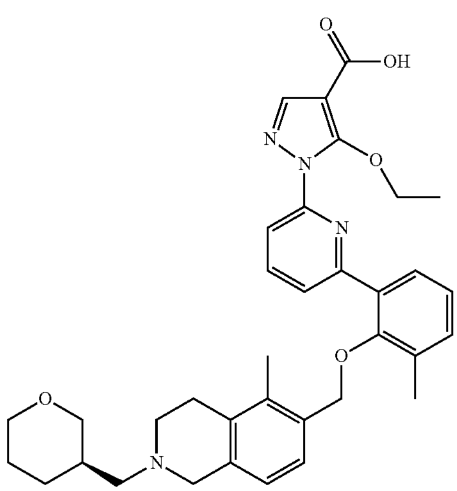 [SMILES: CCOc1c(C(=O)O)cnn1-c1cccc(-c2cccc(C)c2OCc2ccc3c(c2C)CCN(C[C@H]2CCCOC2)C3)n1] |
TABLE 1-continued
| Cpd No. | Structure |
|---|---|
| 154 | 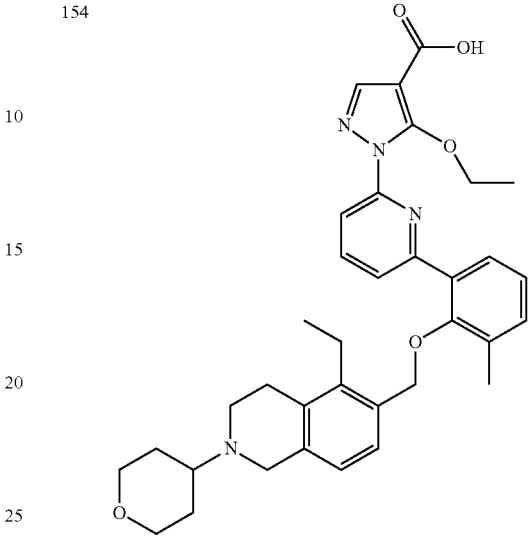 |
| 155 | 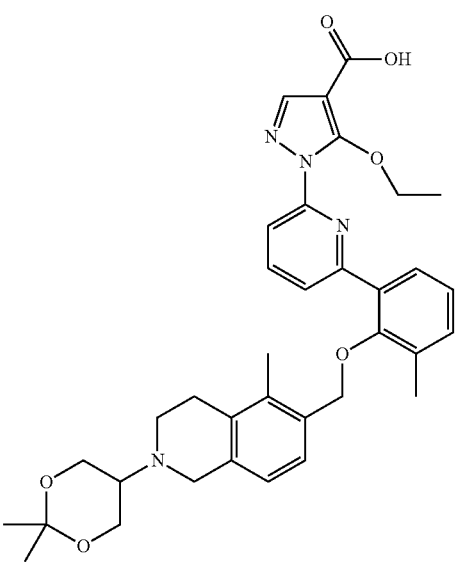 [SMILES: CCOc1c(C(=O)O)cnn1-c1cccc(-c2cccc(C)c2OCc2ccc3c(c2C)CCN(C2COC(C)(C)OC2)C3)n1] |

TABLE 1-continued
| Cpd No. | Structure |
|---|---|
| 156 | 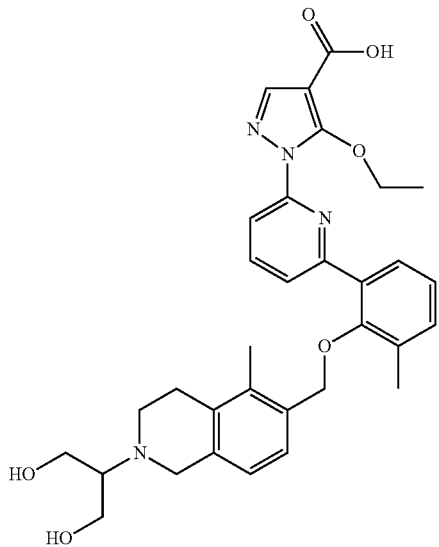 [SMILES: CCOc1c(C(=O)O)cnn1-c1cccc(-c2cccc(C)c2OCc2ccc3c(c2C)CCN(C(CO)CO)C3)n1] |
| 157 | 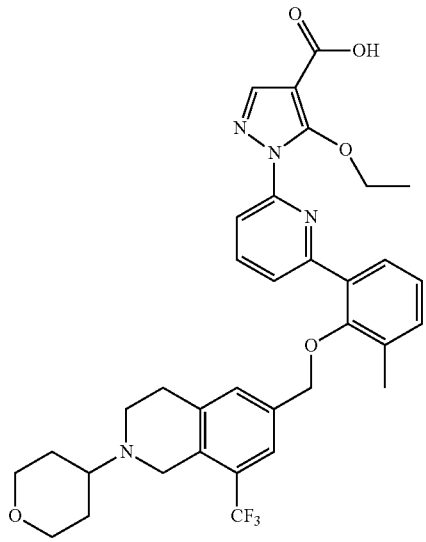 [SMILES: CCOc1c(C(=O)O)cnn1-c1cccc(-c2cccc(C)c2OCc2cc3c(c(C(F)(F)F)c2)CN(C2CCOCC2)CC3)n1] |
TABLE 1-continued
| Cpd No. | Structure |
|---|---|
| 158 | 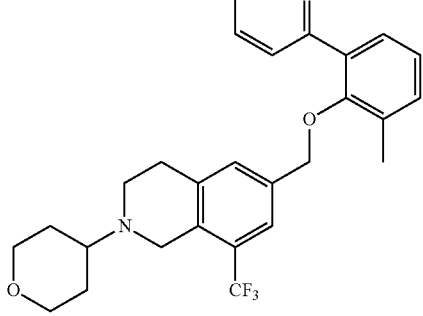 |
| 159 | 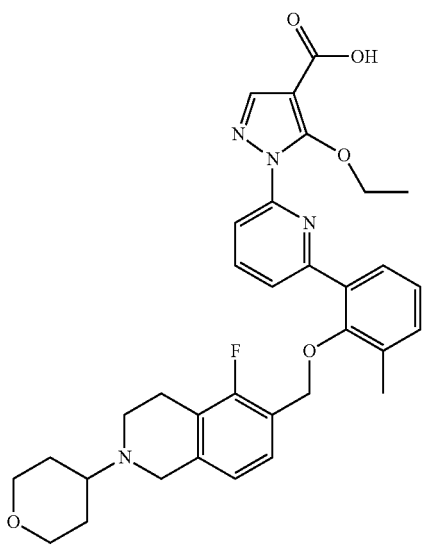 |
| 160 | 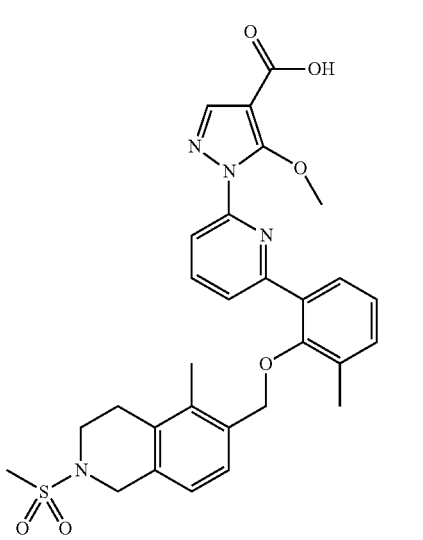 [SMILES: COc1c(C(=O)O)cnn1-c1cccc(-c2cccc(C)c2OCc2ccc3c(c2C)CCN(S(C)(=O)=O)C3)n1] |

TABLE 1-continued

| Cpd No. | Structure |
|---|---|
| 161 | (structure) |
| 162 | (structure) |
| 163 | (structure) |
| 164 | (structure) |
| 165 | (structure) |
| 166 | (structure) |

TABLE 1-continued
| Cpd No. | Structure |
|---|---|
| 167 | 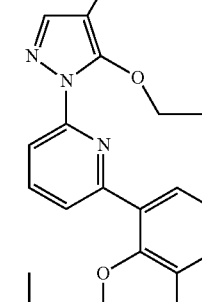 |
| 168 | 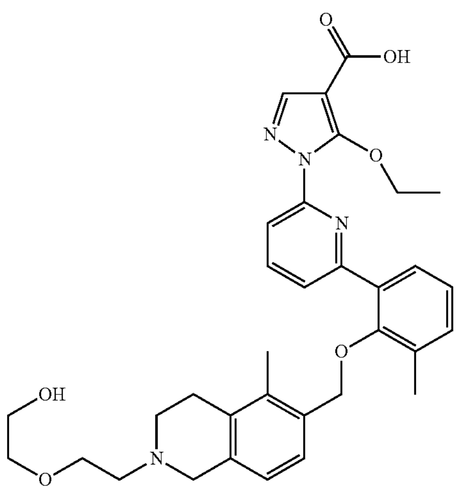 [SMILES: CCOc1c(C(=O)O)cnn1-c1cccc(-c2cccc(C)c2OCc2ccc3c(c2C)CCN(CCOCCO)C3)n1] |
| 169 | 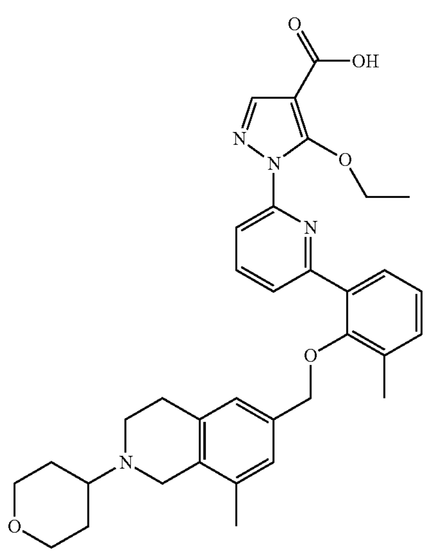 [SMILES: CCOc1c(C(=O)O)cnn1-c1cccc(-c2cccc(C)c2OCc2cc(C)c3c(c2)CCN(C2CCOCC2)C3)n1] |
| 170 | 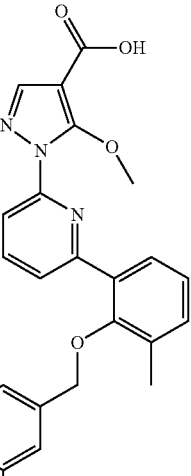 |
| 171 | |
| 172 | 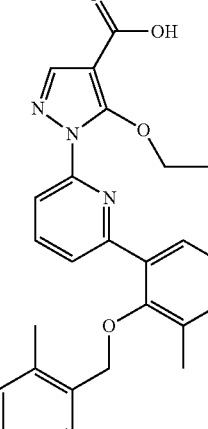 |

TABLE 1-continued
| Cpd No. | Structure |
|---|---|
| 173 | 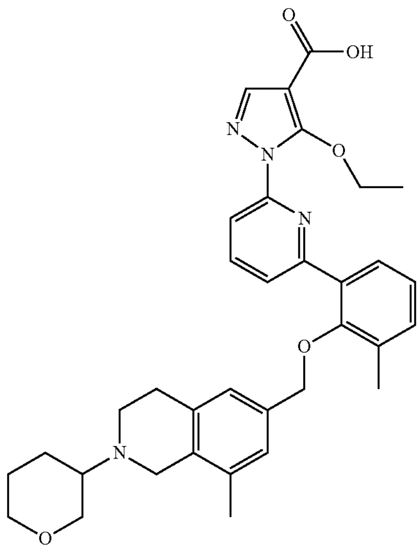 [SMILES: CCOc1c(C(=O)O)cnn1-c1cccc(-c2cccc(C)c2OCc2cc(C)c3c(c2)CCN(C2CCCOC2)C3)n1] |
| 174 | 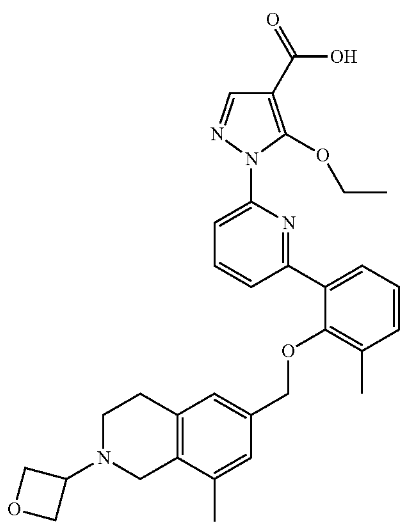 [SMILES: CCOc1c(C(=O)O)cnn1-c1cccc(-c2cccc(C)c2OCc2cc(C)c3c(c2)CCN(C2COC2)C3)n1] |
| 175 | 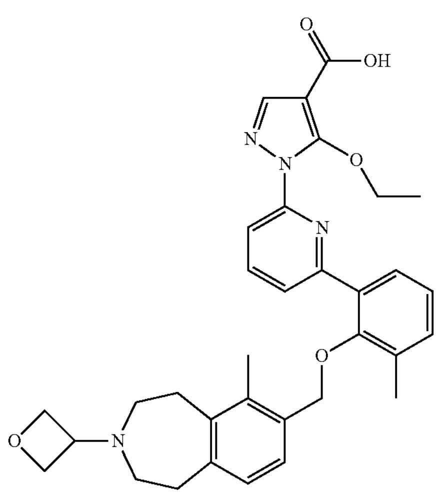 [SMILES: CCOc1c(C(=O)O)cnn1-c1cccc(-c2cccc(C)c2OCc2ccc3c(c2C)CCN(C2COC2)CC3)n1] |
| 176 | 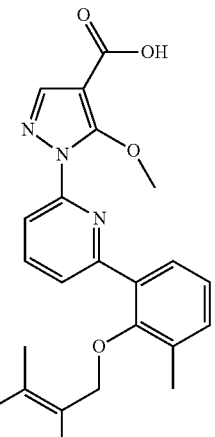 |
| 177 | 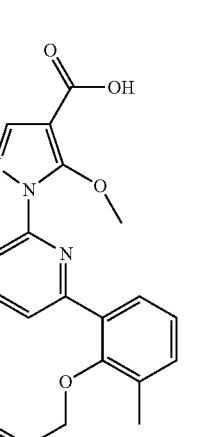 |
| 178 | 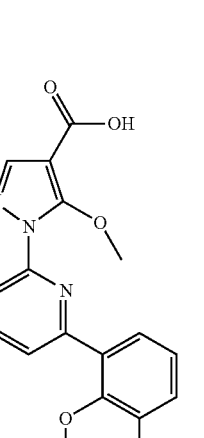 |

TABLE 1-continued

| Cpd No. | Structure |
|---|---|
| 179 | (structure) |
| 180 | (structure) |
| 181 | (structure) |
| 182 | (structure) |
| 183 | (structure) |
| 184 | (structure) |

TABLE 1-continued
| Cpd No. | Structure |
|---|---|
| 185 | 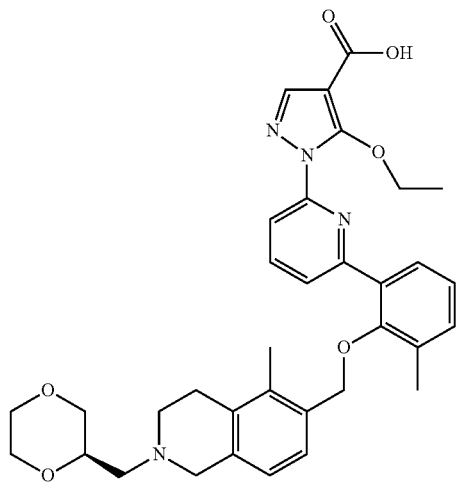 [SMILES: CCOc1c(C(=O)O)cnn1-c1cccc(-c2cccc(C)c2OCc2ccc3c(c2C)CCN(C[C@@H]2COCCO2)C3)n1] |
| 186 | 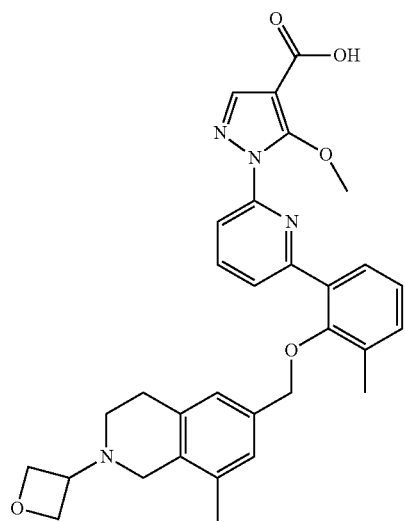 [SMILES: COc1c(C(=O)O)cnn1-c1cccc(-c2cccc(C)c2OCc2cc(C)c3c(c2)CCN(C2COC2)C3)n1] |
| 187 | 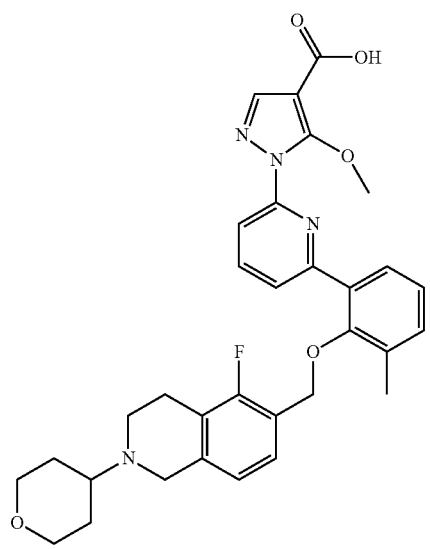 |
| 188 | 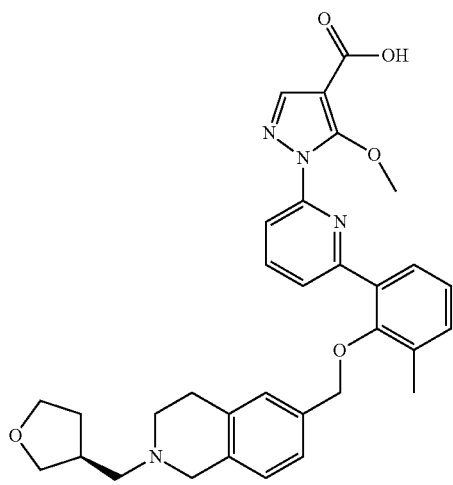 [SMILES: COc1c(C(=O)O)cnn1-c1cccc(-c2cccc(C)c2OCc2ccc3c(c2)CCN(C[C@@H]2CCOC2)C3)n1] |
| 189 | 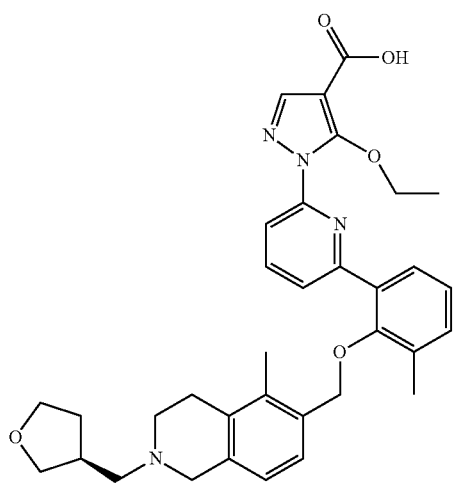 [SMILES: CCOc1c(C(=O)O)cnn1-c1cccc(-c2cccc(C)c2OCc2ccc3c(c2C)CCN(C[C@@H]2CCOC2)C3)n1] |
| 190 | 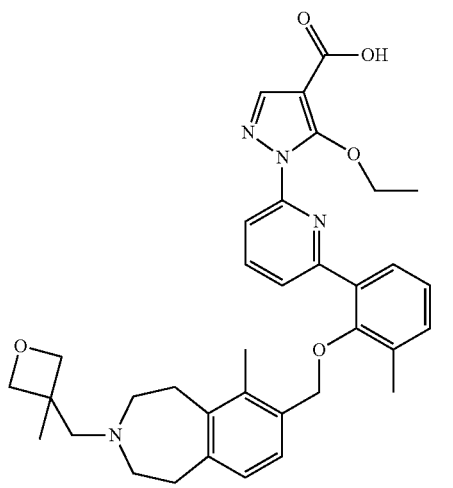 [SMILES: CCOc1c(C(=O)O)cnn1-c1cccc(-c2cccc(C)c2OCc2ccc3c(c2C)CCN(CC2(C)COC2)CC3)n1] |

TABLE 1-continued
| Cpd No. | Structure |
|---|---|
| 191 | 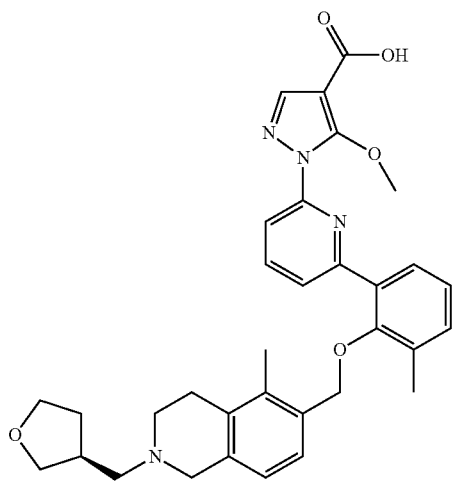 [SMILES: COc1c(C(=O)O)cnn1-c1cccc(-c2cccc(C)c2OCc2ccc3c(c2C)CCN(C[C@@H]2CCOC2)C3)n1] |
| 192 | 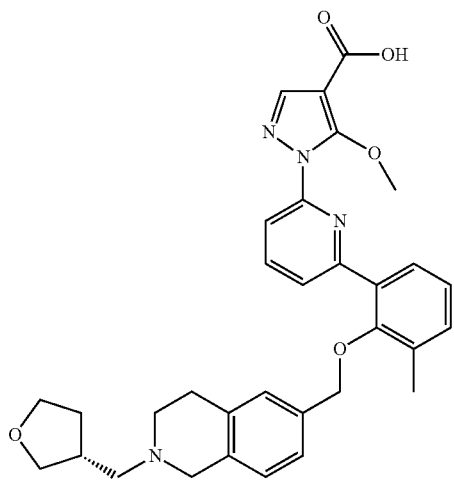 [SMILES: COc1c(C(=O)O)cnn1-c1cccc(-c2cccc(C)c2OCc2ccc3c(c2)CCN(C[C@H]2CCOC2)C3)n1] |
| 193 | 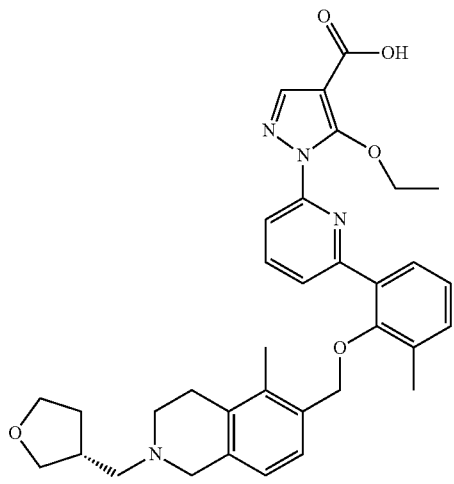 [SMILES: CCOc1c(C(=O)O)cnn1-c1cccc(-c2cccc(C)c2OCc2ccc3c(c2C)CCN(C[C@H]2CCOC2)C3)n1] |
| 194 | 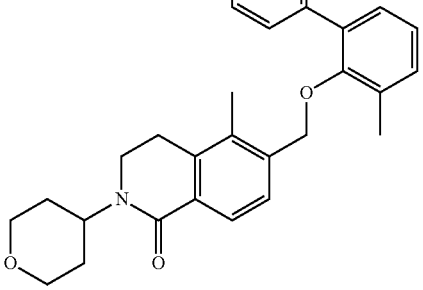 |
| 195 | 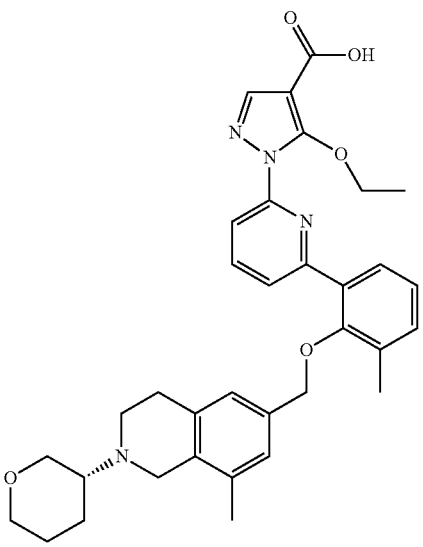 [SMILES: CCOc1c(C(=O)O)cnn1-c1cccc(-c2cccc(C)c2OCc2cc(C)c3c(c2)CCN([C@@H]2CCCOC2)C3)n1] |
| 196 | 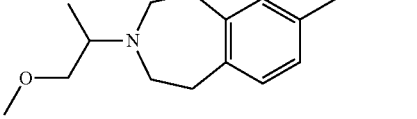 |

TABLE 1-continued
| Cpd No. | Structure |
|---|---|
| 197 | 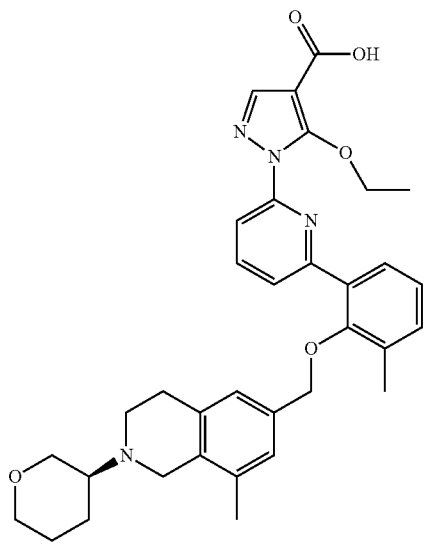 [SMILES: CCOc1c(C(=O)O)cnn1-c1cccc(-c2cccc(C)c2OCc2cc(C)c3c(c2)CCN([C@H]2CCCOC2)C3)n1] |
| 198 | 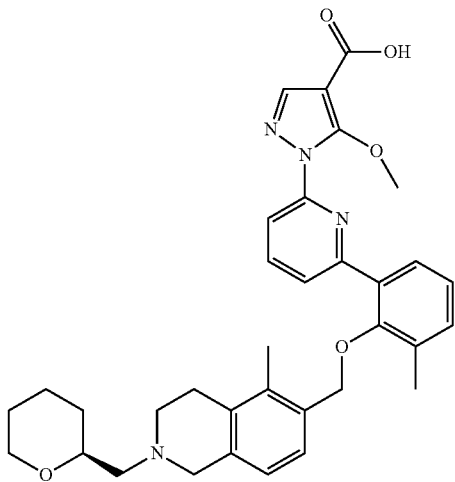 |
| 199 | 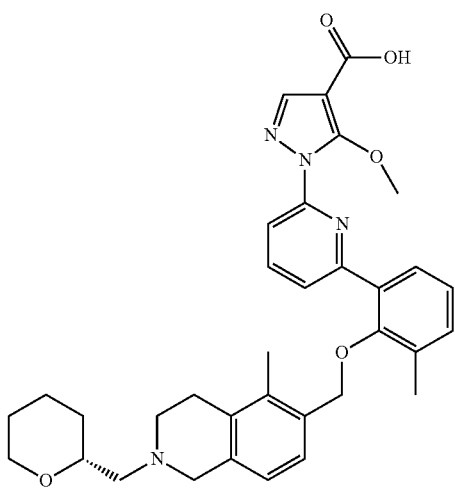 [SMILES: COc1c(C(=O)O)cnn1-c1cccc(-c2cccc(C)c2OCc2ccc3c(c2C)CCN(C[C@H]2CCCCO2)C3)n1] |
| 200 | 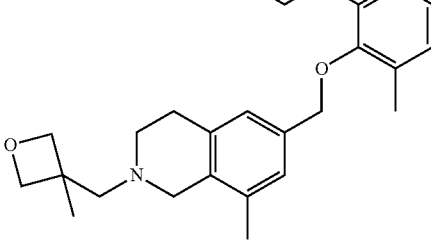 |
| 201 | 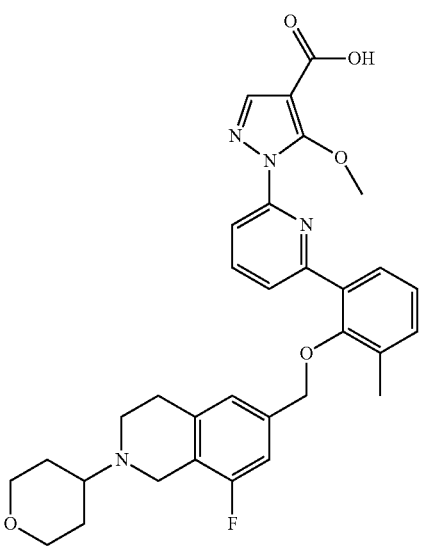 |
| 202 | 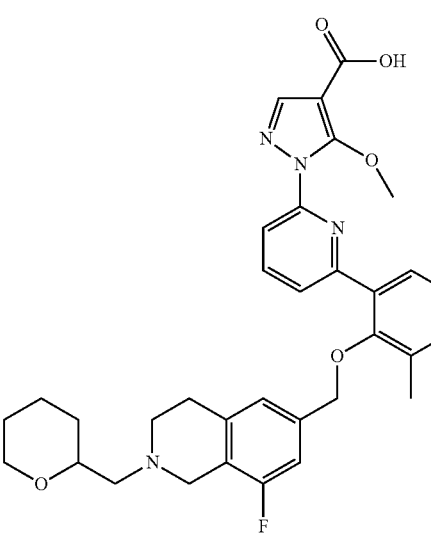 |

TABLE 1-continued

| Cpd No. | Structure |
|---|---|
| 203 | 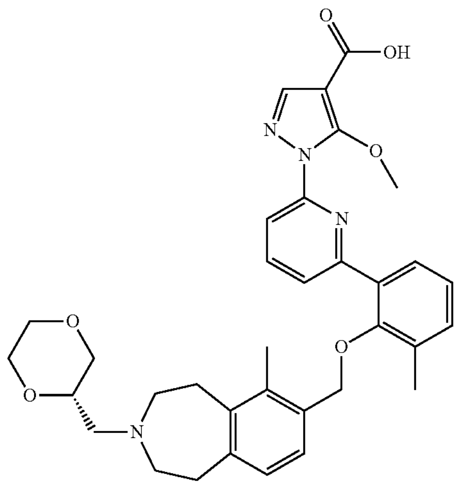 [SMILES: COc1c(C(=O)O)cnn1-c1cccc(-c2cccc(C)c2OCc2ccc3c(c2C)CCN(C[C@H]2COCCO2)CC3)n1] |
| 204 | 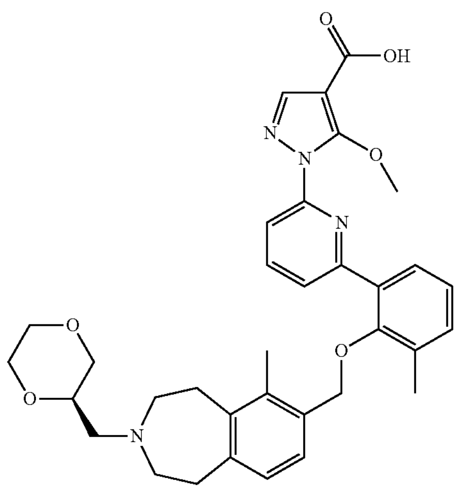 [SMILES: COc1c(C(=O)O)cnn1-c1cccc(-c2cccc(C)c2OCc2ccc3c(c2C)CCN(C[C@@H]2COCCO2)CC3)n1] |
| 205 | 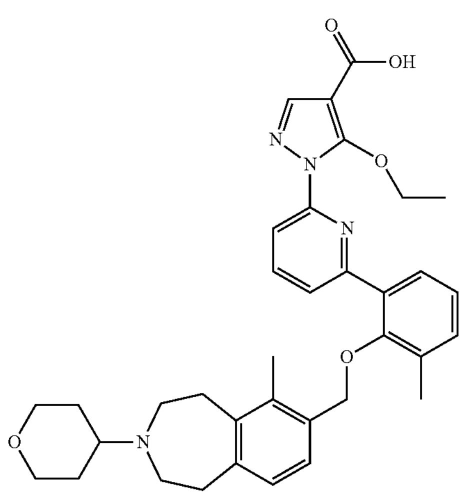 [SMILES: CCOc1c(C(=O)O)cnn1-c1cccc(-c2cccc(C)c2OCc2ccc3c(c2C)CCN(C2CCOCC2)CC3)n1] |
| 206 | 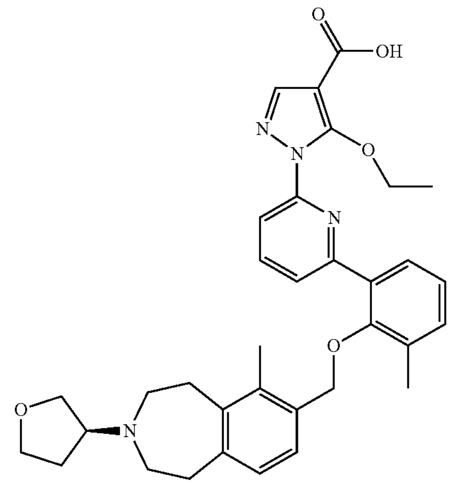 [SMILES: CCOc1c(C(=O)O)cnn1-c1cccc(-c2cccc(C)c2OCc2ccc3c(c2C)CCN([C@H]2CCOC2)CC3)n1] |
| 207 | 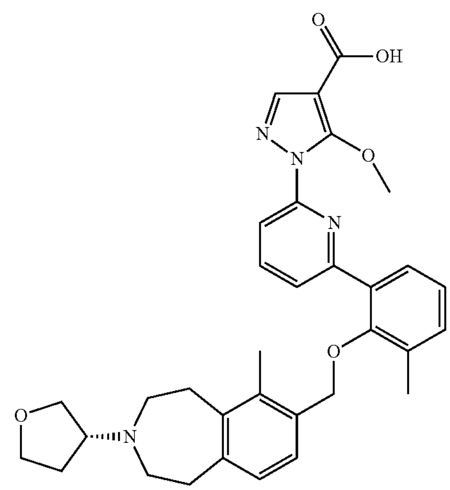 [SMILES: COc1c(C(=O)O)cnn1-c1cccc(-c2cccc(C)c2OCc2ccc3c(c2C)CCN([C@@H]2CCOC2)CC3)n1] |
| 208 | 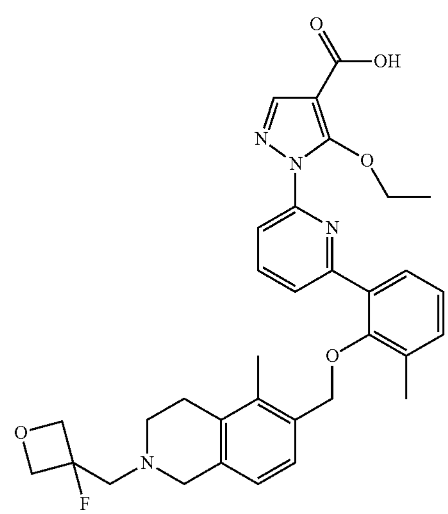 [SMILES: CCOc1c(C(=O)O)cnn1-c1cccc(-c2cccc(C)c2OCc2ccc3c(c2C)CCN(CC2(F)COC2)C3)n1] |

TABLE 1-continued
| Cpd No. | Structure |
|---|---|
| 209 | 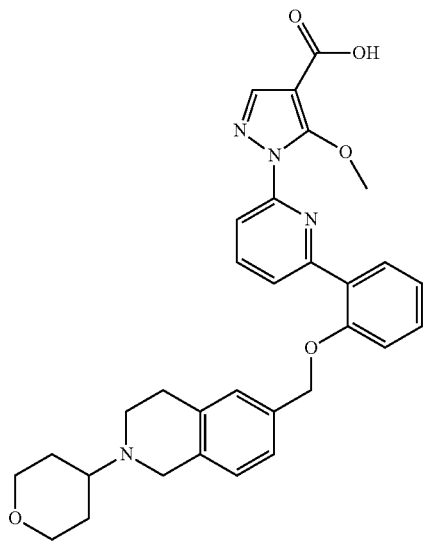 [SMILES: COc1c(C(=O)O)cnn1-c1cccc(-c2ccccc2OCc2ccc3c(c2)CCN(C2CCOCC2)C3)n1] |
| 210 | 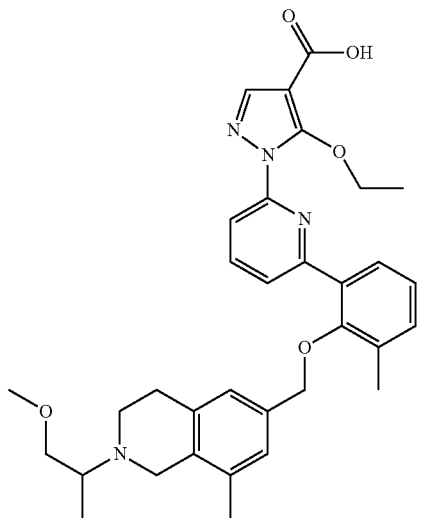 [SMILES: CCOc1c(C(=O)O)cnn1-c1cccc(-c2cccc(C)c2OCc2cc(C)c3c(c2)CCN(C(C)COC)C3)n1] |
| 211 | 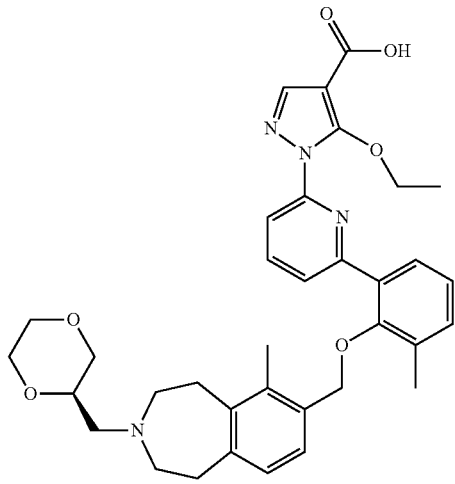 [SMILES: CCOc1c(C(=O)O)cnn1-c1cccc(-c2cccc(C)c2OCc2ccc3c(c2C)CCN(C[C@@H]2COCCO2)CC3)n1] |
| 212 | 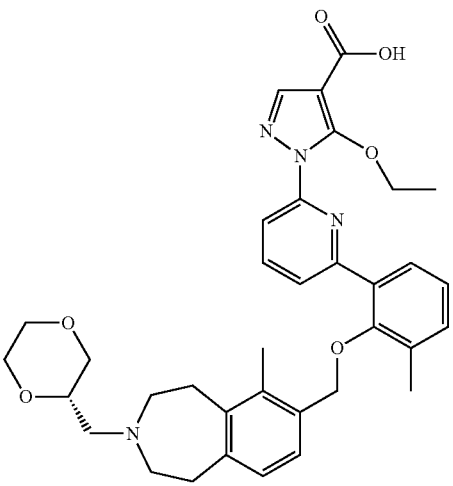 [SMILES: CCOc1c(C(=O)O)cnn1-c1cccc(-c2cccc(C)c2OCc2ccc3c(c2C)CCN(C[C@H]2COCCO2)CC3)n1] |
| 213 | 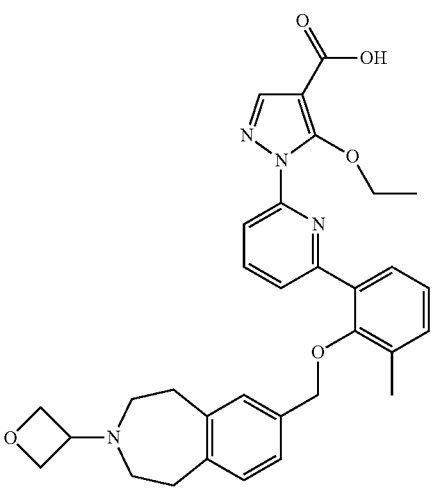 [SMILES: CCOc1c(C(=O)O)cnn1-c1cccc(-c2cccc(C)c2OCc2ccc3c(c2)CCN(C2COC2)CC3)n1] |
| 214 | 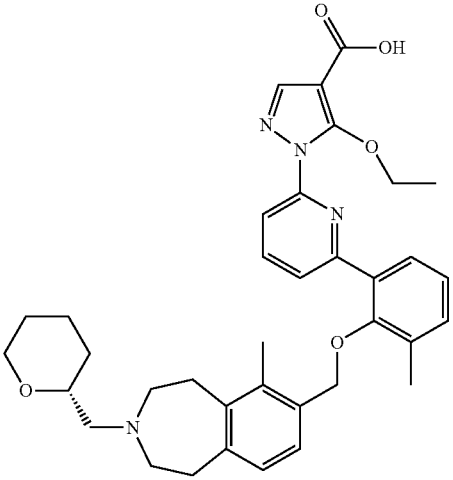 |

TABLE 1-continued
| Cpd No. | Structure |
|---|---|
| 215 | 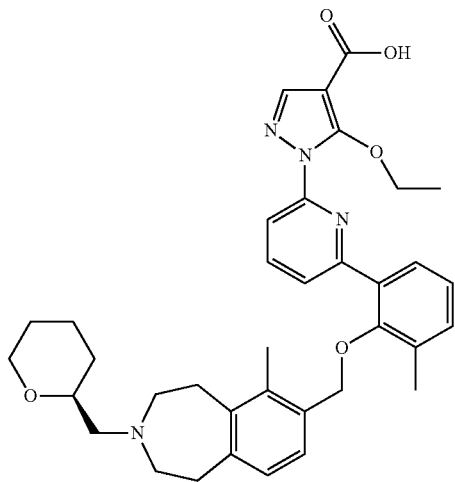 |
| 216 | 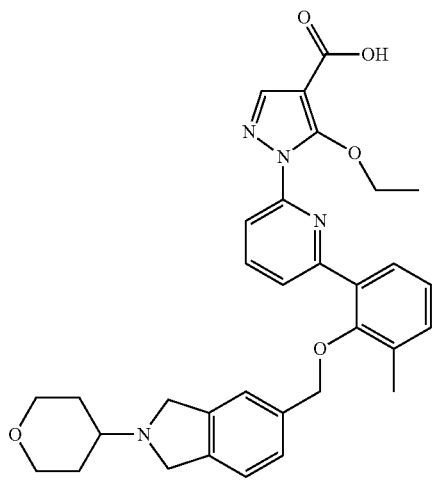 [SMILES: CCOc1c(C(=O)O)cnn1-c1cccc(-c2cccc(C)c2OCc2ccc3c(c2)CN(C2CCOCC2)C3)n1] |
| 217 | 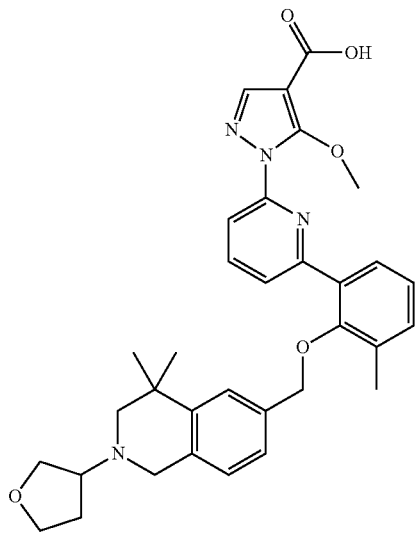 [SMILES: COc1c(C(=O)O)cnn1-c1cccc(-c2cccc(C)c2OCc2ccc3c(c2)C(C)(C)CN(C2CCOC2)C3)n1] |
| 218 | 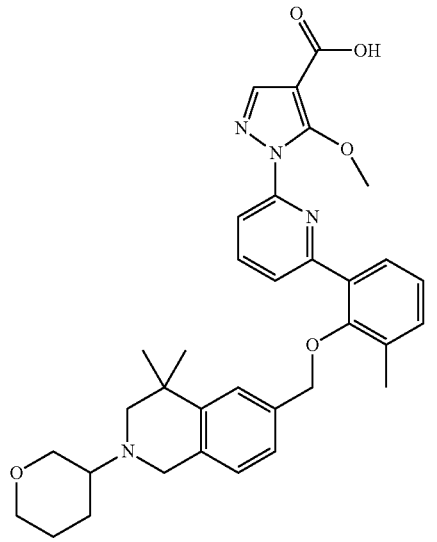 [SMILES: COc1c(C(=O)O)cnn1-c1cccc(-c2cccc(C)c2OCc2ccc3c(c2)C(C)(C)CN(C2CCCOC2)C3)n1] |
| 219 | 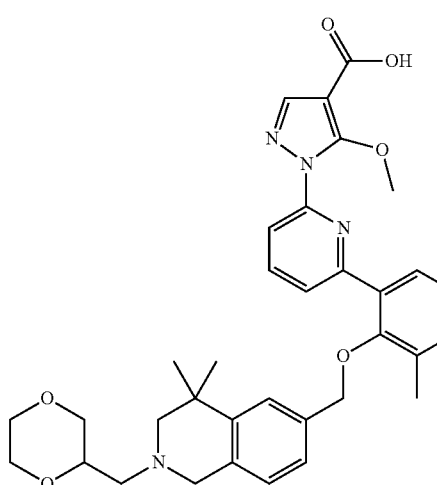 |
| 220 | 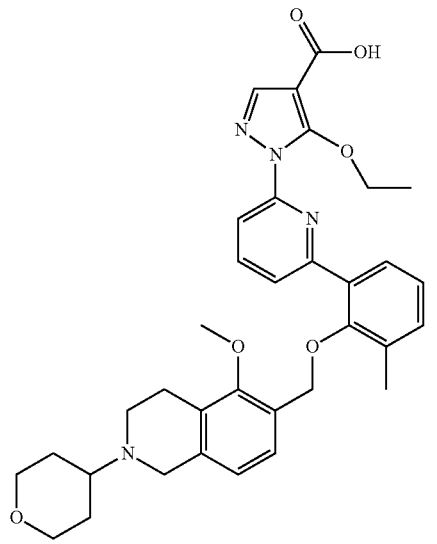 [SMILES: CCOc1c(C(=O)O)cnn1-c1cccc(-c2cccc(C)c2OCc2ccc3c(c2OC)CCN(C2CCOCC2)C3)n1] |

TABLE 1-continued
| Cpd No. | Structure |
|---|---|
| 221 | 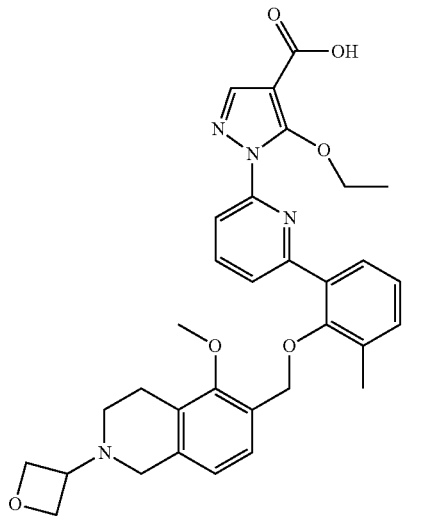 [SMILES: CCOc1c(C(=O)O)cnn1-c1cccc(-c2cccc(C)c2OCc2ccc3c(c2OC)CCN(C2COC2)C3)n1] |
| 222 | 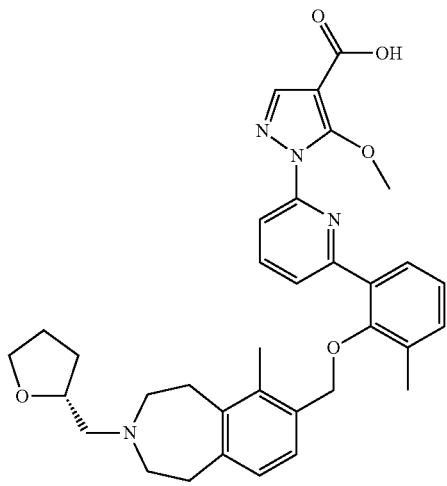 [SMILES: COc1c(C(=O)O)cnn1-c1cccc(-c2cccc(C)c2OCc2ccc3c(c2C)CCN(C[C@H]2CCCO2)CC3)n1] |
| 223 | 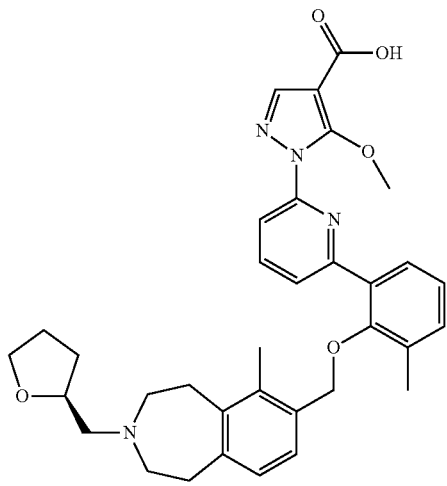 [SMILES: COc1c(C(=O)O)cnn1-c1cccc(-c2cccc(C)c2OCc2ccc3c(c2C)CCN(C[C@@H]2CCCO2)CC3)n1] |
TABLE 1-continued
| Cpd No. | Structure |
|---|---|
| 224 | 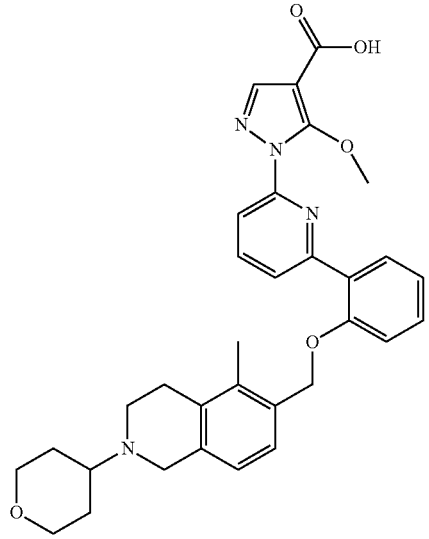 [SMILES: COc1c(C(=O)O)cnn1-c1cccc(-c2ccccc2OCc2ccc3c(c2C)CCN(C2CCOCC2)C3)n1] |
| 225 | 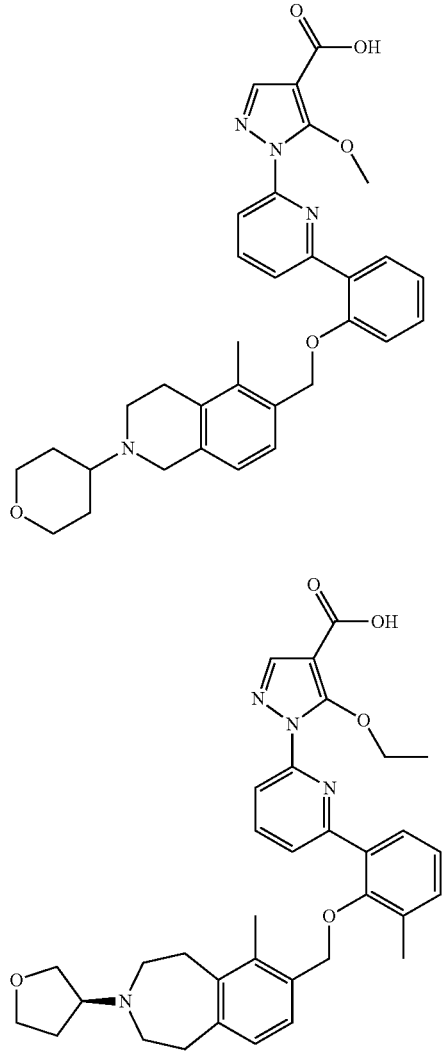 |
| 226 | 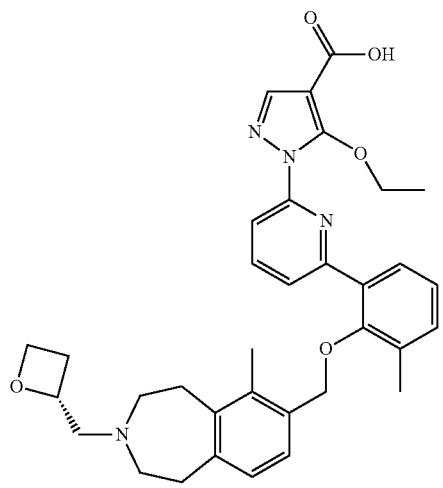 [SMILES: CCOc1c(C(=O)O)cnn1-c1cccc(-c2cccc(C)c2OCc2ccc3c(c2C)CCN(C[C@H]2CCO2)CC3)n1] |

TABLE 1-continued
| Cpd No. | Structure |
|---|---|
| 227 | 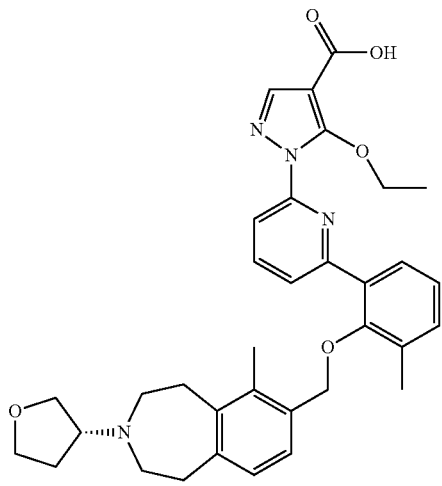 [SMILES: CCOc1c(C(=O)O)cnn1-c1cccc(-c2cccc(C)c2OCc2ccc3c(c2C)CCN([C@@H]2CCOC2)CC3)n1] |
| 228 | 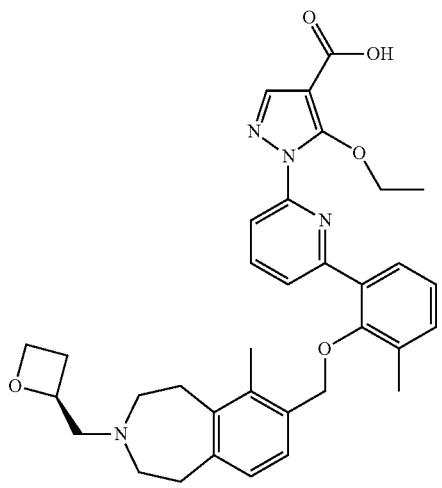 [SMILES: CCOc1c(C(=O)O)cnn1-c1cccc(-c2cccc(C)c2OCc2ccc3c(c2C)CCN(C[C@@H]2CCO2)CC3)n1] |
| 229 | 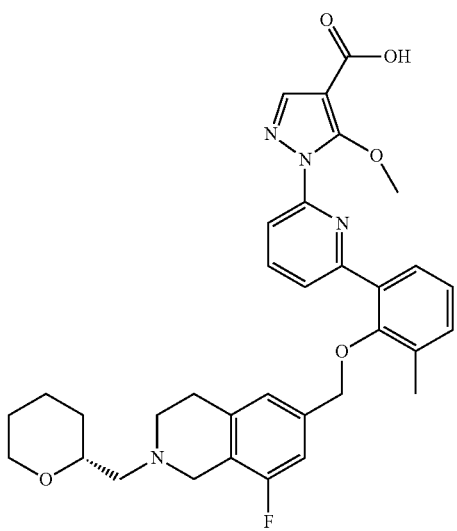 [SMILES: COc1c(C(=O)O)cnn1-c1cccc(-c2cccc(C)c2OCc2cc(F)c3c(c2)CCN(C[C@H]2CCCCO2)C3)n1] |
| 230 | 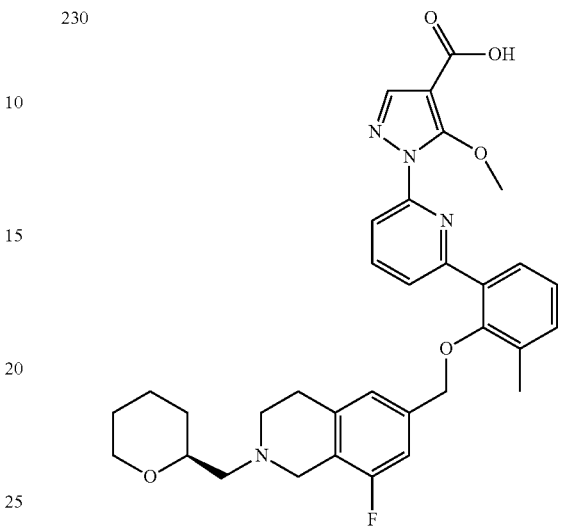 |
| 231 | 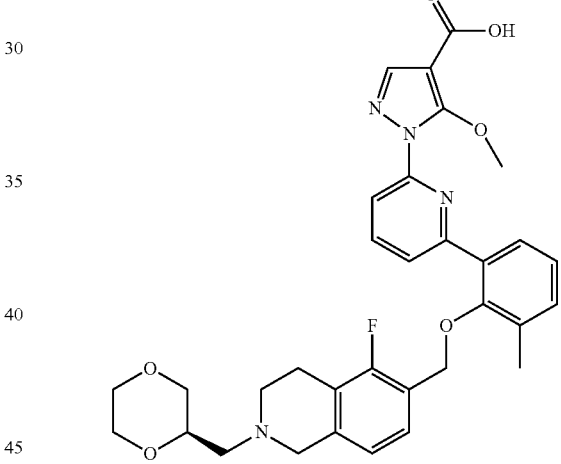 |
| 232 | 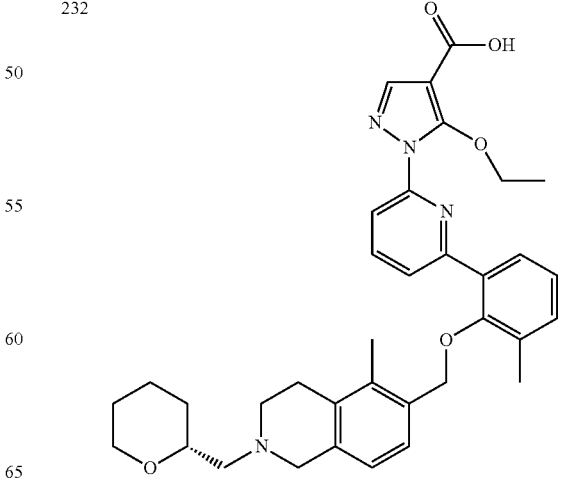 |

TABLE 1-continued

| Cpd No. | Structure |
|---|---|
| 233 | 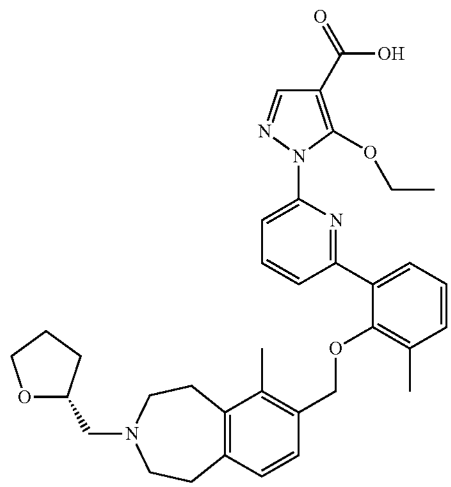 [SMILES: CCOc1c(C(=O)O)cnn1-c1cccc(-c2cccc(C)c2OCc2ccc3c(c2C)CCN(C[C@H]2CCCO2)CC3)n1] |
| 234 | 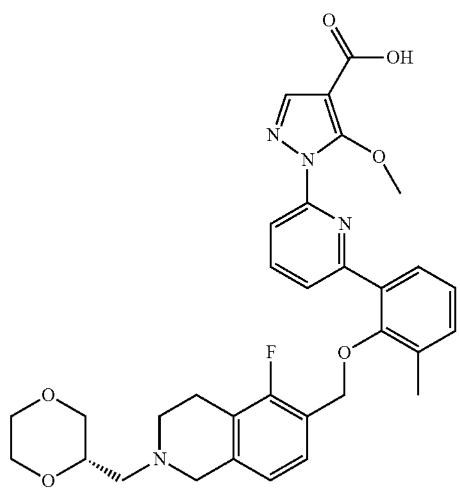 |
| 235 | 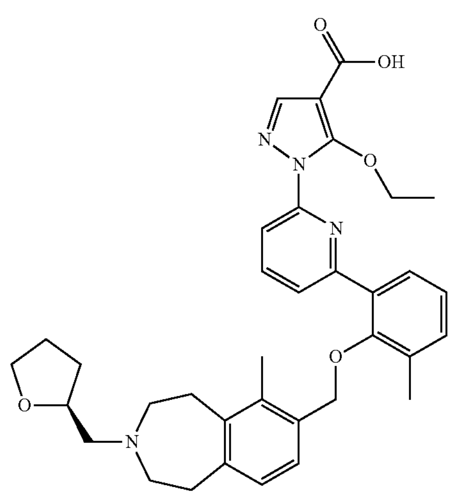 [SMILES: CCOc1c(C(=O)O)cnn1-c1cccc(-c2cccc(C)c2OCc2ccc3c(c2C)CCN(C[C@@H]2CCCO2)CC3)n1] |
| 236 | |
| 237 | |
| 238 | |

TABLE 1-continued

| Cpd No. | Structure |
|---|---|
| 239 | (structure) |
| 240 | (structure) |
| 241 | (structure) |
| 242 | (structure) |
| 243 | (structure) |
| 244 | (structure) |

TABLE 1-continued

| Cpd No. | Structure |
|---|---|
| 245 | (structure) |
| 246 | (structure) |
| 247 | (structure) |
| 248 | (structure) |
| 249 | (structure) |

TABLE 1-continued
| Cpd No. | Structure |
|---|---|
| 250 | 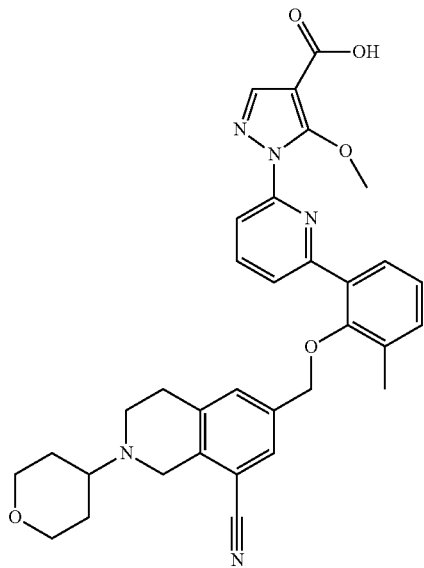 [SMILES: COc1c(C(=O)O)cnn1-c1cccc(-c2cccc(C)c2OCc2cc(C#N)c3c(c2)CCN(C2CCOCC2)C3)n1] |
| 251 | 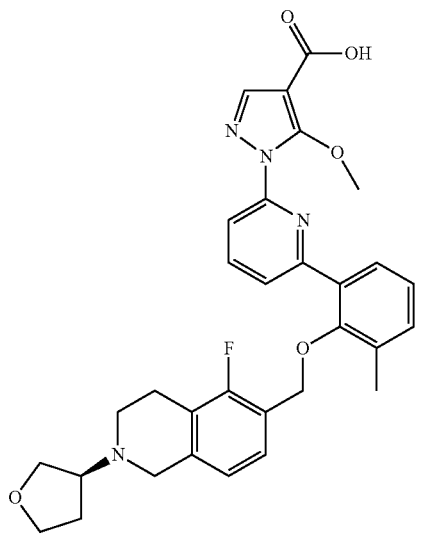 [SMILES: COc1c(C(=O)O)cnn1-c1cccc(-c2cccc(C)c2OCc2ccc3c(c2F)CCN([C@H]2CCOC2)C3)n1] |
| 252 | 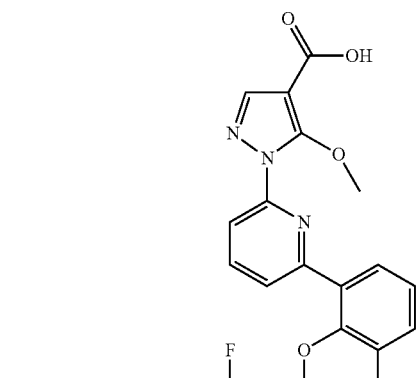 |
| 253 | 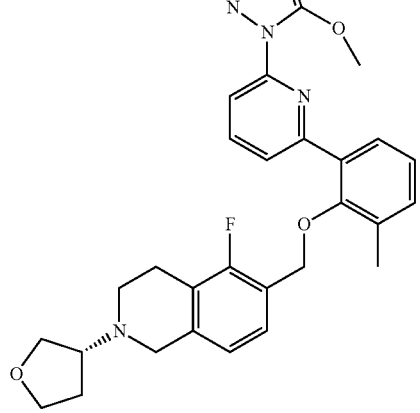 |
| 254 | 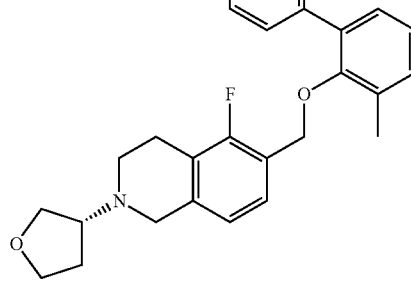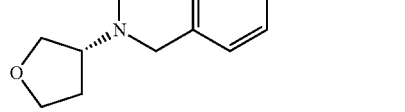 |

TABLE 1-continued

| Cpd No. | Structure |
|---|---|
| 255 | 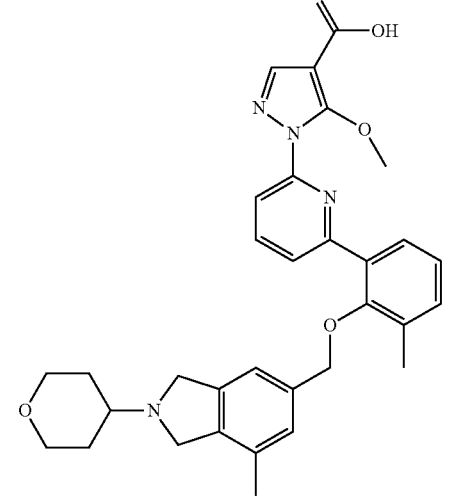 |
| 256 | 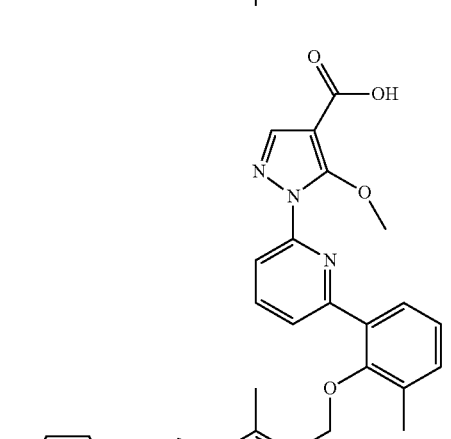 |
| 257 | 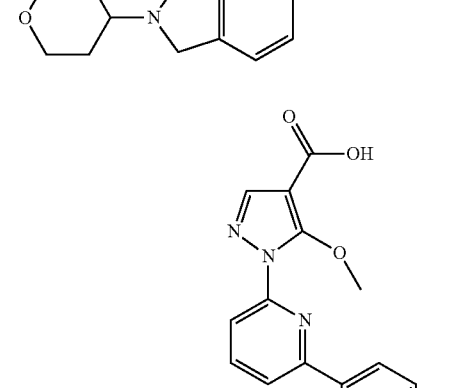 |

TABLE 1-continued

| Cpd No. | Structure |
|---|---|
| 258 | 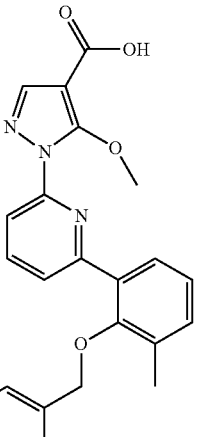 |

In one embodiment, the invention relates to any of the compounds depicted in Table 1 above and the pharmaceutically acceptable salts thereof.

In another embodiment the invention relates to the group of compounds depicted in Table 1 consisting of compound number 1, 2, 3, 4, 5, 7, 8, 9, 12, 15, 16, 18, 21, 27, 28, 30, 31, 35, 36, 39, 41, 42, 44, 45, 46, 47, 48, 57, 59, 62, 68, 77, 78, 79, 80, 82, 83, 84, 85, 86, 88, 92, 93, and 94 and the pharmaceutically acceptable salts thereof.

In another embodiment the invention relates to the group of compounds depicted in Table 1 consisting of compound number 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 136, 137, 139, 140, 141, 142, 145, 146, 152, 153, 154, 155, 157, 158, 159, 161, 162, 163, 164, 165, 166, 167, 169, 170, 171, 172, 173, 174, 175, 176, 177, 178, 179, 180, 181, 184, 185, 186, 187, 188, 189, 191, 193, 194, 195, 196, 197, 198, 199, 201, 202, 203, 204, 205, 206, 207, 208, 210, 211, 212, 213, 214, 215, 216, 220, 222, 223, 224, 225, 227, 229, 230, 231, 232, 233, 234, 235, 236, 237, 238, 239, 240, 241, 242, 243, 244, 246, 247, 248, 249, 250, 251, 252, 253, 254, 255, 256, 257 and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed herein above in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3] heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

General Synthetic Methods

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

Compounds of formula I may be prepared as described in Scheme 1

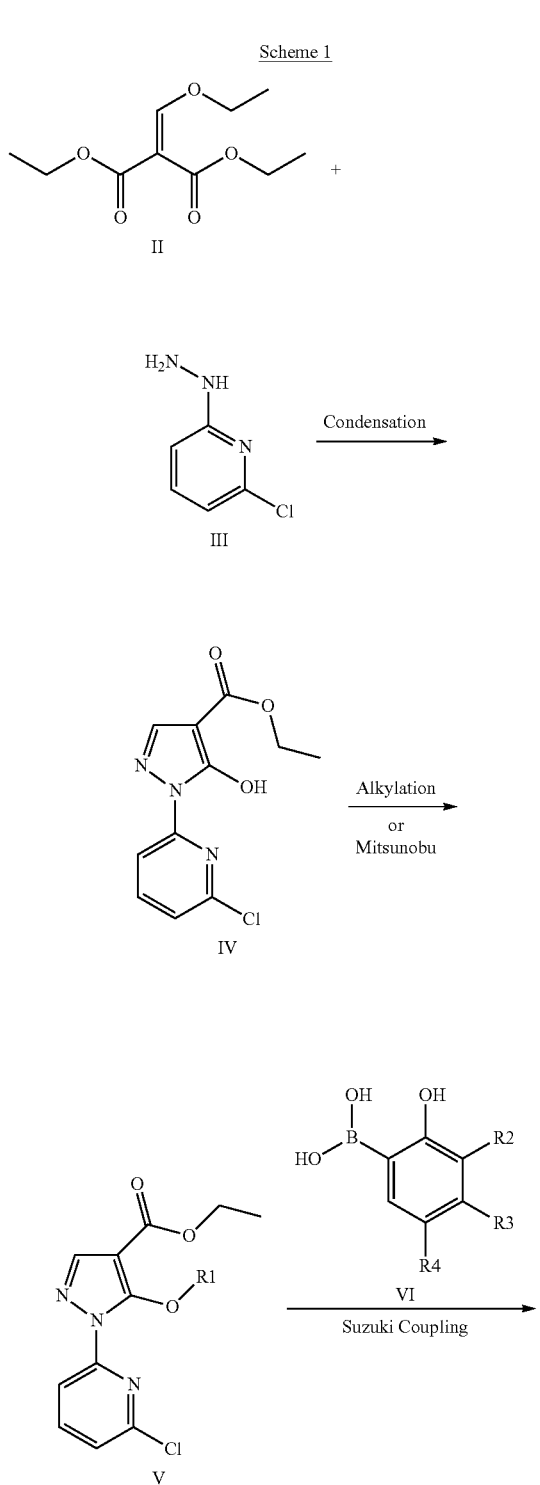

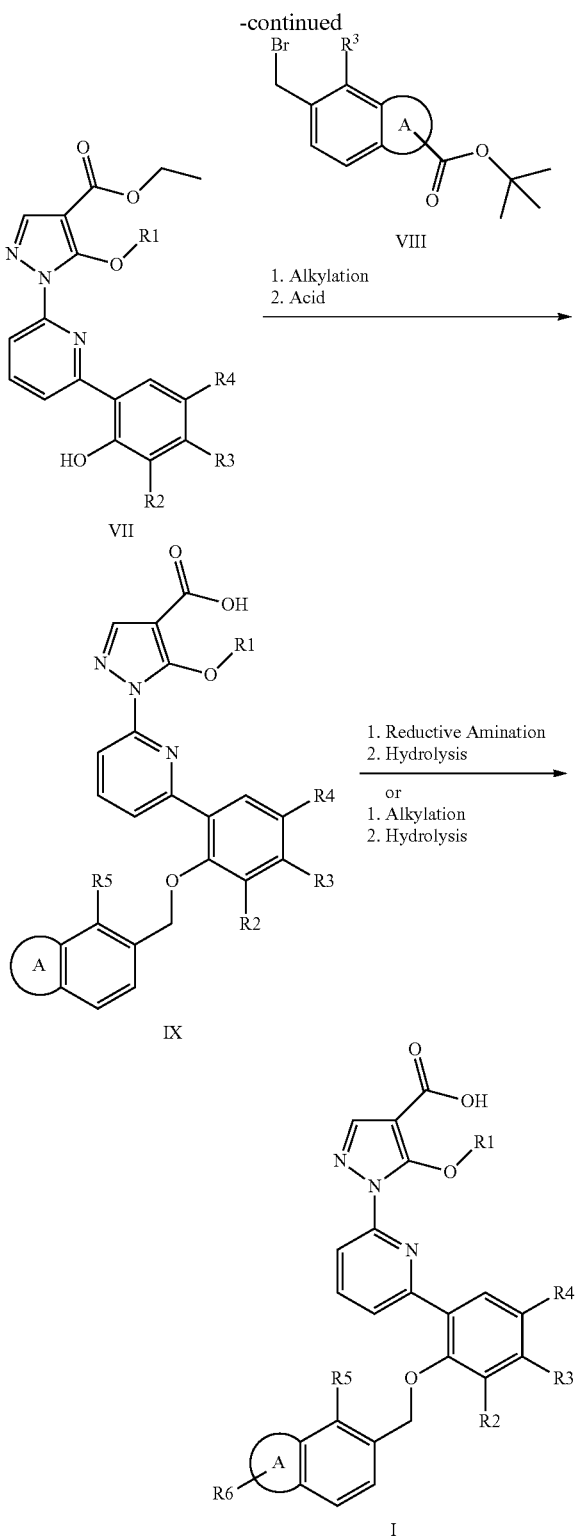

Chloropyridine, V, is coupled with boron species, VI, in the presence of a palladium catalyst such as tetrakis(triphenyl) phosphine (0) and a suitable base such as $Na_2CO_3$ in aqueous 1,2-DME (1,2-dimethoxyethane) under microwave irradiation at 120° C. to provide VII. Alkylation of the phenol intermediate, VII with alkyl bromide VIII, where X=Cl, I or Br using a base such as cesium carbonate ($Cs_2CO_3$) in a solvent such as acetone at about 50° C. Subsequent deprotection of the t-Boc group with a suitable acid such as trifluoroacetic acid (TFA) provides compound IX. Reductive amination of amine, IX, with the desired ketone or aldehyde using an appropriate hydride source such as $NaBH_3CN$ in a solvent such as MeOH containing an organic acid such as AcOH at about 50° C., followed by in situ hydrolysis with a base such as aqueous LiOH affords the desired compound of formula I. Alternatively, alkylations of amine, IX with alkyl halides in the presence of a suitable base such as cesium carbonate ($Cs_2CO_3$) or N,N-diisopropylethylamine (DIPEA) in a solvent such as MeCN (acetonitrile) followed by hydrolysis of the ester provides the desired compound of formula I.

UPLC/MS Methods

Retention times (RT) reported for compounds in the Synthetic Examples section are obtained by UPLC/MS using one of the following methods:

For each of the methods, the following are identical:

UPLC/MS system components—Acquity UPLC with PDA, SQ and ELS detectors.

PDA conditions—Detection: 210 to 400 nm. Sampling rate: 20 pts/sec. Filter response: fast.

ELSD conditions—Gain: 1000. Sampling rate: 20 pts/sec. Drift tube temp: 55° C. Nebulizer mode: cooling. Gas pressure: 41 psi.

MS conditions—Instrument: Acquity SQD with ESCi source. Ionization mode: ESI+/−.

Capillary voltage: 3.5 kV. Cone voltage: 5 V. Extractor: 1.3 V. Source temp: 150° C.

Desolvation temp: 350° C. Desolvation gas: 800 L/hr. Cone gas: 50 L/hr.

Conditions specific to each method are as follows

Method A1

Column—Waters BEH C18, 2.1×50 mm, 1.7 um particle diameter.

Description and Gradient: Medium polar fast gradient method. ESI+/− ion mode 80-1000 Da.

Gradient: 90% A to 100% B in 1.19 minutes hold at 100% B to 1.70 minutes. Flow rate 0.8 mL/min. A=(95% Water 5% Acetonitrile 0.05% Formic Acid) B=(Acetonitrile 0.05% Formic Acid).

Sample Injection Volume: 1 uL

Method A2

Column—Waters BEH C18, 2.1×50 mm, 1.7 um particle diameter.

Description and Gradient: Medium polar long gradient method. ESI+/− ion mode 80-1000 Da.

Gradient: 90% A to 100% B in 4.45 minutes hold at 100% B to 4.58 minutes. Flow rate 0.8 mL/min. A=(95% Water 5% Acetonitrile 0.05% Formic Acid) B=(Acetonitrile 0.05% Formic Acid).

Sample Injection Volume: 2 uL

Method B1

Column—CSH 2.1×50 mm C18, 1.7 um particle diameter.

Description and Gradient: Medium polar fast gradient method. ESI+/− ion mode 80-1000 Da.

Gradient: 90% A to 100% B in 1.19 minutes hold at 100% B to 1.70 minutes. Flow rate 0.8 mL/min. A=(95% Water 5% Acetonitrile 0.05% Formic Acid) B=(Acetonitrile 0.05% Formic Acid).

As illustrated above, diester II (R=Me or Et) and hydrazine III are refluxed in a suitable solvent such as ethanol with a suitable base such as potassium carbonate ($K_2CO_3$) yielding hydroxy pyrazole IV. Compound IV is alkylated, for example by using trimethylsilyldiazomethane in some cases or $R^1I$ and a suitable base such as cesium carbonate ($Cs_2CO_3$). Alternatively, Mitsunobu conditions are employed with ethanol to yield the desired alkoxy pyrazole chloropyridine V (R'=Et).

Sample Injection Volume: 1 uL

Method B2

Column—CSH 2.1×50 mm C18, 1.7 um particle diameter.

Description and Gradient: Medium polar long gradient method. ESI+/− ion mode 80-1000 Da.

Gradient: 90% A to 100% B in 4.45 minutes hold at 100% B to 4.58 minutes. Flow rate 0.8 mL/min. A=(95% Water 5% Acetonitrile 0.05% Formic Acid) B=(Acetonitrile 0.05% Formic Acid).

Sample Injection Volume: 2 uL

Method A1 is used for all of the compounds except for compounds noted for which Method A2, Method B1, or Method B2 is used.

SYNTHETIC EXAMPLES

Final compounds are designated by compound numbers corresponding to the compound numbers in Table 1. Intermediates are given hyphenated numbers corresponding to the figures and numbers shown in the scheme for each example.

Example 1

Preparation of intermediate 1-[6-(2-hydroxy-3-methyl-phenyl)-pyridin-2-yl]-5-isopropoxy-1H-pyrazole-4-carboxylic acid ethyl ester (1-6)

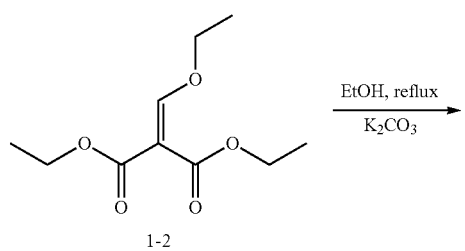

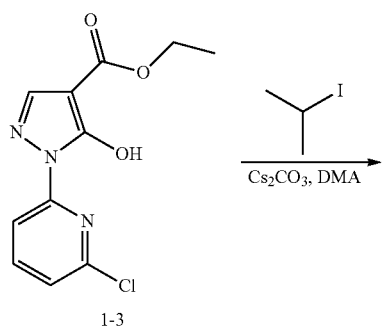

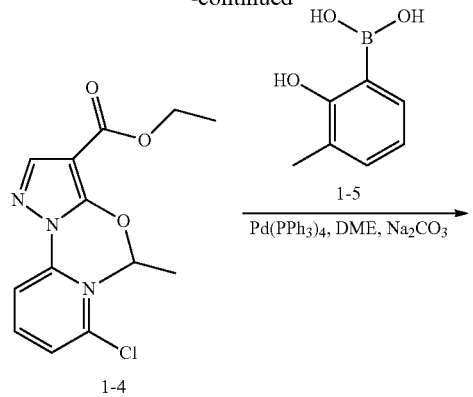

To a round bottom flask containing EtOH (200 mL), $K_2CO_3$ (20.05 g, 55.720 mmol), and 1-1 (10.00 g, 69.65 mmol) is added 1-2 (13.95 mL, 69.65 mmol). The resulting mixture is refluxed for 3 h. The reaction is cooled and the solid is collected by filtration. This solid is removed from the fritted funnel and is placed into a beaker to which is added 250 mL of 1.0 N HCl (excessive bubbling). The solution is confirmed to be acidic (pH 2) and then dichloromethane (500 mL) is added. The mixture is stirred until all solid is dissolved. The organic layer is collected, dried over $MgSO_4$, and concentrated to afford 1-3 (17.18 g) as an off-white solid.

A reaction mixture of 1-3 (0.50 g, 1.87 mmol), 2-iodopropane (372.92 μL, 3.74 mmol), $Cs_2CO_3$ (0.91 g, 2.80 mmol) in DMA (9.0 mL) is heated at 150° C. in a microwave reactor for 10 min. The mixture is added to water and is extracted with EtOAc (2×). The organic layers are washed with water, brine, dried over $MgSO_4$, and concentrated. The crude is purified by silica gel chromatography using a gradient of 12-100% EtOAc in heptane to yield the desired product 1-4 (0.41 g).

To a microwave vial is added 1-4 (1.00 g, 3.29 mmol), 1-5 (0.69 g, 4.52 mmol), $Pd(PPh_3)_4$ (0.37 g, 0.32 mmol), DME (15.0 mL), and 2.0 M $Na_2CO_3$ (4.36 mL, 8.72 mmol). The reaction mixture is heated in microwave reactor at 120° C. for 20 min. The reaction is extracted with dichloromethane (2×), washed with water, brine, dried over $Na_2SO_4$, and concentrated. The resulting material is purified by silica gel chromatography using a gradient of 12-100% EtOAc in heptane to yield the desired product 1-6 (0.41 g).

Example 2

Preparation of intermediate 1-[6-(2-hydroxy-3-methyl-phenyl)-pyridin-2-yl]-5-methoxy-1H-pyrazole-4-carboxylic acid ethyl ester (2-8)

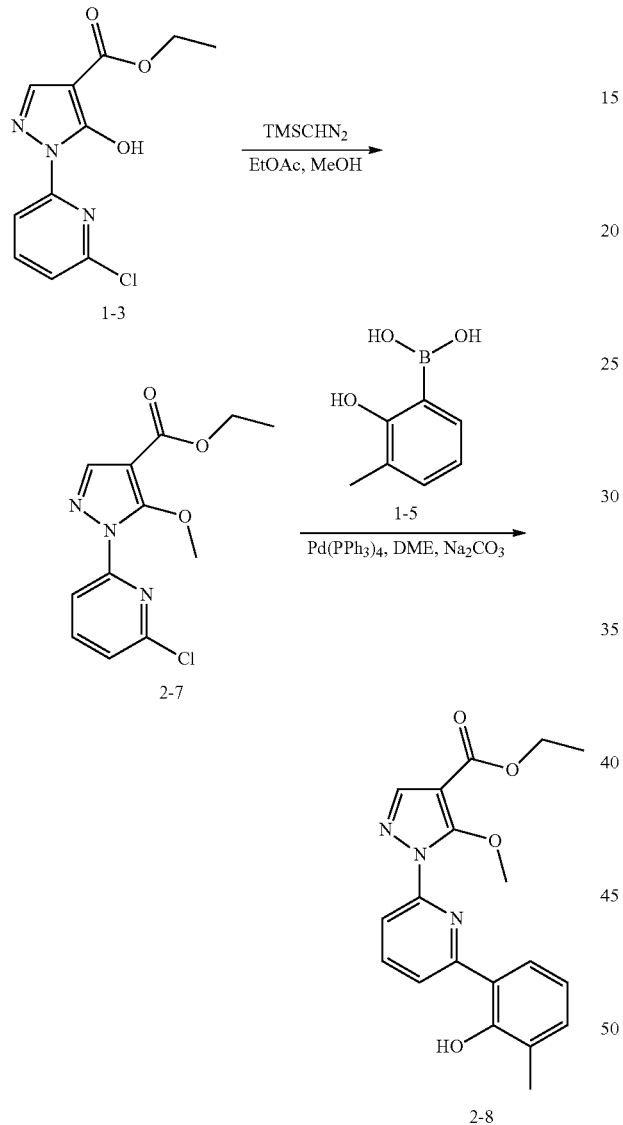

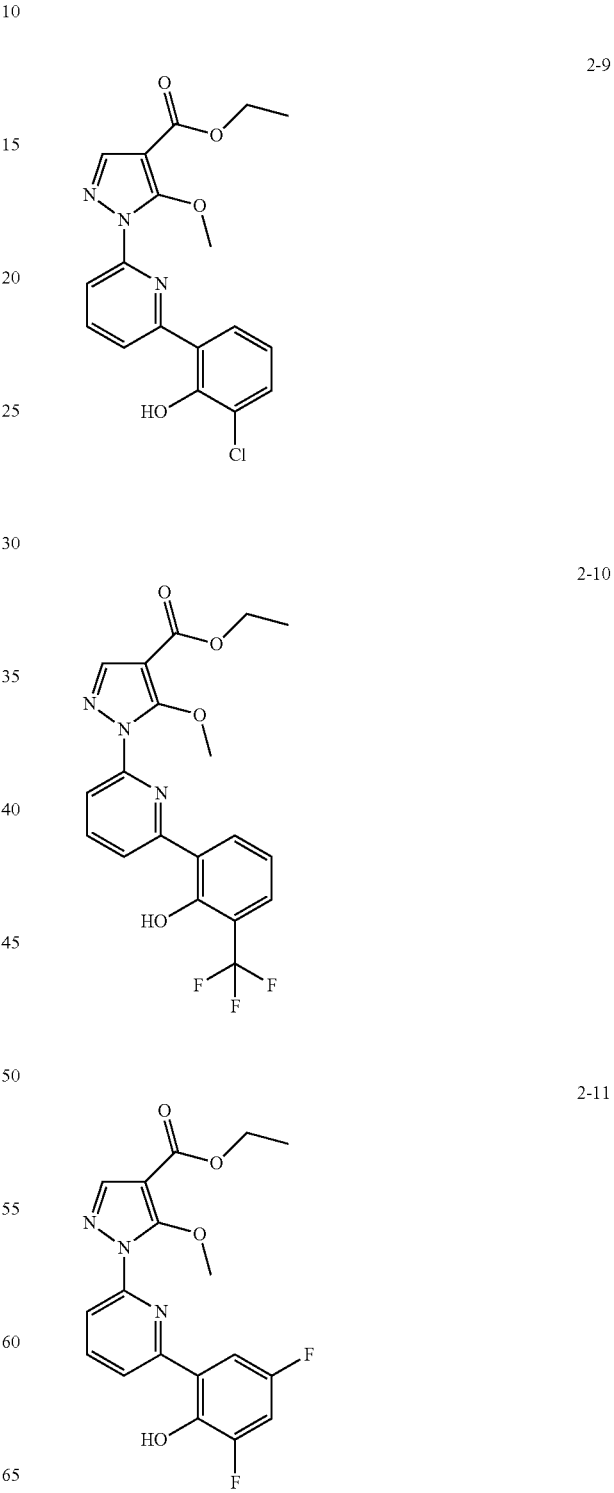

Intermediate 1-3 (7.00 g, 26.15 mmol) is dissolved in 1:1 mixture EtOAc/MeOH (50.0 mL). 2.0 M TMSCHN$_2$ in hexanes (42.70 mL, 85.40 mmol) is then added slowly via a syringe. The reaction is stirred for 3 h and is quenched by the addition of acetic acid (4.0 mL). The mixture is stirred for 10 min and then concentrated. The resulting residue is purified by silica gel chromatography using a gradient of 12-100% EtOAc in heptane to yield the desired product 2-7 (4.460 g) as an off-white solid.

To a microwave vial is added 2-7 (1.50 g, 5.33 mmol), 1-5 (0.890 g, 5.86 mmol), Pd(PPh$_3$)$_4$ (0.62 g, 0.532 mmol), DME (12.0 mL), and 2.0 M Na$_2$CO$_3$ (6.922 mL, 13.85 mmol). The reaction mixture is heated in a microwave reactor at 120° C. for 20 min. The reaction is extracted with dichloromethane (2×), washed with water, brine, dried over MgSO$_4$, and concentrated. The resulting material is purified by silica gel chromatography using a gradient of 12-100% EtOAc in heptane to yield the desired product 2-8 (1.17 g).

The following intermediates are synthesized in a similar fashion from the appropriate reagents:

Example 3

Preparation of intermediate 5-ethoxy-1-[6-(2-hydroxy-3-methyl-phenyl)-pyridin-2-yl]-1H-pyrazole-4-carboxylic acid ethyl ester (3-15)

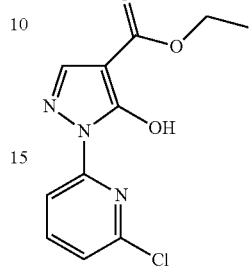

1-(6-Chloro-pyridin-2-yl)-5-hydroxy-1H-pyrazole-4-carboxylic acid ethyl ester, 1-3, (3.50 g, 13.08 mmol) is dissolved in THF (90.0 mL). Triphenylphosphine (3.77 g, 14.383 mmol) and ethanol (1.14 mL, 19.614 mmol) are added and the reaction is cooled to 0° C. The resulting suspension is slowly dissolved at 0° C. as diisopropyl azodicarboxylate (3.09 mL, 15.691 mmol) is added dropwise over 10 min. The reaction mixture is allowed to warm to ambient temperature and is stirred for 16 h. The reaction is concentrated in vacuo and the residue is dissolved in a minimal amount of dichloromethane and subjected to silica gel chromatography using a gradient of 3-50% EtOAc in heptane to yield the desired product 3-14 (3.33 g).

To a microwave vial is added 3-14 (250.0 mg, 0.85 mmol), 1-5 (134.9 mg, 0.89 mmol), Pd(PPh₃)₄ (60.05 mg, 0.05

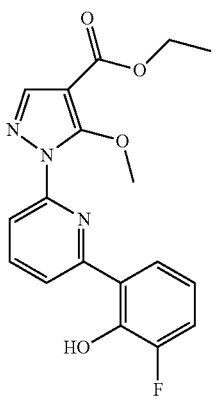

2-13

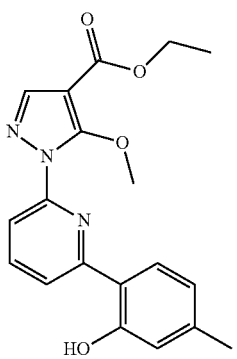

2-14

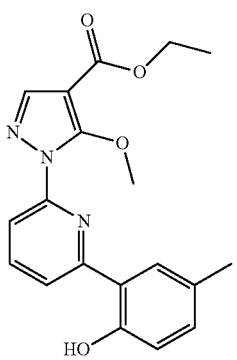

mmol), DME (5.0 mL), and 2.0 M Na₂CO₃ (1.06 mL, 2.11 mmol). The reaction mixture is heated in a microwave reactor at 120° C. for 20 min. The reaction is extracted with dichloromethane (2×), washed with water, brine, dried over MgSO₄, and concentrated. The resulting material is purified by silica gel chromatography using a gradient of 12-100% EtOAc in heptane to yield the desired product, 3-15 (227.0 mg).

The following intermediate is synthesized in a similar fashion from the appropriate reagents:

3-16

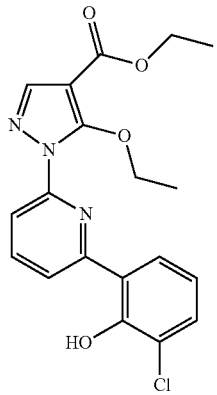

3-17

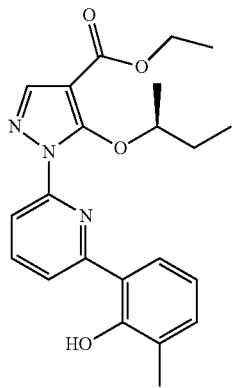

3-18

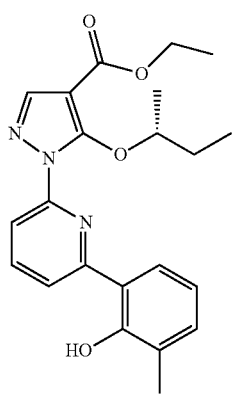

-continued 3-19

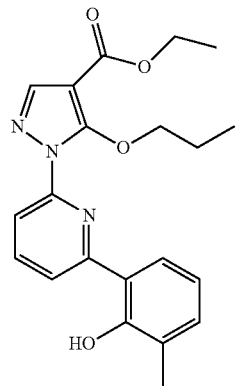

3-20

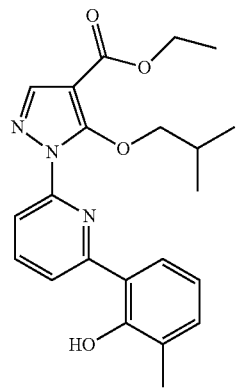

3-21

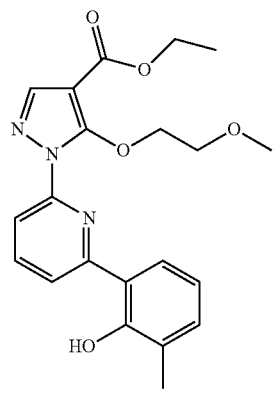

3-22

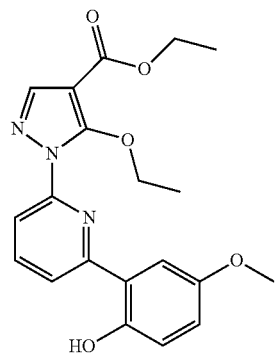

-continued

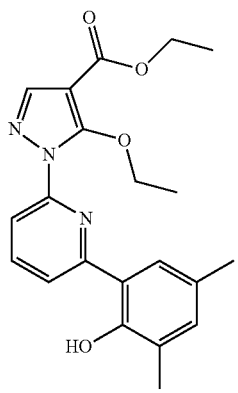

3-23

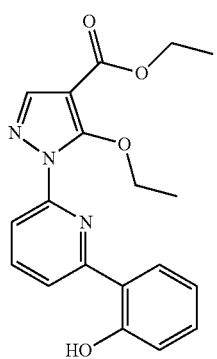

3-24

Example 4

Preparation of intermediate 6-bromomethyl-3,4-dihydro-1H-isoquinoline-2-carboxylic acid tert-butyl ester (4-19)

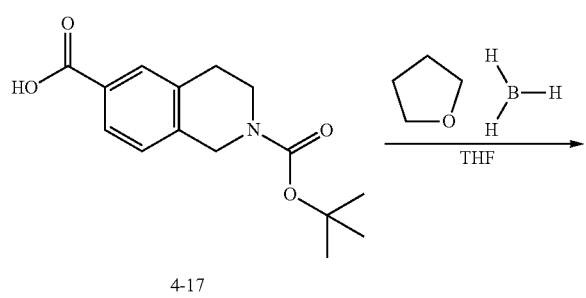

-continued

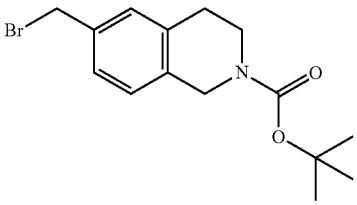

4-19

Compound 4-17 (12.50 g, 45.08 mmol) is dissolved in dry THF (125.0 mL) under nitrogen at 25° C. Borane THF complex (99.17 mL, 99.17 mmol) is added via syringe and the mixture is stirred at 25° C. for 16 h. Water (10.0 mL) is slowly added and then 2.0 M $Na_2CO_3$ (15.0 mL). This mixture is stirred for 15 min and then is diluted with EtOAc and the organic layers are collected. The organics are rinsed with 1.0 M HCl, dried over $MgSO_4$, and concentrated in vacuo to afford an oil. The oil is purified by silica gel chromatography using a gradient of 10-80% EtOAc in heptane to yield the desired product, 4-18 (11.78 g), as a white solid.

To a solution of alcohol, 4-18, (9.50 g, 36.08 mmol) and N,N-diisopropylethylamine (9.43 mL, 54.11 mmol) in dichloromethane (200.0 mL) is added triphenylphosphine dibromide (23.79 g, 54.11 mmol) at 0° C. The reaction is stirred for 1 h and concentrated in vacuo. The resulting residue is purified by silica gel chromatography using a gradient of 7-60% EtOAc in heptanes to yield the desired product, 4-19 (8.74 g), as a white solid.

The following intermediates are synthesized in similar fashion from the appropriate reagents:

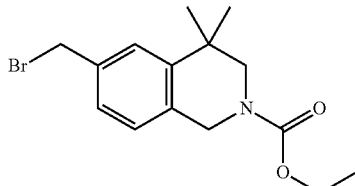

4-20

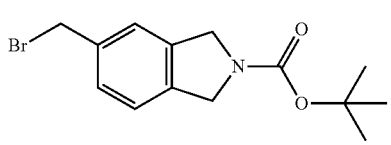

4-21

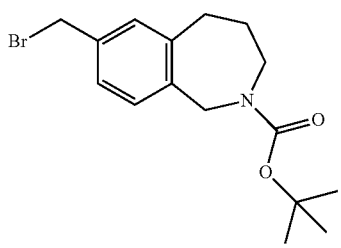

4-22

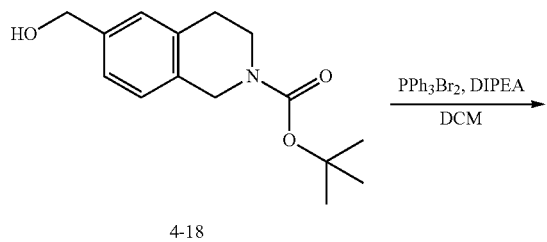

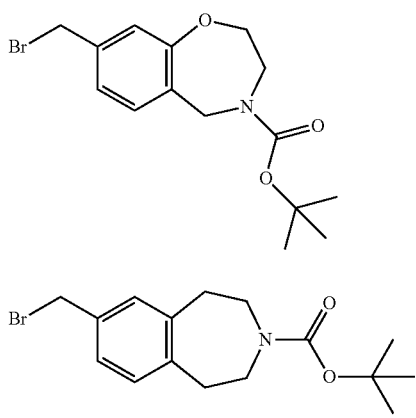
Example 5
Preparation of intermediate 6-bromomethyl-5-methyl-3,4-dihydro-1H-isoquinoline-2-carboxylic acid tert-butyl ester (5-34)
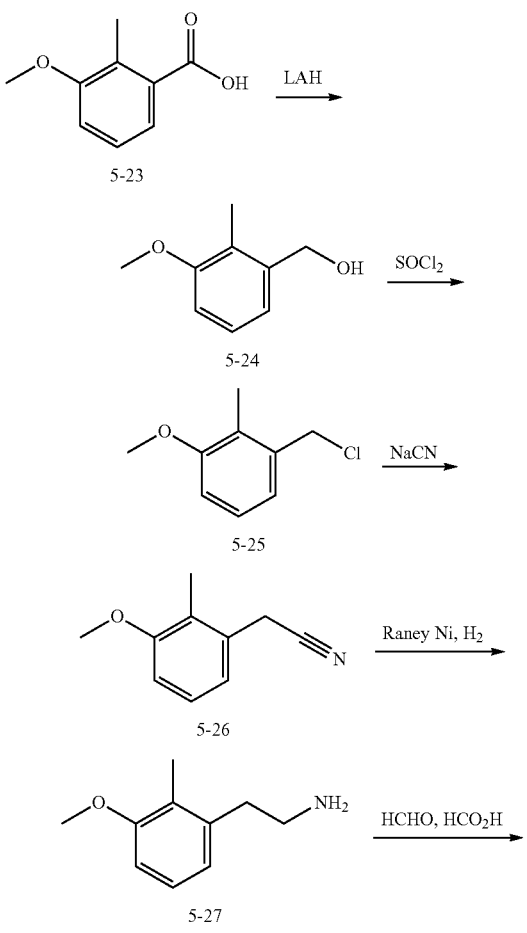
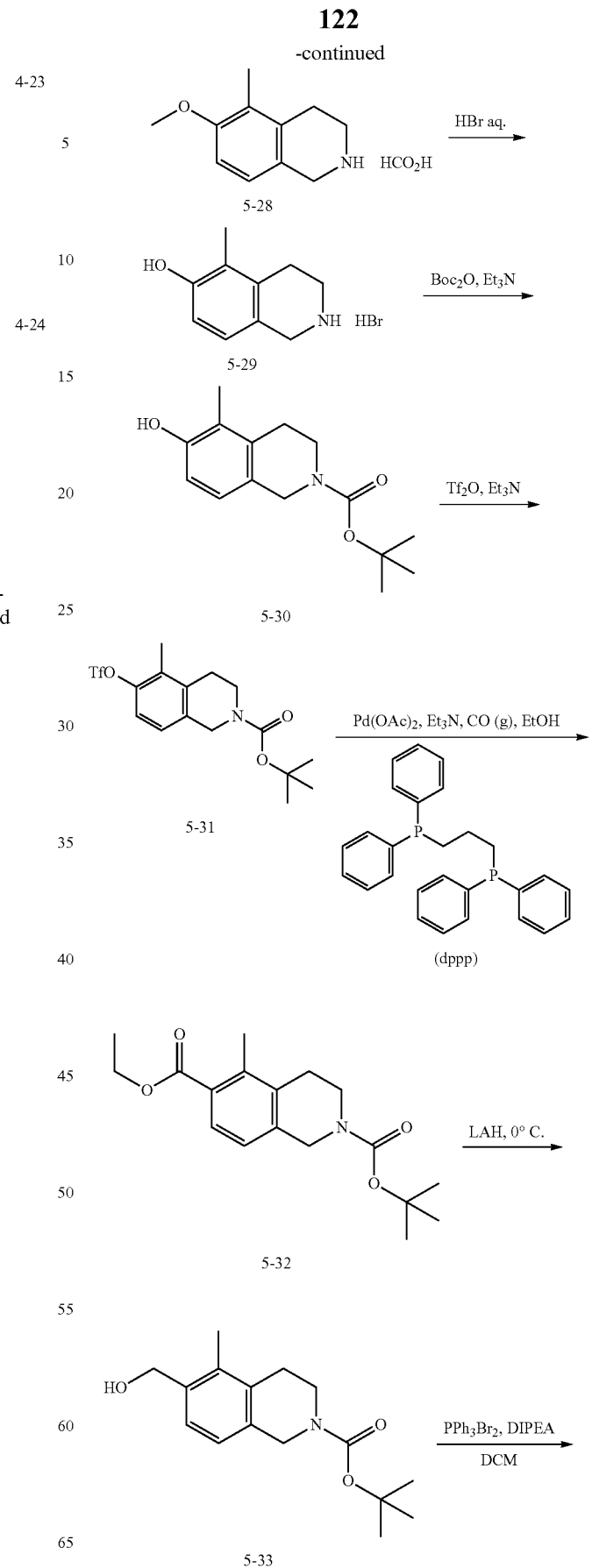

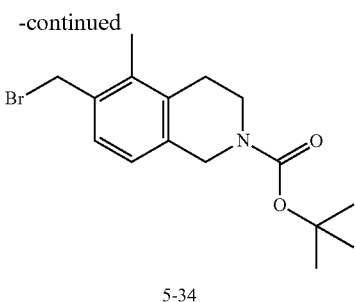

5-34

A solution of acid 5-23 (350.0 g, 2.10 mol) in THF (1.4 L) is added to a slurry of LAH (95.9 g, 1.40 mol) in THF (2.5 L) at 0° C. The mixture is stirred at room temperature for 0.5 h, then heated to reflux for 1 h. The mixture is then cooled to 0° C., and slowly quenched by the addition of saturated aqueous ammonium chloride solution. A large excess of solid $Na_2SO_4$ and EtOAc are added, then the solids are collected by filtration. The filtrate is concentrated in vacuo to afford crude 5-24 (350.0 g) which is used directly in the next step.

To a solution of compound 5-24 (294.0 g, 1.90 mol) in dichloromethane (2.2 L) at −10° C. is added thionyl chloride ($SOCl_2$) (460.0 g, 3.90 mol). Then the reaction mixture is heated to reflux for 1 h, followed by concentration in vacuo to provide crude 5-25 (298.0 g) which is used directly in the next step.

A mixture of compound 5-25 (298.0 g, 1.8 mol) and NaCN (154.5 g, 2.1 mol) in DMF (1.2 L) is stirred at room temperature for 12 h, then extracted with EtOAc and $H_2O$. The organic layer is dried over $Na_2SO_4$, filtered, and concentrated in vacuo. The residue is purified by silica gel chromatography (petroleum ether:EtOAc=50:1) to deliver intermediate 5-26 (230.0 g).

A mixture of compound 5-26 (180.0 g, 1.10 mol), Raney Ni (40.0 g) and aqueous ammonia (250.0 mL) in MeOH (1.0 L) is stirred under $H_2$ (50 psi) at room temperature for 5 h. The mixture is then filtered and concentrated to give compound 5-27 (165.0 g) that is used directly in the next step.

A solution of compound 5-27 (165.0 g, 1.0 mol) and aqueous formaldehyde (HCHO) (37 wt %, 30 g, 1.0 mol) in formic acid ($HCO_2H$) (1.5 L) is stirred at 50° C. overnight, then the solvent is removed in vacuo to afford compound 5-28 (150.0 g) which is used directly in the next step.

Compound 5-28 (150.0 g, 847 mmol) is suspended in aqueous HBr (48%, 1.0 L), then heated to 100° C. overnight. Removal of the solvent in vacuo provides compound 5-29 (195.0 g) which is used directly in the next step.

To a solution of compound 5-29 (195.0 g, 799 mmol) in THF (1.0 L) and $H_2O$ (1.0 L) is added $Et_3N$ (242.0 g, 2.4 mol) and $Boc_2O$ (174.0 g, 799 mmol). The resulting mixture is stirred at room temperature overnight, then extracted with EtOAc. The combined organic phases are washed with brine, dried over $Na_2SO_4$, filtered and concentrated in vacuo. The crude product is purified by silica gel chromatography (using 10:1 petroleum ether:EtOAc) to provide compound 5-30 (100.0 g).

To a solution of compound 5-30 (100.0 g, 380 mmol) and $Et_3N$ (76.8 g, 760 mmol) in dichloromethane (1.5 L) cooled to 0° C. is added triflic anhydride ($Tf_2O$) (107.0 g, 380 mmol) via addition funnel. Upon complete addition of $Tf_2O$, the solution is warmed to room temperature for 5 h. The reaction mixture is then treated with $H_2O$ and dichloromethane, and the organic phase is separated, washed with brine, dried over $Na_2SO_4$, filtered, and concentrated in vacuo. The residue is purified by silica gel chromatography (using 20:1 petroleum ether:EtOAc) to provide compound 5-31 (105.0 g).

Compound 5-31 (50.0 g, 127 mmol) is combined with palladium (II) acetate ($Pd(OAc)_2$) (5.0 g), dppp (5.0 g) and $Et_3N$ (25.7 g, 254 mmol) in EtOH (1.0 L), then stirred at 80° C. overnight under CO at a pressure of 4 MPa. The mixture is cooled to room temperature, then the solids are removed by filtration. The filtrate is concentrated in vacuo, and the remaining residue is purified by silica gel chromatography (using 20:1 petroleum ether:EtOAc) to provide compound 5-32 (25.0 g).

To a solution of LAH (12.5 g, 330 mmol) in THF (400 mL) cooled to −30° C. is added dropwise a solution of compound 5-32 (35.0 g, 110 mmol) in THF (400 mL) over 30 min. After addition, the reaction mixture is stirred at 0° C. for 30 min, then treated with $H_2O$ and dichloromethane. The organic phase is separated, washed with brine, dried over $Na_2SO_4$, filtered, and concentrated in vacuo. The crude product is purified by silica gel chromatographyl (using 10:1 petroleum ether:EtOAc) to provide the desired intermediate 5-33 (21.1 g).

To a solution of alcohol, 5-33, (6.00 g, 21.63 mmol) and N,N-diisopropylethylamine (5.65 mL, 32.45 mmol) in dichloromethane (200.0 mL) is added triphenylphosphine dibromide (14.27 g, 32.45 mmol) at 0° C. The reaction is stirred for 1 h and concentrated in vacuo. The resulting residue is purified by silica gel chromatography using a gradient of 7-60% EtOAc in heptanes to yield the desired product, 5-34 (6.60 g), as a white solid.

Example 6

Preparation of intermediate 6-Bromomethyl-5-chloro-3,4-dihydro-1H-isoquinoline-2-carboxylic acid tert-butyl ester (6-39)

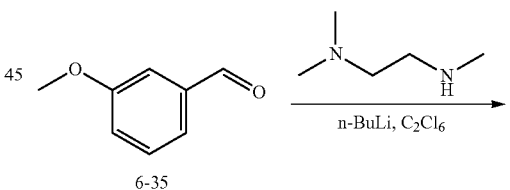

6-35

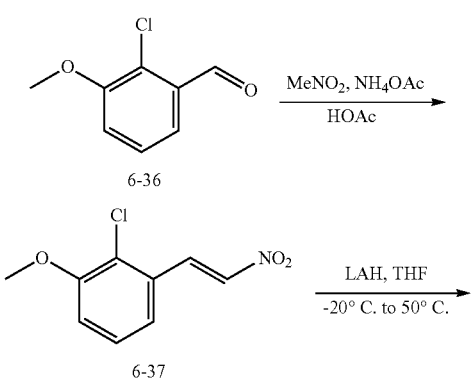

6-36

6-37

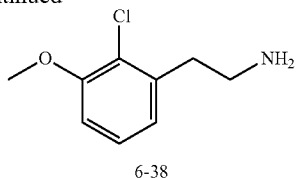

6-38

To a solution of N,N,N'-trimethyl-ethane-1,2-diamine (45.0 g, 442.0 mmol) in THF (500 mL) is added a solution of n-BuLi (177.0 mL, 442 mmol) at −40° C. under $N_2$. The mixture is stirred at −40° C. for 30 min. After the mixture is cooled to −70° C., compound 6-35 (50.0 g, 368 mmol) in THF (250 mL) is added to the reaction mixture. The mixture is allowed to warm to 0° C. and stirred for 30 min. Then the reaction mixture is cooled to −78° C. and n-BuLi (177.0 mL, 442 mmol) is added. The mixture is allowed to warm to 10° C. and is cooled to −30° C. before it is added to a solution of $C_2Cl_6$ (287.0 g, 1.1 mol) in THF (600 mL). The mixture is stirred 2 h at room temperature. The reaction mixture is poured into 1000 mL of 10% HCl solution and extracted with EtOAc. The organic layers are washed with brine, dried over $Na_2SO_4$, concentrated, and purified by silica gel chromatography to give compound 6-36 (36.7 g).

To a solution of compound 6-36 (105.0 g, 615 mmol) in HOAc (700 mL) is added $NH_4OAc$ (47.4 g, 615 mmol) at room temperature under $N_2$. To this reaction mixture is added $MeNO_2$ (188.0 g, 3.08 mol) and the mixture is warmed to 40° C. for 12 h and then is stirred at 85° C. for 6 h. TLC showed the reaction is completed. The mixture is quenched with H2O and is extracted with dichloromethane. The organic layers are washed with brine, dried over Na2SO4, concentrated, and purified by silica gel chromatography to give compound 6-37 (97.5 g).

To a solution of compound 6-37 (48.0 g, 225 mmol) in THF (900 mL) is added LAH (34.1 g, 899 mol) at −20° C. The mixture is stirred at room temperature for 5 h and 50° C. for 30 min. The mixture is quenched with $H_2O$ and is extracted with dichloromethane. The organic layers are washed with brine, dried over $Na_2SO_4$, and concentrated to give compound 6-38 (28.0 g) which is used directly in the next step.

The following compound is prepared from intermediate 6-38 according to the procedure described in Example 5:

6-39

Example 7

Preparation of 5-isopropoxy-1-(6-{3-methyl-2-[2-(tetrahydro-pyran-4-yl)-1,2,3,4-tetrahydro-isoquinolin-6-ylmethoxy]-phenyl}-pyridin-2-yl)-1H-pyrazole-4-carboxylic acid (1)

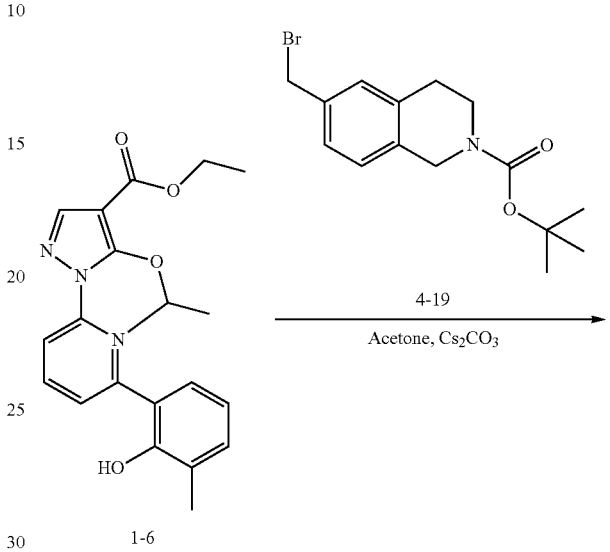

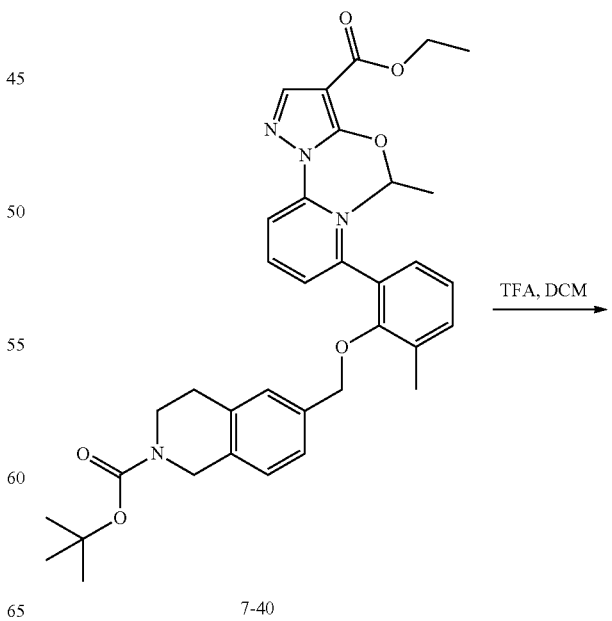

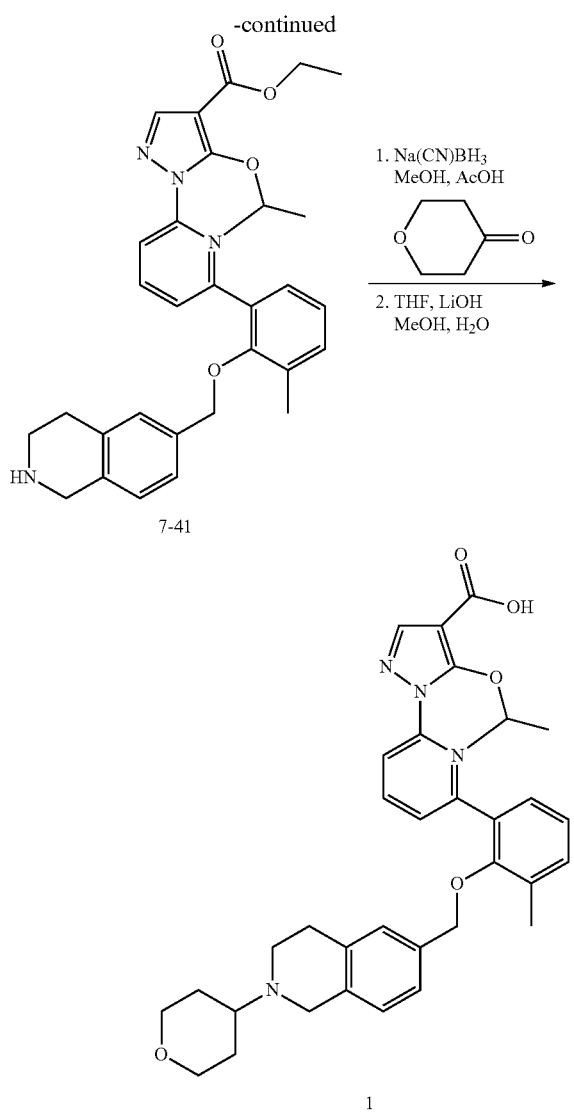

Intermediate 1-6 (373.0 mg, 0.88 mmol), bromide 4-19 (287.1 mg, 0.88 mmol) and Cs$_2$CO$_3$ (573.5 mg, 1.76 mmol) are combined in acetone (11.0 mL) and heated to 50° C. for 5 h. The reaction mixture is extracted with EtOAc, washed with brine, dried over MgSO$_4$, and concentrated. The resulting material is purified by silica gel chromatography (using a gradient of 5-100% EtOAc/heptane) to provide the desired intermediate, 7-40 (502.0 mg).

The carbamate, 7-40, (496.0 mg, 0.79 mmol) is dissolved in dichloromethane (4.0 mL) and treated with TFA (1.0 mL) at room temperature. After 1 h the mixture is neutralized with saturated NaHCO$_3$ solution and the layers are separated with a hydrophobic frit. The organic filtrate is concentrated to afford 7-41 (375.0 mg).

Amine 7-41 (98.0 mg, 0.19 mmol) is combined with 4 Å molecular sieves (30 mg), tetrahydropyran 4-one (28 µL, 0.28 mmol), AcOH (20 µL), and Na(CN)BH$_3$ (24 mg, 0.38 mmol) in MeOH (4 mL). The mixture is stirred at room temperature for 30 min, and then heated to 50° C. for 12 h. The mixture is diluted with THF (1.0 mL) and water (1 mL). To this is added LiOH (42.8 mg, 1.86 mmol) and the reaction is heated to 50° C. for 2 h. It is then concentrated under N$_2$, triturated with 1:1 MeOH/DMSO, filtered through a 0.45 micron syringe filter, and the filtrate is purified by gradient elution (10-100% MeCN/water+0.1% HCO$_2$H) on a Gilson RP-HPLC. Concentrated in vacuo to afford title compound 1 (64.0 mg). MS, electrospray, m/z=583.3 [M+H], RT 0.71 min.

Example 7A

Procedure is equivalent to Example 7, however during reductive amination step Na(OAc)$_3$BH in dichloromethane is substituted for NaCNBH$_3$/AcOH/MeOH.

The following compounds from Table 1 are prepared according to the procedure described in Example 7, using the appropriate starting materials and purification conditions Compound 2: MS, electrospray, m/z=617.3 [M+H], RT 0.79 min;

Compound 37: MS, electrospray, m/z=541.3 [M+H], RT 0.75 min;

Compound 38: MS, electrospray, m/z=571.4 [M+H], RT 0.76 min;

Compound 39: MS, electrospray, m/z=555.3 [M+H], RT 0.73 min;

Compound 40: MS, electrospray, m/z=583.3 [M+H], RT 0.73 min;

Compound 41: MS, electrospray, m/z=569.3 [M+H], RT 0.73 min;

Compound 42: MS, electrospray, m/z=583.3 [M+H], RT 0.75 min;

Compound 109: MS, electrospray, m/z=569.4 [M+H], RT 0.77 min;

Resolution: ChiralPak AD-H Prep 40% i-Propanol(1% iPrNH$_2$):CO$_2$ @ 80 ml/min., 100 bar, 25° C.

Compound 111: MS, electrospray, m/z=569.4 [M+H], RT 0.77 min;

Resolution: ChiralPak AD-H Prep 40% i-Propanol(1% iPrNH$_2$):CO$_2$ @ 80 ml/min., 100 bar, 25° C.

Compound 113: MS, electrospray, m/z=583.3 [M+H], RT 0.75 min;

Resolution: Lux Cellulose 2 Prep 60% MeOH (1% iPrNH$_2$): CO$_2$ @ 55 ml/min., 100 bar, 25° C.

Compound 115: MS, electrospray, m/z=583.3 [M+H], RT 0.75 min;

Resolution: Lux Cellulose 2 Prep 60% MeOH (1% iPrNH$_2$): CO$_2$ @ 55 ml/min., 100 bar, 25° C.

Compound 144: MS, electrospray, m/z=569.4 [M+H], RT 0.77 min.

The following compounds from Table 1 are prepared according to the procedure described in Example 7, using phenol, 1-6, bromide, 5-34, and other appropriate starting materials and purification conditions:

Compound 43: MS, electrospray, m/z=555.4 [M+H], RT 0.77 min;

Compound 44: MS, electrospray, m/z=585.4 [M+H], RT 0.80 min;

Compound 45: MS, electrospray, m/z=569.3 [M+H], RT 0.75 min;

Compound 46: MS, electrospray, m/z=597.4 [M+H], RT 0.76 min;

Compound 47: MS, electrospray, m/z=583.3 [M+H], RT 0.76 min;

Compound 48: MS, electrospray, m/z=597.4 [M+H], RT 0.77 min;

Compound 104: MS, electrospray, m/z=597.5 [M+H], RT 0.80 min;

Compound 116: MS, electrospray, m/z=597.4 [M+H], RT 0.77 min;

Resolution: Lux Cellulose 2 Prep 65% MeOH (1% iPrNH$_2$): CO$_2$ @ 60 ml/min., 125 bar, 25° C.
Compound 117: MS, electrospray, m/z=597.4 [M+H], RT 0.77 min;
Resolution: Lux Cellulose 2 Prep 65% MeOH (1% iPrNH$_2$): CO$_2$ @ 60 ml/min., 125 bar, 25° C.
Compound 122: MS, electrospray, m/z=581.5 [M+H], RT 0.72 min;
Resolution: RegisPack Prep 15% IPA (1% diethylamine): CO$_2$ @ 12 ml/min., 120 bar, 40° C.
Compound 123: MS, electrospray, m/z=581.5 [M+H], RT 0.72 min.
Resolution: RegisPack Prep 15% IPA (1% diethylamine): CO$_2$ @ 12 ml/min., 120 bar, 40° C.

The following compounds from Table 1 are prepared according to the procedure described in Example 7, using phenol, 2-8, bromide, 4-19, and other appropriate starting materials and purification conditions:
Compound 3: MS, electrospray, m/z=555.3 [M+H], RT 0.64 min;
Compound 5: MS, electrospray, m/z=587.2 [M−H], RT 0.78 min;
Compound 8: MS, electrospray, m/z=527.2 [M+H], RT 0.69 min;
Compound 12: MS, electrospray, m/z=555.3 [M+H], RT 0.68 min;
Compound 13: MS, electrospray, m/z=513.2 [M+H], RT 0.70 min;
Compound 14: MS, electrospray, m/z=541.3 [M+H], RT 0.77 min;
Compound 15: MS, electrospray, m/z=541.2 [M+H], RT 0.68 min;
Compound 23: MS, electrospray, m/z=543.3 [M+H], RT 0.70 min;
Compound 24: MS, electrospray, m/z=525.2 [M+H], RT 0.72 min;
Compound 25: MS, electrospray, m/z=539.3 [M+H], RT 0.75 min;
Compound 61: MS, electrospray, m/z=583.3 [M+H], RT 0.72 min;
Compound 62: MS, electrospray, m/z=583.4 [M+H], RT 0.72 min;
Compound 73: MS, electrospray, m/z=611.4 [M+H], RT 0.75 min;
Compound 75: MS, electrospray, m/z=593.4 [M−H], RT 0.72 min;
Compound 81: MS, electrospray, m/z=585.1 [M+H], Method A2, RT 1.42 min;
Compound 86: MS, electrospray, m/z=569.4 [M+H], RT 0.78 min;
Compound 87: MS, electrospray, m/z=581.4 [M+H], RT 0.80 min;
Compound 90: MS, electrospray, m/z=583.4 [M+H], RT 0.80 min;
Compound 91: MS, electrospray, m/z=583.4 [M+H], RT 0.83 min;
Compound 92: MS, electrospray, m/z=571.4 [M+H], RT 0.79 min;
Compound 102: MS, electrospray, m/z=609.4 [M+H], RT 0.83 min;
Compound 103: MS, electrospray, m/z=609.4 [M+H], RT 0.89 min;
Compound 188: MS, electrospray, m/z=555.3 [M+H], RT 0.58 min;
Compound 192: MS, electrospray, m/z=555.3 [M+H], RT 0.58 min.

The following compounds from Table 1 are prepared according to the procedure described in Example 7, using phenol, 2-8, bromide, 4-20, and other appropriate starting materials and purification conditions:
Compound 10: MS, electrospray, m/z=555.2 [M+H], RT 0.82 min;
Compound 89: MS, electrospray, m/z=583.4 [M+H], Method A2, RT 1.80 min.

The following compounds from Table 1 are prepared according to the procedure described in Example 7a, using phenol, 2-8, bromide, 4-20, and other appropriate starting materials and purification conditions:
Compound 217: MS, electrospray, m/z=569.3 [M+H], 1.45 min (method B2);
Compound 218: MS, electrospray, m/z=583.3 [M+H], 1.52 min (method B2);
Compound 219: MS, electrospray, m/z=599.3 [M+H], 1.46 min (method B2);

The following compounds from Table 1 are prepared according to the procedure described in Example 7, using phenol, 2-8, bromide, 4-21, and other appropriate starting materials and purification conditions:
Compound 59: MS, electrospray, m/z=541.3 [M+H], RT 0.66 min;
Compound 85: MS, electrospray, m/z=513.2 [M+H], RT 0.71 min.

The following compound from Table 1 is prepared according to the procedure described in Example 7, using phenol, 2-8, bromide, 4-22, and other appropriate starting materials and purification conditions:
Compound 100: MS, electrospray, m/z=569.4 [M+H], RT 0.77 min.

The following compound from Table 1 is prepared according to the procedure described in Example 7, using phenol, 2-8, bromide, 4-23, and other appropriate starting materials and purification conditions:
Compound 130: MS, electrospray, m/z=571.4 [M+H], RT 0.69 min (Method B1);

The following compounds from Table 1 are prepared according to the procedure described in Example 7, using phenol, 2-8, bromide, 5-34, and other appropriate starting materials and purification conditions:
Compound 16: MS, electrospray, m/z=541.2 [M+H], RT 0.70 min;
Compound 27: MS, electrospray, m/z=569.3 [M+H], RT 0.70 min;
Compound 28: MS, electrospray, m/z=569.3 [M+H], RT 0.70 min;
Compound 30: MS, electrospray, m/z=555.3 [M+H], RT 0.77 min;
Compound 31: MS, electrospray, m/z=555.3 [M+H], RT 0.70 min.

The following compounds from Table 1 are prepared according to the procedure described in Example 7a, using phenol, 2-8, bromide, 5-34, and other appropriate starting materials and purification conditions:
Compound 105: MS, electrospray, m/z=555.4 [M+H], RT 0.72 min
Resolution: Chirapak AD-H, 20×250 mm; MeOH to 30 mg/mL, 35% EtOH (1% DEA) in heptane over 18 min, ambient temp. and collection at 290 nm;
Compound 106: MS, electrospray, m/z=555.4 [M+H], RT 0.72 min
Resolution: Chirapak AD-H, 20×250 mm; MeOH to 30 mg/mL, 35% EtOH (1% DEA) in heptane over 18 min, ambient temp. and collection at 290 nm;

Compound 127: MS, electrospray, m/z=569.4 [M+H], RT 0.76 min;

Compound 139: MS, electrospray, m/z=585.4 [M+H], RT 0.74 min

Resolution: Chiracel OD-H, 20×250 mm; 10% MeOH in $CO_2$ at 55.5 g/min over 28 min, 140 Bar, 40° C. and collection at 254 nm;

Compound 140: MS, electrospray, m/z=569.4 [M+H], RT 0.74 min

Resolution: Chiracel OD-H, 20×250 mm; 10% MeOH in $CO_2$ at 58 g/min over 30 min, 120 Bar, 40° C. and collection at 254 nm;

Compound 141: MS, electrospray, m/z=569.4 [M+H], RT 0.74 min

Resolution: Chiracel OD-H, 20×250 mm; 10% MeOH in $CO_2$ at 58 g/min over 30 min, 120 Bar, 40° C. and collection at 254 nm;

Compound 142: MS, electrospray, m/z=585.4 [M+H], RT 0.74 min

Resolution: Chiracel OD-H, 20×250 mm; 10% MeOH in $CO_2$ at 55.5 g/min over 28 min, 140 Bar, 40° C. and collection at 254 nm;

Compound 191: MS, electrospray, m/z=569.3 [M+H], RT 0.61 min;

Compound 198: MS, electrospray, m/z=583.3 [M+H], RT 0.66 min (method B1);

Resolution: LUX Amylose-2, 21×250 mm 35% (1:1:1 MeOH:EtOH:iPA)+$Et_2NH$:$CO_2$, 80 ml/min, 110 bar, 40° C.

Compound 199: MS, electrospray, m/z=583.3 [M+H], RT 0.66 min (method B1).

Resolution: LUX Amylose-2, 21×250 mm 35% (1:1:1 MeOH:EtOH:iPA)+$Et_2NH$:$CO_2$, 80 ml/min, 110 bar, 40° C.

The following compounds from Table 1 are prepared according to the procedure described in Example 7, using phenol, 2-8, bromide, 6-39, and other appropriate starting materials and purification conditions:

Compound 17: MS, electrospray, m/z=561.2 [M+H], RT 0.77 min;

Compound 18: MS, electrospray, m/z=589.3 [M+H], RT 0.73 min;

Compound 19: MS, electrospray, m/z=589.3 [M+H], RT 0.73 min;

Compound 20: MS, electrospray, m/z=559.3 [M+H], RT 0.76 min;

Compound 21: MS, electrospray, m/z=575.3 [M+H], RT 0.83 min;

Compound 22: MS, electrospray, m/z=575.3 [M+H], RT 0.73 min.

The following compound from Table 1 is prepared according to the procedure described in Example 7, using phenol, 2-9, bromide, 4-19, and other appropriate starting materials and purification conditions:

Compound 7: MS, electrospray, m/z=547.2 [M+H], RT 0.71 min.

The following compounds from Table 1 are prepared according to the procedure described in Example 7, using phenol, 2-10, bromide, 4-19, and other appropriate starting materials and purification conditions:

Compound 9: MS, electrospray, m/z=581.2 [M+H], RT 0.73 min;

Compound 83: MS, electrospray, m/z=609.4 [M+H], RT 0.79 min.

The following compound from Table 1 is prepared according to the procedure described in Example 7, using phenol, 2-10, bromide, 4-21, and other appropriate starting materials and purification conditions:

Compound 93: MS, electrospray, m/z=595.3 [M+H], RT 0.80 min.

The following compounds from Table 1 are prepared according to the procedure described in Example 7, using phenol, 2-10, bromide, 5-34, and other appropriate starting materials and purification conditions:

Compound 84: MS, electrospray, m/z=623.4 [M+H], RT 0.83 min;

Compound 88: MS, electrospray, m/z=595.3 [M+H], RT 0.80 min;

Compound 107: MS, electrospray, m/z=607.4 [M+H], RT 0.77 min;

Resolution: Chirapak AD-H, 30×250 mm; 50% Isopropanol:Hexane with 1% Isopropylamine @ 88 mL/min, 100 bar $CO_2$, ambient temp.

Compound 108: MS, electrospray, m/z=607.4 [M+H], RT 0.77 min.

Resolution: Chirapak AD-H, 30×250 mm; 50% Isopropanol:Hexane with 1% Isopropylamine @ 88 mL/min, 100 bar $CO_2$, ambient temp.

The following compounds from Table 1 are prepared according to the procedure described in Example 7, using phenol, 2-11, bromide, 4-19, and other appropriate starting materials and purification conditions:

Compound 52: MS, electrospray, m/z=547.3 [M−H], RT 0.70 min;

Compound 53: MS, electrospray, m/z=575.3 [M−H], RT 0.71 min.

The following compound from Table 1 is prepared according to the procedure described in Example 7, using phenol, 2-12, bromide, 4-19, and other appropriate starting materials and purification conditions:

Compound 63: MS, electrospray, m/z=559.3 [M+H], RT 0.65 min.

The following compound from Table 1 is prepared according to the procedure described in Example 7, using phenol, 2-13, bromide, 4-19, and other appropriate starting materials and purification conditions:

Compound 98: MS, electrospray, m/z=555.4 [M+H], RT 0.76 min.

The following compound from Table 1 is prepared according to the procedure described in Example 7, using phenol, 2-13, bromide, 5-34, and other appropriate starting materials and purification conditions:

Compound 99: MS, electrospray, m/z=569.4 [M+H], RT 0.79 min.

The following compound from Table 1 is prepared according to the procedure described in Example 7a, using phenol, 2-14, bromide, 5-34, and other appropriate starting materials and purification conditions:

Compound 124: MS, electrospray, m/z=569.4 [M+H], RT 0.71 min

The following compounds from Table 1 are prepared according to the procedure described in Example 7, using phenol, 3-15, bromide, 4-19, and other appropriate starting materials and purification conditions:

Compound 6: MS, electrospray, m/z=541.2 [M+H], RT 0.73 min;

Compound 32: MS, electrospray, m/z=527.3 [M+H], RT 0.73 min;

Compound 34: MS, electrospray, m/z=569.3 [M+H], RT 0.71 min;

Compound 35: MS, electrospray, m/z=555.3 [M+H], RT 0.71 min;

Compound 36: MS, electrospray, m/z=569.3 [M+H], RT 0.73 min;

Compound 110: MS, electrospray, m/z=555.4 [M+H], RT 0.75 min;
Resolution: ChiralPak AD-H Prep 30% EtOH:$CO_2$ @ 80 ml/min., 100 bar, 25° C.
Compound 112: MS, electrospray, m/z=555.4 [M+H], RT 0.75 min.
Resolution: ChiralPak AD-H Prep 30% EtOH:$CO_2$ @ 80 ml/min., 100 bar, 25° C.

The following compound from Table 1 is prepared according to the procedure described in Example 7, using phenol, 3-15, bromide, 4-22, and other appropriate starting materials and purification conditions:
Compound 245: MS, electrospray, m/z=583.1 [M+H], RT 0.62 min.

The following compound from Table 1 is prepared according to the procedure described in Example 7, using phenol, 3-15, bromide, 4-23, and other appropriate starting materials and purification conditions:
Compound 131: MS, electrospray, m/z=585.4 [M+H], RT 1.21 min (Method B1);

The following compounds from Table 1 are prepared according to the procedure described in Example 7, using phenol, 3-15, bromide, 4-24, and other appropriate starting materials and purification conditions:
Compound 205: MS, electrospray, m/z=583.3 [M+H], RT 0.67 min (Method B1);
Compound 213: MS, electrospray, m/z=555.3 [M+H], RT 0.67 min (Method B1);

The following compounds from Table 1 are prepared according to the procedure described in Example 7, using phenol, 3-15, bromide, 5-34, and other appropriate starting materials and purification conditions:
Compound 114: MS, electrospray, m/z=583.5 [M+H], RT 0.62 min;
Compound 125: MS, electrospray, m/z=569.4 [M+H], RT 1.25 min (Method B2);
Resolution: LUX 5 u Cellulose 2 Prep, 23% MeOH (1% Et2NH) in CO2 at 78 ml/min over 21 minutes, 160 Bar, 40° C.
Compound 126: MS, electrospray, m/z=569.4 [M+H], RT 1.25 min (Method B2);
Resolution: LUX 5 u Cellulose 2 Prep, 23% MeOH (1% Et2NH) in CO2 at 78 ml/min over 21 minutes, 160 Bar, 40° C.
Compound 128: MS, electrospray, m/z=583.5 [M+H], RT 1.31 min (Method B2);
Resolution: Chiralcel OD-H, 20×250 mm 5.8% MeOH (~1% Et2NH) in CO2 at 85 g/min, 160 Bar, 40 C.
Compound 129: MS, electrospray, m/z=583.5 [M+H], RT 1.31 min (Method B2);
Resolution: Chiralcel OD-H, 20×250 mm 5.8% MeOH (~1% Et2NH) in CO2 at 85 g/min, 160 Bar, 40 C.

The following compounds from Table 1 are prepared according to the procedure described in Example 7a, using phenol, 3-15, bromide, 4-23, and other appropriate starting materials and purification conditions:
Compound 216: MS, electrospray, m/z=555.3 [M+H], RT 0.64 min (Method B1);
Compound 247: MS, electrospray, m/z=557.1 [M+H], RT 1.21 min (Method B2);

The following compounds from Table 1 are prepared according to the procedure described in Example 7a, using phenol, 3-15, bromide, 5-34, and other appropriate starting materials and purification conditions:
Compound 146: MS, electrospray, m/z=597.4 [M+H], RT 0.65 min (Method B1);
Compound 152: MS, electrospray, m/z=597.4 [M+H], RT 0.65 min (Method B1);
Resolution: Chiralcel OD-H, 20×250 mm 5.8% MeOH (~1% $Et_2NH$) in $CO_2$ at 85 g/min, 160 Bar, 40° C.;
Compound 153: MS, electrospray, m/z=597.4 [M+H], RT 0.65 min (Method B1);
Resolution: Chiralcel OD-H, 20×250 mm 5.8% MeOH (~1% $Et_2NH$) in $CO_2$ at 85 g/min, 160 Bar, 40° C.;
Compound 155: MS, electrospray, m/z=613.4 [M+H], RT 0.55 min (Method B1);
Compound 156: MS, electrospray, m/z=573.4 [M+H], RT 0.43 min (Method B1);
Compound 163: MS, electrospray, m/z=625.3 [M+H], RT 0.77 min;
Compound 164: MS, electrospray, m/z=555.3 [M+H], RT 0.71 min;
Compound 172: MS, electrospray, m/z=597.3 [M+H], RT 1.31 min (Method B2);
Compound 179: MS, electrospray, m/z=613.1 [M+H], RT 0.67 min (Method B1);
Compound 189: MS, electrospray, m/z=583.5 [M+H], RT 0.63 min
Compound 193: MS, electrospray, m/z=583.51 [M+H], RT 0.63 min
Compound 208: MS, electrospray, m/z=587.3 [M+H], RT 1.48 min (Method B2);
Compound 236: MS, electrospray, m/z=597.3 [M+H], RT 1.54 min (Method A2);
Resolution: LUX 5 u Cellulose 1 Prep 7% EtOH:Heptane @ 10 ml/min
Compound 238: MS, electrospray, m/z=569.2 [M+H], RT 0.60 min;

The following compounds from Table 1 are prepared according to the procedure described in Example 7a, using phenol, 3-17, bromide, 5-34, and other appropriate starting materials and purification conditions:
Compound 135: MS, electrospray, m/z=611.5 [M+H], RT 0.86 min;
Compound 136: MS, electrospray, m/z=611.5 [M+H], RT 0.83 min;
Compound 137: MS, electrospray, m/z=597.5 [M+H], RT 0.84 min;

The following compound from Table 1 is prepared according to the procedure described in Example 7a, using phenol, 3-18, bromide, 5-34, and other appropriate starting materials and purification conditions:
Compound 148: MS, electrospray, m/z=609.4 [M+H], RT 0.81 min;

The following compound from Table 1 is prepared according to the procedure described in Example 7a, using phenol, 3-19, bromide, 5-34, and other appropriate starting materials and purification conditions:
Compound 133: MS, electrospray, m/z=597.5 [M+H], RT 0.81 min.

The following compound from Table 1 is prepared according to the procedure described in Example 7a, using phenol, 3-20, bromide, 5-34, and other appropriate starting materials and purification conditions:
Compound 134: MS, electrospray, m/z=611.5 [M+H], RT 0.85 min;

The following compounds from Table 1 are prepared according to the procedure described in Example 7a, using phenol, 3-21, bromide, 5-34, and other appropriate starting materials and purification conditions:
Compound 149: MS, electrospray, m/z=613.3 [M+H], RT 0.74 min;
Compound 150: MS, electrospray, m/z=599.5 [M+H], RT 0.72 min;
Compound 151: MS, electrospray, m/z=613.3 [M+H], RT 0.74 min;

The following compound from Table 1 is prepared according to the procedure described in Example 7a, using phenol, 3-22, bromide, 4-19, and other appropriate starting materials and purification conditions:
Compound 183: MS, electrospray, m/z=573.1 [M+H], RT 0.53 min.

The following compound from Table 1 is prepared according to the procedure described in Example 7a, using phenol, 3-22, bromide, 5-34, and other appropriate starting materials and purification conditions:

Compound 182: MS, electrospray, m/z=585.9 [M+H], RT 0.55 min.

The following compound from Table 1 is prepared according to the procedure described in Example 7a, using phenol, 3-22, bromide, 4-19, and other appropriate starting materials and purification conditions:

Compound 181: MS, electrospray, m/z=570.7 [M+H], RT 0.61 min.

The following compound from Table 1 is prepared according to the procedure described in Example 7a, using phenol, 3-22, bromide, 5-34, and other appropriate starting materials and purification conditions:

Compound 180: MS, electrospray, m/z=583.7 [M+H], RT 0.64 min.

The following compound from Table 1 is prepared according to the procedure described in Example 7a, using phenol, 3-22, bromide, 4-19, and other appropriate starting materials and purification conditions:

Compound 209: MS, electrospray, m/z=541.4 [M+H], RT 0.52 min.

The following compound from Table 1 is prepared according to the procedure described in Example 7a, using phenol, 3-22, bromide, 5-34, and other appropriate starting materials and purification conditions:

Compound 224: MS, electrospray, m/z=556.7 [M+H], RT 0.52 min.

Example 8

Preparation of 5-ethoxy-1-(6-{2-[2-(2-fluoro-1-methyl-ethyl)-1,2,3,4-tetrahydro-isoquinolin-6-yl-methoxy]-3-methyl-phenyl}-pyridin-2-yl)-1H-pyrazole-4-carboxylic acid (49)

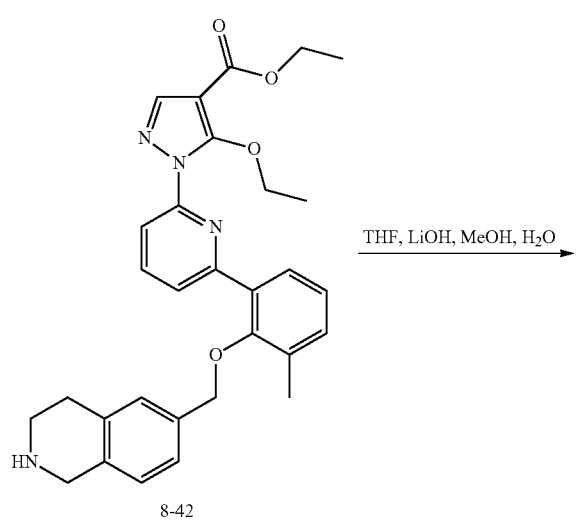

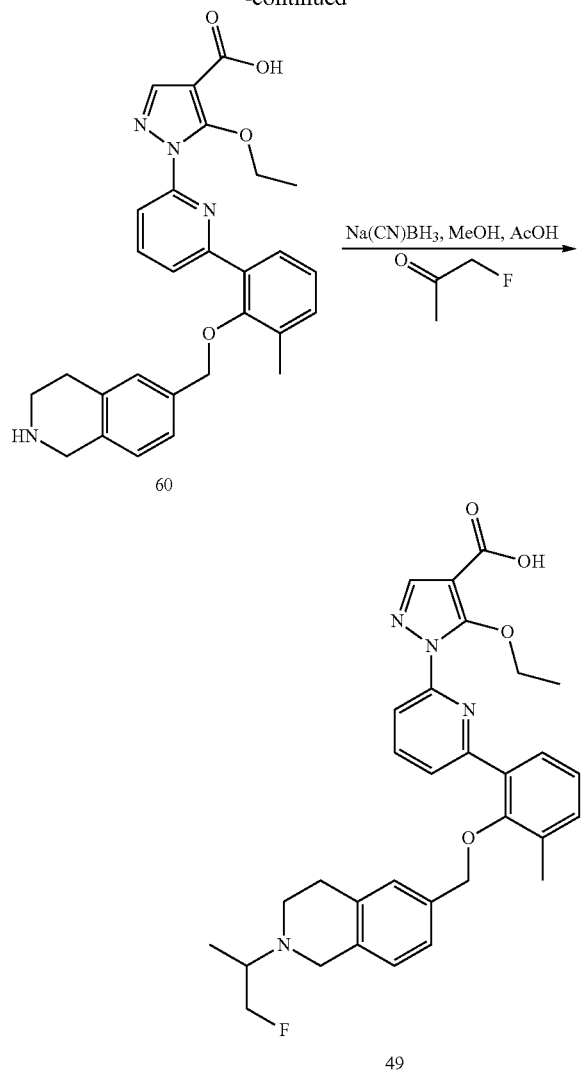

Amine, 8-42 (2.94 g, 5.74 mmol) is dissolved in methanol (20 mL), THF (20 mL) and water (10 mL). To this solution is added LiOH (0.971 g, 40.60 mmol) and the mixture is heated at 50° C. for 2 h. The reaction is cooled to room temperature and concentrated in vacuo. The crude product is purified by reverse phase column chromatography on C18 (using a solvent gradient of 5-95% MeCN/H$_2$O+0.1% TFA) to provide 60 (2.94 g). MS, electrospray, m/z=485.1 [M+H], RT 0.68 min).

Amino acid 60 (78.0 mg, 0.15 mmol) is combined with 4 Å molecular sieves (20 mg), 1-fluoro-propan-2-one (100 µL), AcOH (25.0 µL), and Na(CN)BH$_3$ (29.2 mg, 0.44 mmol) in MeOH (4 mL). The mixture is stirred at room temperature for 30 min and then heated to 50° C. for 12 h. It is then concentrated under N$_2$, triturated with 1:1 MeOH/DMSO, filtered through a 0.45 micron syringe filter, and the filtrate is purified by gradient elution (10-100% MeCN/water+0.1% HCO2H) on a Gilson RP-HPLC. Concentrated in vacuo to afford title compound 49 (70.0 mg). MS, electrospray, m/z=545.3 [M+H], RT 0.72 min.

The following compounds from Table 1 are prepared according to the procedure described in Example 8, using appropriate starting materials and purification conditions Compound 64: MS, electrospray, m/z=583.4 [M+H], RT 0.70 min;
Compound 65: MS, electrospray, m/z=597.4 [M+H], RT 0.75 min;
Compound 66: MS, electrospray, m/z=597.4 [M+H], RT 0.72 min;
Compound 67: MS, electrospray, m/z=625.5 [M+H], RT 0.78 min;
Compound 68: MS, electrospray, m/z=569.4 [M+H], RT 0.68 min;
Compound 69: MS, electrospray, m/z=583.4 [M+H], RT 0.70 min;
Compound 70: MS, electrospray, m/z=605.4 [M+H], RT 0.71 min;
Compound 71: MS, electrospray, m/z=569.4 [M+H], RT 0.71 min;
Compound 76: MS, electrospray, m/z=597.4 [M+H], RT 0.79 min;
Compound 77: MS, electrospray, m/z=569.4 [M+H], RT 0.69 min;
Compound 78: MS, electrospray, m/z=583.4 [M+H], RT 0.71 min;
Compound 79: MS, electrospray, m/z=597.4 [M+H], RT 0.75 min;
Compound 80: MS, electrospray, m/z=611.4 [M+H], RT 0.74 min;
Compound 94: MS, electrospray, m/z=587.4 [M+H], RT 0.80 min;
Compound 95: MS, electrospray, m/z=597.4 [M+H], RT 0.82 min.

The following compounds from Table 1 are prepared according to the procedure described in Example 8, using phenol, 3-16, bromide, 4-19, and other appropriate starting materials and purification conditions:
Compound 50: MS, electrospray, m/z=505.2 [M+H], RT 0.66 min;
Compound 51: MS, electrospray, m/z=561.3 [M+H], RT 0.70 min;
Compound 54: MS, electrospray, m/z=589.3 [M+H], RT 0.72 min;
Compound 55: MS, electrospray, m/z=575.2 [M+H], RT 0.71 min;
Compound 56: MS, electrospray, m/z=563.3 [M+H], RT 0.74 min;
Compound 57: MS, electrospray, m/z=623.3 [M+H], RT 0.80 min;
Compound 58: MS, electrospray, m/z=563.2 [M+H], RT 0.76 min.

Example 9

Preparation of intermediate 3,3-difluoro-cyclobutanecarbaldehyde (9-44)

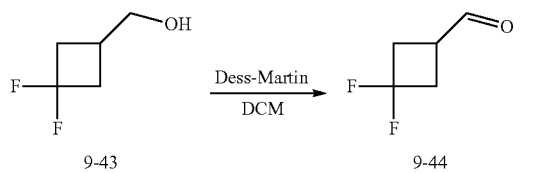 [SMILES: OCC1CC(F)(F)C1 ; O=CC1CC(F)(F)C1]

Dess-Martin periodinane (2.6 g, 6.1 mmol) is added to a mixture of 3,3-difluorocyclobutylmethanol, 9-43, (0.5 g, 4.0 mmol) and NaHCO$_3$ (1.4 g, 16.0 mmol) in dichloromethane (10 mL) at room temperature. The resulting slurry is stirred in the dark for 15 h and then poured into a solution of saturated aqueous NaHCO$_3$. The resulting mixture is filtered through a hydrophobic frit with excess dichloromethane. The organic filtrate is washed with saturated aqueous Na$_2$S$_2$O$_5$, and then separated with another hydrophobic frit. The filtrate is dried over MgSO$_4$, and then filtered through a pad of diatomaceous earth using dichloromethane. All but about 5 mL of dichloromethane is removed by short path distillation at atmospheric pressure (50° C. bath temperature). The remaining solution is cooled to −78° C. for 15 min to precipitate residual periodinane solids. The solvent is removed by syringe and passed through a 0.45 micron Millipore filter. The filtrate containing the crude aldehyde 9-44 (~0.1M in dichloromethane) is used as is without further purification or concentration.

Example 10

Preparation of 1-(6-{2-[2-(3,3-difluoro-cyclobutylmethyl)-1,2,3,4-tetrahydro-isoquinolin-6-ylmethoxy]-3-methyl-phenyl}-pyridin-2-yl)-5-isopropoxy-1H-pyrazole-4-carboxylic acid (4)

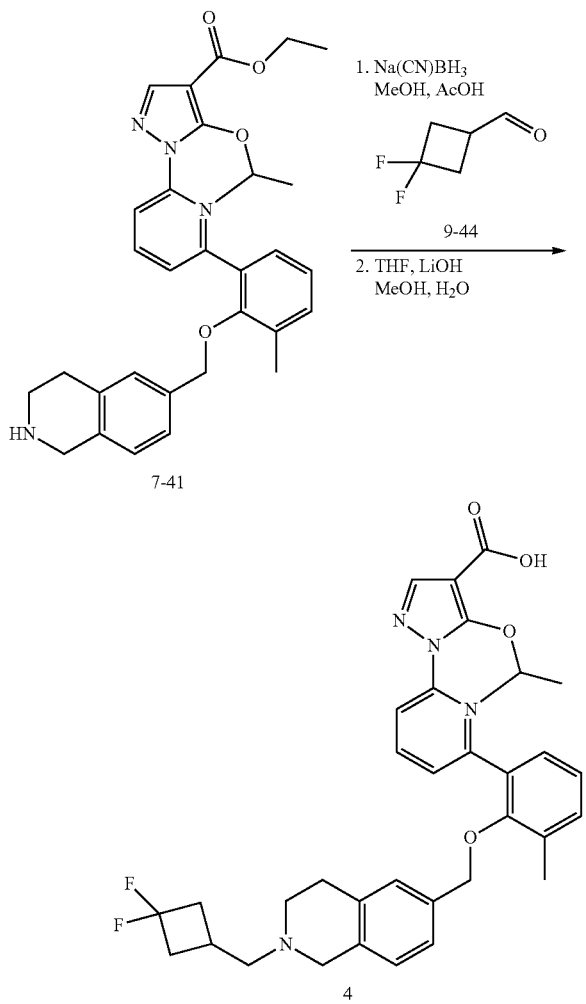

Amine 7-41 (56.0 mg, 0.11 mmol) is combined with 4 Å molecular sieves (20 mg), 3,3-difluoro-cyclobutanecarboxaldehyde, 9-44, (100 μL, 0.21 mmol), AcOH (20 μL), and Na(CN)BH₃ (20.01 mg, 0.32 mmol) in MeOH (2.0 mL). The mixture is stirred at room temperature for 30 min, and then heated to 50° C. for 12 h. The mixture is diluted with THF (1.0 mL) and water (1.0 mL). To this is added LiOH (14.68 mg, 0.64 mmol) and the reaction is heated to 50° C. for 2 h. It is then concentrated under $N_2$, triturated with 1:1 MeOH/DMSO, filtered through a 0.45 micron syringe filter, and the filtrate is purified by gradient elution (10-100% MeCN/water+0.1% HCO2H) on a Gilson RP-HPLC. Concentrated in vacuo to afford title compound 4 (40.0 mg). MS, electrospray, m/z=603.4 [M+H], RT 0.78 min.

The following compounds from Table 1 are prepared according to the procedure described in Example 10, using the appropriate amine, other appropriate starting materials and purification conditions:

Compound 26: MS, electrospray, m/z=575.3 [M+H], RT 0.73 min;
Compound 29: MS, electrospray, m/z=589.3 [M+H], RT 0.77 min;
Compound 82: MS, electrospray, m/z=561.3 [M+H], RT 0.82 min;
Compound 96: MS, electrospray, m/z=589.4 [M+H], RT 0.96 min.

Example 11

Preparation of intermediate
2,2-difluoro-cyclopropanecarbaldehyde (10-46)

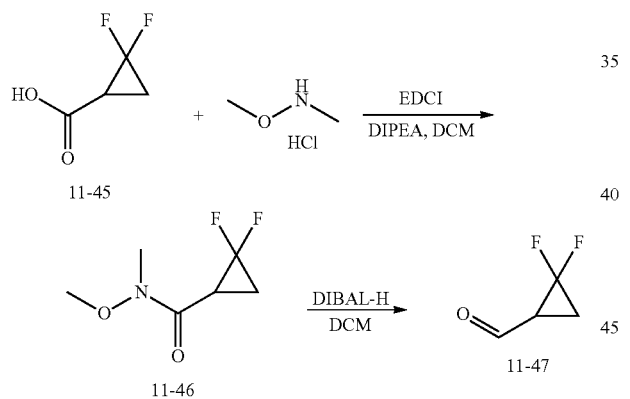

EDCI (1.4 g, 7.1 mmol) is added to a mixture of N,O-dimethylamine hydrochloride (600 mg, 6.2 mmol) and 2,2-difluorocyclopropane carboxylic acid, 11-45, (580 mg, 4.8 mmol) in dichloromethane (15 mL) at room temperature. N,N-Diisopropylethylamine (3.3 mL, 19.0 mmol) is added and the mixture is stirred for 3 h. A solution of 1N HCl is added, followed by vigorous stirring for 10 min. The organic phase is separated using a hydrophobic fit and applied directly to a 10 g $SiO_2$ samplet. The crude material is purified on a 50 g HP-Sil SNAP cartridge (Biotage) eluting with 9:1 dichloromethane/MeOH. The solvent is removed from product containing fractions via short-path distillation at atmospheric pressure (bath temp of 70° C.) to afford 11-46 (605 mg).

A solution of 11-46, (605 mg, 3.66 mmol) in dichloromethane at −78° C. is treated dropwise with DIBAL-H (4.2 mL, 1.0 M in dichloromethane) and then is stirred 2.5 h at −78° C. The reaction is quenched by addition of saturated aqueous Rochelle salt solution. An equal volume of water is added and the mixture is warmed to room temperature. The mixture is vigorously stirred for 3 h, followed by separation of the organic phase with a hydrophobic frit. The dichloromethane is removed by short path distillation at atmospheric pressure (bath temp=62° C.) to afford 11-47 (389 mg).

Example 12

Preparation of 1-(6-{2-[2-(2,2-difluoro-cyclopropyl-methyl)-1,2,3,4-tetrahydro-isoquinolin-6-yl-methoxy]-3-methyl-phenyl}-pyridin-2-yl)-5-methoxy-1H-pyrazole-4-carboxylic acid (72)

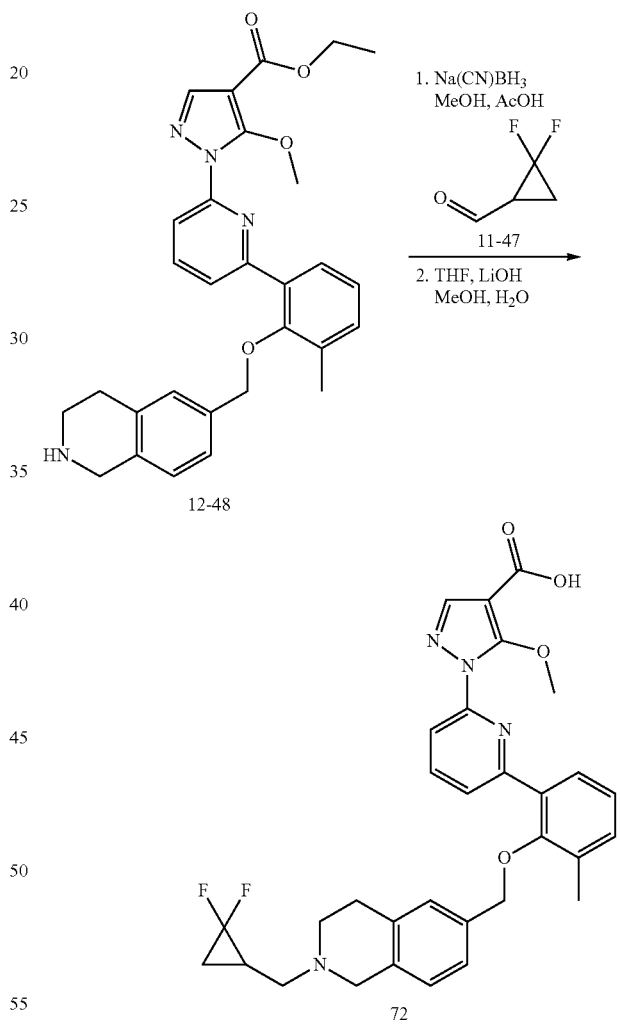

Amine 12-48 (90.0 mg, 0.18 mmol) is combined with 4 Å molecular sieves (20 mg), 2,2-difluoro-cyclopropanecarboxaldehyde, 11-47, (60.0 mg, 0.54 mmol), AcOH (20 μL), and Na(CN)BH₃ (34.0 mg, 0.54 mmol) in MeOH (4.0 mL). The mixture is stirred at room temperature for 30 min, and then heated to 50° C. for 12 h. The mixture is diluted with THF (1.0 mL) and water (1.0 mL). To this is added LiOH (33.00 mg, 1.43 mmol) and the reaction is heated to 50° C. for 2 h. It is then concentrated under $N_2$, triturated with 1:1 MeOH/DMSO, filtered through a 0.45 micron syringe filter, and the filtrate is purified by gradient elution (10-100% MeOH/water+0.1% HCO₂H) on a Gilson RP-HPLC. Concentrated in vacuo to afford title compound 72 (7.0 mg). MS, electrospray, m/z=561.3 [M+H], Method A2, RT 1.59 min.

Example 13

Preparation of 5-methoxy-1-(6-{3-methyl-2-[2-(2,2,2-trifluoro-ethyl)-1,2,3,4-tetrahydro-isoquinolin-6-ylmethoxy]-phenyl}-pyridin-2-yl)-1H-pyrazole-4-carboxylic acid (11)

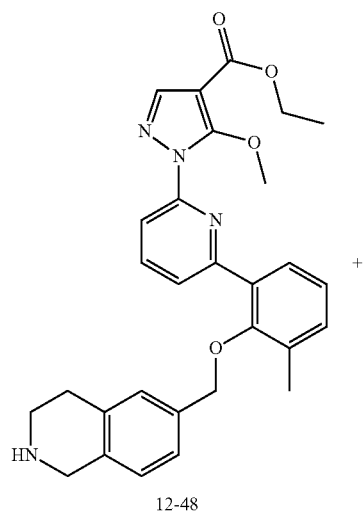

12-48

+

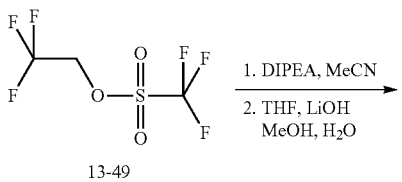

13-49

1. DIPEA, MeCN
2. THF, LiOH MeOH, H₂O

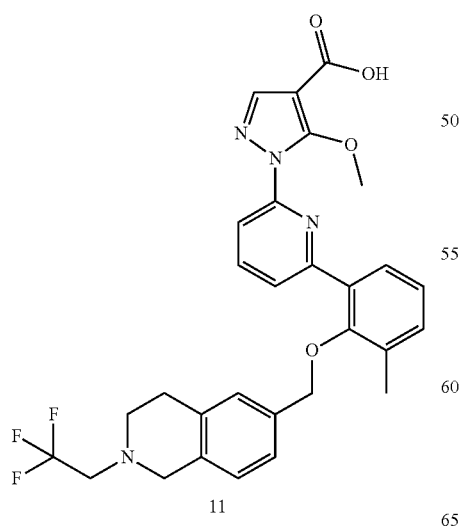

11

2,2,2-Trifluoroethyl triflate, 13-49, (36.0 uL, 0.23 mmol) is added to a mixture of intermediate 12-48 (106.0 mg, 0.21 mmol) and N,N-diisopropylethylamine (190 µL, 1.10 mmol) in MeCN (5.0 mL). The mixture is heated to 45° C. for 4 h and then concentrated in vacuo. The remaining residue is redissolved in 5 mL of THF/MeOH/water (2:2:1) and treated with LiOH (25.0 mg, 1.10 mmol). The mixture is then heated to 50° C. for 2 h prior to removal of the solvents in vacuo. The remaining crude residue is purified by gradient elution on a 30 g KP-C18 SNAP cartridge (Biotage) using a gradient of 5-95% MeCN/water+0.1% TFA to afford title compound 11 (103 mg). MS, electrospray, m/z=553.2 [M+H], Method A2, RT 1.13 min.

Example 14

Preparation of intermediate 1-methyl-5-oxo-pyrrolidine-3-carbaldehyde (14-51)

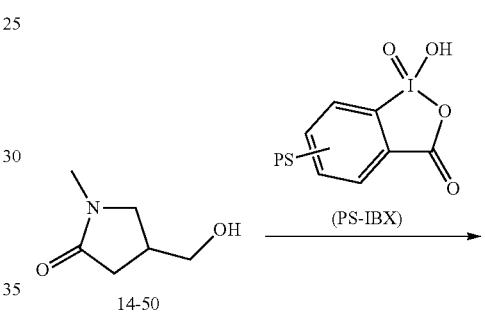

14-50

(PS-IBX)

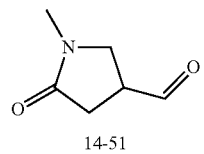

14-51

Alcohol 14-50 (0.20 g, 1.55 mmol) is combined with polystyrene-bound IBX resin (5.81 g) in dichloromethane (20.0 mL) in a sealed 40 mL vial and is rotated end over end for 20 h. The reaction mixture is filtered away from the resin, and the resin is rinsed several times [first with dichloromethane (10 mL), then with a 1:1 dichloromethane/MeOH (20 mL), again with 1:1 dichloromethane/MeOH (20 mL), and finally with dichloromethane (10 mL)]. The combined filtrates are concentrated under a stream of $N_2$ to yield a mixture of 14-50 and desired product 14-51.

Example 15

Preparation of 5-ethoxy-1-(6-{3-methyl-2-[2-(1-methyl-5-oxo-pyrrolidin-3-ylmethyl)-1,2,3,4-tetrahydro-isoquinolin-6-ylmethoxy]-phenyl}-pyridin-2-yl)-1H-pyrazole-4-carboxylic acid (97)

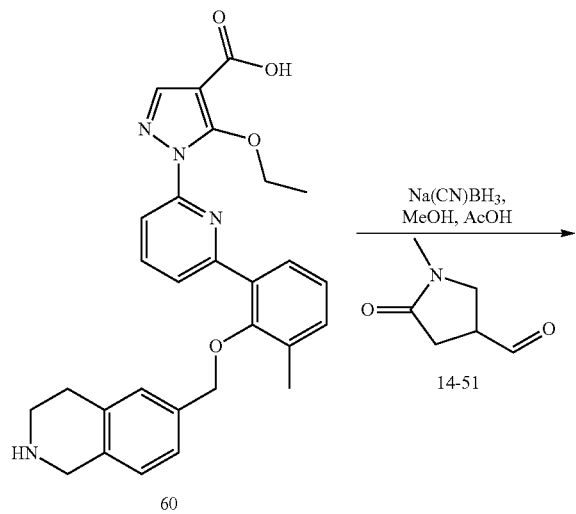

Amino acid 60 (40.0 mg, 0.07 mmol) is combined with 4 Å molecular sieves (20 mg), 14-51 (51.0 mg, 0.200 mmol), AcOH (15.0 µL), and Na(CN)BH$_3$ (13.2 mg, 0.20 mmol) in MeOH (2.0 mL). The mixture is stirred at room temperature for 30 min and then heated to 50° C. for 12 h. The crude is purified by reverse phase column chromatography on C18 (using a solvent gradient of 5-95% MeCN/H$_2$O+0.1% TFA) to afford title compound 97 (27.0 mg). MS, electrospray, m/z=596.4 [M+H], RT 0.80 min.

Example 16

Preparation of 5-ethoxy-1-(6-{3-methyl-2-[2-(tetrahydro-furan-2-ylmethyl)-1,2,3,4-tetrahydro-isoquinolin-6-ylmethoxy]-phenyl}-pyridin-2-yl)-1H-pyrazole-4-carboxylic acid (101)

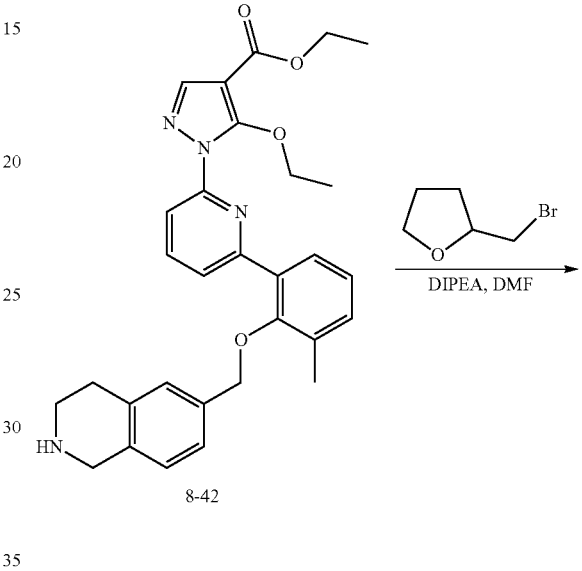

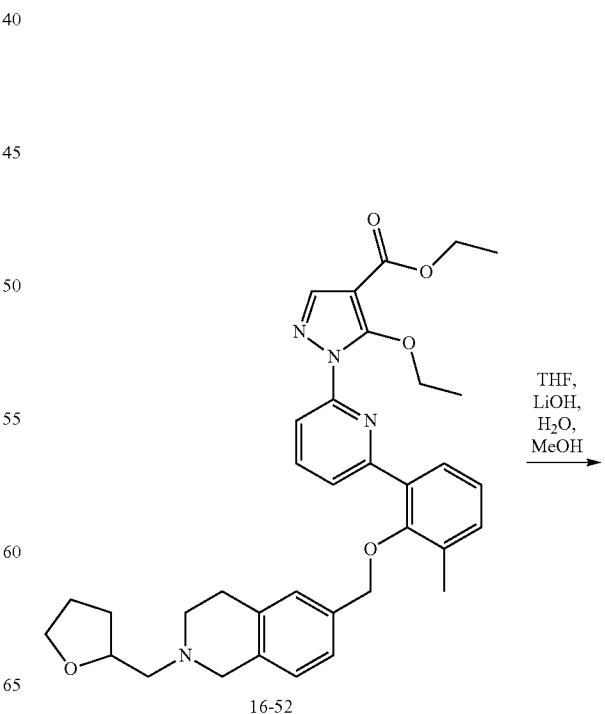

145
-continued

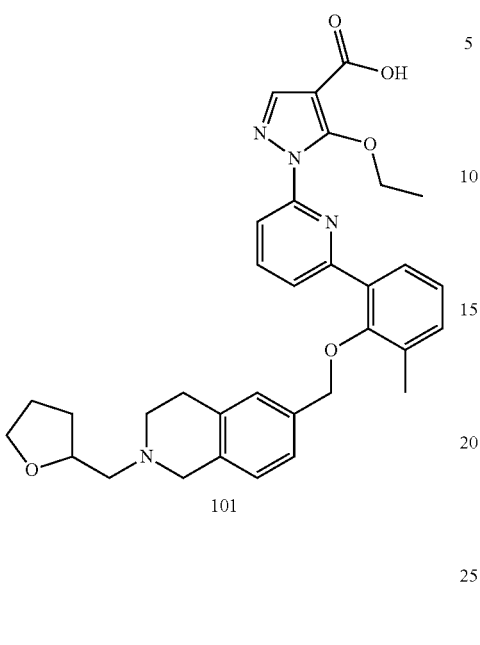

101

To a mixture of amine 8-42 (100.0 mg, 0.20 mmol) and N,N-diisopropylethylamine (0.10 mL, 0.59 mmol) in DMF (1.00 mL) is added 2-bromomethyltetrahydrofuran (8.0 mg, 0.05 mmol) in DMF (0.06 mL). The mixture is irradiated at 100° C. for 10 min and cooled to room temperature. Excess bromide (76.0 mg) is added and the reaction is irradiated multiple times and then stirred at room temperature for 24 h. The reaction mixture is filtered and the filtrate is purified by HPLC (using a solvent gradient of 10-95% MeCN/H$_2$O+ 0.1% Formic Acid) to provide 16-52 (6.0 mg).

16-52 (6.0 mg) is diluted with THF (1.0 mL), water (1.0 mL) and MeOH (1.0 mL). To this is added LiOH (5.0 mg) and the reaction is heated to 50° C. for 2 h. The reaction mixture is cooled to room temperature, acidified with 4 N HCl in 1,4-dioxane, and filtered. The filtrate is purified by HPLC (using a solvent gradient of 10-95% MeCN/H$_2$O+0.1% Formic Acid) to provide title compound 101 (1.0 mg). MS, electrospray, m/z=569.4 [M+H], RT 0.88 min.

The following compounds from Table 1 are prepared according to the procedure described in Example 16, using the appropriate starting materials and purification conditions Compound 138: MS, electrospray, m/z=639.4 [M+H], RT 1.16 min;

Compound 160: MS, electrospray, m/z=563.3 [M+H], RT 0.96 min.

146

Example 17

Preparation of 1-(6-{2-[2-(2-hydroxy-2-methyl-propyl)-1,2,3,4-tetrahydro-isoquinolin-6-ylmethoxy]-3-methyl-phenyl}-pyridin-2-yl)-5-methoxy-1H-pyrazole-4-carboxylic acid (33)

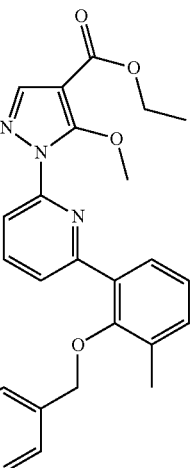

12-48

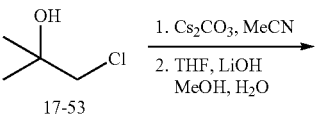

17-53

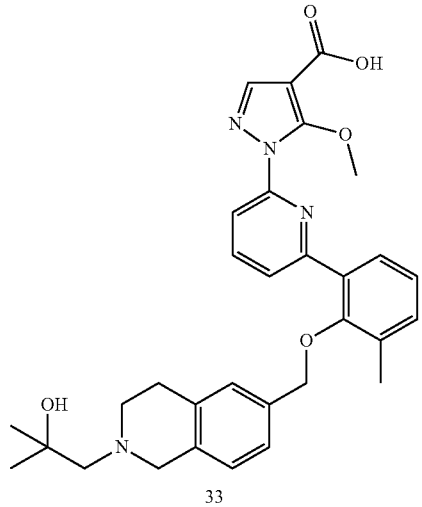

33

Intermediate 12-48 (90.0 mg, 0.18 mmol) is dissolved in MeCN (5.0 mL) to which is added Cs$_2$CO$_3$ (117.9 mg, 0.36 mmo) and chloride 17-53 (29.5 mg, 0.27 mmol). The mixture is heated to 50° C. for 10 h. The reaction was cooled, extracted with EtOAc, washed with brine, dried over MgSO$_4$, and concentrated. The resulting material is purified by gradient elution on a 30 g KP-C18 SNAP cartridge (Biotage) using a gradient of 15-65% MeCN/water+0.1% TFA to afford the intermediate ester. The ester is dissolved in 5 mL of THF/MeOH/water (2:2:1) and treated with LiOH (25.0 mg, 1.10 mmol). The mixture is then heated to 50° C. for 2 h prior to removal of the solvents in vacuo. The remaining crude residue is purified by gradient elution on a 30 g KP-C18 SNAP cartridge (Biotage) using a gradient of 15-65% MeCN/water+0.1% TFA to afford title compound 33 (103.0 mg). MS, electrospray, m/z=543.2 [M+H], RT 0.68 min.

The following compounds from Table 1 are prepared according to the procedure described in Example 17, using the appropriate starting materials and purification conditions Compound 74: MS, electrospray, m/z=577.3 [M+H], RT 0.67 min;

Compound 168: MS, electrospray, m/z=587.3 [M+H], RT 0.70 min.

Example 18

Preparation of 6-Bromomethyl-8-trifluoromethyl-3,4-dihydro-1H-isoquinoline-2-carboxylic acid tert-butyl ester (18-10)

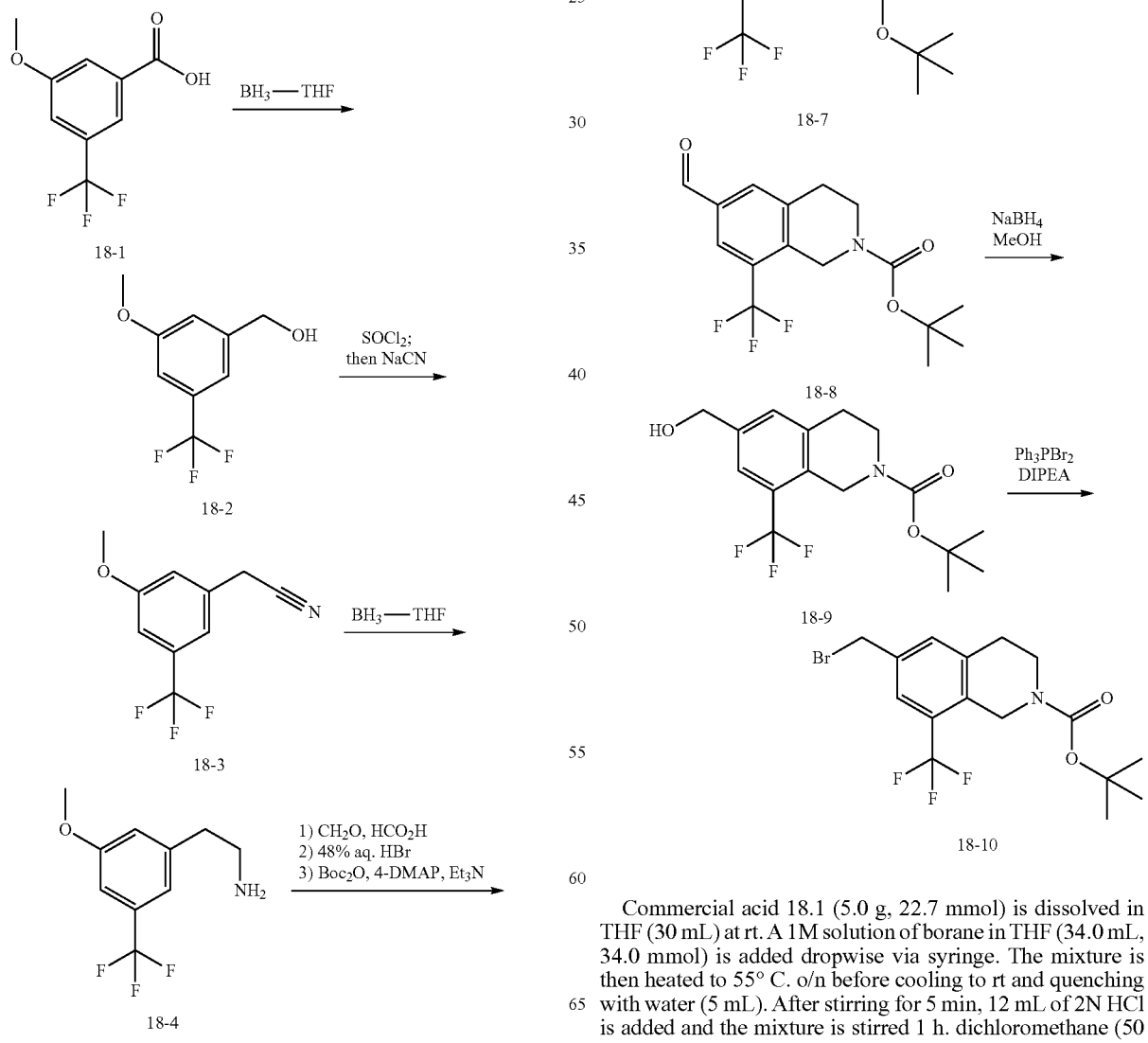

Commercial acid 18.1 (5.0 g, 22.7 mmol) is dissolved in THF (30 mL) at rt. A 1M solution of borane in THF (34.0 mL, 34.0 mmol) is added dropwise via syringe. The mixture is then heated to 55° C. o/n before cooling to rt and quenching with water (5 mL). After stirring for 5 min, 12 mL of 2N HCl is added and the mixture is stirred 1 h. dichloromethane (50 mL) and water (50 mL) are then added, and the resulting phases are separated with a hydrophobic frit. The organic layer is further dried over Na$_2$SO$_4$, then refiltered. Concentrated in vacuo to affords an oil that is purified by gradient elution (5-100% EtOAc/heptane) on a 100 g KP-Sil SNAP cartridge (Biotage). Concentration of the product fractions delivers intermediate 18.2 (3.2 g)

Thionyl chloride (SOCl$_2$) (2.3 mL, 31.5 mmol) is added to a solution of alcohol 18.2 (3.2 g, 15.5 mmol) in dichloromethane (20 mL) under N$_2$ at −10° C. After 5 min, the cooling bath is removed and the mixture is heated to reflux for 6 h. The resulting solution is cooled to rt and concentrated in vacuo. The remaining residue is then azeotroped with PhMe (2×10 mL) and then dissolved in DMF (20 mL). Solid NaCN (840 mg, 17.1 mmol) is added and the mixture is heated to 45° C. o/n. Upon cooling to rt, the mixture is diluted with water (25 mL), brine (25 mL), and EtOAc (50 mL). The layers are separated, and the organics are dried over Na$_2$SO$_4$, filtered, and concentrated in vacuo. Crude product is purified by gradient elution (5-100% EtOAc/heptane) on a 100 g KP-Sil SNAP cartridge (Biotage). Product fractions concentrated in vacuo to afford 18-3 (3.0 g).

A 1M solution of borane in THF (35 mL, 35 mmol) is added dropwise via syringe to a solution of 18-3 (3.0 g, 13.9 mmol) in THF (25 mL) at rt. The mixture is then heated to 55° C. o/n before cooling to rt, and quenching with water (5 mL). After 5 min of stirring, conc. HCl (8 mL) is added and stirring is continued for 1 h. The mixture is then diluted with water (20 mL), and treated with solid NaOH until alkaline. dichloromethane (50 mL) and brine (25 mL) are added, then the layers are separated with a hydrophobic frit. The crude amine is purified by gradient elution (5-95% MeCN/water+0.1% TFA) on a 120 g KP-C18 SNAP cartridge (Biotage). Concentration of the fractions in in vacuo affords an intermediate TFA salt (2.93 g) that is dissolved in HCO$_2$H (30 mL) and treated with 37% aq. HCHO (0.66 mL, 8.8 mmol). The mixture is stirred at 50° C. o/n, then concentrated in vacuo to afford a crude solid that is immediately dissolved in 48% aq. HBr (25 mL). This solution is heated to 100° C. o/n, then concentrated in vacuo. The crude material is azeotroped with PhMe (3×15 mL), then slurried in dichloromethane (50 mL) and DMF (10 mL). Et$_3$N (1.9 mL, 0.82 mmol) and a few crystals of 4-DMAP are added. Boc$_2$O (2.0 g, 9.1 mmol) is added in one portion, and the mixture is stirred at rt o/n. Saturated NH4Cl solution (50 mL) is added and the layers are separated with a hydrophobic frit. The organic is concentrated in vacuo to afford a crude residue that is purified by gradient elution (5-100% EtOAc/heptane) on a 100 g KP-Sil SNAP cartridge (Biotage). Concentration of the product fractions afforded 18-5 (540 mg).

Tf$_2$O (0.27 mL, 1.6 mmol) is added via syringe to a mixture of 18-5 (540 mg, 1.46 mmol), Et$_3$N (0.31 mL, 2.2 mmol) and 4-DMAP (18 mg, 0.15 mmol) in dichloromethane (25 ml) cooled to 0° C. The mixture is stirred with warming to rt o/n, and then quenched with sat. NaHCO$_3$ (30 mL). The resulting layers are separated with a hydrophobic frit, and the organics are concentrated under N$_2$. The crude residue is purified by gradient elution (5-30% EtOAc/heptane) on a 50 g HP-Sil SNAP cartridge (Biotage). Concentration of the product fractions in vacuo affords 18-6 (460 mg).

Triflate 18-6 (460 mg, 1.02 mmol) is combined with vinylboronic acid-pyridine complex (250 mg, 1.04 mmol) and Pd(PPh$_3$)$_4$ (60 mg, 0.05 mmol) in a mixture of DME (9 mL) and 2M aq. Na$_2$CO$_3$ solution. The mixture is irradiated in Biotage microwave at 120° C. for 40 min. Upon cooling, then mixture is concentrated under N$_2$, and the crude solids and triturated with dichloromethane. The dichloromethane filtrate is then purified by gradient elution (5-80% EtOAc/heptane) using a 50 g HP-Sil SNAP cartridge (Biotage). Product fractions concentrated in vacuo to afford 18-7 (275 mg).

Styrene 18-7 (275 mg, 0.84 mmol) and NaIO$_4$ (630 mg, 2.95 mmol) are combined in a mixture of THF (12 mL) and water (3 mL) at rt. OsO$_4$ (0.13 mL, 0.017 mmol, 4 wt % in H$_2$O) is added via syringe and the resulting slurry is stirred vigorously o/n at rt. The slurry is then filtered through a frit, and concentrated in vacuo. The remaining residue is dissolved in dichloromethane (20 mL), and washed with saturate aq. thiosulfate solution (25 mL). The layers are then separated with a hydrophobic frit, and the organic concentrated in vacuo. Purification of the crude residue by gradient elution (5-60% EtOAc/heptane) on a 25 g HP-Sil SNAP cartridge (Biotage) affords 18-8 (228 mg).

Aldehyde 18-8 (225 mg, 0.683 mmol) is dissolved in THF (5 mL) and then MeOH (5 mL). Solid NaBH$_4$ (40 mg, 1.1 mmol) is added, and the mixture is stirred at rt for 20 min. Aqueous sat. NH$_4$Cl (ca 50 mL) is added and the mixture is stirred for 15 min. EtOAc (100 ml) and brine (100 mL) are added, then the layers are separated. The organic is dried over Na$_2$SO$_4$, filtered, and concentrated in vacuo. The crude product is purified by gradient elution (5-100% EtOAc/heptane) on a 50 g HP-Sil SNAP cartridge (Biotage). Concentration of the product fractions in vacuo affords 18-9 (225 mg).

Solid Ph$_3$PBr$_2$ (450 mg, 1.02 mmol) is added to a mixture of 18-9 (225 mg, 0.68 mmol) and DIPEA (0.21 mL, 1.2 mmol) in dichloromethane at 0° C. The mixture is stirred for 1 hour, and then concentrated in vacuo. The crude bromide is purified by gradient elution (5-40% EtOAc/heptanes) on a 25 g HP-SII SNAP cartridge (Biotage) to afford 18-10 (248 mg).

Similarly, the following bromides were prepared from the appropriate starting materials as described in Example 18:

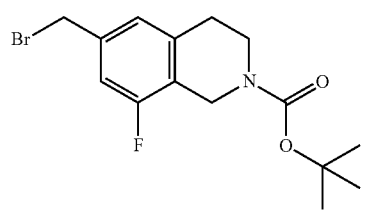

18-11

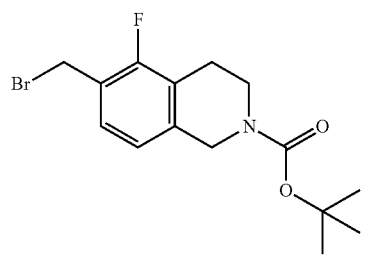

18-12

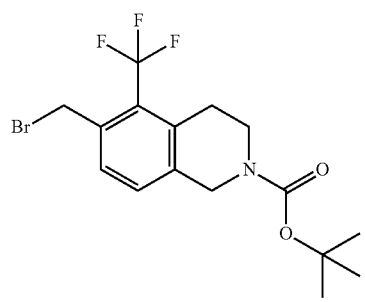

18-13

The following compound from Table 1 is prepared according to the procedure described in Example 7a, using phenol, 2-8, bromide, 18-10, and other appropriate starting materials and purification conditions:
Compound 158: MS, electrospray, m/z=623.3 [M+H], RT 1.34 min (Method B2).

The following compound from Table 1 is prepared according to the procedure described in Example 7a, using phenol, 3-15, bromide, 18-10, and other appropriate starting materials and purification conditions:
Compound 157: MS, electrospray, m/z=637.3 [M+H], RT 0.67 min (Method B2).

The following compounds from Table 1 are prepared according to the procedure described in Example 7a, using phenol, 2-8, bromide, 18-11, and other appropriate starting materials and purification conditions:
Compound 201: MS, electrospray, m/z=573.3 [M+H], RT 1.14 min (Method B2);
Compound 202: MS, electrospray, m/z=589.3 [M+H], RT 1.14 min (Method B2);
Compound 229: MS, electrospray, m/z=587.3 [M+H], RT 1.46 min (Method B2);
Resolution: LUX 5 u Cellulose 3 Prep 14% (1:1:1 MeOH:EtOH:iPA):CO$_2$, 40° C., 110 bar, 80 ml/min
Compound 230: MS, electrospray, m/z=559.3 [M+H], RT 1.46 min (Method B2).
Resolution: LUX 5 u Cellulose 3 Prep 14% (1:1:1 MeOH:EtOH:iPA):CO$_2$, 40° C., 110 bar, 80 ml/min
Compound 253: MS, electrospray, m/z=559.4 [M+H], RT 1.20 min (Method A2) (Med Polar Long).
Compound 254: MS, electrospray, m/z=559.3 [M+H], RT 1.20 min (Method A2) (Med Polar Long).

The following compounds from Table 1 are prepared according to the procedure described in Example 7a, using phenol, 2-8, bromide, 18-12, and other appropriate starting materials and purification conditions:
Compound 177: MS, electrospray, m/z=545.2 [M+H], RT 0.68 min (Method B1);
Compound 187: MS, electrospray, m/z=575.3 [M+H], RT 1.13 min (Method B2);
Compound 231: MS, electrospray, m/z=589.3 [M+H], RT 1.26 min (Method B2);
Resolution: LUX 5 u Cellulose 4 Prep 20% 1:1:1 MeOH:EtOH:iPA (0.1% Et$_2$NH):CO$_2$ @ 75 ml/min., 130 bar, 40° C.
Compound 234: MS, electrospray, m/z=589.3 [M+H], RT 1.26 min (Method B2);
Resolution: LUX 5 u Cellulose 4 Prep 20% 1:1:1 MeOH:EtOH:iPA (0.1% Et$_2$NH):CO$_2$ @ 75 ml/min., 130 bar, 40° C.
Compound 251: MS, electrospray, m/z=559.4 [M+H], RT 1.18 min (Method A2) (Med Polar Long).
Resolution: ChiralPak AD-H Prep 45% 3:1 hexane:EtOH (1% iPrNH$_2$):CO$_2$ @ 80 ml/min., 100 bar, 25° C.
Compound 252: MS, electrospray, m/z=559.3 [M+H], RT 1.18 min (Method A2) (Med Polar Long).
Resolution: ChiralPak AD-H Prep 45% 3:1 hexane:EtOH (1% iPrNH$_2$):CO$_2$ @ 80 ml/min., 100 bar, 25° C.

The following compound from Table 1 is prepared according to the procedure described in Example 7a, using phenol, 2-8, bromide, 18-13, and other appropriate starting materials and purification conditions:
Compound 166: MS, electrospray, m/z=623.3 [M+H], RT 1.30 min (Method B2).

The following compound from Table 1 is prepared according to the procedure described in Example 7a, using phenol, 3-15, bromide, 18-12, and other appropriate starting materials and purification conditions:
Compound 159: MS, electrospray, m/z=587.3 [M+H], RT 0.61 min (Method B1).

The following compound from Table 1 is prepared according to the procedure described in Example 7a, using phenol, 3-15, bromide, 18-13, and other appropriate starting materials and purification conditions:
Compound 165: MS, electrospray, m/z=637.3 [M+H], RT 1.42 min (Method B2).

Example 19

Preparation of intermediate 7-Hydroxymethyl-6-methyl-1,2,4,5-tetrahydro-benzo[d]azepine-3-carboxylic acid tert-butyl ester (19-14)

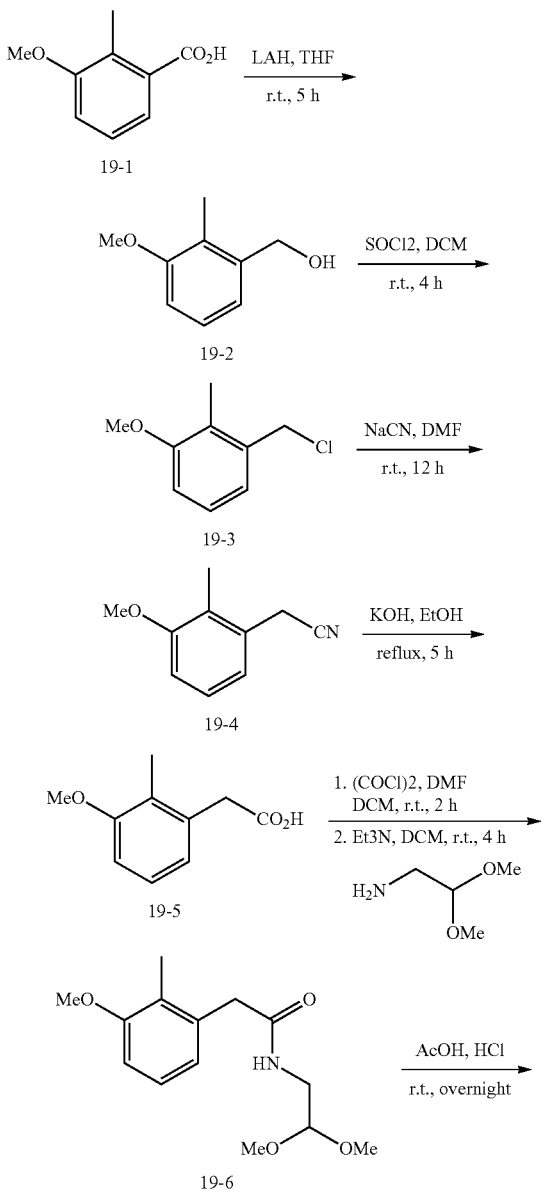

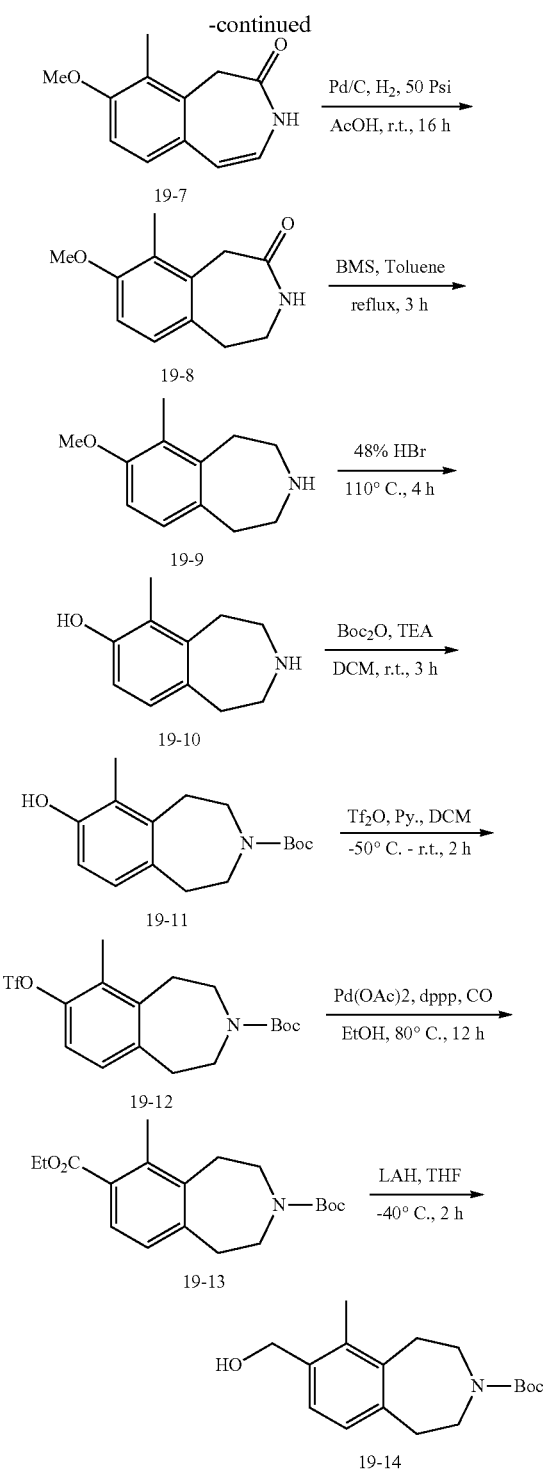

A solution of compound 19-1 (100 g, 0.465 mol) in THF (800.000 ml) is added to a mixture of LAH (166 g, 1.395 mol) in anhydrous THF (200 ml) at 0° C. The mixture is stirred at room temperature for 0.5 h, then is refluxed for 1 h. TLC showed the reaction is completed. A saturated aqueous NH$_4$Cl (200 ml) is slowly added to the mixture. Then EtOAc and Na$_2$SO$_4$ are added. The mixture is stirred for 1 h, and then is filtered and washed by PE to afford compound 19-2.

To a solution of compound 19-2 (360.000 g, 2.365 mol) in dichloromethane (3000.000 ml) is added SOCl$_2$ (562.980 g, 4.731 mol) at −10° C. Then the reaction mixture is refluxed for 4 h. The mixture is concentrated to afford crude compound 19-3 which is used directly in the next step.

A mixture of compound 19-3 (334.000 g, 1.957 mol) and NaCN (168.096 g, 2.290 mol) in DMF (1000.000 ml) is stirred at room temperature overnight. The mixture is extracted with EtOAc and H$_2$O. The organic layer is dried and concentrated, and purified by chromatography on silica gel (PE:EA=50:1) to give compound 19-4 as a yellow oil.

A mixture of compound 19-4 (1608.000 g, 9.975 mol), KOH (1117.221 g, 19.950 mol) in EtOH (15000.000 ml) is heated to reflux for 5 h. TLC showed the reaction is completed. The solvent is removed under reduced pressure. The residue is adjusted to pH=1. The mixture is filtered and the filter cake is dried to yield compound 19-5.

Compound 19-5 (737.000 g, 4.090 mol) is added to a stirred solution of (COCl)$_2$ (8.180 mol) and DMF (70.000 ml) in dichloromethane (7370.000 ml) under N$_2$ atmosphere, followed by stirring for 2 h. TLC showed the reaction is completed. Then the mixture is evaporated. The residue was added to a stirred solution of 2,2-dimethoxyethyl-1-amine (429.996 g, 4.090 mol) and Et$_3$N (454.388 g, 4.499 mol) in dichloromethane (1000 ml) at room temperature for 2 h. TLC showed the reaction is completed. The mixture is evaporated and the residue is purified by column to give compound 19-6.

A solution of compound 19-6 (1053 g, 3.939 mol) in AcOH (2 L) and HCl (2 L) is stirred at room temperature for 16 h. TLC showed the reaction is completed. The mixture is evaporated. The residue is crystallized, washed with H$_2$O and EtOH, and then the solid is filtered and dried to give compound 19-7.

A mixture of Pd/C (4 g) and compound 19-7 (40.000 g, 0.197 mol) in AcOH (2 L) is stirred at room temperature under H$_2$ for 16 h. LCMS showed the reaction is completed. The mixture is filtered, evaporated, and the residue is crystallized with EtOH. The solid is filtered and dried to give compound 19-8.

To a stirred solution of compound 19-8 (130.000 g, 0.633 mol) in THF (1300.000 ml) is added BMS (127.000 ml, 1.267 mol) slowly under N$_2$ atmosphere, meanwhile the temperature is maintained below −5° C., followed by stirring for 16 h. LCMS showed the reaction is completed. The reaction is quenched with conc. HCl and then the mixture is refluxed for 2 h. The solvent is evaporated and the residue is separated with dichloromethane and H$_2$O. The aqueous phase is adjusted to pH=9 and the solid is filtered and dried to give compound 19-9.

A solution of compound 19-9 (220.000 g, 1.150 mol) in 48% HBr aqueous (1800.000 ml) is stirred at 110° C. for 4 h under N$_2$ atmosphere. LCMS showed the reaction is completed. The mixture is evaporated to give crude compound 19-10.

A mixture of compound 19-10 (267.000 g, 1.506 mol), Boc$_2$O (492.595 g, 2.260 mol) and TEA (380.368 g, 3.766 mol) in dichloromethane (2670.000 ml) is stirred at room temperature for 2 h. The reaction is monitored by TLC. When compound 19-10 is consumed, the reaction mixture is concentrated under reduce pressure and the residue was purified by column chromatography to give compound 19-11.

A mixture of compound 19-11 (267.000 g, 0.963 mol) and Tf$_2$O (271.468 g, 0.963 mol) in (2670.000 ml) is stirred at room temperature for 2 h under N$_2$ atmosphere. TLC showed the reaction is completed. The reaction mixture is concentrated under reduce pressure and the residue is purified by column to give compound 19-12.

A mixture of compound 19-12 (20.000 g, 0.049 mol), dppp (2.000 g), Pd(OAc)$_2$ (2.000 g) and TEA (9.868 g, 0.098 mol)

in EtOH (400.000 ml) is stirred at 80° C. for 12 h under CO atmosphere. The reaction is monitored by TLC. When the reaction is completed, the reaction mixture is concentrated under reduce pressure and the residue is purified by column chromatography to give compound 19-13.

To a stirred solution of compound 19-13 (22.000 g, 0.066 mol) in THF (300.000 ml) is slowly added LAH (2.507 g, 0.066 mol), meanwhile the temperature is maintained below −40° C. After addition is completed, the mixture is stirred at room temperature for 2 h. TLC showed the reaction is completed and the reaction is quenched with $H_2O$. The solvent is removed under reduced pressure and the residue is separated with dichloromethane and $H_2O$, the organic phase is dried over anhydrous $Na_2SO_4$, and evaporated. The residue was purified by column to give compound 19-14.

Bromination of the alcohol is performed similarly to that of Example 4 to yield intermediate 7-Bromomethyl-6-methyl-1,2,4,5-tetrahydro-benzo[d]azepine-3-carboxylic acid tert-butyl ester 19-15.

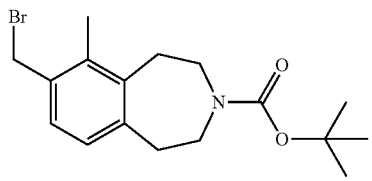

19-15

The following compounds from Table 1 are prepared according to the procedure described in Example 7a, using phenol, 2-8, bromide, 19-15, and other appropriate starting materials and purification conditions:
Compound 176: MS, electrospray, m/z=555.3 [M+H], RT 1.19 min (Method B2);
Compound 184: MS, electrospray, m/z=583.3 [M+H], RT 1.24 min (Method B2);
Compound 206: MS, electrospray, m/z=569.3 [M+H], RT 1.26 min (Method B2);
Resolution: LUX 5 u Cellulose 4 Prep, 20% MeOH:EtOH:IPA (1:1:1) (0.1% $Et_2NH$) in $CO_2$ at 705 ml/min, 130 Bar, 40° C.
Compound 207: MS, electrospray, m/z=569.3 [M+H], RT 1.26 min (Method B2);
Resolution: LUX 5 u Cellulose 4 Prep, 20% MeOH:EtOH:IPA (1:1:1) (0.1% $Et_2NH$) in $CO_2$ at 705 ml/min, 130 Bar, 40° C.
Compound 222: MS, electrospray, m/z=583.3 [M+H], RT 1.40 min (Method B2);
Resolution: LUX 5 u Cellulose 1 Prep, 12% MeOH:IPA (1% $Et_2NH$) in $CO_2$ at 70 ml/min, 105 Bar, 40° C.
Compound 223: MS, electrospray, m/z=583.4 [M+H], RT 1.42 min (Method B2);
Resolution: LUX 5 u Cellulose 1 Prep, 12% MeOH:IPA (1% $Et_2NH$) in $CO_2$ at 70 ml/min, 105 Bar, 40° C.

The following compounds from Table 1 are prepared according to the procedure described in Example 7a, using phenol, 3-15, bromide, 19-15, and other appropriate starting materials and purification conditions:
Compound 162: MS, electrospray, m/z=597.3 [M+H], RT 1.34 min (Method B2);
Compound 175: MS, electrospray, m/z=569.3 [M+H], RT 1.31 min (Method B2);
Compound 190: MS, electrospray, m/z=597.2 [M+H], RT 0.63 min (Method B1);
Compound 196: MS, electrospray, m/z=585.3 [M+H], RT 0.67 min (Method B1);
Compound 203: MS, electrospray, m/z=599.3 [M+H], RT 0.67 min (Method B1)
Resolution: Chirapak AD-H, 20×250 mm; 20% EtOH:Heptane@ 8 mL/min, ambient temp.
Compound 204: MS, electrospray, m/z=599.3 [M+H], RT 0.67 min (Method B1)
Resolution: Chirapak AD-H, 20×250 mm; 20% EtOH:Heptane@ 8 mL/min, ambient temp.
Compound 211: MS, electrospray, m/z=613.3 [M+H], RT 1.43 min (Method B2);
Resolution: LUX 5 u Cellulose 1 Prep 20% iPA+$Et_2NH$:Heptane @ 9 ml/min
Compound 212: MS, electrospray, m/z=613.3 [M+H], RT 1.43 min (Method B2);
Resolution: LUX 5 u Cellulose 1 Prep 20% iPA+$Et_2NH$:Heptane @ 9 ml/min
Compound 214: MS, electrospray, m/z=611.3 [M+H], RT 1.61 min (Method B2);
Resolution: LUX 5 u Cellulose 1 Prep 30% iPA:$CO_2$, 110 bar, 75 ml/min, 40° C.
Compound 215: MS, electrospray, m/z=611.3 [M+H], RT 1.61 min (Method B2);
Resolution: LUX 5 u Cellulose 1 Prep 30% iPA:$CO_2$, 110 bar, 75 ml/min, 40° C.
Compound 225: MS, electrospray, m/z=583.3 [M+H], RT 1.41 min (Method B2);
Resolution: LUX 5 u Cellulose 4 Prep 20% 1:1:1 MeOH:EtOH:iPA (0.1% $Et_2NH$):$CO_2$ @ 75 g/min., 110 bar, 40° C.
Compound 226: MS, electrospray, m/z=583.3 [M+H], RT 1.44 min (Method B2);
Resolution: ESI Industries CC4 Prep 55% 1:1 hexane:MeOH (3% iPrOH, 0.1% $iPrNH_2$):$CO_2$ @ 80 ml/min., 100 bar, 25° C.
Compound 227: MS, electrospray, m/z=583.3 [M+H], RT 1.41 min (Method B2);
Resolution: LUX 5 u Cellulose 4 Prep
20% 1:1:1 MeOH:EtOH:iPA (0.1% $Et_2NH$):$CO_2$ @ 75 g/min., 110 bar, 40° C.
Compound 235: MS, electrospray, m/z=583.3 [M+H], RT 1.41 min (Method B2);
Resolution: LUX 5 u Cellulose 4 Prep
20% 1:1:1 MeOH:EtOH:iPA (0.1% $Et_2NH$):$CO_2$ @ 75 g/min., 110 bar, 40° C.
Compound 228: MS, electrospray, m/z=583.3 [M+H], RT 1.44 min (Method B2);
Resolution: ESI Industries CC4 Prep 55% 1:1 hexane:MeOH (3% iPrOH, 0.1% $iPrNH_2$):$CO_2$ @ 80 ml/min., 100 bar, 25° C.
Compound 232: MS, electrospray, m/z=597.3 [M+H], RT 1.54 min (Method A2);
Resolution: LUX 5 u Cellulose 1 Prep 7% EtOH:Heptane @ 10 ml/min
Compound 233: MS, electrospray, m/z=597.3 [M+H], RT 1.50 min (Method A2);
Resolution: LUX 5 u Cellulose 4 Prep 20% EtOH:$CO_2$, 80 ml/min, 110 bar, 40° C.
Compound 235: MS, electrospray, m/z=597.3 [M+H], RT 1.50 min (Method A2);

Example 20

Preparation of intermediate 5-Bromomethyl-4,7-dimethyl-1,3-dihydro-isoindole-2-carboxylic acid tert-butyl ester (20-4)

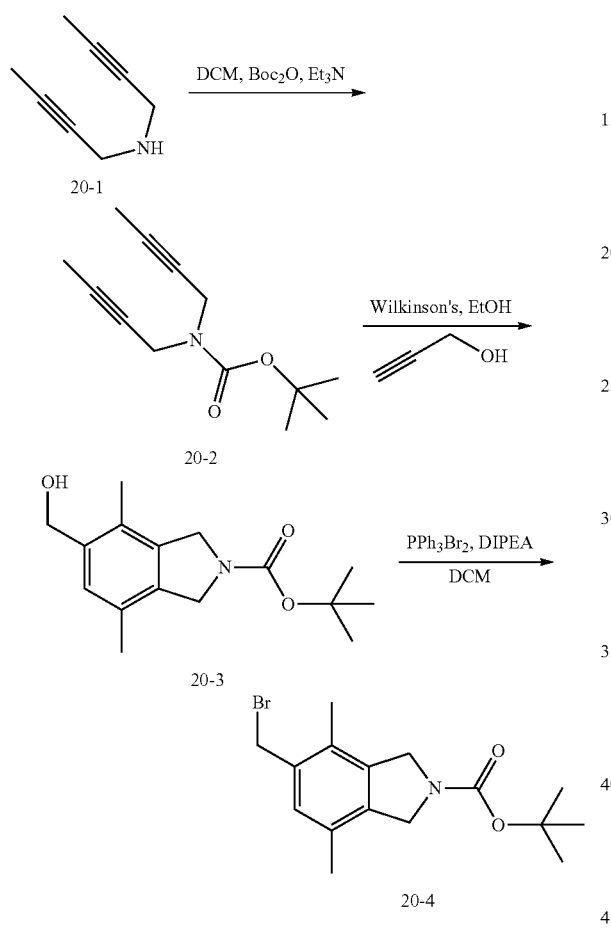

To a 100 mL round bottom flask is added amine 20-1 (0.500 g, 4.13 mmol) which is dissolved in dichloromethane (15.0 mL). The reaction mixture is cooled to 0° C. and triethylamine (1.15 mL, 8.25 mmol) and BOC$_2$O (1.35 g, 6.19 mmol) are added. The reaction is warmed to room temperature and stirred overnight. The reaction is extracted with dichloromethane, washed with water and brine, dried over MgSO$_4$ and concentrated. The resulting residue is purified by silica gel chromatography using a gradient of 12-100% EtOAc in heptanes. The desired fractions are collected and concentrated yielding an oil (0.556 g).

Propargyl alcohol (0.579 mL, 9.94 mmol) is added dropwise at 0° C. to a solution of diacetylene 20-2 (0.550 g, 2.49 mmol) in anhydrous ethanol (15.0 mL). Wilkinson's catalyst (0.229 g, 0.249 mmol) is added and the mixture is stirred for 16 h at room temperature. The crude reaction is concentrated and subjected to silica gel chromatography using a gradient of 10-80% EtOAc in heptanes. The desired fractions are collected and concentrated yielding an off-white solid (0.125 g).

To a solution of alcohol 20-3 (125 mg, 0.451 mmol) and N,N-diisopropylethylamine (0.118 mL, 0.676 mmol) in dichloromethane (5.0 mL) is added triphenylphosphine dibromide (297 mg, 0.676 mmol) at 0° C. The reaction is stirred for 2 h and concentrated in vacuo. The resulting residue is purified by silica gel chromatography using a gradient of 7-60% EtOAc in heptanes to yield the desired product 20-4 (35.0 mg) as a white solid.

The following compounds from Table 1 are prepared according to the procedure described in Example 7a, using phenol, 2-8, bromide, 20-4, and other appropriate starting materials and purification conditions:

Compound 145: MS, electrospray, m/z=569.3 [M+H], RT 0.75 min;

Compound 246: MS, electrospray, m/z=585.0 [M+H], RT 1.40 min (Method B2);

Example 21

Preparation of intermediate 6-Bromomethyl-5,8-dimethyl-3,4-dihydro-1H-isoquinoline-2-carboxylic acid tert-butyl ester (21-8)

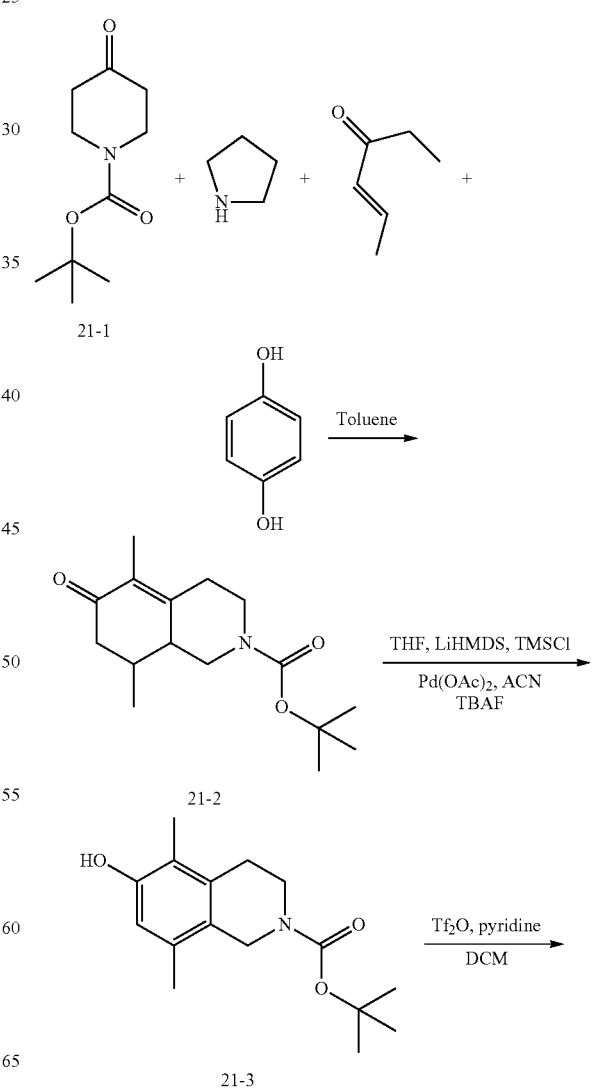

-continued

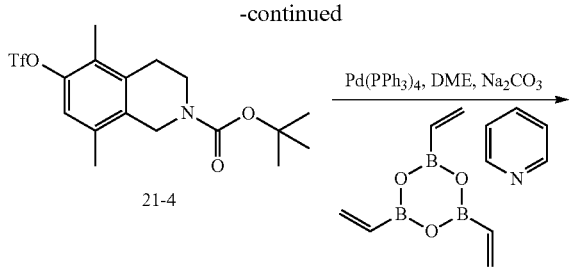

21-4

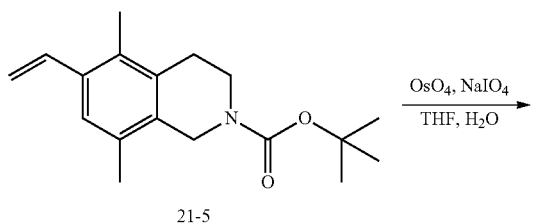

21-5

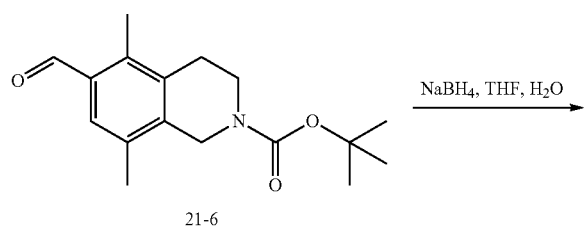

21-6

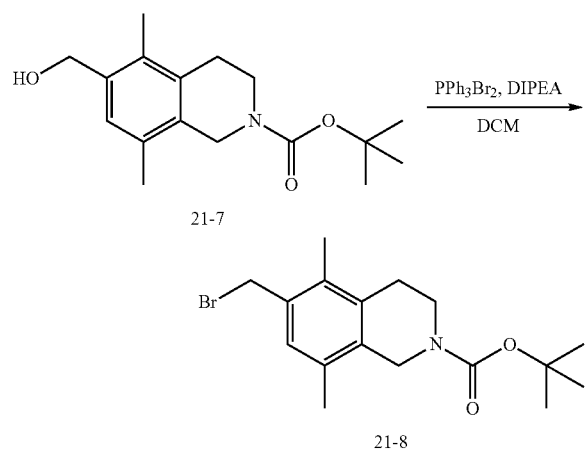

21-7

21-8

Ketone 21-1 (14.00 g, 70.27 mmol) and pyrrolidine (8.71 mL, 106.0 mmol) are dissolved in toluene (60 mL) and the mixture is refluxed under Dean Stark conditions for 24 h. The reaction is then concentrated in vacuo. The resulting residue is dissolved in toluene (60 mL) and treated with 4-hexen-3-one (8.32 mL, 70.27 mmol) and hydroquinone (0.080 g, 0.727 mmol). The solution is heated to reflux for 24 h and then diluted with EtOAc and washed with 1N HCl. The combined organics are dried and concentrated in vacuo to afford a viscous oil. The material is purified by silica gel chromatography using a gradient of 20-100% EtOAc in heptanes to afford a yellow solid (11.74 g).

A 1.0 M LiHMDS solution (42.95 mL) is added dropwise to a solution of intermediate 21-2 (10.00 g, 35.79 mmol) in THF (50.0 mL) at −78° C. This mixture is stirred at −78° C. for an additional 30 min. TMS-Cl (5.45 mL, 42.95 mmol) is added dropwise and stirred at −78° C. for 2 h. The reaction is warmed to room temperature and diluted with diethyl ether (200 mL). This mixture is added to a saturated $Na_2CO_3$ solution and the phases are separated. The combined organics are dried and concentrated in vacuo. The residue is dissolved in ACN (50.0 mL) and $Pd(OAc)_2$ (8.04 g, 35.79 mmol) is added. The resulting mixture is cooled in a water bath to maintain reaction temp below 35° C. and stirred overnight. The reaction is filtered through celite and the filtrate is concentrated in vacuo. The residue is taken up in 200 mL EtOAc then treated with 1.0 M TBAF solution (50.0 mL). This mixture is stirred for 30 min and then washed with 1N HCl and 10% sodium thiosulfate solution. The organics are dried and concentrated. The material is purified by silica gel chromatography using a gradient of 20-80% EtOAc in heptanes to afford an off-white solid (6.11 g).

To a solution of starting material 21-3 (1.50 g, 5.41 mmol) in dichloromethane (25.0 mL) at room temperature is added pyridine (0.871 mL, 10.82 mmol). The solution is cooled to −30° C. and $Tf_2O$ (1.00 mL, 5.95 mmol) is added dropwise. The reaction is stirred at −30° C. for 1 h and then is warmed to room temperature. It is concentrated in vacuo and the residue is diluted with EtOAc, washed with 1 N HCl, saturated $NaHCO_3$, brine, dried over $MgSO_4$, and concentrated. The resulting material is purified by silica gel chromatography using a gradient of 12-100% EtOAc in heptanes to yield a white solid (1.61 g).

Triflate 21-4 (1.00 g, 2.44 mmol) is combined with the boronate (0.647 g, 2.69 mmol) and $Pd(PPh_3)_4$ (0.144 g, 0.124 mmol) in a mix of DME (15.0 mL) and 2.0 M $Na_2CO_3$ (1.27 mL). The reaction is irradiated in MW at 120° C. for 40 min. It is concentrated under $N_2$ and is purified by silica gel chromatography using a gradient of 12-100% EtOAc in heptanes. The desired fractions are concentrated to afford a white solid (0.662 g).

Substrate 21-5 (1.029 g, 3.58 mmol), $NaIO_4$ (2.34 g, 10.94 mmol), 2.5 wt % $OsO_4$ in t-BuOH (1.0 mL), THF (12.4 mL) and $H_2O$ (2.4 mL) are combined at room temperature, then stirred overnight in the dark. The reaction mixture is diluted with water and dichloromethane. The layers are separated with a hydrophobic frit. The organics are dried over $Na_2SO_4$, filtered, and concentrated. The residue is purified by silica gel chromatography using a gradient of 12-100% EtOAc in heptanes to yield an amber oil (0.786 g).

Aldehyde 21-6 (0.785 g, 2.71 mmol) is dissolved in THF (5.0 mL) and MeOH (5.0 mL). The mixture is cooled to 0° C. and $NaBH_4$ (0.156 g, 4.07 mmol) is added. The reaction is stirred at room temperature for 30 min. The reaction is quenched with aq. $NH_4Cl$ and is stirred for 10 min. It is extracted with EtOAc, washed with $NH_4Cl$, brine, dried over $MgSO_4$, and concentrated. The resulting material is purified by silica gel chromatography using a gradient of 12-100% EtOAc in heptanes. The desired fractions are collected to yield the desired product 21-7 (0.626 g) as a white solid.

To a solution of alcohol 21-7 (0.300 g, 1.030 mmol) and N,N-diisopropylethylamine (0.269 mL, 1.54 mmol) in dichloromethane (10.0 mL) is added triphenylphosphine dibromide (0.679 g, 1.54 mmol) at 0° C. The reaction is stirred for 2 h and concentrated in vacuo. The resulting residue is purified by silica gel chromatography using a gradient of 7-60% EtOAc in heptanes to yield the desired product 21-8 (0.338 g) as a white solid.

Similarly, the following bromides were prepared from the appropriate starting materials as described in Example 21:

21-9

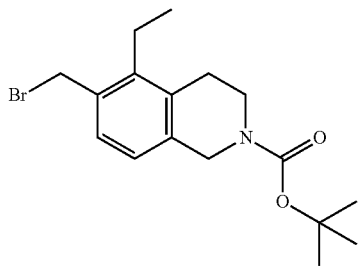

The following compounds from Table 1 are prepared according to the procedure described in Example 7a, using phenol, 2-8, bromide, 21-8, and other appropriate starting materials and purification conditions:
Compound 120: MS, electrospray, m/z=583.5 [M+H], RT 0.74 min;
Compound 178: MS, electrospray, m/z=555.3 [M+H], RT 0.64 min (Method B1).

The following compound from Table 1 is prepared according to the procedure described in Example 7a, using phenol, 3-15, bromide, 21-8, and other appropriate starting materials and purification conditions:
Compound 132: MS, electrospray, m/z=597.5 [M+H], RT 0.83 min.

The following compound from Table 1 is prepared according to the procedure described in Example 7a, using phenol, 3-15, bromide, 21-9, and other appropriate starting materials and purification conditions:
Compound 154: MS, electrospray, m/z=597.7 [M+H], RT 0.81 min.

Example 22

Preparation of intermediates 5-Bromomethyl-4-methyl-1,3-dihydro-isoindole-2-carboxylic acid tert-butyl ester (22-5) and 6-Bromomethyl-4-methyl-1,3-dihydro-isoindole-2-carboxylic acid tert-butyl ester (22-6)

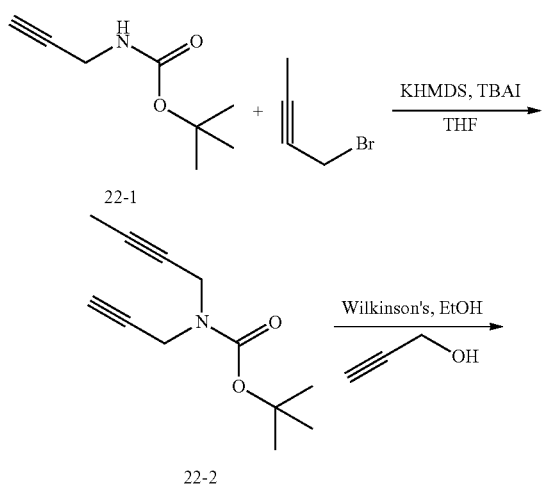

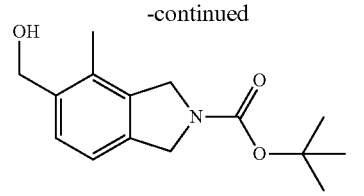

22-3

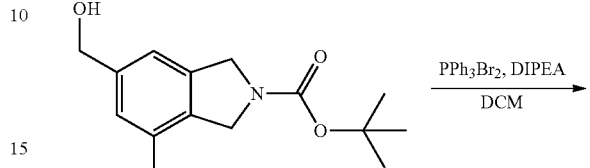

22-4

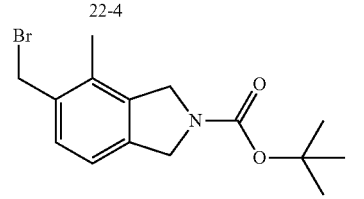

22-5

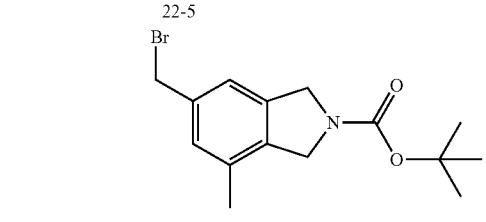

22-6

To a stirred solution of Boc-amine 22-1 (2.00 g, 12.89 mmol) in THF (30.0 mL) and tetrabutylammonium iodide (0.476 g, 1.29 mmol) is added 0.5 M KHMDS solution (25.8 mL) and the mixture is stirred for 30 min at room temperature. The bromide (1.69 mL, 19.33 mmol) is added dropwise and the mixture is stirred for 30 min at room temperature and then is refluxed for 2 h. The reaction is quenched with saturated NH₄Cl and extracted with EtOAc. The combined organics are dried with MgSO₄ and concentrated in vacuo. The crude material is purified by silica gel chromatography using a gradient of 5-40% EtOAc in heptanes to yield the desired product (2.13 g) as a colorless oil.

Propargyl alcohol (2.39 mL, 41.11 mmol) is added dropwise at 0° C. to a solution of diacetylene 22-2 (2.13 g, 10.28 mmol) in anhydrous ethanol (50.0 mL). Wilkinson's catalyst (0.95 g, 1.028 mmol) is added to the mixture and it stirred overnight at room temperature. The crude reaction is concentrated in vacuo and subjected to silica gel chromatography using a gradient of 10-80% EtOAc in heptanes. The desired fractions are collected and concentrated to afford both regioisomers 22-3 and 22-4 (1.93 g). The mixture is carried on to the next step.

To a solution of the mixture of alcohols 22-3 and 22-4 (1.93 g, 7.33 mmol) and N,N-diisopropylethylamine (1.91 mL, 10.98 mmol) in dichloromethane (50.0 mL) is added triphenylphosphine dibromide (4.73 g, 10.98 mmol) at 0° C. The reaction is stirred for 2 h and concentrated in vacuo. The resulting residue is purified by silica gel chromatography using a gradient of 7-60% EtOAc in heptanes to yield the mixture of regioisomers 22-5 and 22-6 (2.12 g) as a white solid.

The following compounds from Table 1 are prepared according to the procedure described in Example 7a, using phenol, 2-8, bromide, 22-5, and other appropriate starting materials and purification conditions:

Compound 256: MS, electrospray, m/z=555.4 [M+H], RT 1.13 min (Method A2);

Compound 257: MS, electrospray, m/z=527.3 [M+H], RT 1.12 min (Method A2).

The following compounds from Table 1 are prepared according to the procedure described in Example 7a, using phenol, 2-8, bromide, 22-6, and other appropriate starting materials and purification conditions:

Compound 255: MS, electrospray, m/z=555.4 [M+H], RT 1.15 min (Method A2);

Compound 258: MS, electrospray, m/z=527.3 [M+H], RT 1.16 min (Method A2).

The following compound from Table 1 is prepared according to the procedure described in Example 7a, using phenol, 3-15, bromide, 22-5, and other appropriate starting materials and purification conditions:

Compound 119: MS, electrospray, m/z=569.3 [M+H], RT 1.13 min (Method A2);

The following compound from Table 1 is prepared according to the procedure described in Example 7a, using phenol, 3-15, bromide, 22-6, and other appropriate starting materials and purification conditions:

Compound 118: MS, electrospray, m/z=569.3 [M+H], RT 1.11 min (Method A2);

Example 23

Preparation of intermediate 5-Bromomethyl-6-methyl-1,3-dihydro-isoindole-2-carboxylic acid tert-butyl ester (23-3)

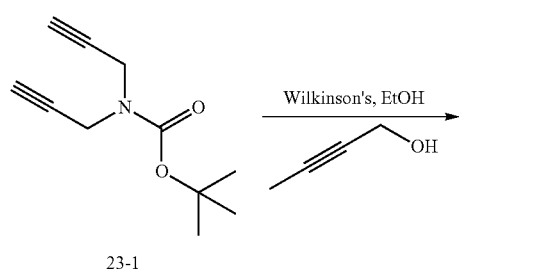

23-1

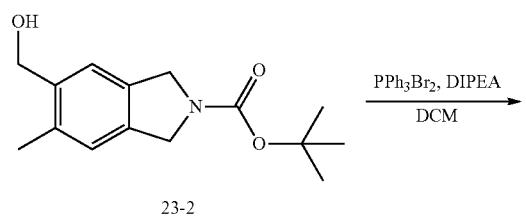

23-2

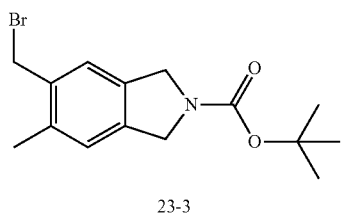

23-3

The alcohol (0.968 mL, 12.94 mmol) is added dropwise at 0° C. to a solution of diacetylene 23-1 (500 mg, 2.59 mmol) in anhydrous ethanol (12.0 mL). Wilkinson's catalyst (239.4 mg, 0.259 mmol) is added to the mixture and it stirred overnight at room temperature. The crude reaction is concentrated in vacuo and subjected to silica gel chromatography using a gradient of 10-80% EtOAc in heptanes. The desired fractions are collected and concentrated yielding a solid (105 mg).

To a solution of alcohol 23-2 (105 mg, 0.399 mmol) and N,N-Diisopropylethylamine (0.104 mL, 0.598 mmol) in dichloromethane (7.0 mL) is added triphenylphosphine dibromide (263 mg, 0.598 mmol) at 0° C. The reaction is stirred for 2 h and concentrated in vacuo. The resulting residue is purified by silica gel chromatography using a gradient of 7-60% EtOAc in heptanes to yield 23-3.

The following compound from Table 1 is prepared according to the procedure described in Example 7a, using phenol, 2-8, bromide, 23-3, and other appropriate starting materials and purification conditions:

Compound 143: MS, electrospray, m/z=555.4 [M+H], RT 0.74 min.

Example 24

Preparation of 5-Ethoxy-1-(6-{3-methyl-2-[5-methyl-2-(tetrahydro-pyran-4-carbonyl)-1,2,3,4-tetrahydro-isoquinolin-6-ylmethoxy]-phenyl}-pyridin-2-yl)-1H-pyrazole-4-carboxylic acid (Compound 147)

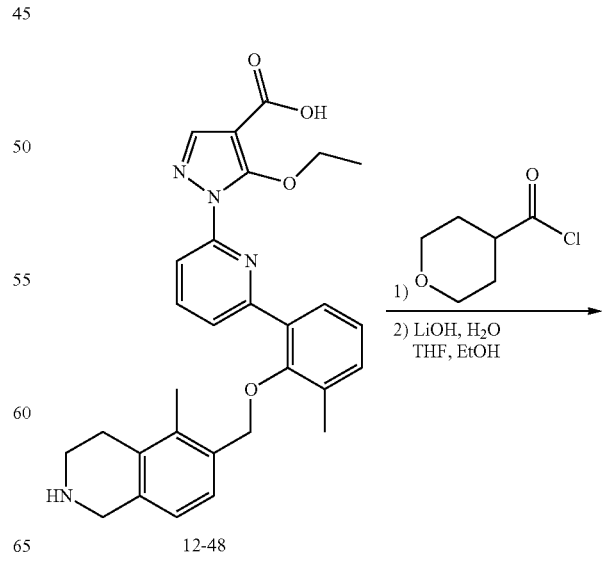

12-48

-continued

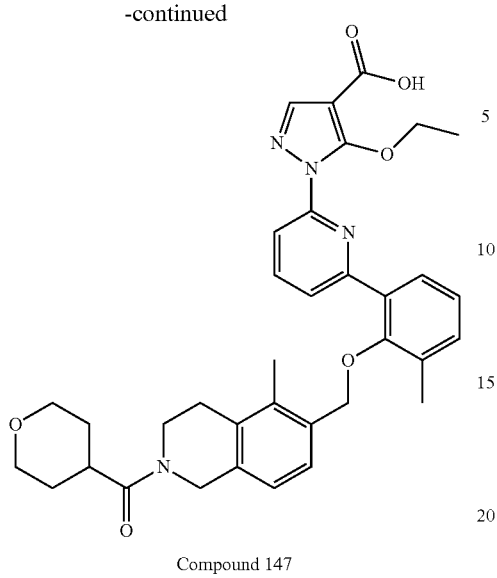

Compound 147

Amine 12-48 (122 mg, 0.232 mmol) is combined with DMAP (2 mg, 0.02 mmol) and DIPEA (60 µL, 0.34 mmol) in dichloromethane (5 mL) at rt. Tetrahydro-2H-pyran-4-carbonyl chloride (40 µL, 0.23 mmol) is added, and the mixture is stirred overnight at rt. The mixture is applied directly to a samplet, and then purified by elution with 100% dichloromethane on a 50 g HP-Sil SNAP cartridge (Biotage). Concentration in vacuo affords the intermediate ester (31 mg) that is used immediately in the next step.

Ester (30 mg) is dissolved in EtOH/H$_2$O/THF (1, 0.5, 0.5 mL) and treated with LiOH (26 mg, 1.2 mmol). The mixture is stirred at 45° C. o/n, and then concentrated under N$_2$. The residue is then purified by gradient elution (5-95% MeCN/water+0.1% TFA) on a 12 g KP-C18 SNAP cartridge (Biotage). The product is concentrated in vacuo, to afford Compound 150 (26 mg).

Compound 147: MS, electrospray, m/z=611.3 [M+H], RT 1.04 min (Method B1)

Example 25

Preparation of intermediate 6-Bromomethyl-8-methyl-3,4-dihydro-1H-isoquinoline-2-carboxylic acid tert-butyl ester (25-14)

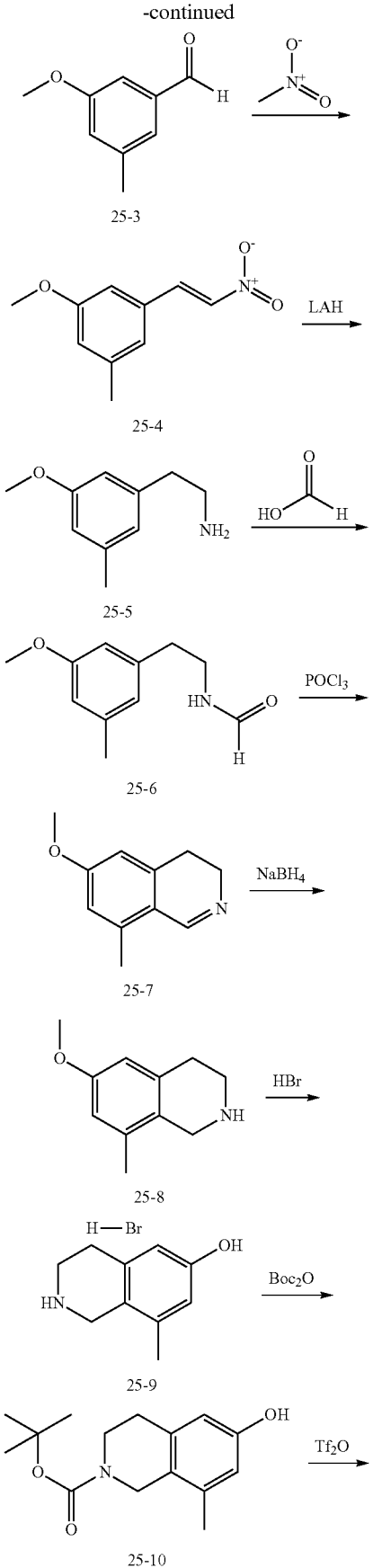

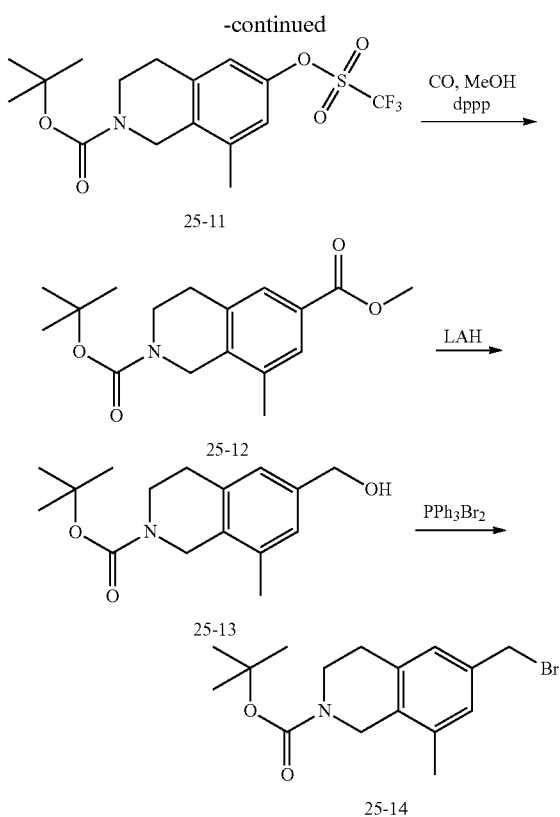

To a mixture of 25-01 (185 g; 0.940 mol), K$_2$CO$_3$ (437 g, 3.17 mol) in acetone (2 L) is added MeI (424 g, 2.99 mol). The mixture is stirred at 40° C. for 16 h. After filtration, the mixture is purified by silica gel column (PE:EtOAc=500:1) to give 1-Bromo-3-methoxy-5-methyl-benzene, 25-02 (189 g) as a light yellow oil.

To a mixture of 25-02 (200 g, 0.995 mol) in dry THF (1.70 L) is added dropwise n-BuLi (438 ml; 1.09 mol) at −70° C. After stirring for 1 h at −70° C., dry DMF (76.3 g, 1.04 mol) is added dropwise at −70° C. and stirred for 1 h at −70° C. The mixture is poured into NH$_4$Cl (1.00 L) and extracted with EtOAc (500 mL×3), washed with brine (500 mL×2), dried over Na$_2$SO$_4$ and concentrated to give 3-Methoxy-5-methyl-benzaldehyde, 25-03 (147 g) as a yellow oil.

The mixture of 25-03 (150 g, 0.999 mol) and NH$_4$OAc (30.8 g, 0.40 mol) in MeNO$_2$ (1.5 L) is refluxed for 16 h. The mixture is concentrated, then diluted with EtOAc (1000 mL), washed with water (1 L), brine (100 mL), the organic layers are dried over Na$_2$SO$_4$ and concentrated. The mixture is triturated with PE:EtOAc=10:1 for 10 minutes, filtered to give 1-Methoxy-3-methyl-5-((E)-2-nitro-vinyl)-benzene, 25-04 (80 g) as yellow solid.

To a mixture of LiAlH$_4$ (78.6 g, 2.00 mol) in dry THF (1 L) is added 25-04 (78 g, 0.404 mol) in portions at 0° C. in THF (200 mL) and stirred for 16 h at 70° C. The mixture is cooled to 0° C., quenched slowly with water (78 mL), 15% NaOH (78 mL) and water (235 mL). After filtration, the mixture is concentrated to give 2-(3-Methoxy-5-methyl-phenyl)-ethylamine, 25-05 (40 g) as a light yellow oil.

The mixture of compound 25-05 (66 g, 0.40 mol) and formic acid (73.5 g, 1.60 mol) in dioxane (600 mL) is stirred for 16 h at 90° C. The mixture was concentrated to give N-[2-(3-Methoxy-5-methyl-phenyl)-ethyl]-formamide, 25-06 (77 g) as yellow solid.

To a solution of 25-06 (76.0 g, 0.354 mol) in dichloromethane (2.5 L) is added POCl$_3$ (155 g, 1.01 mol) at 15° C. and refluxed for 3 h. The solution is concentrated, to the residue is added water (1.5 L), toluene (1.5 L) and 20% NaOH (500 mL), then refluxed for 1 h and cooled. The mixture is diluted with EtOAc (500 mL×3), washed with water (1 L×2), brine (100 mL×2), the combined organics were dried over Na$_2$SO$_4$ and concentrated. It is purified by silica gel column (PE:EtOAc=10:1) to give 6-Methoxy-8-methyl-3,4-dihydroisoquinoline, 25-07 (58.5 g) as brown oil.

To a solution of 25-07 (58.5 g, 0.334 mol) in MeOH (500 mL) is added NaBH$_4$ (63.3 g, 1.67 mol) at 0° C. and the mixture is maintained at 0° C. for 4 h. The solution is quenched with 1N HCl (100 mL), pH is adjusted to 8 by addition of NaHCO$_3$, extracted with dichloromethane (300 mL×2), the combined organics are dried over Na$_2$SO$_4$ and concentrated to afford 6-Methoxy-8-methyl-3,4-dihydro-isoquinoline, 25-08 (83 g, crude) as brown oil.

A solution of crude 25-08 (83 g, 0.47 mol) in HBr (40% in water, 500 mL) is heated to 90° C. for 12 h. The solution is evaporated under reduced pressure to obtain 8-Methyl-1,2,3,4-tetrahydro-isoquinolin-6-ol hydrobromide, 25-09. To this crude residue is added Boc$_2$O (72 g, 0.33 mol) and triethylamine (63 g, 0.62 mol) and the resulting mixture is stirred for 12 h at 15° C., then diluted with dichloromethane (1500 mL) and water (100 mL). The organics layer is washed with 0.5 N HCl (100 mL) and brine (100 mL), dried, concentrated, and purified by silica gel column (PE:EtOAc=30:1) to give 6-Hydroxy-8-methyl-3,4-dihydro-1H-isoquinoline-2-carboxylic acid tert-butyl ester, 25-10 (33.4 g) as a white solid.

To a solution of 25-10 (33 g; 0.113 mol) and pyridine (20.1 g, 0.254 mol) in dry dichloromethane (300 mL) is added Tf$_2$O (39.4 g, 0.139 mol) drop-wise at −30° C. and stirred for 1 h at −30° C. Then the solution is warmed to 15° C. and stirred for 8 h. The mixture is diluted with dichloromethane (500 mL) and water (100 mL), and the combined organics are concentrated and then purified by silica gel column (PE:EtOAc=50:1) to give 8-Methyl-6-trifluoromethanesulfonyloxy-3,4-dihydro-1H-isoquinoline-2-carboxylic acid tert-butyl ester, 25-11 (43 g) as a white solid.

A solution of 25-11 (43 g, 0.109 mol), Et$_3$N (33.0 g, 0.327 mol), DPPP (4.53 g) and Pd(OAc)$_2$ (5 g) in MeOH (500 mL) is stirred under 3 MPa pressure of CO at 90° C. for 2 days. After filtration and concentration the residue is purified by silica gel chromatography (PE:EtOAc=50:1) to afford 8-Methyl-3,4-dihydro-1H-isoquinoline-2,6-dicarboxylic acid 2-tert-butyl ester 6-methyl ester, 25-12 (21 g) as a colorless oil.

To a solution of 25-12 (21 g, 0.693 mol) in dry THF (500 mL) is added LiAlH$_4$ (7.4 g, 208 mmol) at −50° C. The mixture is stirred at −50° C. for 1 h, and then 0° C. for 30 min. The reaction is slowly quenched with H$_2$O (7.4 mL), 15% NaOH (7.4 mL), and H$_2$O (22.2 mL) and then filtered. The filtrate is concentrated and purified by prep-HPLC and concentrated. The residue is extracted with dichloromethane (1 L×2), the combined organics were dried over Na$_2$SO$_4$ and concentrated to give 6-Hydroxymethyl-8-methyl-3,4-dihydro-1H-isoquinoline-2-carboxylic acid tert-butyl ester, 25-13 (14.8 g) as a colorless oil.

To a solution of 25-13 (13.4 g, 0.485 mol) and DIEA (11.8 mL, 0.679 mol) in dichloromethane (200 mL) at −30° C. is added triphenylphosphine dibromide (26.6 g, 0.606 mol). The resulting mixture is stirred 1 h, over which time cold bath is allowed to warm to −10° C. Volatiles are stripped from the −10° C. mixture, the residue is suspended in dichloromethane (50 mL), and the filtrate is purified by chromatography (silica gel, 5-40% EtOAc in heptane) to provide the desired intermediate 25-14 (16.2 g) as a white solid.

Similarly, the following bromides were prepared from the appropriate starting materials as described in Example 25:

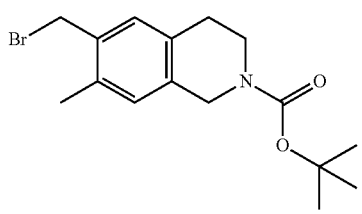

25-15

The following compound from Table 1 is prepared according to the procedure described in Example 7a, using phenol, 1-6, bromide, 25-14, and other appropriate starting materials and purification conditions:
Compound 161: MS, electrospray, m/z=597.3 [M+H], RT 0.75 min.

The following compounds from Table 1 are prepared according to the procedure described in Example 7a, using phenol, 2-8, bromide, 25-14, and other appropriate starting materials and purification conditions:
Compound 171: MS, electrospray, m/z=569.3 [M+H], RT 0.68 min;
Compound 186: MS, electrospray, m/z=541.3 [M+H], RT 0.60 min;
Compound 237: MS, electrospray, m/z=569.3 [M+H], RT 0.60 min;
Compound 239: MS, electrospray, m/z=569.3 [M+H], RT 0.60 min;
Compound 240: MS, electrospray, m/z=585.2 [M+H], RT 0.60 min;
Compound 242: MS, electrospray, m/z=555.3 [M+H], RT 0.59 min;
Compound 244: MS, electrospray, m/z=557.3 [M+H], RT 0.62 min.

The following compounds from Table 1 are prepared according to the procedure described in Example 7a, using phenol, 3-15, bromide, 25-14, and other appropriate starting materials and purification conditions:
Compound 169: MS, electrospray, m/z=583.3 [M+H], RT 0.73 min;
Compound 173: MS, electrospray, m/z=583.3 [M+H], RT 0.74 min;
Compound 174: MS, electrospray, m/z=555.3 [M+H], RT 0.72 min;
Compound 195: MS, electrospray, m/z=583.4 [M+H], RT 0.71 min;
Resolution: IC column 15% 1:1:1 MeOH:EtOH:iPA+diethylamine:CO2, 3 ml/min, 40° C., 200 bar
Compound 197: MS, electrospray, m/z=583.4 [M+H], RT 0.71 min;
Resolution: IC column 15% 1:1:1 MeOH:EtOH:iPA+diethylamine:CO2, 3 ml/min, 40° C., 200 bar
Compound 200: MS, electrospray, m/z=583.3 [M+H], RT 0.63 min (Method B1);
Compound 210: MS, electrospray, m/z=571.1 [M+H], RT 0.70 min (Method B1);
Compound 241: MS, electrospray, m/z=569.3 [M+H], RT 0.62 min;
Compound 243: MS, electrospray, m/z=599.3 [M+H], RT 0.63 min;

The following compound from Table 1 is prepared according to the procedure described in Example 7a, using phenol, 2-8, bromide, 25-15, and other appropriate starting materials and purification conditions:
Compound 121: MS, electrospray, m/z=569.4 [M+H], RT 0.72 min.

Example 26

Preparation of intermediate 6-Bromomethyl-8-methyl-3,4-dihydro-1H-isoquinoline-2-carboxylic acid tert-butyl ester (26-12)

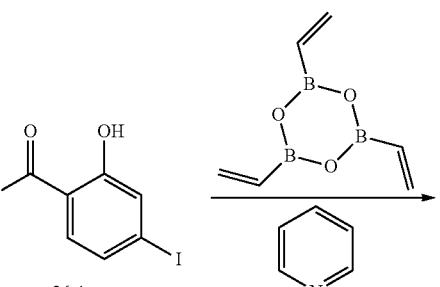

26-1

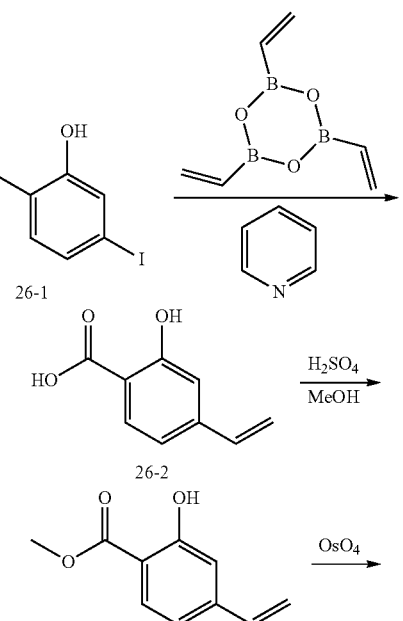

26-2

26-3

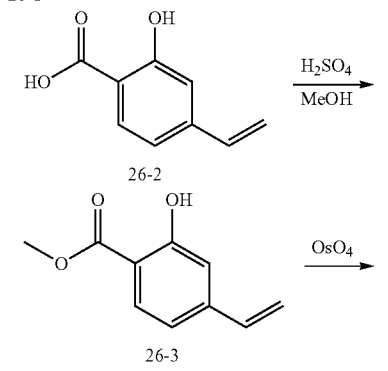

26-4

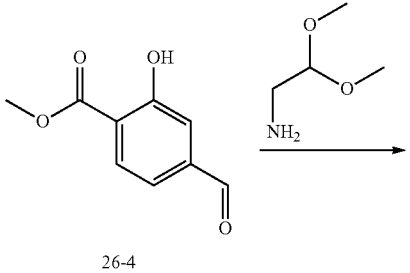

26-5

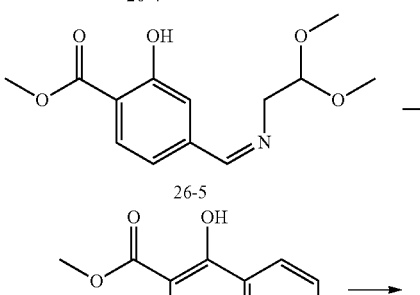

26-6

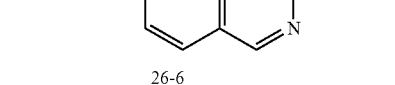

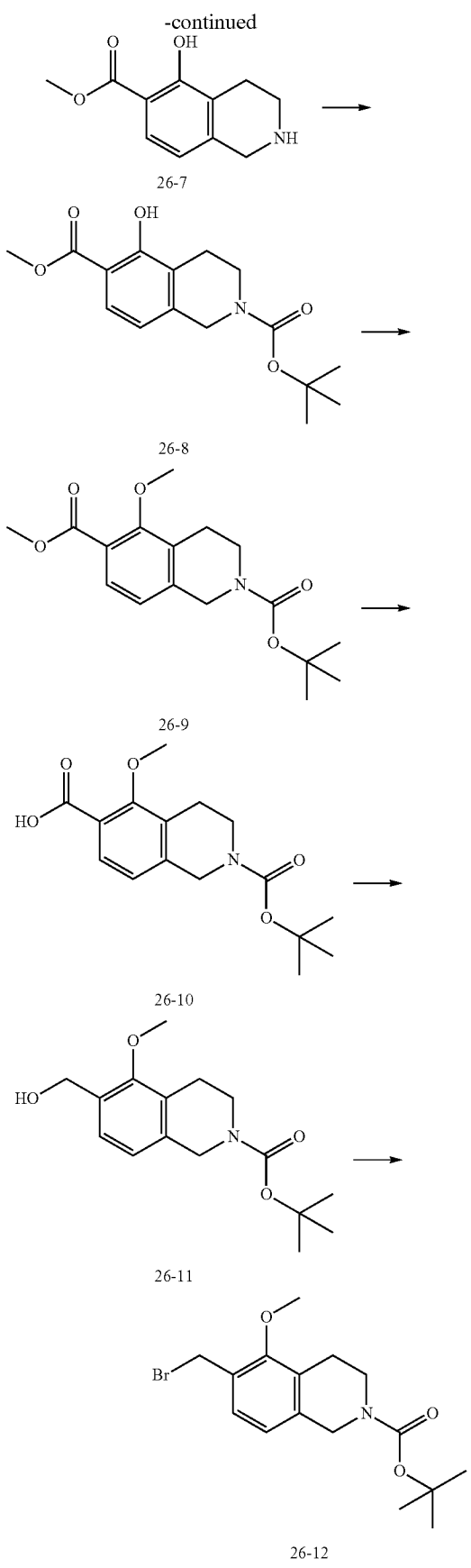

A round-bottom flask is charged with 2-Hydroxy-4-iodo-benzoic acid methyl ester, 26-01 (12.0 g, 43.2 mmol), 2,4,6-Trivinyl-cyclotriboroxane-pyridine complex (11.4 g, 47.5 mmol), tetrakis(triphenylphosphine) palladium (2.49 g, 2.16 mmol), 2.0 M aqueous solution of sodium carbonate (25.9 mL, 51.7 mmol), and 1,2-dimethoxyethane (50 mL), deoxygenated by alternating between vacuum and argon (3×), and refluxed under argon pressure for 3 h, and then stirred 18 h at ambient temperature. Volatiles are stripped in vacuo, the residue is suspended in 1N HCl (800 mL) and extracted with EtOAc (600 mL, 300 mL, and then 300 mL). The combined organic extracts are washed brine, dried over $NaSO_4$, and purified by chromatography (silica gel, 5-30% EtOAc in heptane) to afford 2-Hydroxy-4-vinyl-benzoic acid, 26-02 (3.70 g) and 2-Hydroxy-4-vinyl-benzoic acid methyl ester (0.300 g).

To a solution of 26-02 (3.70 g, 22.0 mmol) and 2-Hydroxy-4-vinyl-benzoic acid methyl ester (0.300 g, 1.69 mmol) in MeOH (50 mL) is added H2SO4 (4.0 mL, 75 mmol). The resulting mixture is refluxed for 16 h and then allowed to cool to room temperature. Ice (100 g) is added and the mixture is stirred. When the ice completely melts, the MeOH is removed under reduced pressure and the aqueous residue is extracted with DCM (2×100 mL). The combined organic extracts are combined, concentrated in vacuo and purified by chromatography (silica gel, 0-5% EtOAc in heptane) to give 2-Hydroxy-4-vinyl-benzoic acid methyl ester, 26-03 (3.75 g) as a clear oil.

To a stirring mixture of 26-03 (3.75 g, 21 mmol) and Sodium metaperiodate (13.8 g, 64.3 mmol) in THF (80 mL) and water (20 mL) is added a 4 wt % solution of osmium tetraoxide in water (3.69 mL, 0.47 mmol). The reaction flask (which warms upon addition of the osmium reagent) is wrapped in aluminum foil to shield contents from light, and the slurry is stirred 16 h. Volatiles are removed under reduced pressure, the residue is diluted with saturated aqueous NaHCO3 (700 mL) and extracted with EtOAc (700 mL, 200 mL, and then 200 mL). Combined organic extracts are concentrated in vacuo and then purified by chromatography (silica gel, 0-50% EtOAc in heptane) to afford 4-Formyl-2-hydroxy-benzoic acid methyl ester, 26-04 (2.25 g) as a yellow solid.

In a round-bottom flask with Dean Stark trap attached, 26-04 (2.25 g, 12 mmol) and amino acetaldehyde dimethyl acetal (1.31 g, 12 mmol) are refluxed in toluene 3 h. Reaction mixture is concentrated in vacuo to afford crude 4-{[2,2-Dimethoxy-ethylimino]-methyl}-2-hydroxy-benzoic acid methyl ester, 26-05 (3.33 g, 12.4 mmol) as a brown oil. To this crude oil is added a large stir bar, polyphosphoric acid (25.0 g), and phosphorous pentoxide (33.0 g, 232 mmol). The resulting, viscous tar is stirred at 80° C. for 5 h. The reaction mixture is diluted with $H_2O$ (600 mL), transferred to a 5 L Erlenmyer flask, and the vigorously stirred mixture is carefully treated with small portions of solid NaHCO3 until said addition no longer cause receiving mixture to foam. Basic aqueous mixture is then extracted with DCM (5×200 mL). The combined organic extracts are washed with $H_2O$ (2×50 mL), dried with Na2SO4, concentrated under vacuo and then purified by choratography (silica gel, 0-100% EtOAc in heptane) to yield 5-Hydroxy-isoquinoline-6-carboxylic acid methyl ester, 26-06 (0.520 g).

26-06 (0.520 g, 2.46 mmol) is dissolved in MeOH (15 mL) and then 4N HCl in dioxane (6.15 mL, 24 mmol) is added. Hydrogenated on an H-Cube apparatus by continuously cycling solution through a $PtO_2$ cartridge at a rate of 1 mL/minute under 10 mbar of $H_2$-pressure for 5 h, then under 50 mbar $H_2$-pressure for 15 h. Reaction mixture is concentrated under reduced pressure to get crude 5-Hydroxy-1,2,3,4-tetrahydro-isoquinoline-6-carboxylic acid methyl ester; hydrochloride, 26-07 (0.90 g) as a red solid. This crude solid is dissolved in DCM (30 mL) and cooled to 0° C. before adding triethylamine (1.65 mL, 11 mmol) and then di-tert-butyl dicarbonate (1.70 mL, 7.39 mmol). Reaction mixture is removed from cold bath, stirred 16 h, concentrated under reduced pressure and purified by chromatography (silica gel, 0-50% EtOAc in heptane). Desired intermediate 5-Hydroxy-3,4-dihydro-1H-isoquinoline-2,6-dicarboxylic acid 2-tert-butyl ester 6-methyl ester 26-08 (0.492 g) co-elutes with di-tert-butyl dicarbonate (1.61 g). The mixture (2.1 g) is dissolved in MeOH (50 mL), K₂CO₃ (2.21 g, 16 mmol) is added and the resulting mixture is stirred 16 h. Supernatant is removed from reaction flask and sediment is triturated with MeOH (2×10 mL). The combined methanolic supernatants are concentrated under reduced pressure, dissolved in EtOAc (50 mL), washed with 1N HCl (3×30 mL), brine (10 mL), dried with Na2SO4, and concentrated in vacuo to get 26-08 (0.422 g). This residue is combined with iodomethane (1.0 mL, 16 mmol), K₂CO₃ (0.20 g, 1.5 mmol), Cs₂CO₃ (0.40 g, 1.5 mmol), and acetone (4.0 mL) and irradiated in microwave at 70° C. for 7 h. Mixture is concentrated under reduced pressure and purified by chromatography (silica gel, 0-100% EtOAc) to afford impure 5-Methoxy-3,4-dihydro-1H-isoquinoline-2,6-dicarboxylic acid 2-tert-butyl ester 6-methyl ester, 26-09 (0.245 g) which was carried forward as is.

Impure 26-09 (0.240 g, 0.51 mmol) is combined with lithium hydroxide (1.22 g, 5.1 mmol) in THF (4.0 mL), MeOH (4.0 mL) and water (2.0 mL). The mixture is heated 45 minutes at 55° C. and then concentrated under reduced pressure. The residue is dissolved in EtOAc (20 mL), washed with 1N HCl (3×50 mL), brine (10 mL), dried with Na₂SO₄, and concentrated in vacuo to give crude 5-Methoxy-3,4-dihydro-1H-isoquinoline-2,6-dicarboxylic acid 2-tert-butyl ester, 26-10 (0.177 g) as a white solid.

To a solution of crude 26-10 (0.177 g, 0.58 mmol) in THF (3 mL) is added a 1M borane in THF solution (1.27 mL, 1.27 mmol) and the resulting mixture is stirred for 18 h. Reaction mixture is concentrated in vacuo and purified by reverse-phase chromatography (C18 silica gel, 5-95% MeCN, in H2O with 0.1% TFA) to get 6-Hydroxymethyl-5-methoxy-3,4-dihydro-1H-isoquinoline-2-carboxylic acid tert-butyl ester, 26-11 (0.125 g) as a clear, colorless residue.

26-11 (0.125 g, 0.43 mmol) and N,N-diisopropylethylamine (0.111 mL, 0.64 mmol) are dissolved in DCM (4.0 mL), the resulting mixture is deoxygenated by alternating between argon and vacuum (3×), and then cooled to −30° C. Triphenylphosphine dibromide (0.262 g, 0.60 mmol) is added and the resulting mixture stirs for 3 h as cold bath warms to −15° C. Reaction mixture is concentrated under reduced pressure and the residue is purified by chromatography (silica gel, 5-50% EtOAc in heptane) to afford desired intermediate 6-Bromomethyl-5-methoxy-3,4-dihydro-1H-isoquinoline-2-carboxylic acid tert-butyl ester, 26-12 (0.103 g).

The following compounds from Table 1 are prepared according to the procedure described in Example 7a, using phenol, 3-15, bromide, 26-12, and other appropriate starting materials and purification conditions:

Compound 220: MS, electrospray, m/z=599.3 [M+H], RT 0.71 min;

Compound 221: MS, electrospray, m/z=571.3 [M+H], RT 0.71 min;

Example 27

5-Methoxy-1-(6-{3-methyl-2-[5-methyl-1-oxo-2-(tetrahydro-pyran-4-yl)-1,2,3,4-tetrahydro-isoquinolin-6-ylmethoxy]-phenyl}-pyridin-2-yl)-1H-pyrazole-4-carboxylic acid

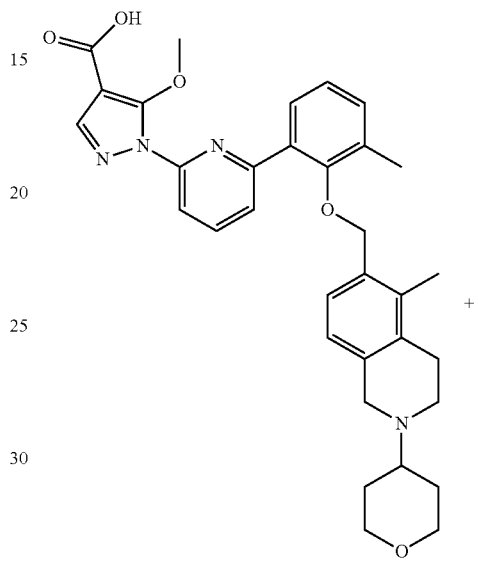

Compound 27

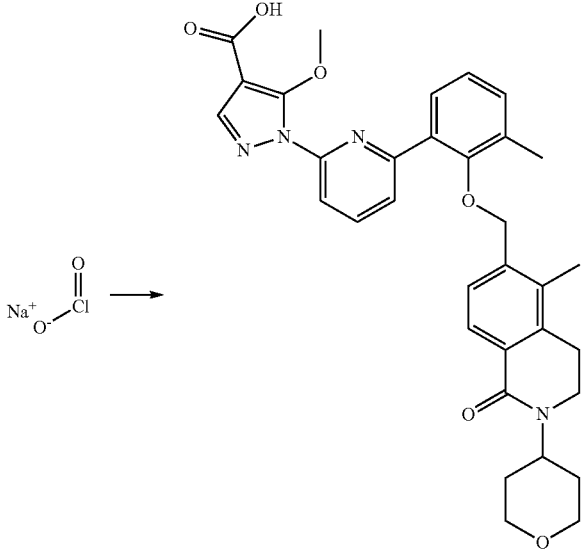

Compound 167

To a suspension of compound 27 (0.065 g, 0.11 mmol) in a 4:1 mixture of 1,1,2,2,-tetrachloroethane:water (1.2 mL) is added sodium chlorite (0.035 g, 0.39 mmol). The mixture was heated at 55° C. for 2 hours then cooled to room temperature and the mixture purified by C18 flash reverse phase chromatography to afford the title compound (0.009 g).

Compound 167: MS, electrospray, m/z=584.8 [M+H], RT 1.01 min.

The following compound is prepared according to the above procedure using Compound 114 as the appropriate starting materials and purification conditions:

Compound 194: MS, electrospray, m/z=597.22 [M+H], RT 1.02 min.

Example 28

Preparation of 1-{6-[2-(2-(S)-1-[1,4]Dioxan-2-ylm-ethyl-5-methyl-1,2,3,4-tetrahydro-isoquinolin-6-ylmethoxy)-3-methyl-phenyl]-pyridin-2-yl}-5-ethoxy-1H-pyrazole-4-carboxylic acid

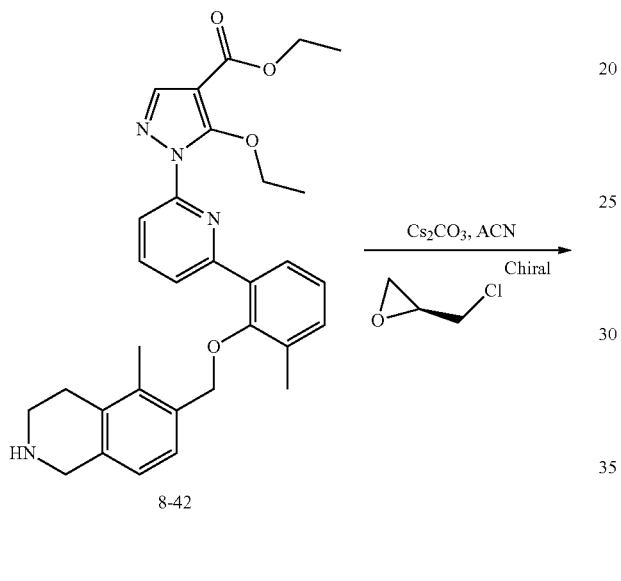

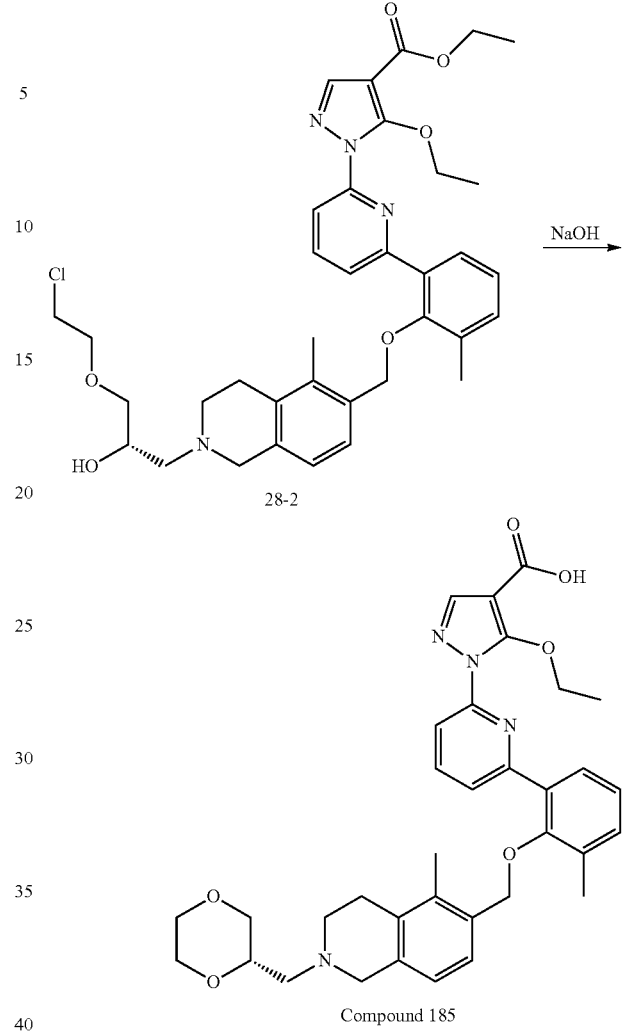

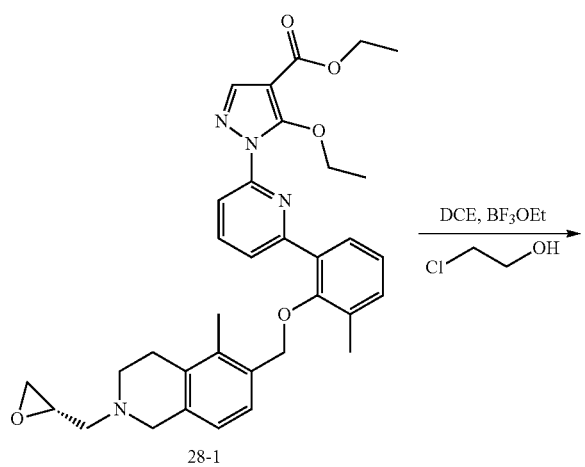

Amine 8-42 (80.0 mg, 0.152 mmol) is dissolved in acetonitrile (3.0 mL) and chloride (16.87 mg, 0.182 mmol) and Cs$_2$CO$_3$ (51.5 mg, 0.243 mmol) are added. The reaction is heated to 60° C. and stirred overnight. LC-MS indicated the desired mass. The reaction is extracted with EtOAc, washed with brine, dried over MgSO$_4$, and concentrated. The resulting residue is subjected to silica gel chromatography using a gradient of 12-100% EtOAc in heptanes. The desired fractions are collected and concentrated to yield the product (43.0 mg).

To a solution of epoxide 28-1 (43.0 mg, 0.074 mmol) and DCE (2.0 mL) is added 2-chloroethanol (0.005 mL, 0.081 mmol) followed by a solution of BF$_3$Et$_2$O (0.01 mL) in DCE. The reaction is stirred at 45° C. overnight. The reaction mixture is cooled to room temperature and is concentrated. The resulting material is carried on crude to the next step.

To starting material 28-2 (40.0 mg) is added a solution of 2.0 M NaOH (2.0 mL). This solution is heated to 90° C. and becomes homogeneous. It is stirred for 3 h and the reaction is cooled to room temperature. It is subjected to a C18 column (20-80% ACN in Water with 0.1% TFA). The desired fractions were collected and concentrated to yield the desired compound 18 (19.1 mg).

Compound 185: MS, electrospray, m/z=599.3 [M+H], RT 0.75 min, Method B1.

The following compound is prepared according to the procedure described in Example 28, using the appropriate starting materials and purification conditions:

Compound 170: MS, electrospray, m/z=599.3 [M+H], RT 0.63 min, Method B1.

Example 29 tert-Butyl 8-ethyl-6(hydroxymethyl)-3,4-dihydroisoquinoline-2(1H)-carboxylate (29-13)

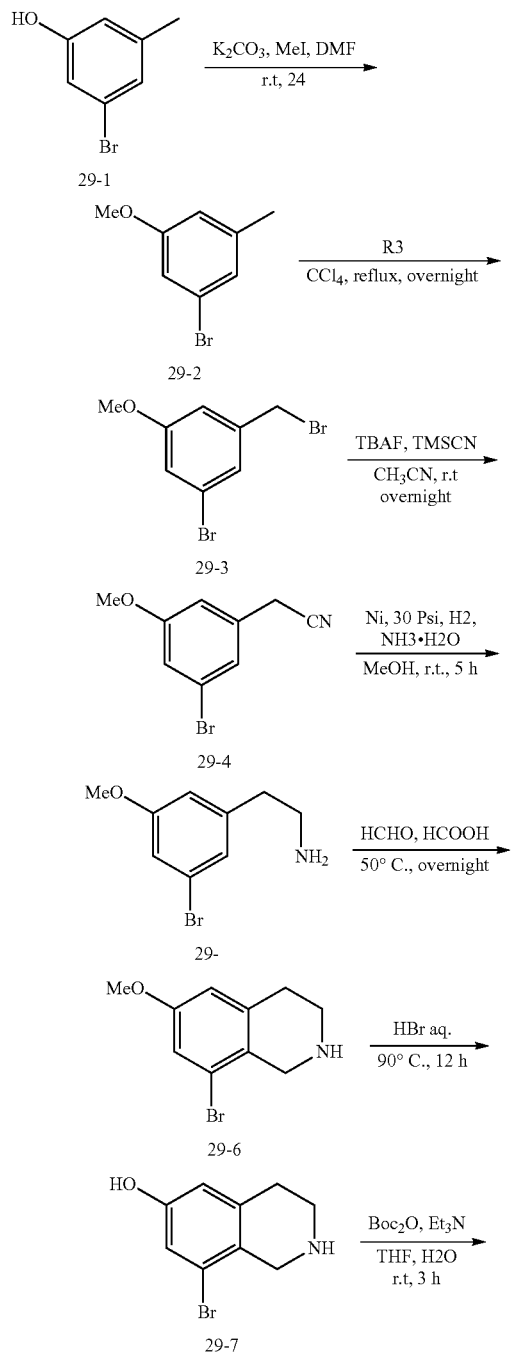

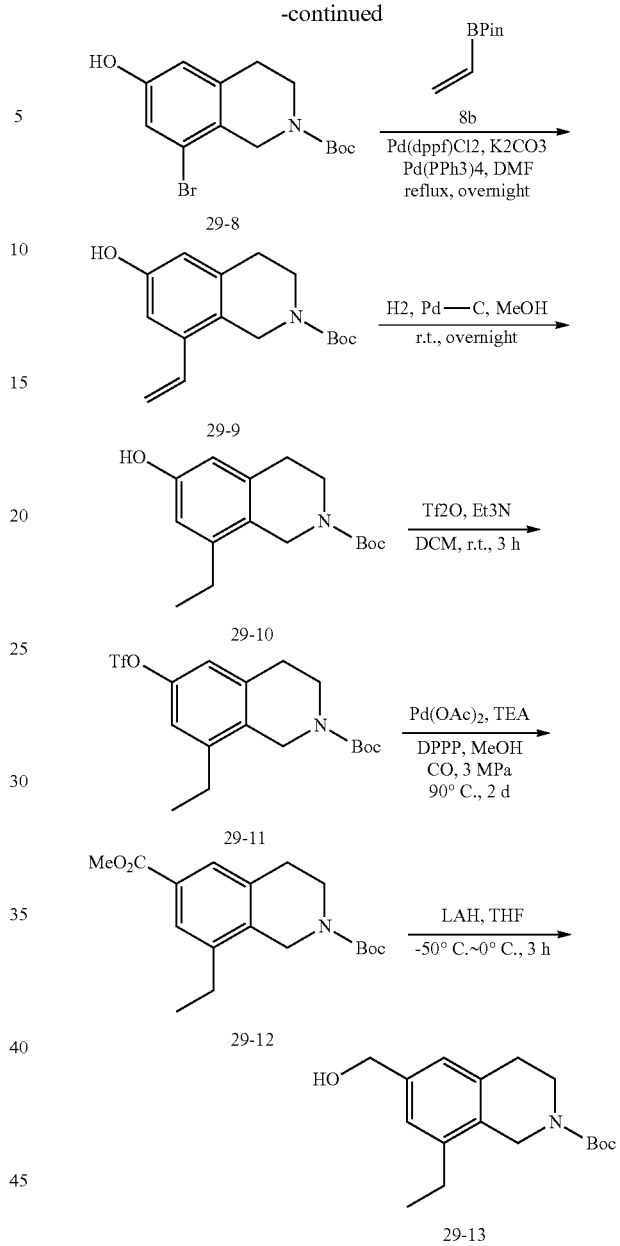

To the mixture of compound 29-1 (300 g, 1.6 mol) and $K_2CO_3$ (665 g, 4.8 mol) in DMF (2000 mL) was added MeI (250 g, 1.8 mol) dropwised at room temperature. The mixture was stirred overnight. TLC showed the reaction is completed. The reaction was quenched by $H_2O$ and extracted with EtOAc. The organic layer was dried, filtered, evaporated under reduced pressure to give the crude product which was purified by chromatography on silica gel to give compound 29-2 (165 g, 52% yield).

The solution of compound 29-2 (100 g, 497.4 mmol), NBS (88.5 g, 497.4 mmol) and AIBN (10 g, 10%) in $CCl_4$ (700 mL) was heated to reflux for 12 h. TLC showed the reaction is completed.

After cooling down to room temperature, the reaction was quenched by $H_2O$ and extracted with EtOAc. The organic layer was dried, filtered and evaporated under reduced pressure to give the crude product which was purified by chromatography on silica gel to give compound 29-3 (48 g, 42% yield).

The solution of compound 29-3 (80 g, 285.7 mmol) and TMSCN (28.2 g, 285.7 mmol) in ACN (600 ml) was stirred at room temperature for 0.5 h. TBAF (74.6 g, 285.7 mmol) was added into the reaction mixture at ice based and the mixture was stirred for 12 h. TLC showed the reaction was completed. The reaction was quenched by $H_2O$ and extracted with EtOAc. The organic layer was dried, filtered and evaporated under reduced pressure to give the crude product which was purified by chromatography on silica gel to give compound 29-4 (39 g, 60% yield).

The solution of compound 29-4 (12 g, 53.1 mmol) and Ni (10 g) in MeOH (80 ml) and $NH_3.H_2O$ (80 ml) was stirred under $H_2$ with a pressure of 50 psi at room temperature for 5 h. TLC showed the reaction was completed. The mixture was filtered and the filtrate was concentrate on vacuum pump to give the crude product (8 g) which was used directly in the next step.

The solution of compound 29-5 (75 g, 326.08 mmol) and HCHO (8.8 g, 293.47 mmol) in $HCO_2H$ (500 ml) was stirred at 50° C. under $N_2$ overnight. LCMS showed the reaction was completed. The solvent was removed under reduced pressure to give the crude product which was purified by chromatography on silica gel to give compound 29-6 (54 g, 64% yield for 2 steps).

The solution of compound 29-6 (45 g, 186 mmol) in aqueous HBr solution (400 ml) was stirred at 90° C. for 12 h. LCMS showed the reaction was completed. The solvent was removed under reduced pressure to give the crude product which was purified by chromatography on silica gel to give compound 29-7 (20.75 g, 53% yield).

The solution of compound 29-7 (20 g, 87.7 mmol), $Boc_2O$ (19.1 g, 87.7 mmol) and TEA (17.7 g, 175.4 mmol) in THF/$H_2O$ (1:1) (200 ml) was stirred at room temperature for 3 h. TLC showed the reaction is completed. The reaction was quenched by $H_2O$ and extracted with EtOAc. The organic layer was dried, filtered and evaporated under reduced pressure to give the crude product which was purified by chromatography on silica gel to give compound 29-8 (20 g, 70% yield).

The solution of compound 29-8 (14 g, 42.7 mmol), $K_2CO_3$ (17.66 g, 128 mmol), Pd(dppf)$Cl_2$ (2.5 g), Pd (PPh$_3$)$_4$ (2.5 g), and compound 29-8B (7.22 g, 46.9 mmol) in DMF (150 ml) was stirred at reflux overnight. TLC showed the reaction is completed. After filtration, the filtrate was concentrate under reduced pressure and the residue was purified by chromatography on silica gel to give compound 29-9 (7.2 g, 61% yield).

The solution of compound 29-9 (7.2 g, 26.2 mmol) and Pd—C (2 g) in MeOH (100 ml) was stirred under $H_2$ with a pressure of 50 psi at room temperature for 12 h. TLC showed the reaction was completed. The mixture was filtered and the filtrate was concentrated to give crude product which was purified by chromatography on silica gel to give compound 29-10 (5.8 g, 80% yield).

The solution of compound 29-10 (5.8 g, 20.9 mmol), $Tf_2O$ (5.9 g, 20.9 mmol) and TEA (6.3 g, 62.7 mmol) in DCM (70 ml) was stirred at room temperature for 3 h. TLC showed the reaction was completed. The reaction was quenched by $H_2O$ and extracted with EtOAc. The organic layer was dried, filtered and evaporated under reduced pressure to give the crude product which was purified by chromatography on silica gel to give compound 29-11 (7 g, 82% yield).

A mixture of compound 29-11 (7 g, 17.1 mmol), Pd(OAc)$_2$ (1.4 g), dppp (1.4 g) and $Et_3N$ (5.2 g, 51.3 mmol) in MeOH (80 mL) was stirred at 80° C. under CO with a pressure of 3 MPa for 2 d. The solid was filtered off and the filtrate was concentrated under reduced pressure. The residue was purified by chromatography on silica gel to give compound 29-12 (4.8 g, 88% yield).

To a solution of LiAlH$_4$ (1.1 g, 30.1 mmol) in THF (10 mL) was added dropwise the solution of compound 29-12 (4.8 g, 15.0 mmol) in THF (50 mL) at −50° C. over 30 min. After addition, the reaction mixture was stirred at 0° C. for 2.5 h. Then the reaction mixture was treated with $H_2O$ and DCM. The organic layer was separated, washed with brine, dried over $Na_2SO_4$, filtered and concentrated under reduced pressure. The residue was purified by chromatography on silica gel to give 29-13 (4.1 g, 92% yield).

Similarly, the bromide was prepared from 29-13 as described in Example 25 producing compound 29-14.

The following compounds from Table 1 are prepared according to the procedure described in Example 7a, using phenol, 2-8, bromide, 29-14, and other appropriate starting materials and purification conditions:

Compound 248: MS, electrospray, m/z=583.3 [M+H], RT 1.29 min (Method A2);
Compound 249: MS, electrospray, m/z=555.3 [M+H], RT 1.37 min (Method A2).

Example 30 tert-Butyl 8-cyano-6-(hydroxymethyl)-3,4-dihydroisoquinoline-2(1H)-carboxylate (30-12)

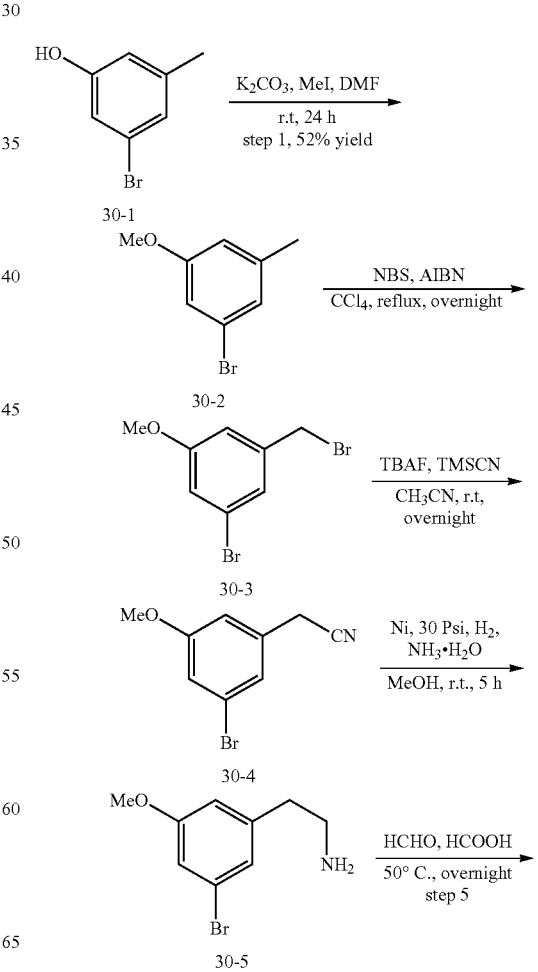

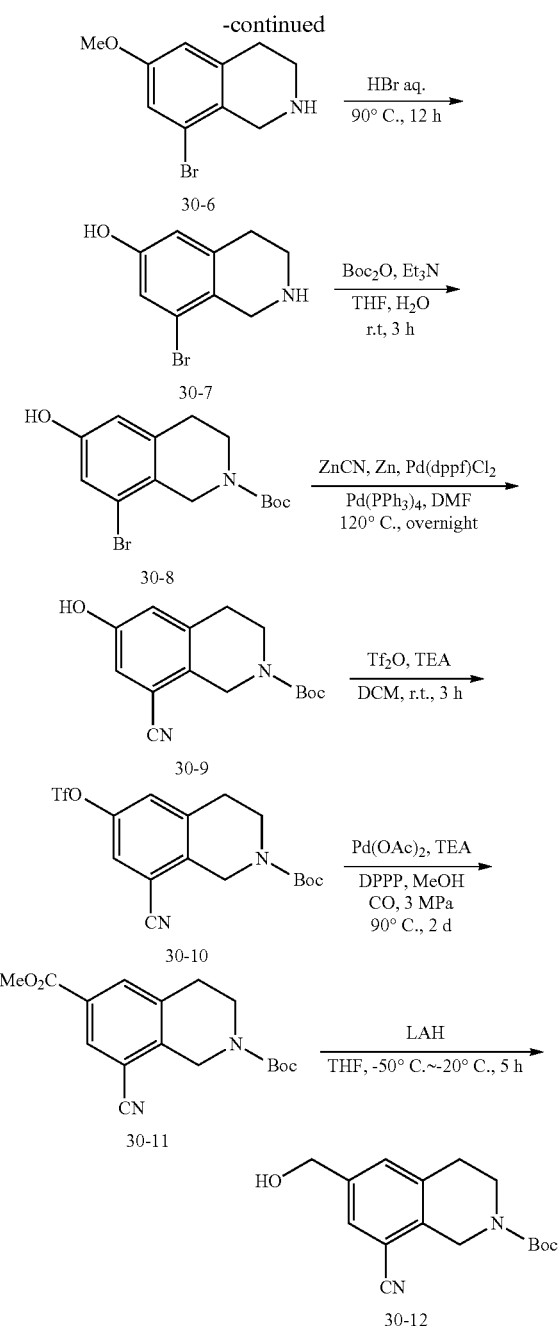

To the mixture of compound 30-1 (300 g, 1.6 mol) and K₂CO₃ (665 g, 4.8 mol) in DMF (2000 mL) was added MeI (250 g, 1.8 mol) dropwised at room temperature. The mixture was stirred overnight. TLC showed the reaction is completed. The reaction was quenched by H₂O and extracted with EtOAc. The organic layer was dried, filtered, evaporated under reduced pressure to give the crude product which was purified by chromatography on silica gel to give compound 30-2 (165 g, 52% yield).

The solution of compound 30-2 (100 g, 497.4 mmol), NBS (88.5 g, 497.4 mmol) and AIBN (10 g, 10%) in CCl₄ (700 mL) was heated to reflux for 12 h. TLC showed the reaction is completed. After cooling down to room temperature, the reaction was quenched by H₂O and extracted with EtOAc. The organic layer was dried, filtered and evaporated under reduced pressure to give the crude product which was purified by chromatography on silica gel to give compound 30-3 (48 g, 42% yield).

The solution of compound 30-3 (80 g, 285.7 mmol) and TMSCN (28.2 g, 285.7 mmol) in ACN (600 ml) was stirred at room temperature for 0.5 h. TBAF (74.6 g, 285.7 mmol) was added into the reaction mixture at ice based and the mixture was stirred for 12 h. TLC showed the reaction was completed. The reaction was quenched by H₂O and extracted with EtOAc. The organic layer was dried, filtered and evaporated under reduced pressure to give the crude product which was purified by chromatography on silica gel to give compound 30-4 (39 g, 60% yield).

The solution of compound 30-4 (12 g, 53.1 mmol) and Ni (10 g) in MeOH (80 ml) and NH₃.H₂O (80 ml) was stirred under H₂ with a pressure of 50 psi at room temperature for 5 h. TLC showed the reaction was completed. The mixture was filtered and the filtrate was concentrate on vacuum pump to give the crude product (8 g) which was used directly in the next step.

The solution of compound 30-5 (75 g, 326.08 mmol) and HCHO (8.8 g, 293.47 mmol) in HCO₂H (500 ml) was stirred at 50° C. under N₂ overnight. LCMS showed the reaction was completed. The solvent was removed under reduced pressure to give the crude product which was purified by chromatography on silica gel to give compound 30-6 (54 g, 64% yield for 2 steps).

The solution of compound 30-6 (45 g, 186 mmol) in aqueous HBr solution (400 ml) was stirred at 90° C. for 12 h. LCMS showed the reaction was completed. The solvent was removed under reduced pressure to give the crude product which was purified by chromatography on silica gel to give compound 30-7 (20.75 g, 53% yield).

The solution of compound 30-7 (20 g, 87.7 mmol), Boc₂O (19.1 g, 87.7 mmol) and TEA (17.7 g, 175.4 mmol) in THF/H₂O (1:1) (200 ml) was stirred at room temperature for 3 h. TLC showed the reaction is completed. The reaction was quenched by H₂O and extracted with EtOAc. The organic layer was dried, filtered and evaporated under reduced pressure to give the crude product which was purified by chromatography on silica gel to give compound 30-8 (20 g, 70% yield).

A solution of compound 30-8 (11 g, 34.8 mmol), Pd(dppf)Cl₂ (2.5 g), Pd (PPh₃)₄ (2.5 g), ZnCN (2.8 g, 31.3 mmol), Zn (1.1 g, 17.4 mmol) in DMF (110 ml) was stirred at reflux overnight. TLC showed the reaction was completed. After filtration, the filtrate was concentrate under reduced pressure and the residue was purified by chromatography on silica gel to give compound 30-9 (6.5 g, 71% yield).

The solution of compound 30-9 (12 g, 43.7 mmol), Tf₂O (12.3 g, 43.7 mmol) and TEA (13.3 g, 131.23 mmol) in DCM (120 ml) was stirred at room temperature for 3 h. TLC showed the reaction was completed. The reaction was quenched by H₂O and extracted with EtOAc. The organic layer was dried, filtered and evaporated under reduced pressure to give the crude product which was purified by chromatography on silica gel to give compound 30-10 (9 g, 51% yield).

A mixture of compound 30-10 (9.5 g, 23.4 mmol), Pd(OAc)₂ (1.9 g), dppp (1.9 g) and Et₃N (7.1 g, 70.1 mmol) in MeOH (90 mL) was stirred at 80° C. under CO with a pressure of 3 MPa for 2 d. The solid was filtered off and the filtrate was concentrated under reduced pressure. The residue was purified by chromatography on silica gel to give compound 30-11 (6 g, 80% yield).

To a solution of LiAlH₄ (1.4 g, 37.9 mmol) in THF (10 mL) was added dropwise the solution of compound 30-11 (6 g, 19.0 mmol) in THF (50 mL) at −50° C. over 30 min. After addition, the reaction mixture was stirred at −20° C. for 4.5 h. Then the reaction mixture was treated with $H_2O$ and DCM. The organic layer was separated, washed with brine, dried over $Na_2SO_4$, filtered and concentrated under reduced pressure. The residue was purified by chromatography on silica gel to give 30-12 (4.1 g, 74% yield).

Similarly, the bromide was prepared from 30-12 as described in Example 25 producing compound 30-13.

The following compound from Table 1 is prepared according to the procedure described in Example 7a, using phenol, 2-8, bromide, 30-13, and other appropriate starting materials and purification conditions:
Compound 250: MS, electrospray, m/z=580.2 [M+H], RT 0.61 min.

Assessment of Biological Activity

Cellular Assay

The sGC cellular activator assay is performed in the presence and absence of 50% human serum (HS) using Chinese hamster ovary cells that have been stably transfected to express the human soluble guanylate cyclase alpha 1 and beta 1 subunits (sGC). Cells are preincubated with 40 microM 1H-[1,2,4]oxadiazolo[4,3-a]quinoxalin-1-one (ODQ), an sGC inhibitor, for one h in buffer containing 0.1% bovine serum albumin and 3-isobutyl-1-methylxanthine (IBMX). Concentration response curves are prepared for test compounds in DMSO. An intermediate dilution of the compounds is performed in either buffer containing IBMX or type AB HS containing IBMX. Diluted compounds are added to cells and they are incubated at room temperature for thirty min. cGMP is measured using a CisBio homogeneous time resolved fluorescence kit and the $EC_{50}$ is calculated for each compound.

Representative compounds of the present invention were tested for activity the above assay. Preferred compounds have an $EC_{50}$ of <1,000 nM in the above assay and more preferred compounds have an $EC_{50}$<200 nM. As examples, data for representative compounds from Table 1 are shown in Table 2.

TABLE 2

| Compound Number | $EC_{50}$ (nM) |
|---|---|
| 1 | 39 |
| 2 | 11 |
| 3 | 29 |
| 4 | 11 |
| 5 | 9. |
| 6 | 87 |
| 7 | 32 |
| 8 | 42 |
| 9 | 59 |
| 10 | 16 |
| 11 | 17 |
| 12 | 26 |
| 13 | 180 |
| 14 | 18 |
| 15 | 28 |
| 16 | 23 |
| 17 | 18 |
| 18 | 8 |
| 19 | 17 |
| 20 | 24 |
| 21 | 17 |
| 22 | 14 |
| 23 | 52 |
| 24 | 54 |
| 25 | 16 |
| 26 | 5 |
| 27 | 14 |
| 28 | 13 |
| 29 | 3.5 |

TABLE 2-continued

| Compound Number | $EC_{50}$ (nM) |
|---|---|
| 30 | 10 |
| 31 | 19 |
| 32 | 170 |
| 33 | 97 |
| 34 | 65 |
| 35 | 29 |
| 36 | 27 |
| 37 | 120 |
| 38 | 66 |
| 39 | 17 |
| 40 | 62 |
| 41 | 27 |
| 42 | 24 |
| 43 | 130 |
| 44 | 44 |
| 45 | 26 |
| 46 | 38 |
| 47 | 22 |
| 48 | 10 |
| 49 | 54 |
| 50 | 990 |
| 51 | 72 |
| 52 | 170 |
| 53 | 110 |
| 54 | 110 |
| 55 | 110 |
| 56 | 820 |
| 57 | 24 |
| 58 | 82 |
| 59 | 31 |
| 60 | — |
| 61 | 59 |
| 62 | 24 |
| 63 | 82 |
| 64 | 71 |
| 65 | 56 |
| 66 | 110 |
| 67 | 320 |
| 68 | 38 |
| 69 | 61 |
| 70 | 180 |
| 71 | 67 |
| 72 | 17 |
| 73 | 250 |
| 74 | 73 |
| 75 | 23 |
| 76 | 160 |
| 77 | 31 |
| 78 | 48 |
| 79 | 33 |
| 80 | 45 |
| 81 | 410 |
| 82 | 8 |
| 83 | 29 |
| 84 | 9 |
| 85 | 22 |
| 86 | 41 |
| 87 | 55 |
| 88 | 28 |
| 89 | 150 |
| 90 | 69 |
| 91 | 75 |
| 92 | 20 |
| 93 | 37 |
| 94 | 45 |
| 95 | 54 |
| 96 | 24 |
| 97 | 67 |
| 98 | 270 |
| 99 | 160 |
| 100 | 170 |
| 101 | 110 |
| 102 | 110 |
| 103 | 110 |
| 104 | 31 |
| 105 | 17 |
| 106 | 27 |
| 107 | 23 |

TABLE 2-continued

| Compound Number | EC$_{50}$ (nM) |
|---|---|
| 108 | 24 |
| 109 | 34 |
| 110 | 45 |
| 111 | 99 |
| 112 | 110 |
| 113 | 24 |
| 114 | 40 |
| 115 | 68 |
| 116 | 28 |
| 117 | 29 |
| 118 | 39 |
| 119 | 57 |
| 120 | 12 |
| 121 | 40 |
| 122 | 23 |
| 123 | 55 |
| 124 | 47 |
| 125 | 27 |
| 126 | 58 |
| 127 | 7.5 |
| 128 | 15 |
| 129 | 17 |
| 130 | 21 |
| 131 | 410 |
| 132 | 11 |
| 133 | 27 |
| 134 | 46 |
| 135 | 54 |
| 136 | 81 |
| 137 | 89 |
| 138 | 54 |
| 139 | 8.4 |
| 140 | 15 |
| 141 | 17 |
| 142 | 62 |
| 143 | 160 |
| 144 | 460 |
| 145 | 13 |
| 146 | 23 |
| 147 | 450 |
| 148 | 43 |
| 149 | 44 |
| 150 | 91 |
| 151 | 130 |
| 152 | 14 |
| 153 | 26 |
| 154 | 28 |
| 155 | 86 |
| 156 | 720 |
| 157 | 25 |
| 158 | 30 |
| 159 | 53 |
| 160 | 110 |
| 161 | 14 |
| 162 | 23 |
| 163 | 55 |
| 164 | 32 |
| 165 | 11 |
| 166 | 6.6 |
| 167 | 30 |
| 168 | 580 |
| 169 | 13 |
| 170 | 28 |
| 171 | 16 |
| 172 | 50 |
| 173 | 13 |
| 174 | 14 |
| 175 | 40 |
| 176 | 9.7 |
| 177 | 35 |
| 178 | 14 |
| 179 | 59 |
| 180 | 28 |
| 181 | 62 |
| 182 | 370 |
| 183 | 980 |
| 184 | 12 |
| 185 | 30 |
| 186 | 16 |
| 187 | 14 |
| 188 | 8.6 |
| 189 | 12 |
| 190 | 23 |
| 191 | 3.3 |
| 192 | 10 |
| 193 | 12 |
| 194 | 87 |
| 195 | 4.7 |
| 196 | 13 |
| 197 | 19 |
| 198 | 5.3 |
| 199 | 9 |
| 200 | 20 |
| 201 | 12 |
| 202 | 12 |
| 203 | 4.4 |
| 204 | 4.5 |
| 205 | 13 |
| 206 | 7.4 |
| 207 | 9.2 |
| 208 | 20 |
| 209 | 200 |
| 210 | 19 |
| 211 | 30 |
| 212 | 36 |
| 213 | 39 |
| 214 | 30 |
| 215 | 37 |
| 216 | 110 |
| 217 | 35 |
| 218 | 62 |
| 219 | 140 |
| 220 | 150 |
| 221 | 210 |
| 222 | 5.4 |
| 223 | 8.5 |
| 224 | 79 |
| 225 | 10 |
| 226 | 12 |
| 227 | 13 |
| 228 | 14 |
| 229 | 3.9 |
| 230 | 13 |
| 231 | 4.6 |
| 232 | 9.5 |
| 233 | 11 |
| 234 | 13 |
| 235 | 20 |
| 236 | 28 |
| 237 | 4.9 |
| 238 | 5.1 |
| 239 | 6.5 |
| 240 | 7.9 |
| 241 | 8 |
| 242 | 11 |
| 243 | 16 |
| 244 | 23 |
| 245 | 280 |
| 246 | 6.5 |
| 247 | 8.6 |
| 248 | 4.2 |
| 249 | 4.6 |
| 250 | 44 |
| 251 | 7 |
| 252 | 10 |
| 253 | 13 |
| 254 | 25 |
| 255 | 9.5 |
| 256 | 14 |
| 257 | 14 |
| 258 | 15 |

Assessment of Solubility

Solubility is measured by the following method.

1. Sample Preparation:

100 uL, 10 mM DMSO stock solution of each compound is prepared in a 96 well plate format. The experiment is done in single determination at 3 pH values (2.2, 4.5 and 6.8). For each pH and one reference, 40 uL of each compound is needed.

Buffer Preparation:

McIlvaine pH 2.2: To 2.076 g citric acid monohydrate and 0.043 g $Na_2HPO_4 \times 2H_2O$ add 100 ml deionized water McIlvaine pH 4.5: To 1.166 g citric acid monohydrate and 1.585 g $Na_2HPO_4 \times 2H_2O$ add 100 ml deionized water McIlvaine pH 6.8: To 0.476 g citric acid monohydrate and 2.753 g $Na_2HPO_4 \times 2H_2O$ add 100 ml deionized water With a suitable liquid handling device (Multipette® or a liquid handler) 390 uL of each buffer solution and 10 uL of compound is added to each well of a 96 deep well plate. The plates are covered firmly and shaken for 24 h on an over head shaker (at 54 RPM) at room temperature. The DMSO content in the final buffer is 2.5% v/v.

After 24 h the plates are centrifuged to remove droplets on the lid before opening (for ~5 min at 2500 RPM).

The filtration is done under vacuum with Millipore 96 well filter plate. Filtrate is collected in a deep well plate and transferred to a suitable plate for UPLC analysis.

The reference plate is prepared by adding 10 uL of compound to 390 uL of 50:50 acetonitrile/water in a 96 deep well plate and transferred to a suitable plate for UPLC analysis. Wells are checked visually for precipitation, any presence noted under comments in reported results.

2. Sample Measurement

The samples are measured with UPLC-UV using the chromatographic method described below.

| | |
|---|---|
| stationary phase | Waters ACQUITY UPLC ® BEH C18 |
| | 1.7 μm |
| | 2.5 × 50 mm |
| mobile phase | |
| solvent A | 0.1% formic acid (pH 3) |
| solvent B | acetonitrile with 0.1% formic acid |
| Gradient | |
| 0 min | 5% B |
| 1.0 min | 95% B |
| 1.3 min | 95% B |
| 1.4 min | 5% B |
| 1.7 min | 5% B |
| column temperature | 40° C. |
| Flow | 0.8 mL/min |
| duration/cycle time | 1.7 min/2.7 min |
| injection volume | 2 μL |
| sample temperature | 20° C. |
| PDA detection | Enable 3D data |
| wavelength | 254 nm |
| sampling rate | 40 points/sec |
| resolution | 4.8 nm |

Waters Empower®2 software is used for generating Sample Sets (according to the plate layout), Sample Set Methods and Instrument Methods.

One Sample Set comprises the methods for three 96 well plates (one reference plate and two sample plates, and includes one Sample Set Method and one Instrument Method).

3. Data Processing and Analysis

The UV chromatograms collected at 254 nm are integrated and processed.

It is assumed that the compound is completely dissolved in the reference solution (50:50 acetonitrile/water)

Solubility data (μg/mL) for compounds from Table 1 is shown in Table 3 below.

TABLE 3

| Compound Number | (pH 2.2) | (pH 4.5) | (pH 6.8) |
|---|---|---|---|
| 1 | 95 | 80 | 87 |
| 2 | 110 | 83 | 88 |
| 3 | 96 | 79 | 81 |
| 4 | 100 | 81 | 83 |
| 5 | 98 | 76 | 72 |
| 6 | 90 | 64 | 81 |
| 7 | 110 | 77 | 91 |
| 8 | 110 | 82 | 98 |
| 9 | 94 | 70 | 82 |
| 10 | 94 | 50 | 73 |
| 11 | 23 | <0.1 | 80 |
| 12 | 110 | 90 | 92 |
| 13 | 100 | 84 | 87 |
| 14 | 110 | 82 | 76 |
| 15 | 110 | 88 | 90 |
| 16 | 95 | 71 | 81 |
| 17 | 97 | 62 | 85 |
| 18 | 110 | 86 | 90 |
| 19 | 96 | 70 | 75 |
| 20 | 95 | 72 | 68 |
| 21 | 96 | 62 | 60 |
| 22 | 97 | 68 | 73 |
| 23 | 99 | 79 | 82 |
| 24 | 95 | 76 | 76 |
| 25 | 91 | 38 | 39 |
| 26 | 100 | 80 | 80 |
| 27 | 110 | 88 | 90 |
| 28 | 110 | 83 | 90 |
| 29 | 110 | 79 | 78 |
| 30 | 100 | 81 | 75 |
| 31 | 110 | 89 | 94 |
| 32 | 91 | 73 | 78 |
| 33 | 93 | 73 | 75 |
| 34 | 82 | 65 | 68 |
| 35 | 93 | 73 | 78 |
| 36 | 91 | 72 | 74 |
| 37 | 92 | 74 | 78 |
| 38 | 110 | 94 | 88 |
| 39 | 93 | 44 | 81 |
| 40 | 99 | 81 | 85 |
| 41 | 96 | 75 | 80 |
| 42 | 93 | 75 | 78 |
| 43 | 95 | 79 | 82 |
| 44 | 100 | 85 | 88 |
| 45 | 82 | 61 | 73 |
| 46 | 100 | 82 | 86 |
| 47 | 87 | 69 | 79 |
| 48 | 100 | 82 | 86 |
| 49 | 92 | 69 | 58 |
| 50 | 120 | 79 | 75 |
| 51 | 110 | 83 | 93 |
| 52 | 83 | 58 | 73 |
| 53 | 84 | 65 | 70 |
| 54 | 100 | 78 | 75 |
| 55 | 98 | 48 | 49 |
| 56 | 87 | 66 | 77 |
| 57 | 95 | 47 | 51 |
| 58 | 111 | 85 | 89 |
| 59 | — | — | — |
| 60 | 117 | 96 | 100 |
| 61 | 130 | 110 | 99 |
| 62 | 110 | 88 | 91 |
| 63 | 110 | 90 | 92 |
| 64 | 100 | 66 | 66 |
| 65 | 110 | 84 | 74 |
| 66 | 63 | 54 | 55 |
| 67 | 90 | 76 | 78 |
| 68 | 85 | 71 | 74 |
| 69 | 91 | 77 | 80 |
| 70 | 86 | 57 | 64 |
| 71 | 94 | 75 | 78 |

TABLE 3-continued

| Compound Number | (pH 2.2) | (pH 4.5) | (pH 6.8) |
|---|---|---|---|
| 72 | 44 | 46 | 67 |
| 73 | 86 | 67 | 71 |
| 74 | 110 | 83 | 95 |
| 75 | 120 | 93 | 90 |
| 76 | 100 | 86 | 89 |
| 77 | 96 | 83 | 87 |
| 78 | 100 | 86 | 89 |
| 79 | 100 | 87 | 89 |
| 80 | 110 | 94 | 95 |
| 81 | 100 | 84 | 79 |
| 82 | 120 | 100 | 97 |
| 83 | 110 | 88 | 95 |
| 84 | 110 | 86 | 89 |
| 85 | 120 | 96 | 110 |
| 86 | 110 | 90 | 91 |
| 87 | 110 | 87 | 90 |
| 88 | 90 | 63 | 75 |
| 89 | 130 | 92 | 81 |
| 90 | 100 | 81 | 81 |
| 91 | 100 | 81 | 81 |
| 92 | 110 | 93 | 96 |
| 93 | 98 | 77 | 81 |
| 94 | 91 | 68 | 73 |
| 95 | 100 | 80 | 84 |
| 96 | 93 | 67 | 75 |
| 97 | 91 | 72 | 77 |
| 98 | 150 | 110 | 99 |
| 99 | 150 | 120 | 110 |
| 100 | 110 | 88 | 97 |
| 101 | 90 | 73 | 74 |
| 102 | 99 | 81 | 82 |
| 103 | 96 | 78 | 81 |
| 104 | 110 | 93 | 97 |
| 105 | 93 | 72 | 75 |
| 106 | 88 | 69 | 73 |
| 107 | 73 | 54 | 58 |
| 108 | 81 | 61 | 65 |
| 109 | 88 | 33 | 36 |
| 110 | 130 | 96 | 120 |
| 111 | 87 | 69 | 75 |
| 112 | 110 | 78 | 94 |
| 113 | 94 | 80 | 84 |
| 114 | 120 | 99 | 100 |
| 115 | 89 | 71 | 43 |
| 116 | — | — | — |
| 117 | 102 | 82 | 85 |
| 118 | 110 | 84 | 92 |
| 119 | 110 | 89 | 97 |
| 120 | 110 | 94 | 97 |
| 121 | 110 | 90 | 93 |
| 122 | 100 | 86 | 82 |
| 123 | 100 | 76 | 73 |
| 124 | 100 | 8.6 | 44 |
| 125 | 110 | 76 | 78 |
| 126 | 96 | 74 | 78 |
| 127 | 130 | 100 | 110 |
| 128 | 93 | 77 | 78 |
| 129 | 95 | 79 | 79 |
| 130 | 130 | 100 | 110 |
| 131 | 130 | 97 | 110 |
| 132 | 130 | 110 | 110 |
| 133 | 120 | 99 | 100 |
| 134 | 110 | 94 | 100 |
| 135 | 110 | 97 | 100 |
| 136 | 120 | 100 | 110 |
| 137 | 110 | 98 | 110 |
| 138 | — | — | — |
| 139 | 130 | 110 | 120 |
| 140 | 140 | 120 | 120 |
| 141 | 130 | 110 | 110 |
| 142 | 120 | 87 | 93 |
| 143 | 160 | 150 | 160 |
| 144 | 110 | 89 | 93 |
| 145 | 110 | 92 | 94 |
| 146 | 100 | 88 | 79 |
| 147 | 1.2 | 3.1 | 75 |
| 148 | 110 | 100 | 94 |
| 149 | 110 | 78 | 81 |
| 150 | 100 | 67 | 78 |
| 151 | 110 | 98 | 85 |
| 152 | 97 | 74 | 74 |
| 153 | 87 | 67 | 65 |
| 154 | 85 | 36 | 57 |
| 155 | 60 | 66 | 73 |
| 156 | — | — | — |
| 157 | 94 | 70 | 62 |
| 158 | 64 | 43 | 41 |
| 159 | 86 | 55 | 51 |
| 160 | <0.1 | 0.93 | 73 |
| 161 | 110 | 91 | 97 |
| 162 | 100 | 83 | 82 |
| 163 | 110 | 75 | 73 |
| 164 | 100 | 72 | 93 |
| 165 | 120 | 58 | 39 |
| 166 | 110 | 51 | 64 |
| 167 | 2.1 | 5.9 | 83 |
| 168 | 110 | 90 | 88 |
| 169 | 120 | 100 | 97 |
| 170 | 120 | 96 | 95 |
| 171 | 120 | 99 | 98 |
| 172 | 110 | 87 | 85 |
| 173 | 130 | 98 | 97 |
| 174 | 99 | 71 | 91 |
| 175 | 110 | 80 | 85 |
| 176 | 100 | 77 | 43 |
| 177 | 110 | 58 | 86 |
| 178 | 100 | 72 | 86 |
| 179 | 43 | 92 | 93 |
| 180 | 100 | 79 | 76 |
| 181 | 110 | 87 | 88 |
| 182 | 110 | 81 | 81 |
| 183 | 110 | 82 | 87 |
| 184 | 89 | 76 | 76 |
| 185 | 100 | 83 | 82 |
| 186 | 110 | 83 | 99 |
| 187 | 100 | 82 | 83 |
| 188 | 89 | 77 | 73 |
| 189 | 89 | 73 | 75 |
| 190 | 100 | 83 | 87 |
| 191 | 100 | 85 | 80 |
| 192 | — | — | — |
| 193 | 100 | 80 | 73 |
| 194 | 0.68 | 2.5 | 78 |
| 195 | 110 | 83 | 80 |
| 196 | 89 | 77 | 85 |
| 197 | 110 | 83 | 79 |
| 198 | 120 | 100 | 93 |
| 199 | 120 | 96 | 92 |
| 200 | 100 | 73 | 73 |
| 201 | 87 | 68 | 66 |
| 202 | 92 | 73 | 70 |
| 203 | 81 | 70 | 72 |
| 204 | 82 | 72 | 73 |
| 205 | 99 | 73 | 81 |
| 206 | 90 | 71 | 76 |
| 207 | 82 | 68 | 73 |
| 208 | 82 | 47 | 57 |
| 209 | 110 | 81 | 84 |
| 210 | 110 | 87 | 87 |
| 211 | 95 | 82 | 78 |
| 212 | 92 | 79 | 75 |
| 213 | 85 | 66 | 72 |
| 214 | 81 | 64 | 69 |
| 215 | 86 | 70 | 76 |
| 216 | — | — | — |
| 217 | 97 | 73 | 69 |
| 218 | 120 | 85 | 75 |
| 219 | 110 | 76 | 74 |
| 220 | 100 | 77 | 86 |
| 221 | 100 | 72 | 94 |
| 222 | 85 | 71 | 73 |
| 223 | 81 | 68 | 69 |
| 224 | 110 | 78 | 13 |
| 225 | 95 | 78 | 81 |

TABLE 3-continued

| Compound Number | (pH 2.2) | (pH 4.5) | (pH 6.8) |
|---|---|---|---|
| 226 | 98 | 83 | 86 |
| 227 | 90 | 73 | 77 |
| 228 | 96 | 78 | 81 |
| 229 | 100 | 81 | 73 |
| 230 | 100 | 84 | 72 |
| 231 | 120 | 92 | 87 |
| 232 | 93 | 74 | 63 |
| 233 | 98 | 73 | 86 |
| 234 | 120 | 97 | 91 |
| 235 | 100 | 83 | 88 |
| 236 | 110 | 96 | 83 |
| 237 | 94 | 55 | 52 |
| 238 | 77 | 55 | 52 |
| 239 | 91 | 71 | 72 |
| 240 | 92 | 69 | 67 |
| 241 | 100 | 81 | 84 |
| 242 | 110 | 79 | 78 |
| 243 | 100 | 82 | 81 |
| 244 | 120 | 99 | 98 |
| 245 | 100 | 79 | 92 |
| 246 | — | — | — |
| 247 | 90 | 75 | 71 |
| 248 | 94 | 75 | 74 |
| 249 | 94 | 67 | 93 |
| 250 | 110 | 81 | 86 |
| 251 | 100 | 72 | 77 |
| 252 | 94 | 73 | 62 |
| 253 | 100 | 75 | 81 |
| 254 | 100 | 64 | 80 |
| 255 | — | — | — |
| 256 | — | — | — |
| 257 | — | — | — |
| 258 | — | — | — |

Assessment of Metabolic Stability

Objective

The 5 time point, high-throughput human liver microsome (HLM) metabolic stability assay is designed to determine in vitro compound metabolism. Compounds are incubated with HLMs at a concentration of 1 uM, at 37° C., for a total of 60 min. The percent of compound remaining at 5, 15, 30, and 60 min is used to calculate the t½ (min), $CL_{int}$ (mL/min/kg), $CL_h$ (mL/min/kg), and % $Q_h$. The assay is based on a 96-well format and can accommodate up to 92 compounds per plate (n=1).

Incubation

Using the 96-well multi-channel head, the Biomek FX, equipped with a Peltier heating block/shaker, is programmed to accomplish the following steps:
 1. Pipette 175 uL of 1.15 mg/mL microsomes into each of the 96 conical inserts (Analytical Sales and Products, catalog number 96PL05) that fit into the plate of the Peltier heating block/shaker (the incubation plate)
 2. Add 5 uL of compounds from the assay plate to the microsomes and shake the mixture at 600 rpm at 42.1° C. for 10 min (a setting of 42.1° C. on the Peltier is required for the samples to incubate at 37° C.)
 3. After 10 min, prompt the user to add the NADPH plate to the deck and add 20 uL from the NADPH plate to the incubation plate to start the reaction
 4. Add 215 uL of 100%, cold acetonitrile containing an internal standard(s) to a 0 minute, 5 minute, 15 minute, 30 minute, and 60 minute "quench" plate
 5. At 0 min, 5 min, 15 min, 30 min, and 60 min into the incubation, aspirate 12 uL from the incubation mixture and add it to the quench solution to stop the reaction
 6. Add 185 uL HPLC grade water to each well of the 0, 5, 15, 30 and 60 minute quench plates to dilute compounds to the appropriate concentration for the mass spectrometer After all time points are collected, the quench plates are sealed with 96-well pierceable plate mats or heat sealing foil and centrifuged at 3000 rpm for 15 min to pellet the microsomes.

Analysis

The plates are analyzed using LC/MS/MS with electron spray ionization (ESI) and the previously determined MRM transitions. The LC method includes the following parameters:

Injection volume: 5 uL
Mobile Phases: 0.1% Formic Acid in Water (A) and 0.1% Formic Acid in Acetonitrile (B) (HPLC grade)
Left and Right Temperature: 35° C.
Run Time: 4.0 min
Column: Thermo Scientific, Aquasil C18, 50×2.1 mm, 5μ, part number 77505-052130, or equivalent
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

If peak shape is poor and cannot be integrated properly, the following LC method can be used:

Injection volume: 5 uL
Mobile Phases: 2.5 mM Ammonium Bicarbonate (A) and 100% Acetonitrile (B) (HPLC grade)
Aqueous Wash: 90% Water, 10% Acetonitrile (HPLC grade)
Organic Wash: 90% Acetonitrile, 10% Water (HPLC grade)
Left and Right Temperature: 35° C.
Run Time: 4.5 min
Column: Phenomex Luna 3 u C18(2) 100 A, 50×2.00 mm
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.30 | 500 | 90.0 | 10.0 |
| 4.50 | 500 | 90.0 | 10.0 |

Using an Excel template in Activitybase, the peak areas corresponding to 5, 15, 30 and 60 min are compared to the peak area at 0 min to calculate the percent of remaining compound using the following equation:

Percent compound remaining=($AUC$ at Time $t$ min/$AUC$ at Time 0 min)×100 where $t$=0, 5, 15, 30 or 60 min.

Time (min) is plotted against the natural logarithm (Ln) of the percent compound remaining to determine the slope. The slope is used to calculate t½ (min) using the equation, t½=0.693/slope.

Clint, Intrinsic Clearance 0.693/$t^{1/2}$*Avg liver wt in g/avg body wt in kg*$f(u)$/
protein concentration in incubation in
mg/mL*mg microsomal protein/g liver 0.693/$t^{1/2}$*26 g/kg*1/1.0 mg/mL*45 mg/g Clh, Hepatic Clearance Hepatic flow*$f(u)$*Clint/(hepatic flow+$f(u)$*Clint)

Qh, % Hepatic Blood Flow (Clh/Hepatic flow)*100

Metabolic stability data (% Qh) for compounds from Table 1 is shown in Table 4 below. Preferred compounds have % Qh values of less than 24.

TABLE 4

| Compound Number. | HLM (% Qh) |
| --- | --- |
| 1 | <24 |
| 2 | <24 |
| 3 | <24 |
| 4 | <24 |
| 5 | <24 |
| 6 | <24 |
| 7 | <24 |
| 8 | <24 |
| 9 | <24 |
| 10 | 30 |
| 11 | 47 |
| 12 | <24 |
| 13 | <24 |
| 14 | 31 |
| 15 | <24 |
| 16 | <24 |
| 17 | 31 |
| 18 | <24 |
| 19 | 29 |
| 20 | 38 |
| 21 | <24 |
| 22 | 33 |
| 23 | <24 |
| 24 | <24 |
| 25 | 29 |
| 26 | 29 |
| 27 | <24 |
| 28 | <24 |
| 29 | 28 |
| 30 | <24 |
| 31 | <24 |
| 32 | <24 |
| 33 | <24 |
| 34 | <24 |
| 35 | <24 |
| 36 | <24 |
| 37 | <24 |
| 38 | <24 |
| 39 | <24 |
| 40 | <24 |
| 41 | <24 |
| 42 | <24 |
| 43 | 26 |
| 44 | <24 |
| 45 | <24 |
| 46 | <24 |
| 47 | <24 |
| 48 | <24 |
| 49 | 48 |
| 50 | 40 |
| 51 | <24 |
| 52 | <24 |
| 53 | <24 |
| 54 | <24 |
| 55 | <24 |
| 56 | <24 |
| 57 | <24 |
| 58 | <24 |

TABLE 4-continued

| Compound Number. | HLM (% Qh) |
| --- | --- |
| 59 | <24 |
| 60 | <24 |
| 61 | <24 |
| 62 | <24 |
| 63 | <24 |
| 64 | <24 |
| 65 | <24 |
| 66 | <24 |
| 67 | <24 |
| 68 | <24 |
| 69 | <24 |
| 70 | <24 |
| 71 | <24 |
| 72 | 47 |
| 73 | 36 |
| 74 | <24 |
| 75 | 31 |
| 76 | <24 |
| 77 | <24 |
| 78 | <24 |
| 79 | <24 |
| 80 | <24 |
| 81 | <24 |
| 82 | <24 |
| 83 | <24 |
| 84 | <24 |
| 85 | <24 |
| 86 | <24 |
| 87 | <24 |
| 88 | <24 |
| 89 | 76 |
| 90 | <24 |
| 91 | <24 |
| 92 | <24 |
| 93 | <24 |
| 94 | <24 |
| 95 | <24 |
| 96 | 30 |
| 97 | <24 |
| 98 | 31 |
| 99 | <24 |
| 100 | 31 |
| 101 | <24 |
| 102 | <24 |
| 103 | 25 |
| 104 | 26 |
| 105 | <24 |
| 106 | <24 |
| 107 | <24 |
| 108 | <24 |
| 109 | <24 |
| 110 | <24 |
| 111 | <24 |
| 112 | <24 |
| 113 | <24 |
| 114 | <24 |
| 115 | 25 |
| 116 | <24 |
| 117 | 25 |
| 118 | <24 |
| 119 | <24 |
| 120 | <24 |
| 121 | <24 |
| 122 | <24 |
| 123 | <24 |
| 124 | <24 |
| 125 | <24 |
| 126 | <24 |
| 127 | <24 |
| 128 | <24 |
| 129 | <24 |
| 130 | 25 |
| 131 | 28 |
| 132 | <24 |
| 133 | <24 |
| 134 | 32 |
| 135 | 29 |
| 136 | <24 |

TABLE 4-continued

| Compound Number. | HLM (% Qh) |
|---|---|
| 137 | <24 |
| 138 | 68 |
| 139 | <24 |
| 140 | <24 |
| 141 | <24 |
| 142 | <24 |
| 143 | <24 |
| 144 | <24 |
| 145 | <24 |
| 146 | <24 |
| 147 | <24 |
| 148 | <24 |
| 149 | <24 |
| 150 | <24 |
| 151 | <24 |
| 152 | <24 |
| 153 | <24 |
| 154 | <24 |
| 155 | <24 |
| 156 | <24 |
| 157 | 31 |
| 158 | <24 |
| 159 | <24 |
| 160 | 44 |
| 161 | <24 |
| 162 | 26 |
| 163 | <24 |
| 164 | <24 |
| 165 | <24 |
| 166 | 27 |
| 167 | <24 |
| 168 | <24 |
| 169 | <24 |
| 170 | <24 |
| 171 | <24 |
| 172 | <24 |
| 173 | <24 |
| 174 | <24 |
| 175 | 31 |
| 176 | 28 |
| 177 | <24 |
| 178 | <24 |
| 179 | <24 |
| 180 | <24 |
| 181 | <24 |
| 182 | <24 |
| 183 | <24 |
| 184 | <24 |
| 185 | <24 |
| 186 | <24 |
| 187 | <24 |
| 188 | <24 |
| 189 | 26 |
| 190 | 43 |
| 191 | <24 |
| 192 | <24 |
| 193 | <24 |
| 194 | <24 |
| 195 | <24 |
| 196 | <24 |
| 197 | <24 |
| 198 | <24 |
| 199 | <24 |
| 200 | 40 |
| 201 | <24 |
| 202 | <24 |
| 203 | <24 |
| 204 | <24 |
| 205 | <24 |
| 206 | <24 |
| 207 | <24 |
| 208 | <24 |
| 209 | <24 |
| 210 | <24 |
| 211 | <24 |
| 212 | <24 |
| 213 | <24 |
| 214 | <24 |
| 215 | <24 |
| 216 | <24 |
| 217 | 89 |
| 218 | 89 |
| 219 | 89 |
| 220 | <24 |
| 221 | <24 |
| 222 | <24 |
| 223 | <24 |
| 224 | <24 |
| 225 | <24 |
| 226 | 52 |
| 227 | 25 |
| 228 | 44 |
| 229 | 34 |
| 230 | <24 |
| 231 | <24 |
| 232 | <24 |
| 233 | 26 |
| 234 | <24 |
| 235 | 29 |
| 236 | <24 |
| 237 | <24 |
| 238 | <24 |
| 239 | 25 |
| 240 | <24 |
| 241 | <24 |
| 242 | <24 |
| 243 | <24 |
| 244 | <24 |
| 245 | <24 |
| 246 | <24 |
| 247 | <24 |
| 248 | <24 |
| 249 | <24 |
| 250 | <24 |
| 251 | <24 |
| 252 | <24 |
| 253 | <24 |
| 254 | <24 |
| 255 | <24 |
| 256 | <24 |
| 257 | <24 |
| 258 | <24 |

Methods of Therapeutic Use

The compounds disclosed herein effectively activate soluble guanylate cyclase. The activation or potentiation of soluble guanylate cyclase is an attractive means for preventing and treating a variety of diseases or conditions associated with deficient sGC activation. Thus, in one embodiment of the invention, there are provided methods of treating diseases that can be alleviated by sGC activation or potentiation. These include:

Cardiovascular and related diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina and thromboembolic disorders;

Inflammatory diseases including psoriasis, multiple sclerosis, arthritis, asthma, and chronic obstructive pulmonary disease;

Hepatic fibrotic disorders including but not limited to cirrhosis of any etiology or fibrosis of specific areas of the liver such as periportal fibrosis which may be caused by immunologic injury, hemodynamic effects and/or other causes;

Renal fibrotic disorders including but not limited to glomerulosclerosis, focal glomerulosclerosis, mesangial fibrosis, interstitial fibrosis due to immunologic injury, hemodynamic effects, diabetes (types I and 2), diabetic nephropathy, IgA nephropathy, lupus nephropathy, membranous nephropathy, hypertension, hemolytic uremic syndrome, multiple glomerulonephritides, interstitial nephritis, tubulointerstitial nephritis again of immunologic and non-immunologic causes;

Pulmonary fibrotic disorders, both diffuse and localized, due to immunologic and non-immunologic causes, including but not limited to idiopathic pulmonary fibrosis, pulmonary fibrosis due to exposure to toxins, chemicals, drugs, and cystic fibrosis;

Cardiac fibrotic disorders due to immunologic and non-immunologic causes including ischemic heart disease (coronary artery disease) and transient and/or sustained decreased blood flow in one or more coronary vessels including possibly related to interventions on coronary arteries or veins, associated with cardiac surgery and/or the use of cardiopulmonary bypass procedures and myocarditis due to viral and non-viral causes, as well as immunologically related myocardial injury potentially due to cross-reactivity to other antigens to which the human body is exposed;

Other diseases mediated at least partially by diminished or decreased soluble guanylate cyclase activity, such as renal disease, diabetes, urologic disorders including overactive bladder, benign prostatic hyperplasia, and erectile dysfunction, and neurological disorders including Alzheimer's disease, Parkinson's disease and neuropathic pain.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner.

Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I

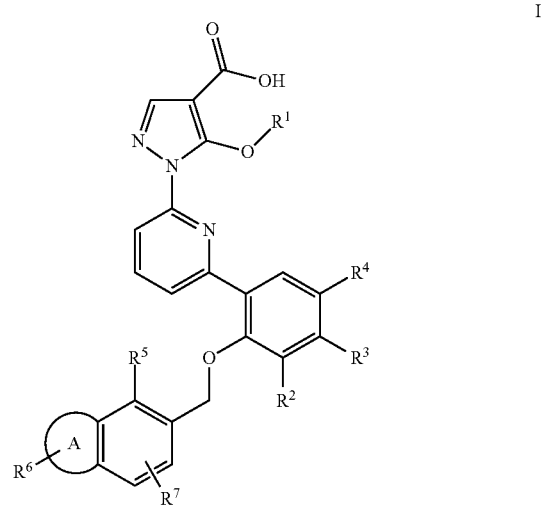

wherein:

A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;

$R^1$ is $C_{1-4}$ alkyl optionally substituted with a methoxy group;

$R^2$ is selected from H, F, Cl, $C_{1-3}$alkyl, —CN, —OMe and —$CF_3$;

$R^3$ is selected from H and —$CH_3$;

$R^4$ is selected from H, F, —$CH_3$ and —OMe;

$R^5$ is selected from H, Cl, —$CH_3$, —$CH_2CH_3$, —$CF_3$, F, and —OMe;

$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl —$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}O(CH_2)_{2-3}OH$, and —$SO_2CH_3$;

$R^7$ is selected from H, —$CH_3$, —$CH_2CH_3$, —$CF_3$, F, and —CN;

n is 0, 1 or 2 or a salt thereof.

2. The compound according to claim 1, wherein:

A is a 5-7 membered saturated heterocyclyl group containing one nitrogen, wherein one carbon of said heterocyclyl group is optionally substituted with one or two $C_{1-3}$alkyl groups;

$R^1$ is $C_{1-3}$alkyl;

$R^4$ is selected from H and F;

$R^5$ is selected from H, Cl and —$CH_3$;

$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl and —$(CH_2)_n$ heteroaryl, wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH and —$SO_2CH_3$; and $R^7$ is H;

or a salt thereof.

3. The compound according to claim 1, wherein:

$R^1$ is methyl, ethyl or isopropyl; and the group

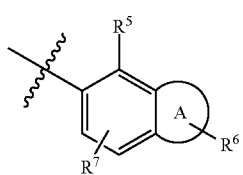

is selected from:

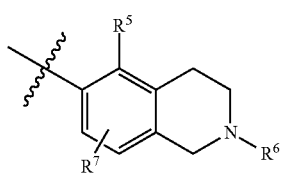,

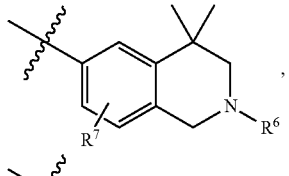,

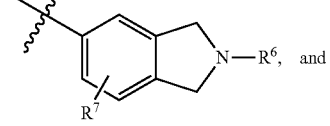, and

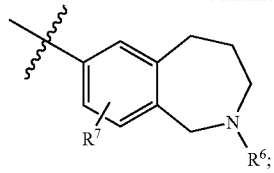;

or a salt thereof.

4. The compound according to claim 1, wherein:

$R^2$ is selected from —$CH_3$, F, Cl, and —$CF_3$; and $R^6$ is selected from H, $C_{1-6}$alkyl, —$(CH_2)_nC_{3-6}$cycloalkyl, —$C(O)C_{1-6}$alkyl and —$(CH_2)_n$ heterocyclyl, wherein said $C_{1-6}$alkyl, —$(CH_2)_n$ cycloalkyl and —$(CH_2)_n$ heterocyclyl are optionally substituted with one to four groups independently selected from $C_{1-3}$alkyl, halogen, $C_{1-3}$alkoxy, —$CF_3$, —OH and —$SO_2CH_3$;

or a salt thereof.

5. The compound according to claim 1, wherein each heterocyclyl referred to in $R^6$ is selected from oxetanyl, tetrahydrofuranyl, tetrahydropyranyl, 2-oxabicyclo[3.2.0]heptanyl, [1,4]dioxanyl, 8-oxabicyclo [3.2.1]octanyl, 1-oxaspiro[4.5]decanyl and pyrrolidin-2-one;

each heteroaryl referred to in $R^6$ is selected from imidazolyl, isoxazolyl, pyrazinyl, pyrazolyl, pyridinyl, pyrimidinyl, thiazolyl and 4,5,6,7-tetrahydrobenzothiazolyl;

and each aryl referred to in $R^6$ is phenyl;

or a salt thereof.

6. The compound according to claim 1, wherein:

$R^6$ is —$(CH_2)_n$ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a salt thereof.

7. The compound according to claim 1, wherein:

$R^2$ is —$CH_3$;

$R^3$ is H;

$R^4$ is H or —$CH_3$;

$R^5$ is H, or —$CH_3$;

$R^7$ is in the position para to $R^5$ and is H, —$CH_3$ or —$CH_2CH_3$;

or a salt thereof.

8. The compound according to claim 1, wherein:

the group

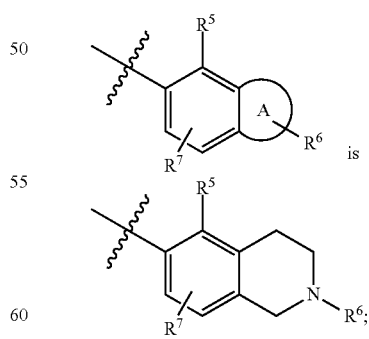

or a salt thereof.

9. The compound according to claim 1, wherein:

$R^3$ is H; and $R^4$ is H;

or a salt thereof.

10. The compound according to claim 1 selected from the group consisting of
| Cpd No. | Structure |
|---|---|
| 1 | 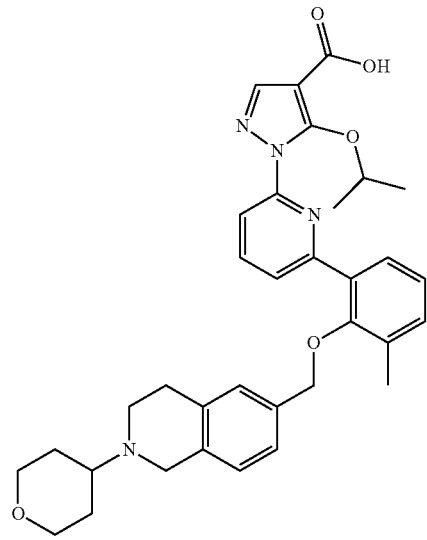 |
| 2 | 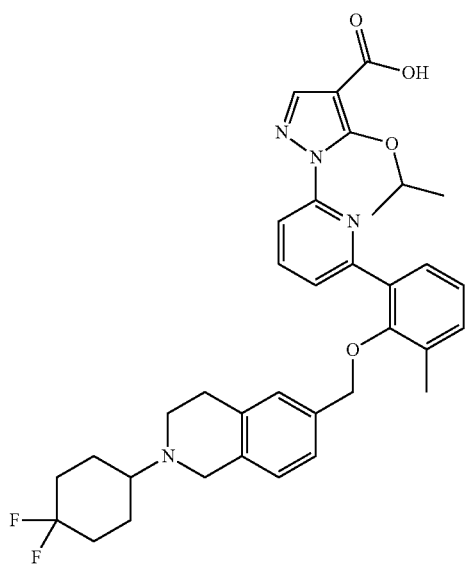 [SMILES: Cc1cccc(-c2cccc(-n3ncc(C(=O)O)c3OC(C)C)n2)c1OCc1ccc2c(c1)CCN(C1CCC(F)(F)CC1)C2] |
-continued
| Cpd No. | Structure |
|---|---|
| 3 | 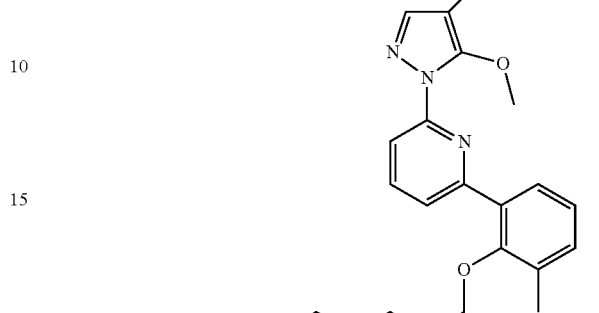 |
| 4 | 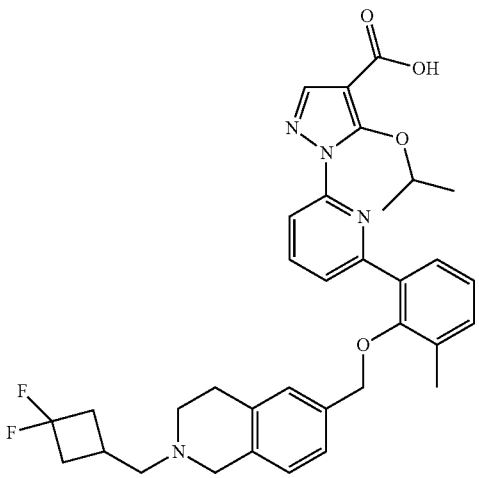 [SMILES: Cc1cccc(-c2cccc(-n3ncc(C(=O)O)c3OC(C)C)n2)c1OCc1ccc2c(c1)CCN(CC1CC(F)(F)C1)C2] |
| 5 | 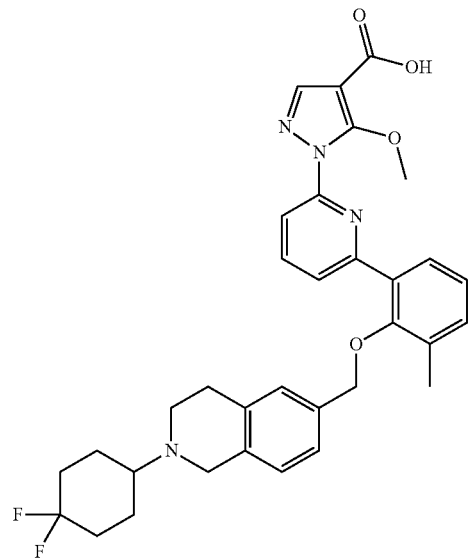 [SMILES: COc1c(C(=O)O)cnn1-c1cccc(-c2cccc(C)c2OCc2ccc3c(c2)CCN(C2CCC(F)(F)CC2)C3)n1] |

-continued
| Cpd No. | Structure |
|---|---|
| 6 | 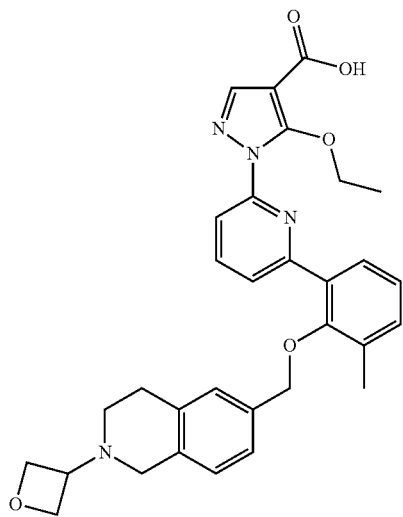 [SMILES: CCOc1c(C(=O)O)cnn1-c1cccc(-c2cccc(C)c2OCc2ccc3c(c2)CCN(C2COC2)C3)n1] |
| 7 | 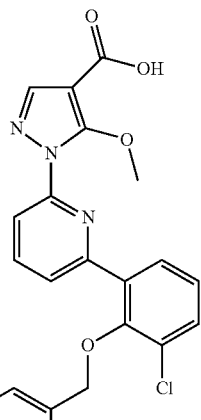 |
| 8 | 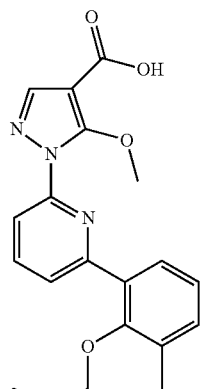 |
-continued
| Cpd No. | Structure |
|---|---|
| 9 | 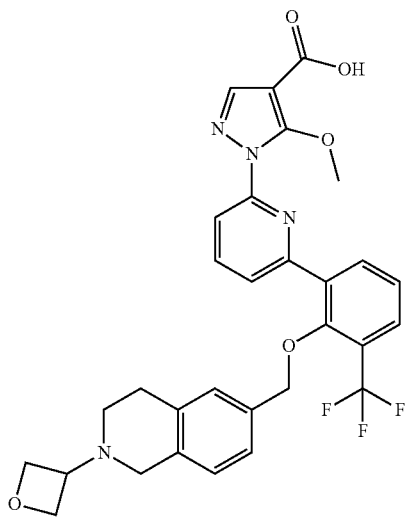 [SMILES: COc1c(C(=O)O)cnn1-c1cccc(-c2cccc(C(F)(F)F)c2OCc2ccc3c(c2)CCN(C2COC2)C3)n1] |
| 10 | 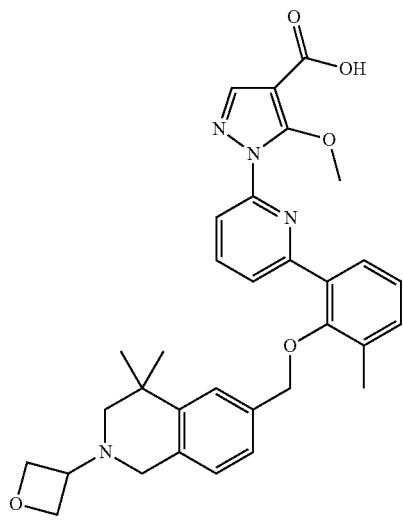 [SMILES: COc1c(C(=O)O)cnn1-c1cccc(-c2cccc(C)c2OCc2ccc3c(c2)C(C)(C)CN(C2COC2)C3)n1] |
| 11 | 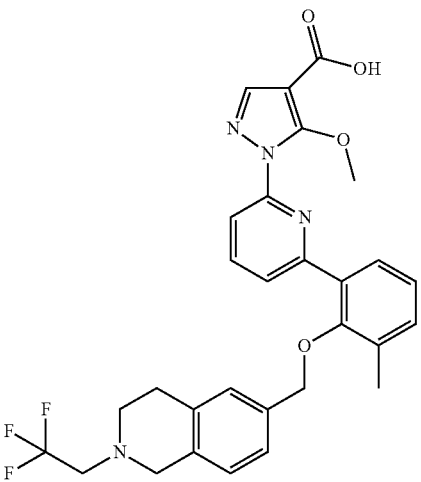 [SMILES: COc1c(C(=O)O)cnn1-c1cccc(-c2cccc(C)c2OCc2ccc3c(c2)CCN(CC(F)(F)F)C3)n1] |

| Cpd No. | Structure |
|---|---|
| 12 | 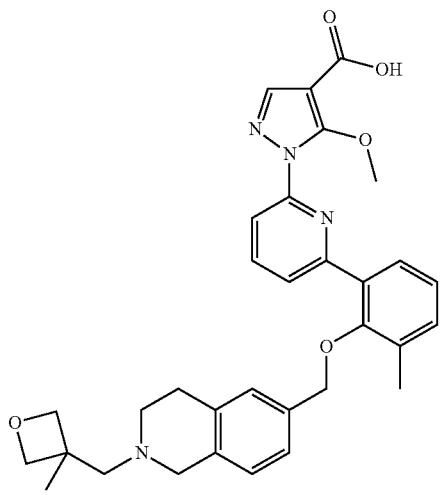 [SMILES: COc1c(C(=O)O)cnn1-c1cccc(-c2cccc(C)c2OCc2ccc3c(c2)CCN(CC2(C)COC2)C3)n1] |
| 13 | 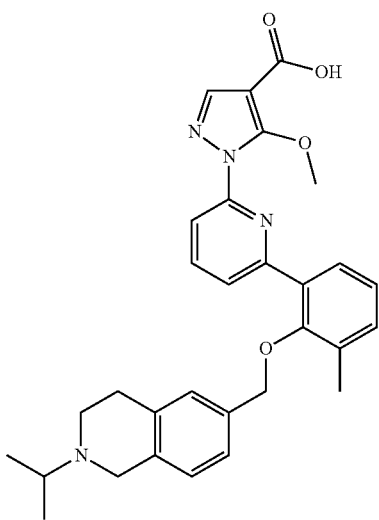 [SMILES: COc1c(C(=O)O)cnn1-c1cccc(-c2cccc(C)c2OCc2ccc3c(c2)CCN(C(C)C)C3)n1] |
| 14 | 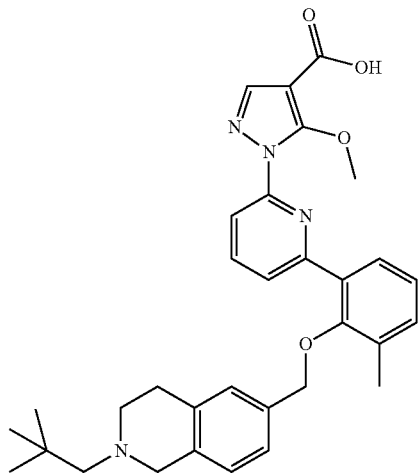 [SMILES: COc1c(C(=O)O)cnn1-c1cccc(-c2cccc(C)c2OCc2ccc3c(c2)CCN(CC(C)(C)C)C3)n1] |
| 15 | 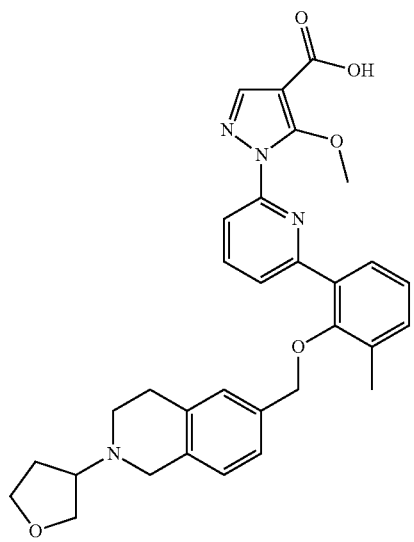 [SMILES: COc1c(C(=O)O)cnn1-c1cccc(-c2cccc(C)c2OCc2ccc3c(c2)CCN(C2CCOC2)C3)n1] |
| 16 | 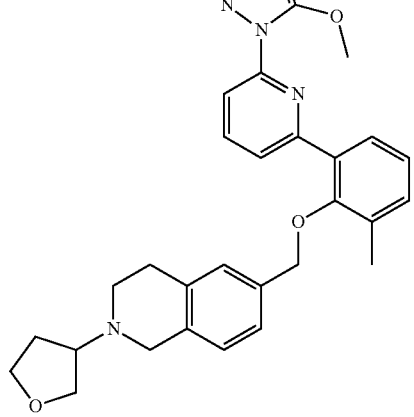 |
| 17 | 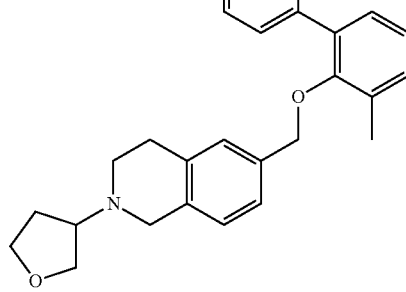 |

| Cpd No. | Structure |
|---|---|
| 18 | 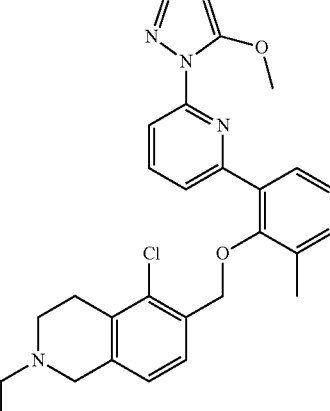 |
| 19 | |
| 20 | |
| Cpd No. | Structure |
|---|---|
| 21 | 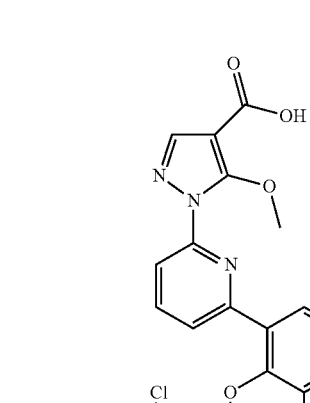 |
| 22 | |
| 23 | |

-continued
| Cpd No. | Structure |
|---|---|
| 24 | 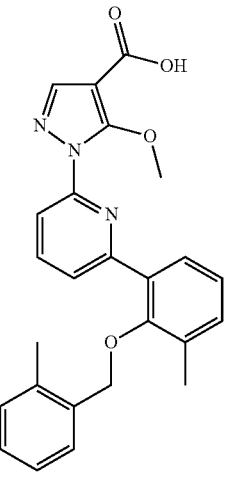 |
| 25 | 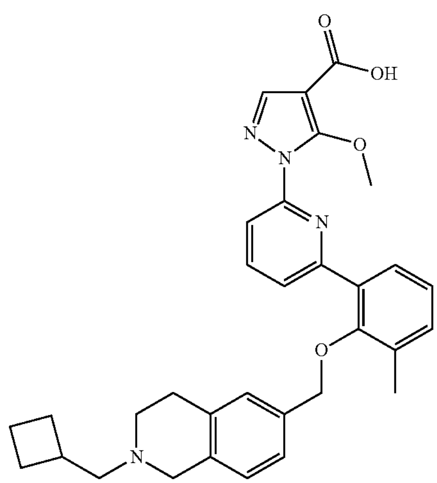 [SMILES: COc1c(C(=O)O)cnn1-c1cccc(-c2cccc(C)c2OCc2ccc3c(c2)CCN(CC2CCC2)C3)n1] |
| 26 | 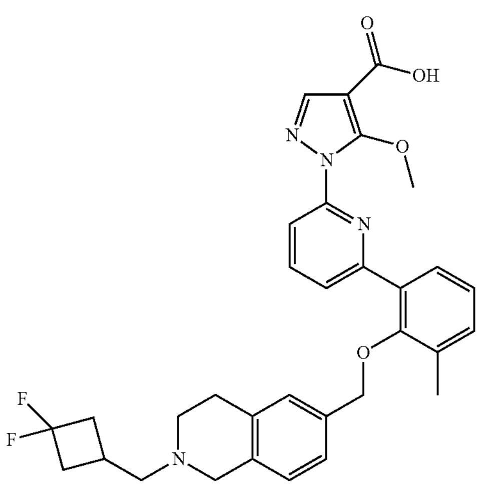 [SMILES: COc1c(C(=O)O)cnn1-c1cccc(-c2cccc(C)c2OCc2ccc3c(c2)CCN(CC2CC(F)(F)C2)C3)n1] |
-continued
| Cpd No. | Structure |
|---|---|
| 27 | 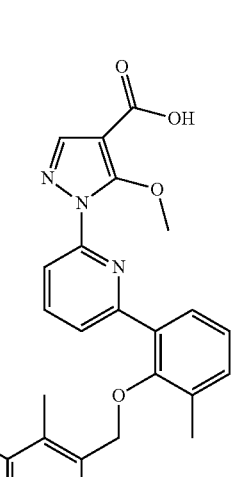 |
| 28 | 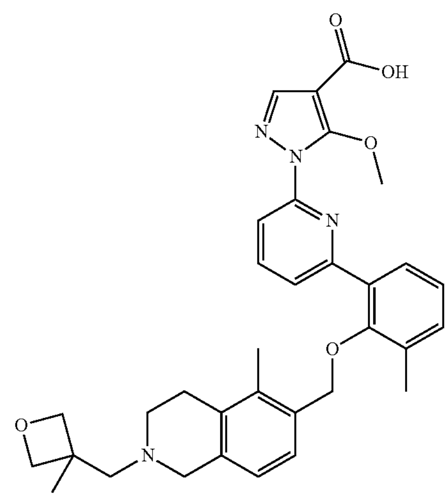 [SMILES: COc1c(C(=O)O)cnn1-c1cccc(-c2cccc(C)c2OCc2ccc3c(c2C)CCN(CC2(C)COC2)C3)n1] |
| 29 | 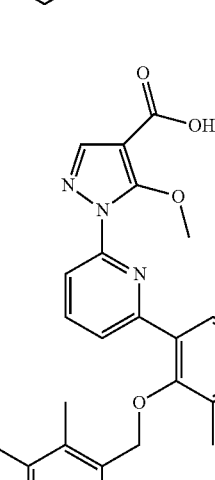 |

| Cpd No. | Structure |
|---|---|
| 30 | 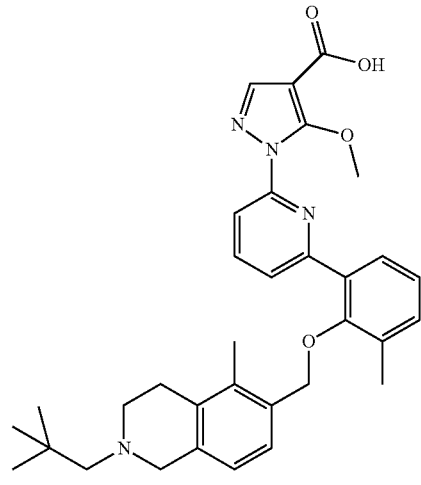 [SMILES: COc1c(C(=O)O)cnn1-c1cccc(-c2cccc(C)c2OCc2ccc3c(c2C)CCN(CC(C)(C)C)C3)n1] |
| 31 | 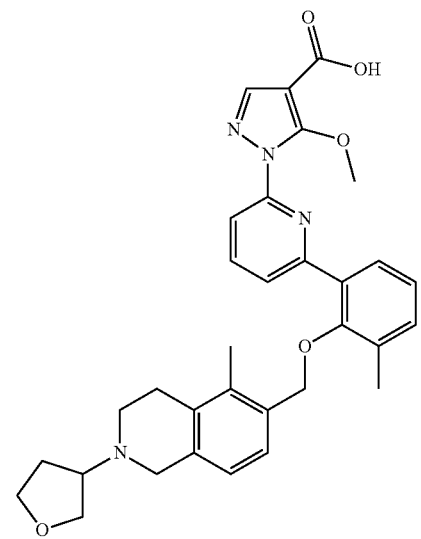 [SMILES: COc1c(C(=O)O)cnn1-c1cccc(-c2cccc(C)c2OCc2ccc3c(c2C)CCN(C2CCOC2)C3)n1] |
| 32 | 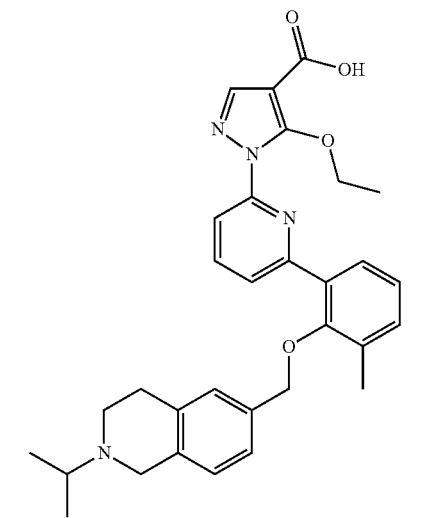 [SMILES: CCOc1c(C(=O)O)cnn1-c1cccc(-c2cccc(C)c2OCc2ccc3c(c2)CCN(C(C)C)C3)n1] |
| Cpd No. | Structure |
|---|---|
| 33 | 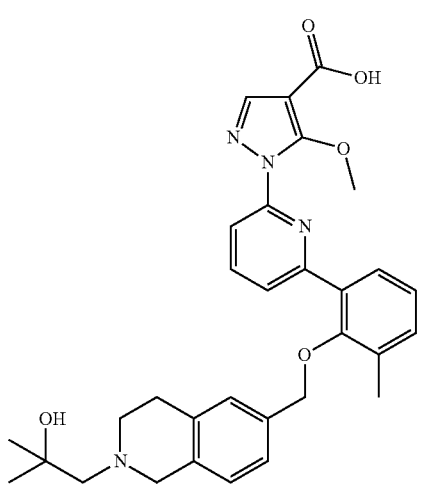 [SMILES: COc1c(C(=O)O)cnn1-c1cccc(-c2cccc(C)c2OCc2ccc3c(c2)CCN(CC(C)(C)O)C3)n1] |
| 34 | 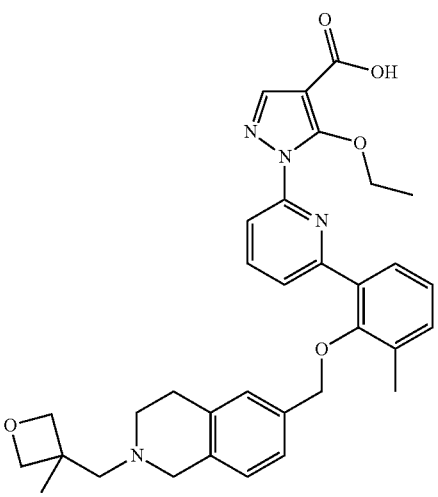 [SMILES: CCOc1c(C(=O)O)cnn1-c1cccc(-c2cccc(C)c2OCc2ccc3c(c2)CCN(CC2(C)COC2)C3)n1] |
| 35 | 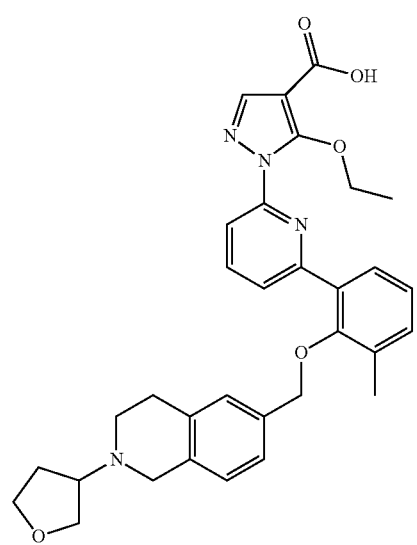 [SMILES: CCOc1c(C(=O)O)cnn1-c1cccc(-c2cccc(C)c2OCc2ccc3c(c2)CCN(C2CCOC2)C3)n1] |

| Cpd No. | Structure |
|---|---|
| 36 | 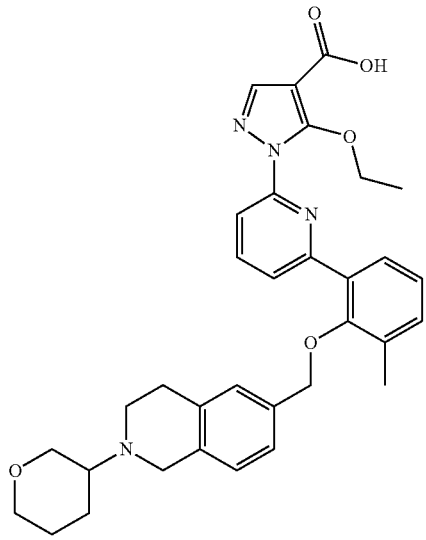 [SMILES: CCOc1c(C(=O)O)cnn1-c1cccc(-c2cccc(C)c2OCc2ccc3c(c2)CCN(C2CCCOC2)C3)n1] |
| 37 | 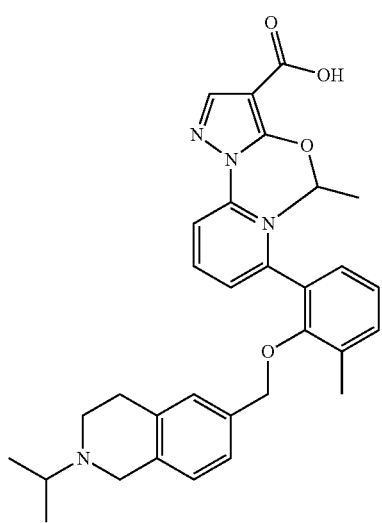 |
| Cpd No. | Structure |
|---|---|
| 38 | 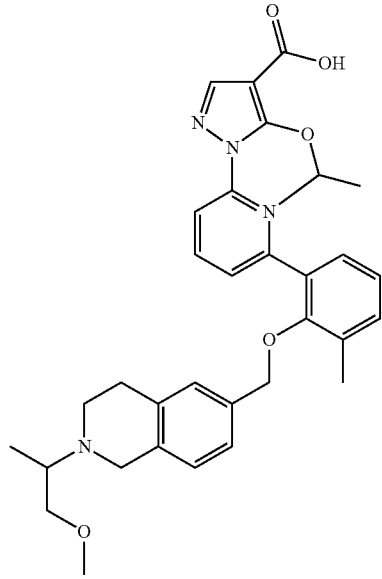 |
| 39 | |
| 40 | 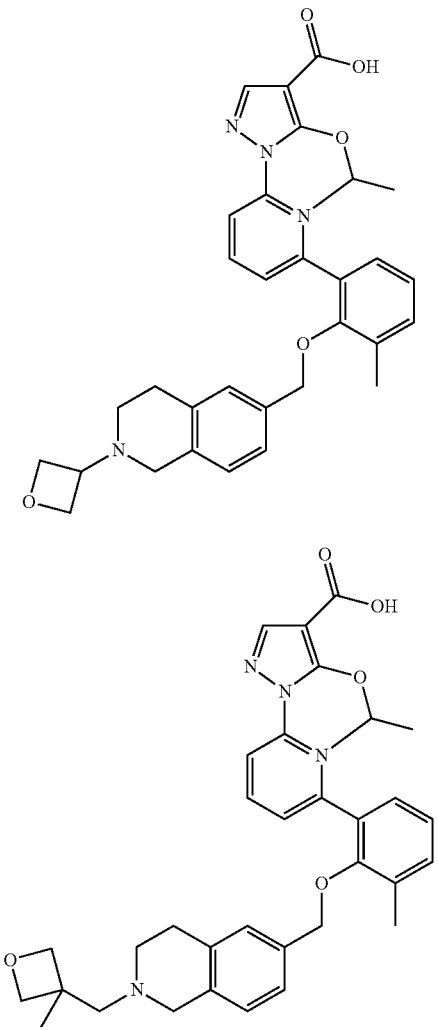 |

| Cpd No. | Structure |
|---|---|
| 41 | 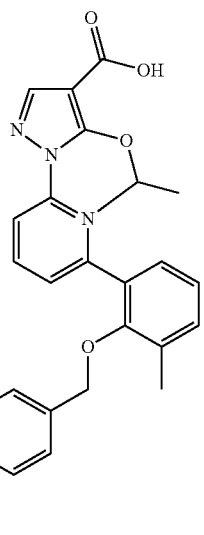 |
| 42 | 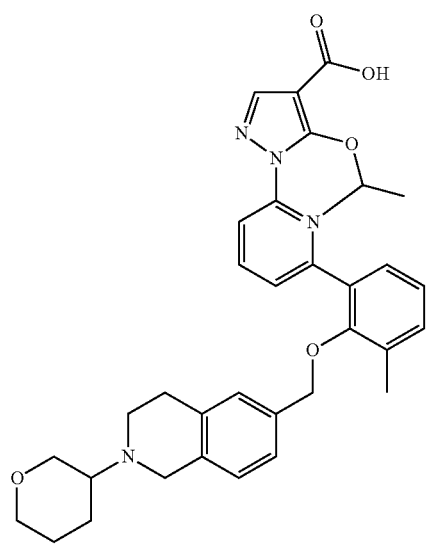 |
| Cpd No. | Structure |
|---|---|
| 43 | 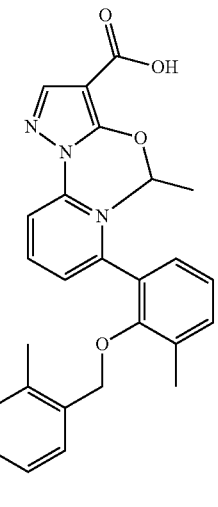 |
| 44 | 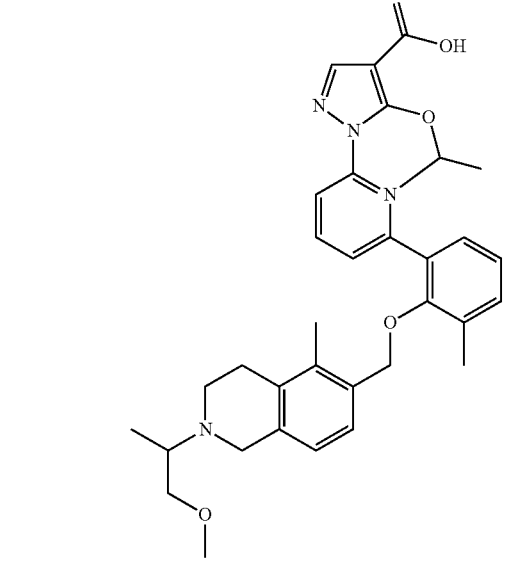 |

| Cpd No. | Structure |
|---|---|
| 45 | 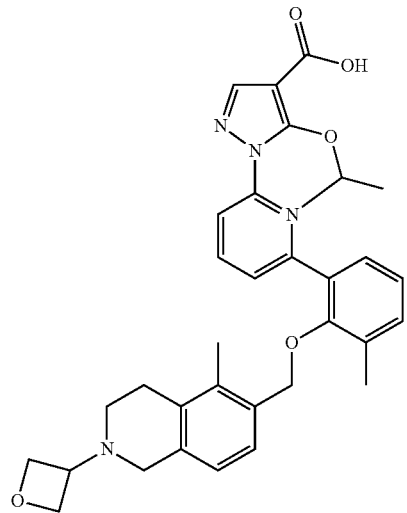 |
| 46 | 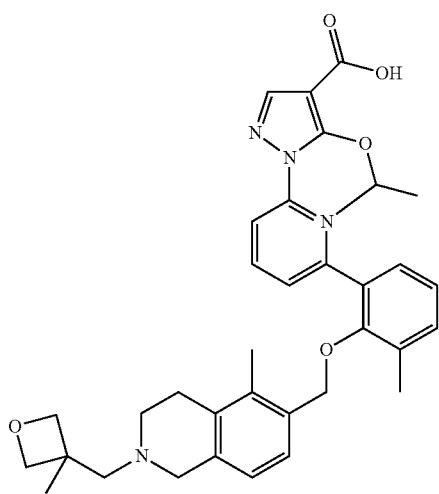 |
| 47 | 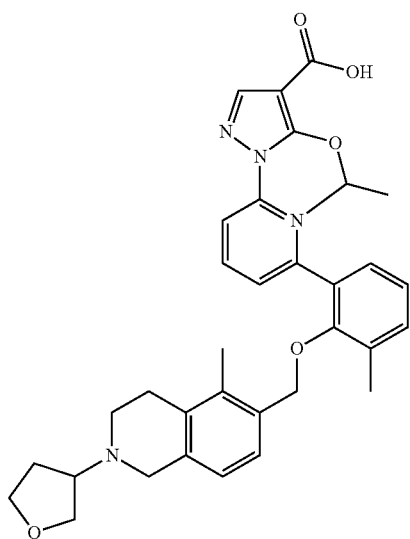 |
| Cpd No. | Structure |
|---|---|
| 48 | 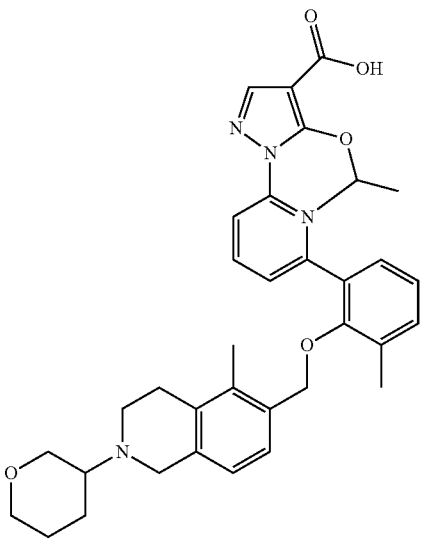 |
| 49 | 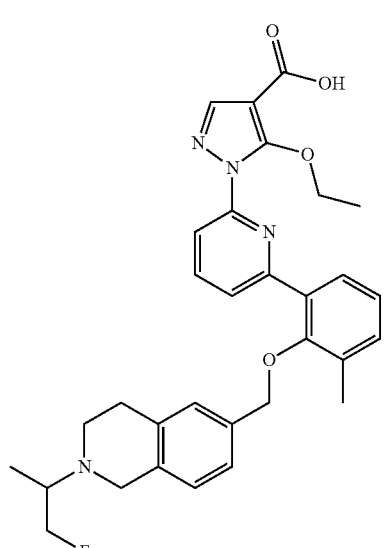 |
| 50 | 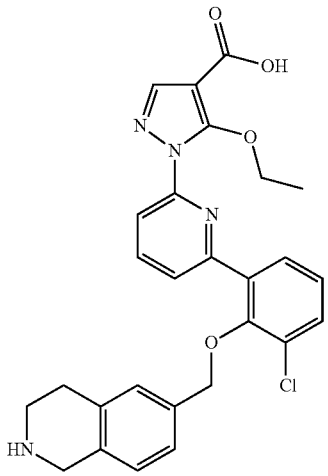 [SMILES: CCOc1c(C(=O)O)cnn1-c1cccc(-c2cccc(Cl)c2OCc2ccc3c(c2)CCNC3)n1] |

-continued
| Cpd No. | Structure |
|---|---|
| 51 | 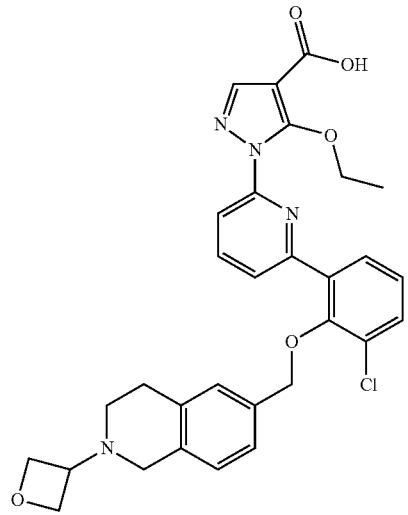 [SMILES: CCOc1c(C(=O)O)cnn1-c1cccc(-c2cccc(Cl)c2OCc2ccc3c(c2)CCN(C2COC2)C3)n1] |
| 52 | 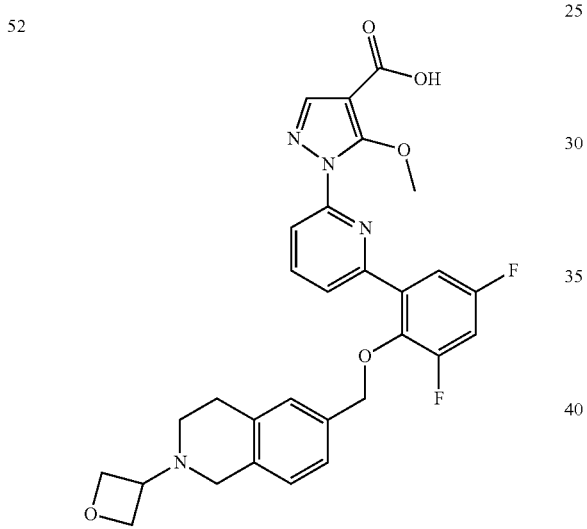 |
| 53 | 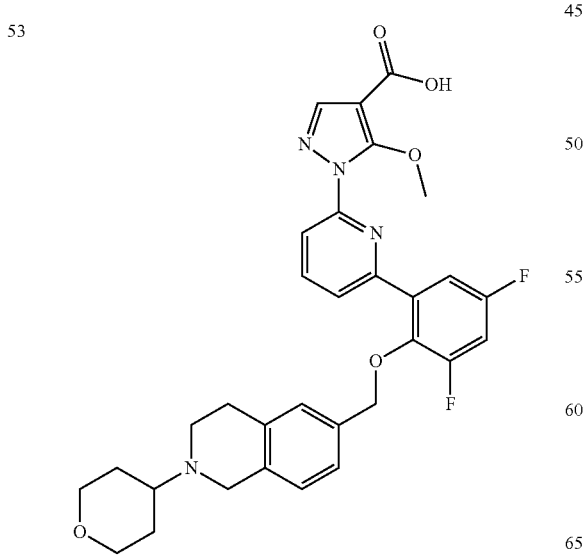 |
-continued
| Cpd No. | Structure |
|---|---|
| 54 | 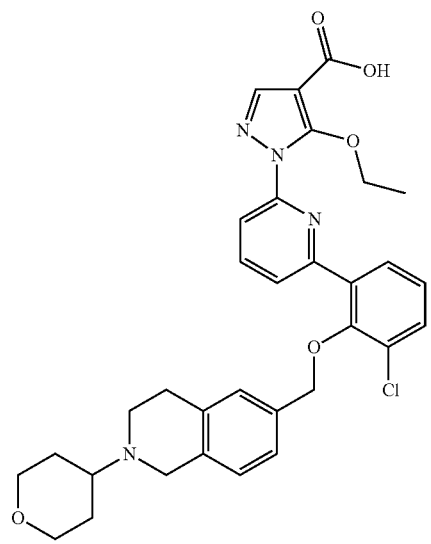 [SMILES: CCOc1c(C(=O)O)cnn1-c1cccc(-c2cccc(Cl)c2OCc2ccc3c(c2)CCN(C2CCOCC2)C3)n1] |
| 55 | 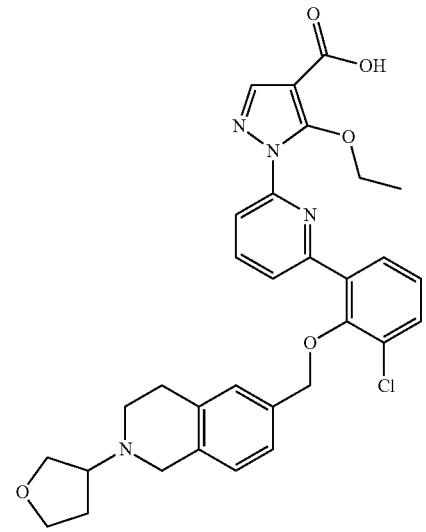 [SMILES: CCOc1c(C(=O)O)cnn1-c1cccc(-c2cccc(Cl)c2OCc2ccc3c(c2)CCN(C2CCOC2)C3)n1] |

| Cpd No. | Structure |
|---|---|
| 56 | 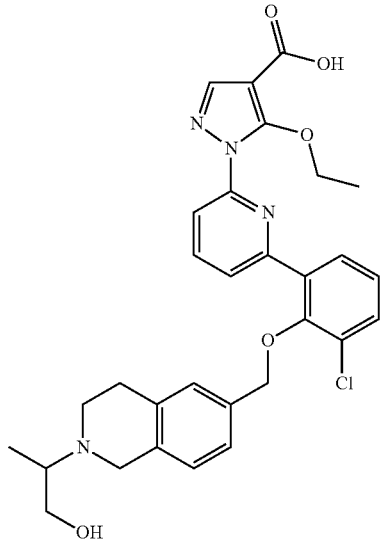 [SMILES: CCOc1c(C(=O)O)cnn1-c1cccc(-c2cccc(Cl)c2OCc2ccc3c(c2)CCN(C(C)CO)C3)n1] |
| 57 | 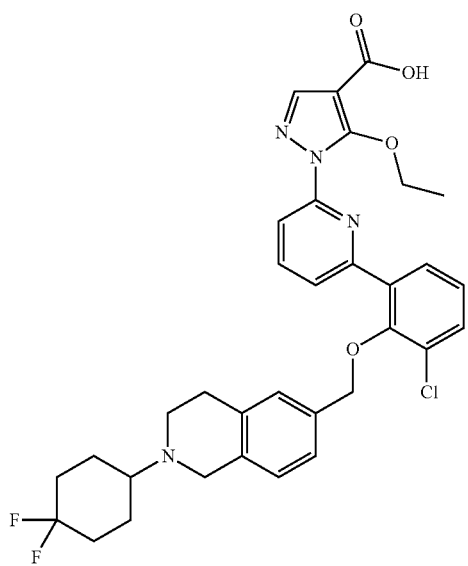 [SMILES: CCOc1c(C(=O)O)cnn1-c1cccc(-c2cccc(Cl)c2OCc2ccc3c(c2)CCN(C2CCC(F)(F)CC2)C3)n1] |
| Cpd No. | Structure |
|---|---|
| 58 | 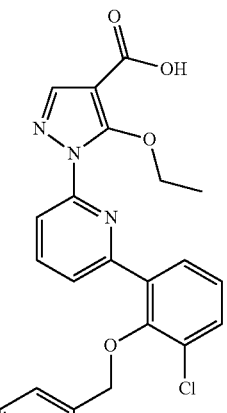 |
| 59 | 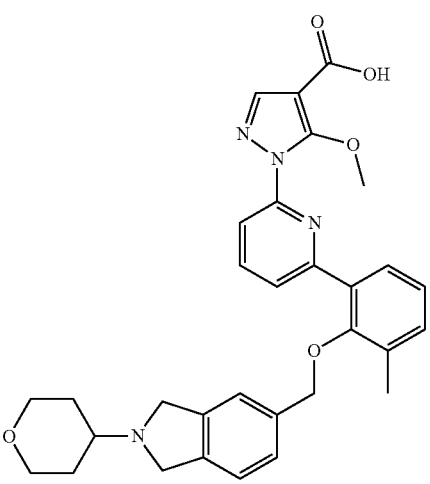 [SMILES: COc1c(C(=O)O)cnn1-c1cccc(-c2cccc(C)c2OCc2ccc3c(c2)CN(C2CCOCC2)C3)n1] |
| 60 | 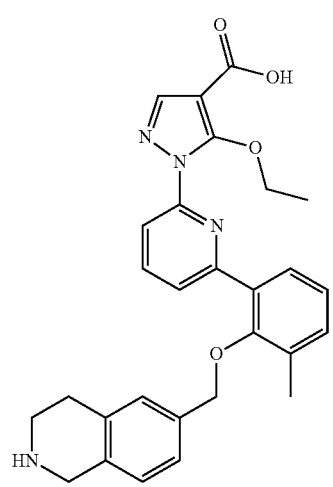 [SMILES: CCOc1c(C(=O)O)cnn1-c1cccc(-c2cccc(C)c2OCc2ccc3c(c2)CCNC3)n1] |

| Cpd No. | Structure |
|---|---|
| 61 | 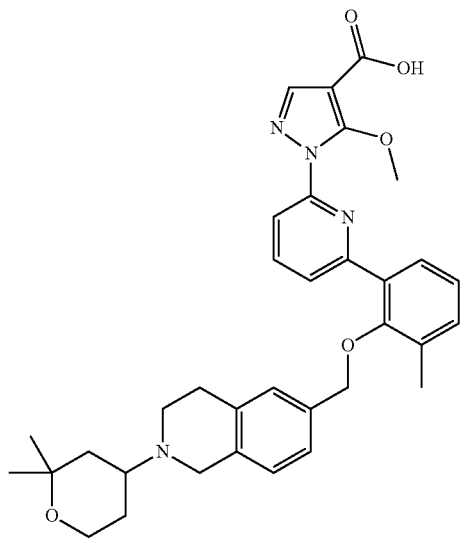 [SMILES: COc1c(C(=O)O)cnn1-c1cccc(-c2cccc(C)c2OCc2ccc3c(c2)CCN(C2CCOC(C)(C)C2)C3)n1] |
| 62 | 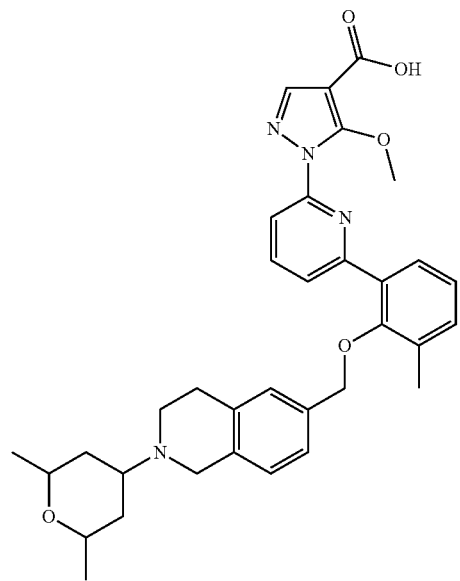 [SMILES: COc1c(C(=O)O)cnn1-c1cccc(-c2cccc(C)c2OCc2ccc3c(c2)CCN(C2CC(C)OC(C)C2)C3)n1] |
| Cpd No. | Structure |
|---|---|
| 63 | 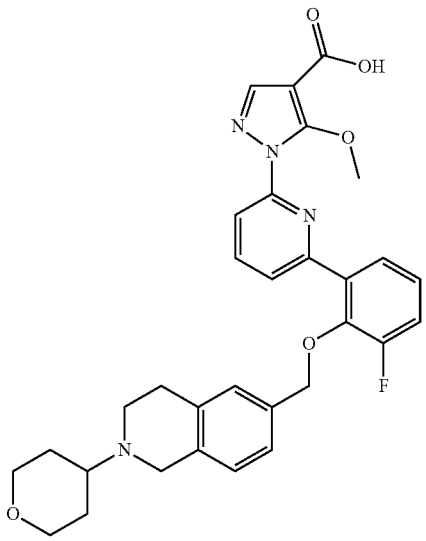 [SMILES: COc1c(C(=O)O)cnn1-c1cccc(-c2cccc(F)c2OCc2ccc3c(c2)CCN(C2CCOCC2)C3)n1] |
| 64 | 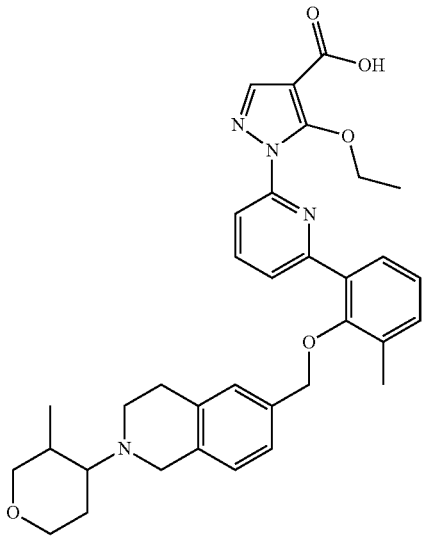 [SMILES: CCOc1c(C(=O)O)cnn1-c1cccc(-c2cccc(C)c2OCc2ccc3c(c2)CCN(C2CCOCC2C)C3)n1] |

| Cpd No. | Structure |
|---|---|
| 65 | 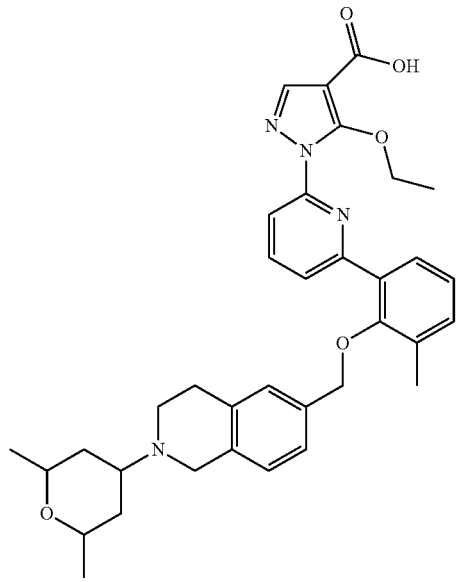 [SMILES: CCOc1c(C(=O)O)cnn1-c1cccc(-c2cccc(C)c2OCc2ccc3c(c2)CCN(C2CC(C)OC(C)C2)C3)n1] |
| 66 | 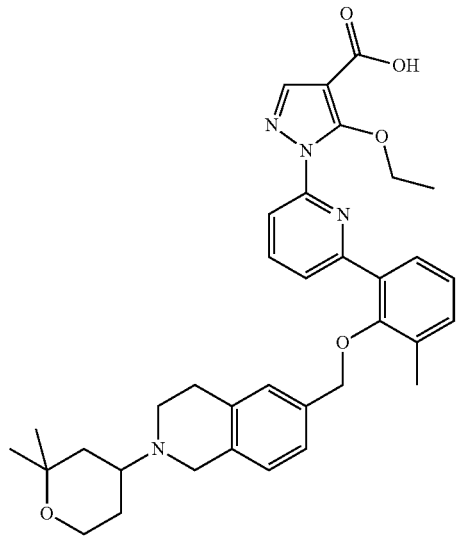 [SMILES: CCOc1c(C(=O)O)cnn1-c1cccc(-c2cccc(C)c2OCc2ccc3c(c2)CCN(C2CCOC(C)(C)C2)C3)n1] |
| Cpd No. | Structure |
|---|---|
| 67 | 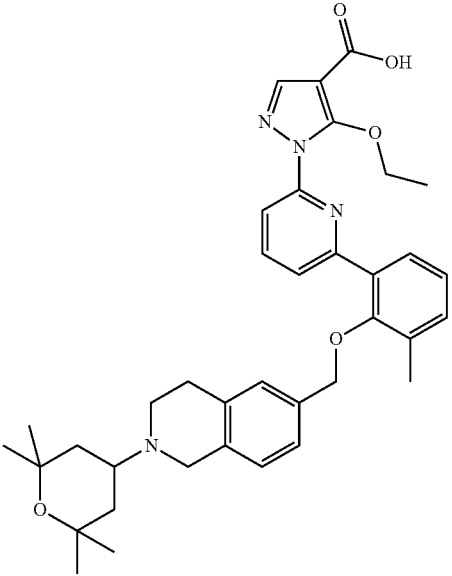 [SMILES: CCOc1c(C(=O)O)cnn1-c1cccc(-c2cccc(C)c2OCc2ccc3c(c2)CCN(C2CC(C)(C)OC(C)(C)C2)C3)n1] |
| 68 | 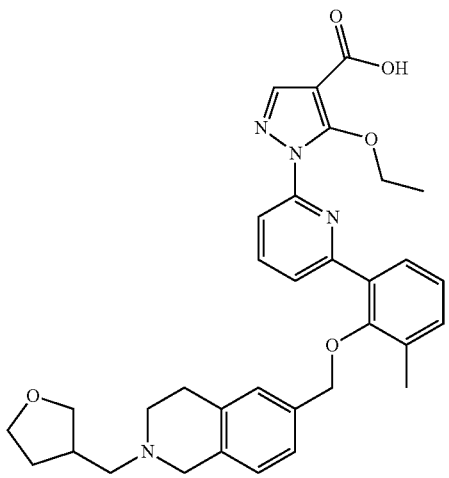 [SMILES: CCOc1c(C(=O)O)cnn1-c1cccc(-c2cccc(C)c2OCc2ccc3c(c2)CCN(CC2CCOC2)C3)n1] |
| 69 | 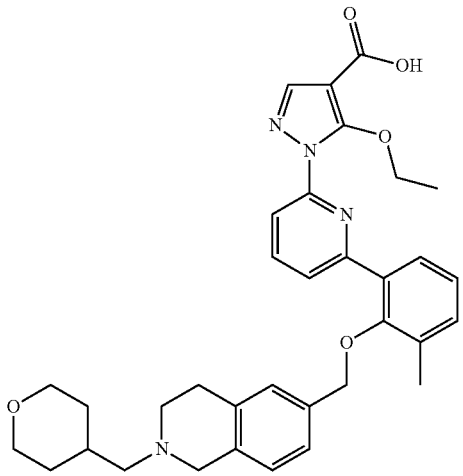 [SMILES: CCOc1c(C(=O)O)cnn1-c1cccc(-c2cccc(C)c2OCc2ccc3c(c2)CCN(CC2CCOCC2)C3)n1] |

-continued
| Cpd No. | Structure |
|---|---|
| 70 | 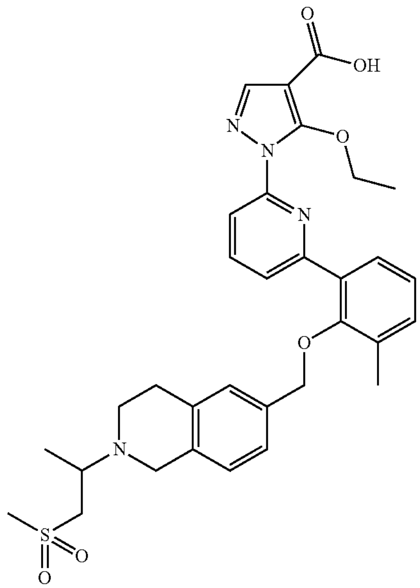 [SMILES: CCOc1c(C(=O)O)cnn1-c1cccc(-c2cccc(C)c2OCc2ccc3c(c2)CCN(C(C)CS(C)(=O)=O)C3)n1] |
| 71 | 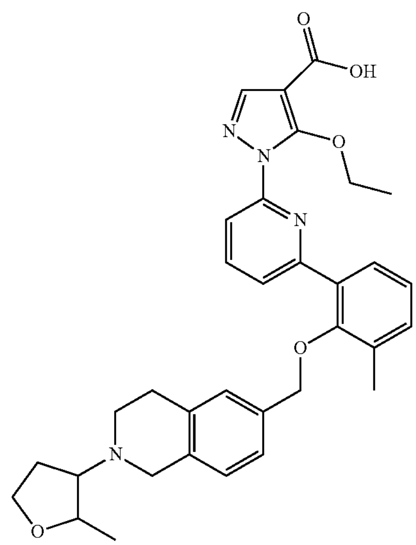 [SMILES: CCOc1c(C(=O)O)cnn1-c1cccc(-c2cccc(C)c2OCc2ccc3c(c2)CCN(C2CCOC2C)C3)n1] |
| 72 | 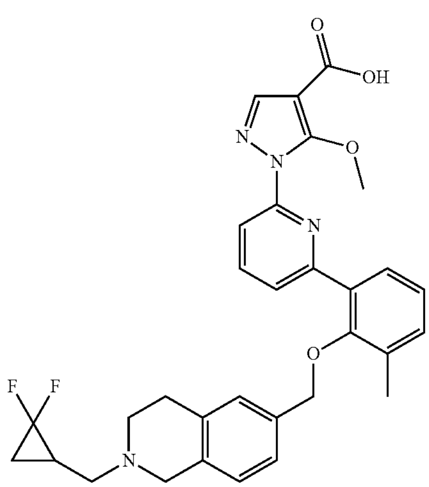 [SMILES: COc1c(C(=O)O)cnn1-c1cccc(-c2cccc(C)c2OCc2ccc3c(c2)CCN(CC2CC2(F)F)C3)n1] |
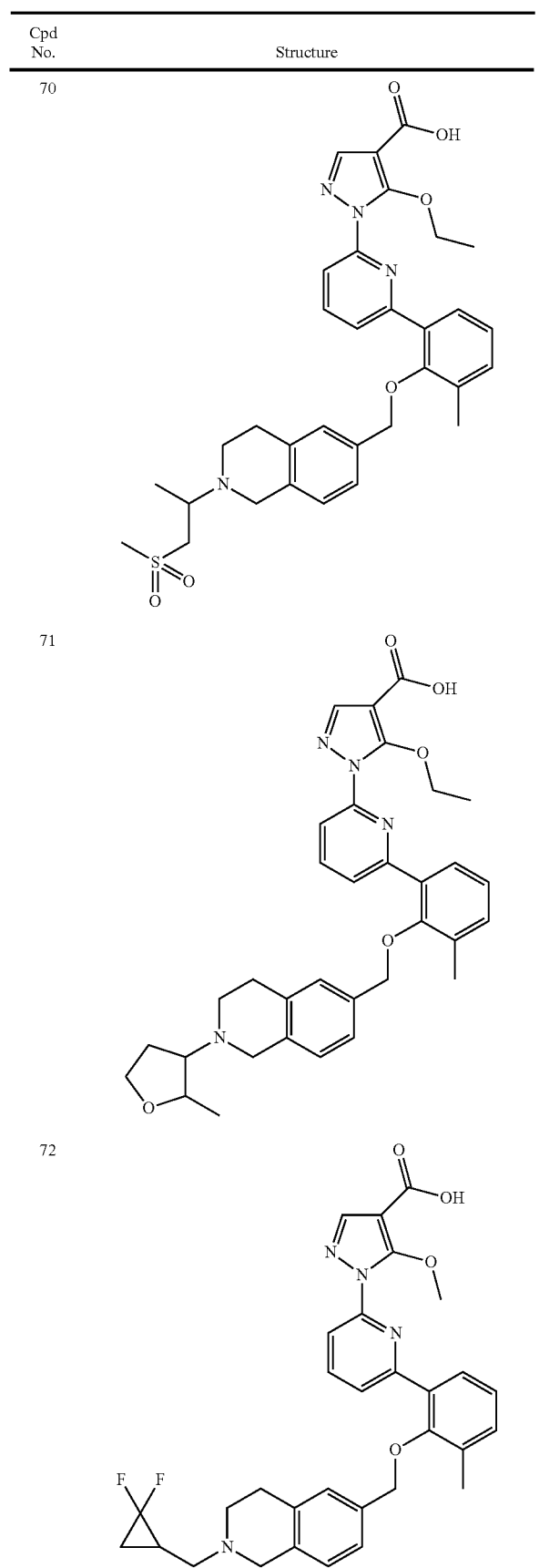
-continued
| Cpd No. | Structure |
|---|---|
| 73 | 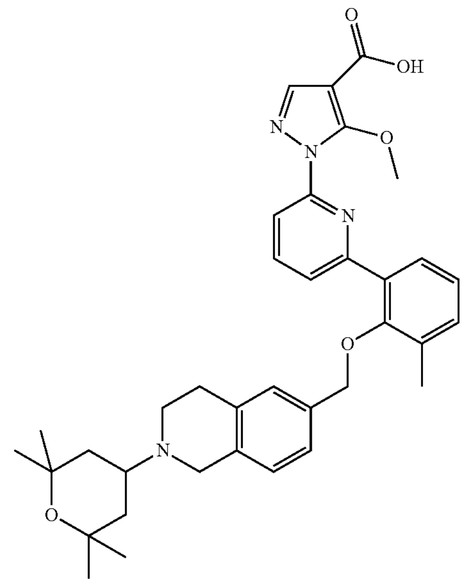 [SMILES: COc1c(C(=O)O)cnn1-c1cccc(-c2cccc(C)c2OCc2ccc3c(c2)CCN(C2CC(C)(C)OC(C)(C)C2)C3)n1] |
| 74 | 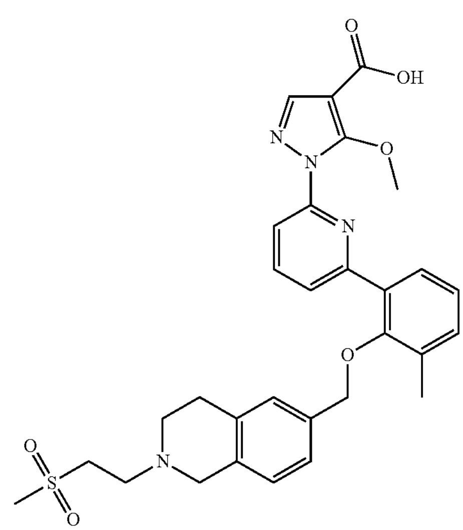 [SMILES: COc1c(C(=O)O)cnn1-c1cccc(-c2cccc(C)c2OCc2ccc3c(c2)CCN(CCS(C)(=O)=O)C3)n1] |
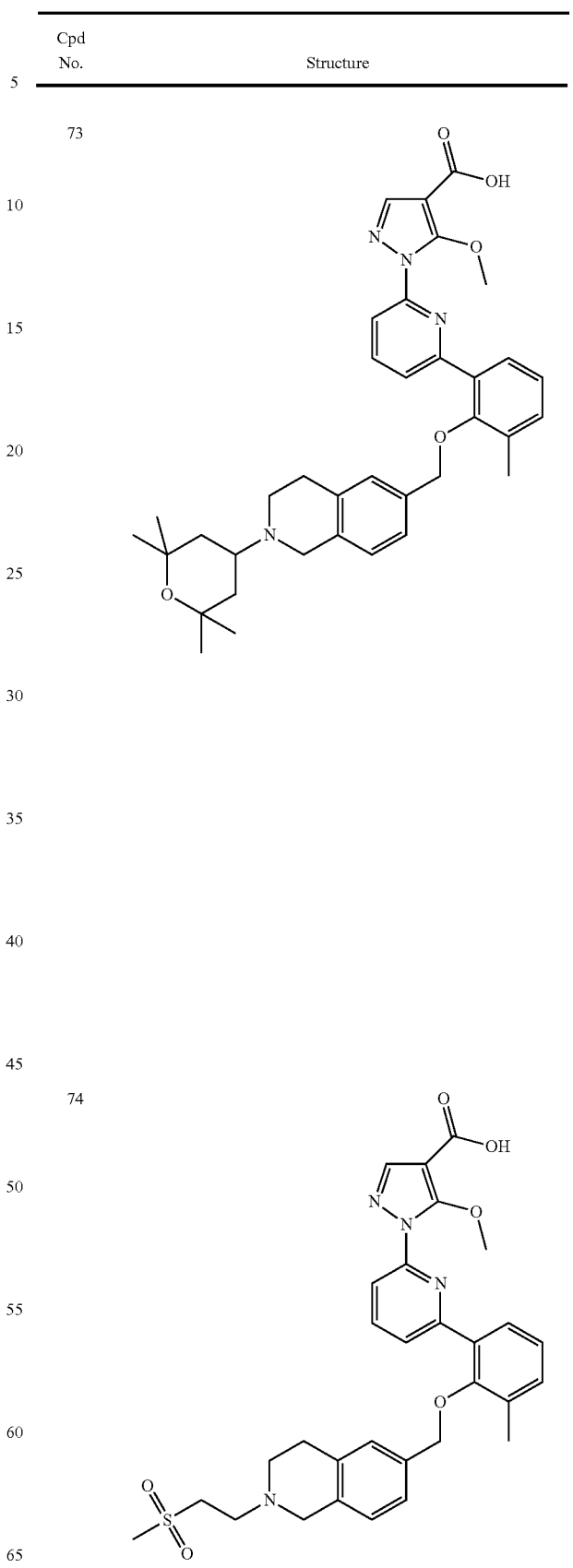

| Cpd No. | Structure |
|---|---|
| 75 | 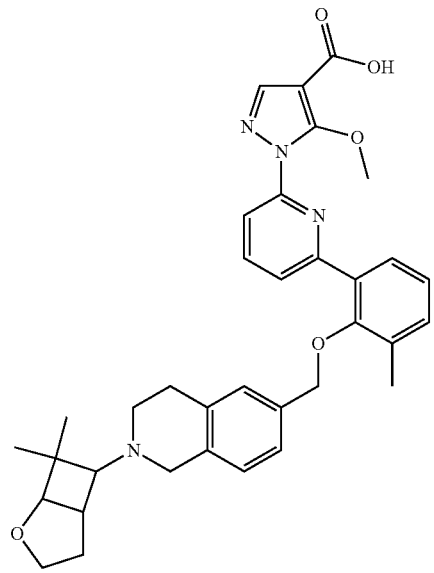 [SMILES: COc1c(C(=O)O)cnn1-c1cccc(-c2cccc(C)c2OCc2ccc3c(c2)CCN(C2C4CCOC4C2(C)C)C3)n1] |
| 76 | 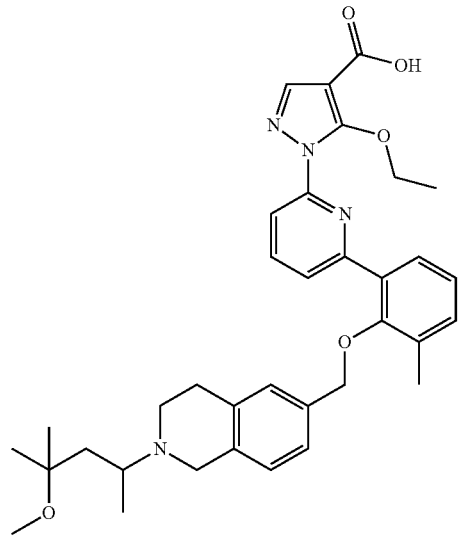 [SMILES: CCOc1c(C(=O)O)cnn1-c1cccc(-c2cccc(C)c2OCc2ccc3c(c2)CCN(C(C)CC(C)(C)OC)C3)n1] |
| Cpd No. | Structure |
|---|---|
| 77 | 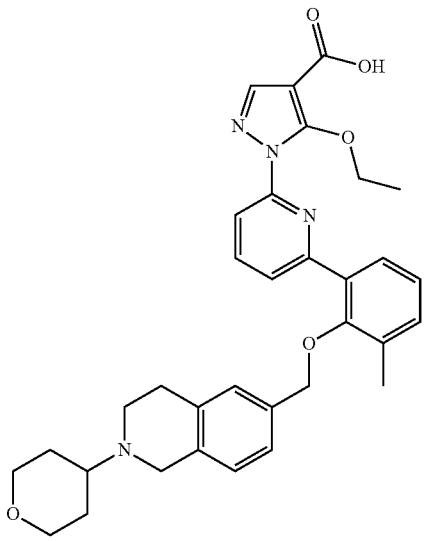 [SMILES: CCOc1c(C(=O)O)cnn1-c1cccc(-c2cccc(C)c2OCc2ccc3c(c2)CCN(C2CCOCC2)C3)n1] |
| 78 | 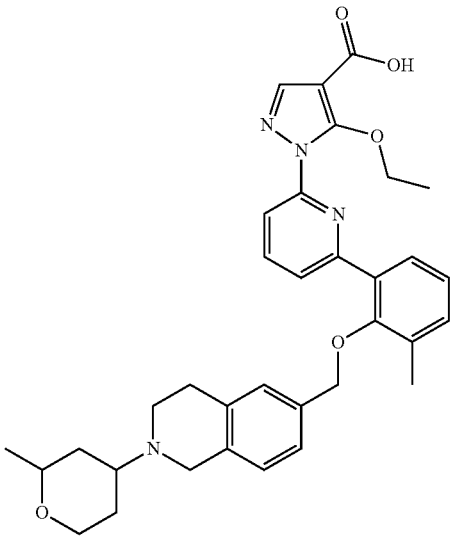 [SMILES: CCOc1c(C(=O)O)cnn1-c1cccc(-c2cccc(C)c2OCc2ccc3c(c2)CCN(C2CCOC(C)C2)C3)n1] |

| Cpd No. | Structure |
|---|---|
| 79 | 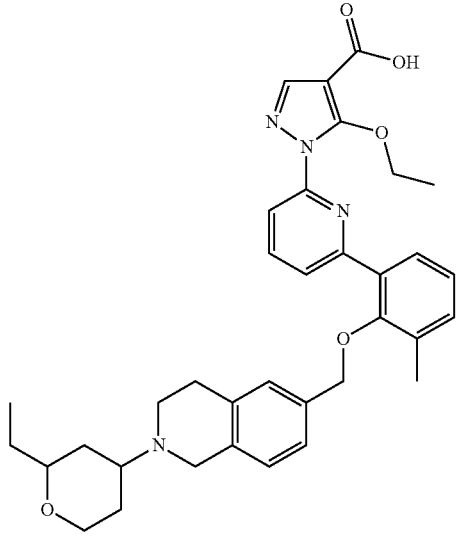 [SMILES: CCOc1c(C(=O)O)cnn1-c1cccc(-c2cccc(C)c2OCc2ccc3c(c2)CCN(C2CCOC(CC)C2)C3)n1] |
| 80 | 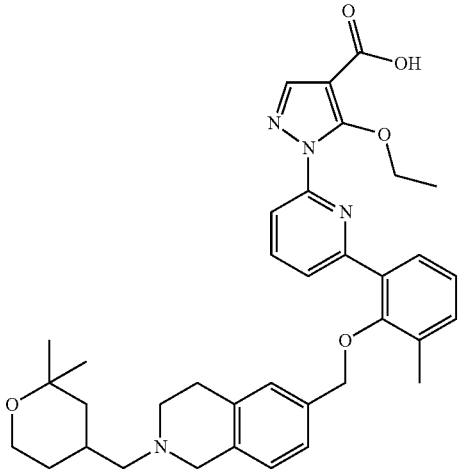 [SMILES: CCOc1c(C(=O)O)cnn1-c1cccc(-c2cccc(C)c2OCc2ccc3c(c2)CCN(CC2CCOC(C)(C)C2)C3)n1] |
| 81 | 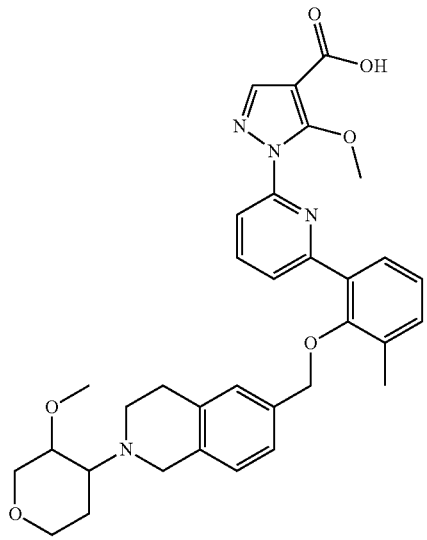 [SMILES: COc1c(C(=O)O)cnn1-c1cccc(-c2cccc(C)c2OCc2ccc3c(c2)CCN(C2CCOCC2OC)C3)n1] |
| Cpd No. | Structure |
|---|---|
| 82 | 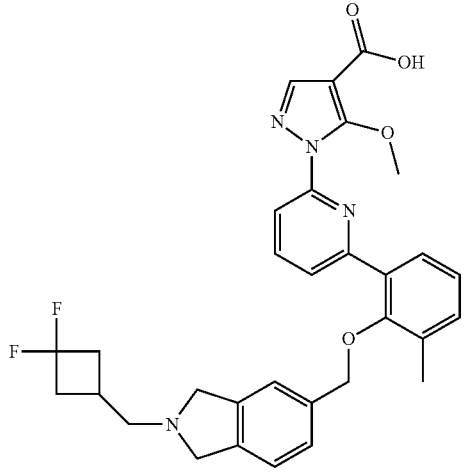 [SMILES: COc1c(C(=O)O)cnn1-c1cccc(-c2cccc(C)c2OCc2ccc3c(c2)CN(CC2CC(F)(F)C2)C3)n1] |
| 83 | 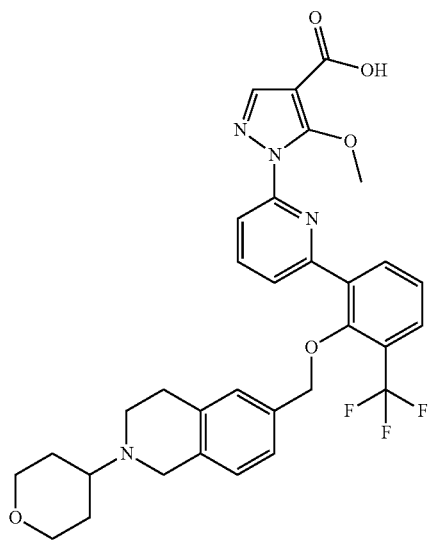 [SMILES: COc1c(C(=O)O)cnn1-c1cccc(-c2cccc(C(F)(F)F)c2OCc2ccc3c(c2)CCN(C2CCOCC2)C3)n1] |
| 84 | 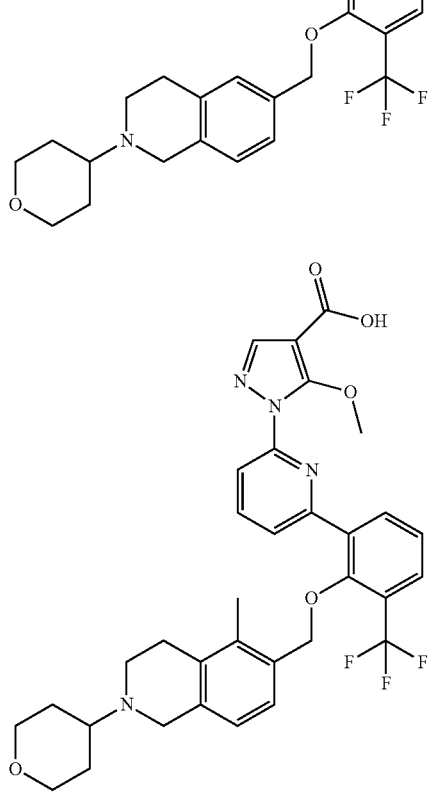 |

| Cpd No. | Structure |
|---|---|
| 85 | 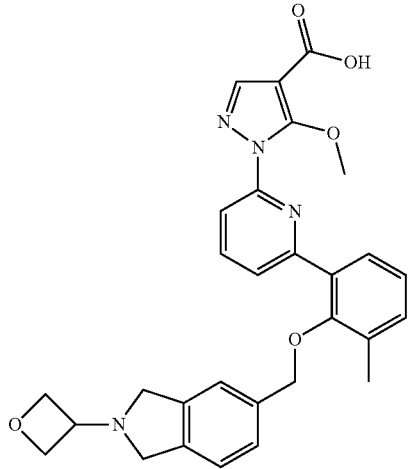 [SMILES: COc1c(C(=O)O)cnn1-c1cccc(-c2cccc(C)c2OCc2ccc3c(c2)CN(C2COC2)C3)n1] |
| 86 | 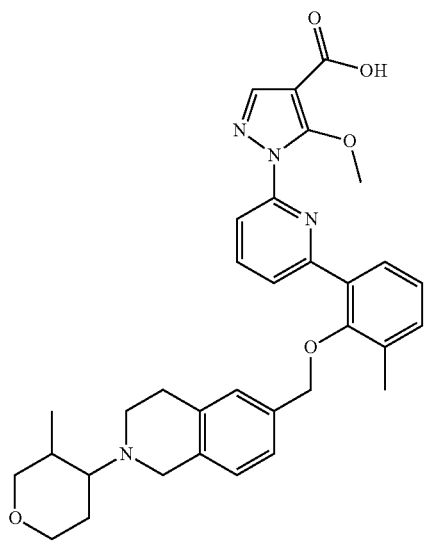 [SMILES: COc1c(C(=O)O)cnn1-c1cccc(-c2cccc(C)c2OCc2ccc3c(c2)CCN(C2CCOCC2C)C3)n1] |
| 87 | 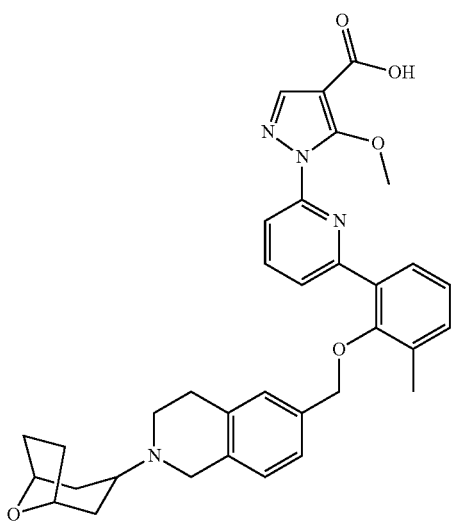 [SMILES: COc1c(C(=O)O)cnn1-c1cccc(-c2cccc(C)c2OCc2ccc3c(c2)CCN(C2CC4CCC(C2)O4)C3)n1] |
| 88 | 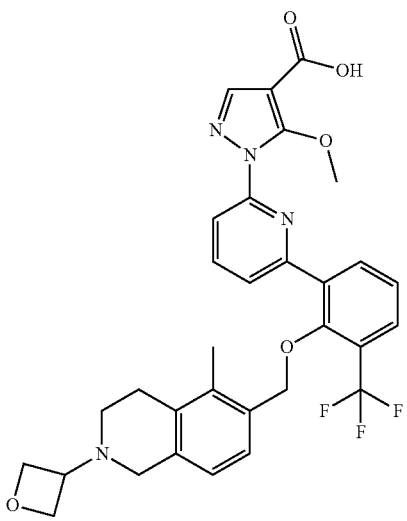 [SMILES: COc1c(C(=O)O)cnn1-c1cccc(-c2cccc(C(F)(F)F)c2OCc2ccc3c(c2C)CCN(C2COC2)C3)n1] |
| 89 | 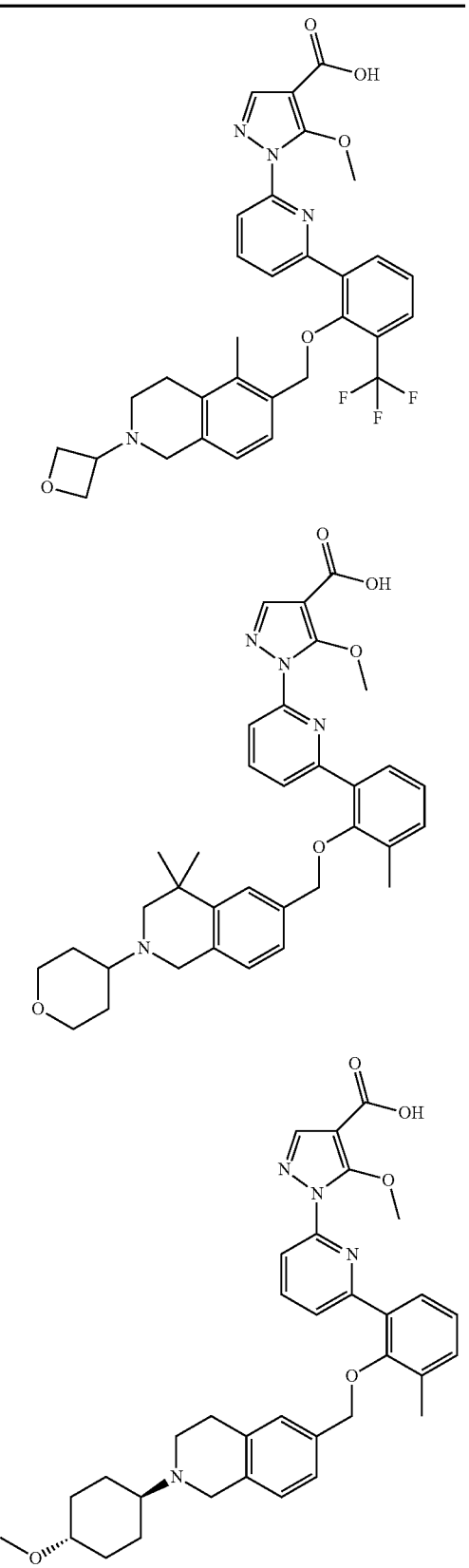 |
| 90 | |

| Cpd No. | Structure |
|---|---|
| 91 | 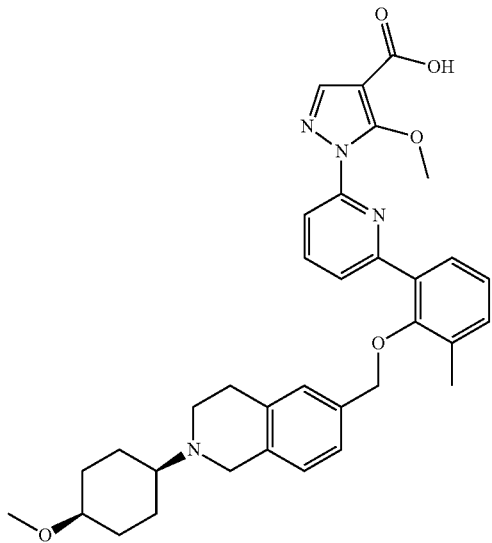 [SMILES: COc1c(C(=O)O)cnn1-c1cccc(-c2cccc(C)c2OCc2ccc3c(c2)CCN([C@H]2CC[C@@H](OC)CC2)C3)n1] |
| 92 | 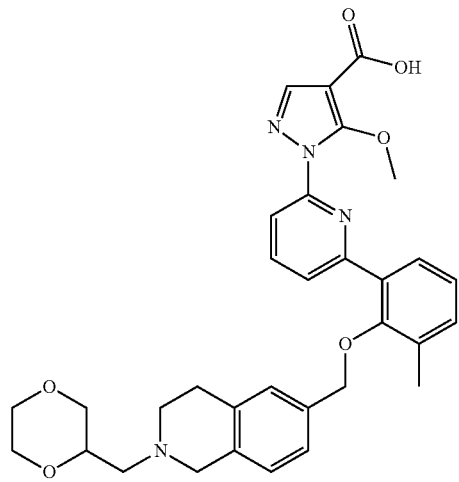 [SMILES: COc1c(C(=O)O)cnn1-c1cccc(-c2cccc(C)c2OCc2ccc3c(c2)CCN(CC2COCCO2)C3)n1] |
| 93 | 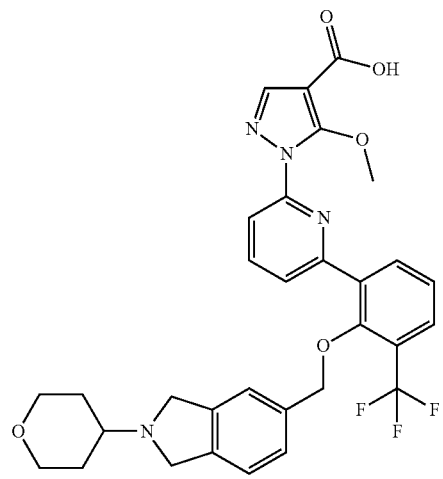 [SMILES: COc1c(C(=O)O)cnn1-c1cccc(-c2cccc(C(F)(F)F)c2OCc2ccc3c(c2)CN(C2CCOCC2)C3)n1] |
| 94 | 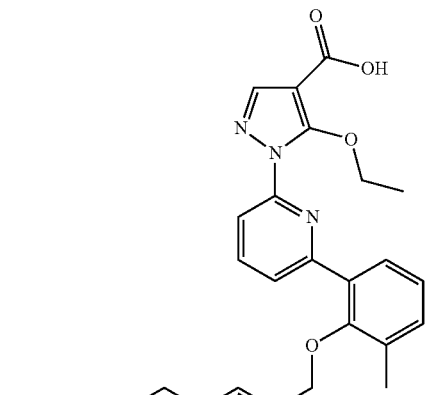 |
| 95 | 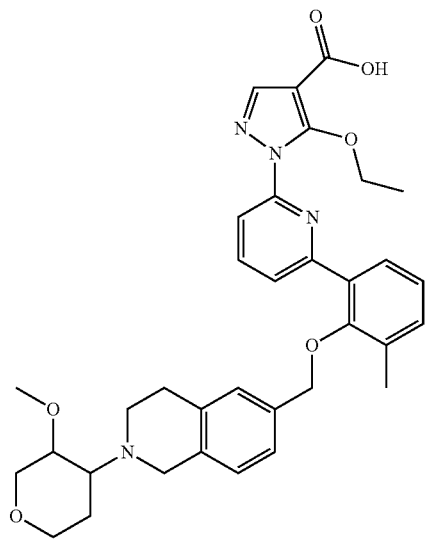 [SMILES: CCOc1c(C(=O)O)cnn1-c1cccc(-c2cccc(C)c2OCc2ccc3c(c2)CCN(C2CCOCC2OC)C3)n1] |
| 96 | 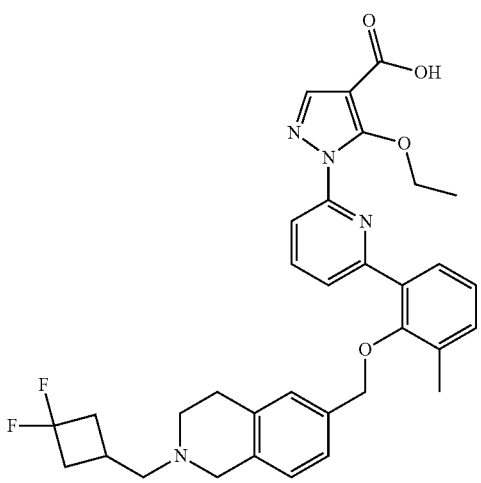 [SMILES: CCOc1c(C(=O)O)cnn1-c1cccc(-c2cccc(C)c2OCc2ccc3c(c2)CCN(CC2CC(F)(F)C2)C3)n1] |

| Cpd No. | Structure |
|---|---|
| 97 | 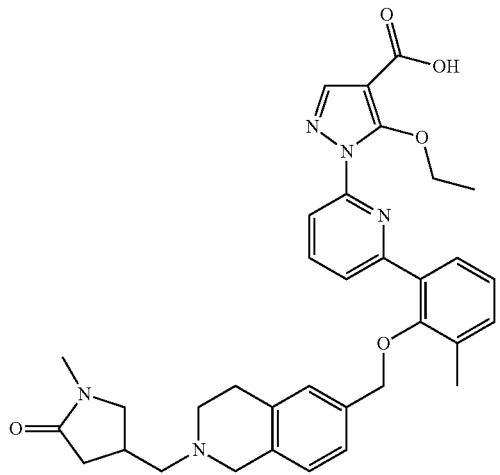 [SMILES: CCOc1c(C(=O)O)cnn1-c1cccc(-c2cccc(C)c2OCc2ccc3c(c2)CCN(CC2CC(=O)N(C)C2)C3)n1] |
| 98 | 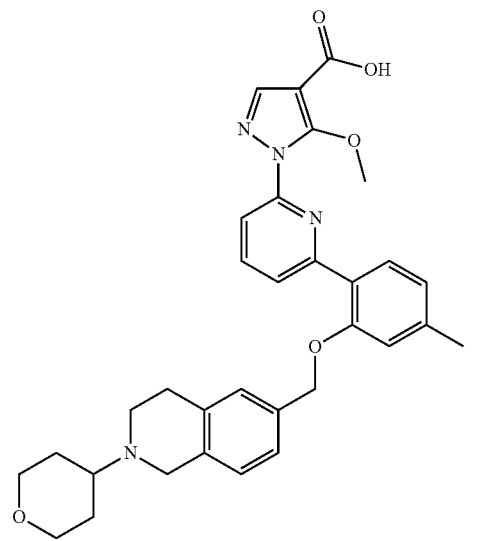 [SMILES: COc1c(C(=O)O)cnn1-c1cccc(-c2ccc(C)cc2OCc2ccc3c(c2)CCN(C2CCOCC2)C3)n1] |
| 99 | 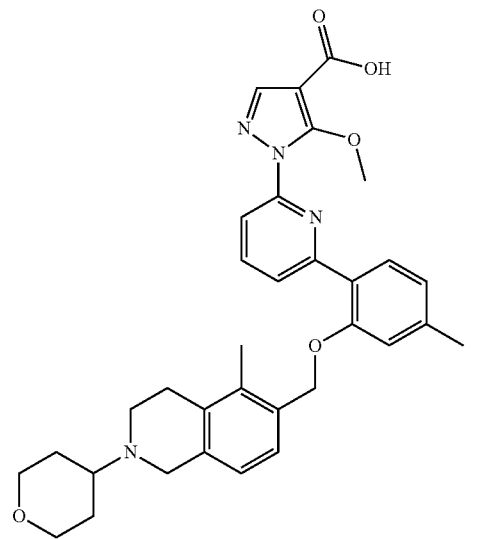 [SMILES: COc1c(C(=O)O)cnn1-c1cccc(-c2ccc(C)cc2OCc2ccc3c(c2C)CCN(C2CCOCC2)C3)n1] |
| Cpd No. | Structure |
|---|---|
| 100 | 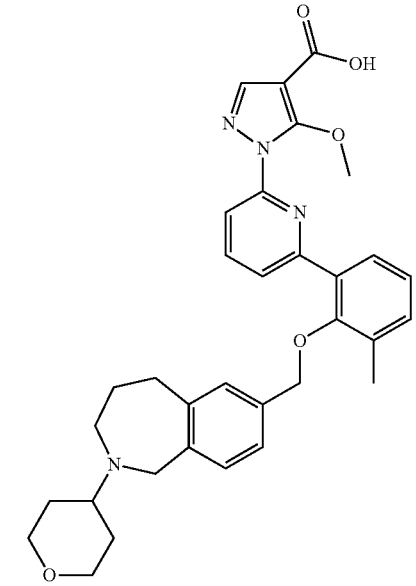 [SMILES: COc1c(C(=O)O)cnn1-c1cccc(-c2cccc(C)c2OCc2ccc3c(c2)CCCN(C2CCOCC2)C3)n1] |
| 101 | 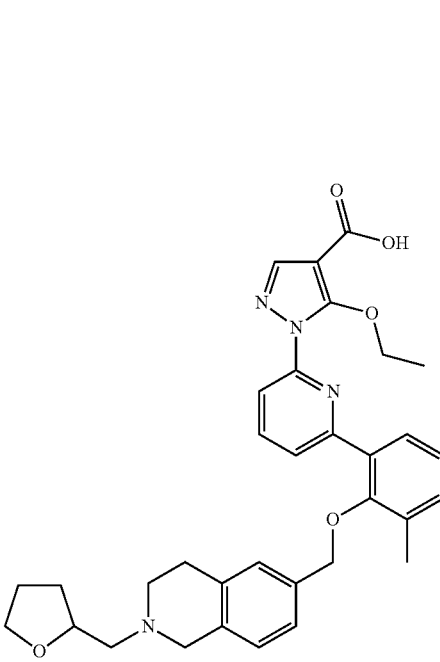 |

| Cpd No. | Structure |
|---|---|
| 102 | 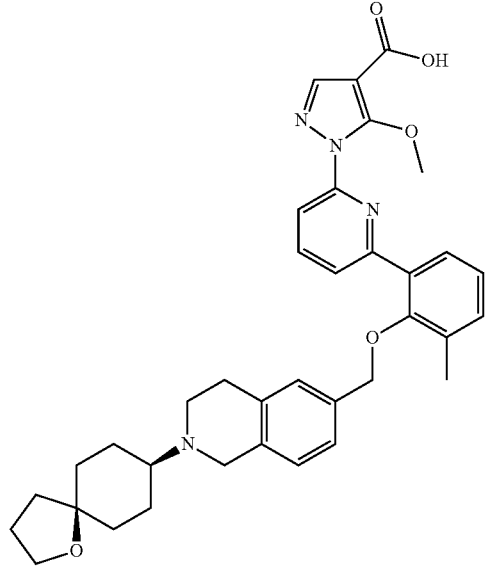 [SMILES: COc1c(C(=O)O)cnn1-c1cccc(-c2cccc(C)c2OCc2ccc3c(c2)CCN([C@H]2CC[C@]4(CCCO4)CC2)C3)n1] |
| 103 | 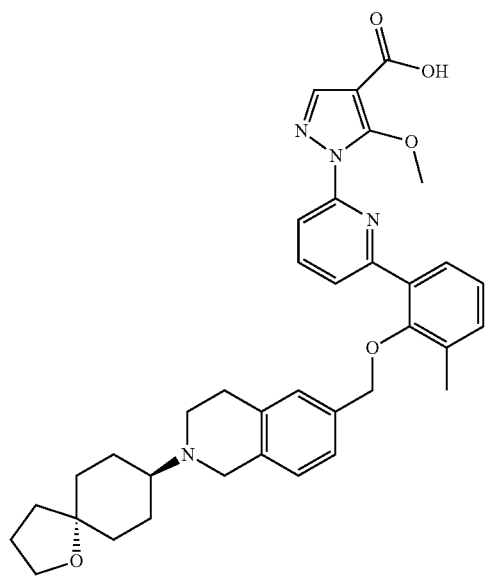 [SMILES: COc1c(C(=O)O)cnn1-c1cccc(-c2cccc(C)c2OCc2ccc3c(c2)CCN([C@H]2CC[C@@]4(CCCO4)CC2)C3)n1] |
| Cpd No. | Structure |
|---|---|
| 104 | 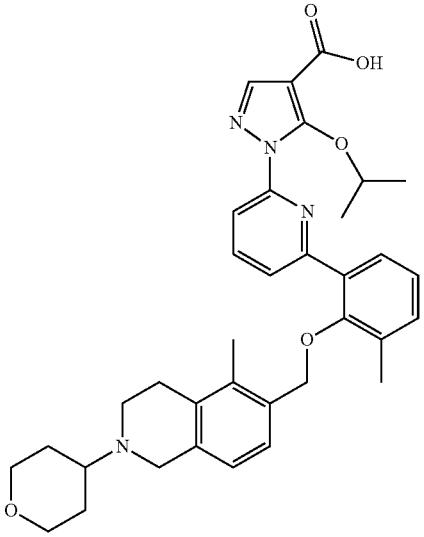 [SMILES: Cc1cccc(-c2cccc(-n3ncc(C(=O)O)c3OC(C)C)n2)c1OCc1ccc2c(c1C)CCN(C1CCOCC1)C2] |
| 105 | 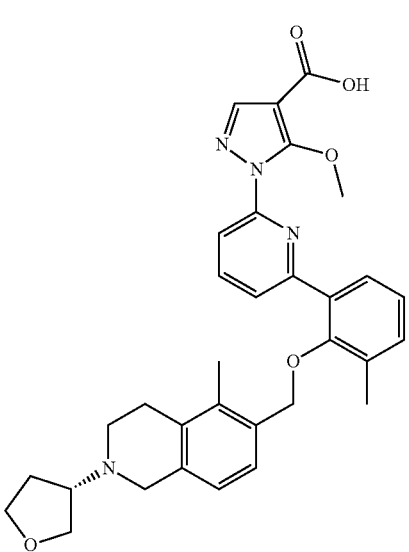 [SMILES: COc1c(C(=O)O)cnn1-c1cccc(-c2cccc(C)c2OCc2ccc3c(c2C)CCN([C@H]2CCOC2)C3)n1] |

| Cpd No. | Structure |
|---|---|
| 106 | 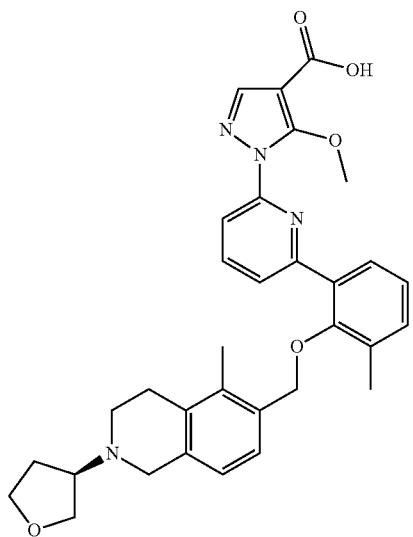 [SMILES: COc1c(C(=O)O)cnn1-c1cccc(-c2cccc(C)c2OCc2ccc3c(c2C)CCN([C@@H]2CCOC2)C3)n1] |
| 107 | 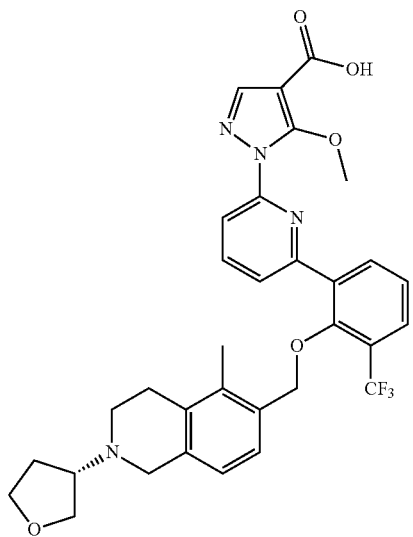 [SMILES: COc1c(C(=O)O)cnn1-c1cccc(-c2cccc(C(F)(F)F)c2OCc2ccc3c(c2C)CCN([C@H]2CCOC2)C3)n1] |
| Cpd No. | Structure |
|---|---|
| 108 | 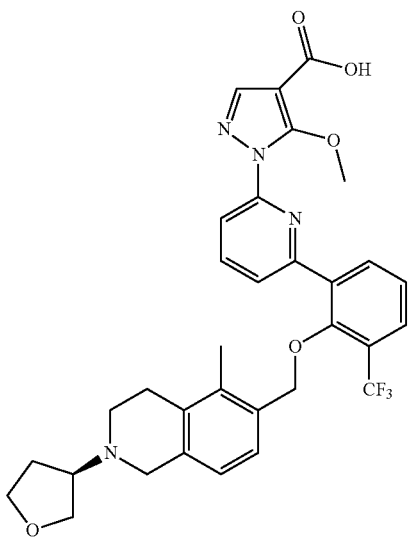 |
| 109 | 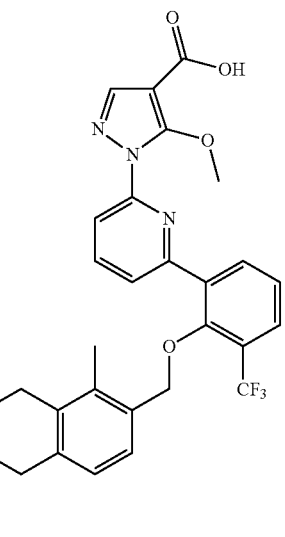 |

-continued
| Cpd No. | Structure |
|---|---|
| 110 | 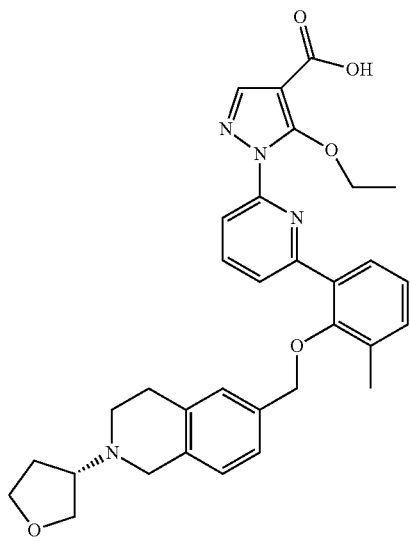 [SMILES: CCOc1c(C(=O)O)cnn1-c1cccc(-c2cccc(C)c2OCc2ccc3c(c2)CCN([C@H]2CCOC2)C3)n1] |
| 111 | 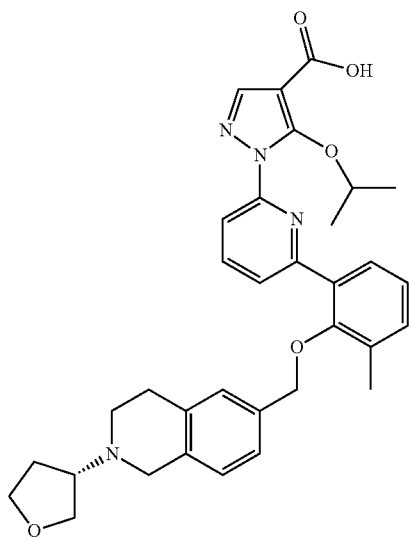 [SMILES: Cc1cccc(-c2cccc(-n3ncc(C(=O)O)c3OC(C)C)n2)c1OCc1ccc2c(c1)CCN([C@H]1CCOC1)C2] |
-continued
| Cpd No. | Structure |
|---|---|
| 112 | 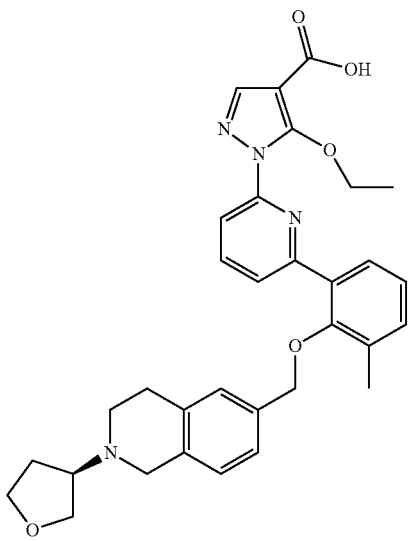 [SMILES: CCOc1c(C(=O)O)cnn1-c1cccc(-c2cccc(C)c2OCc2ccc3c(c2)CCN([C@@H]2CCOC2)C3)n1] |
| 113 | 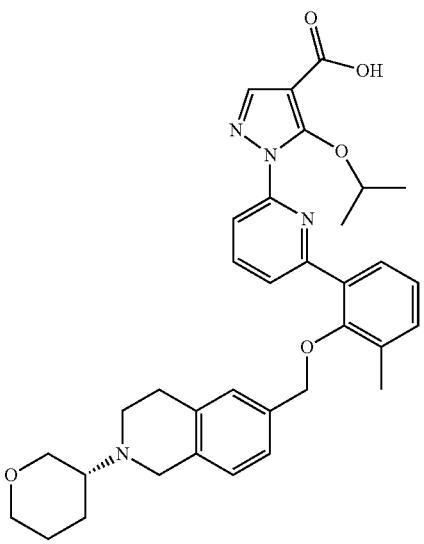 [SMILES: Cc1cccc(-c2cccc(-n3ncc(C(=O)O)c3OC(C)C)n2)c1OCc1ccc2c(c1)CCN([C@@H]1CCCOC1)C2] |

-continued
| Cpd No. | Structure |
|---|---|
| 114 | 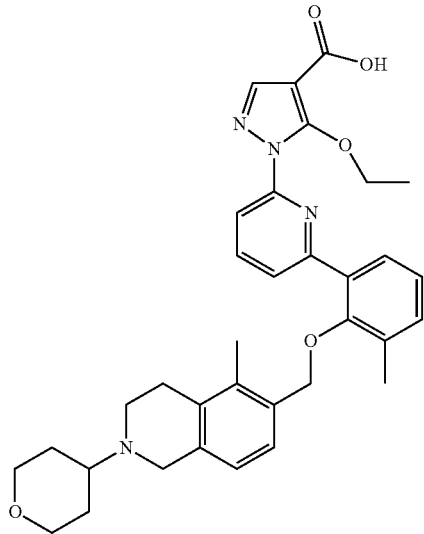 [SMILES: CCOc1c(C(=O)O)cnn1-c1cccc(-c2cccc(C)c2OCc2ccc3c(c2C)CCN(C2CCOCC2)C3)n1] |
| 115 | 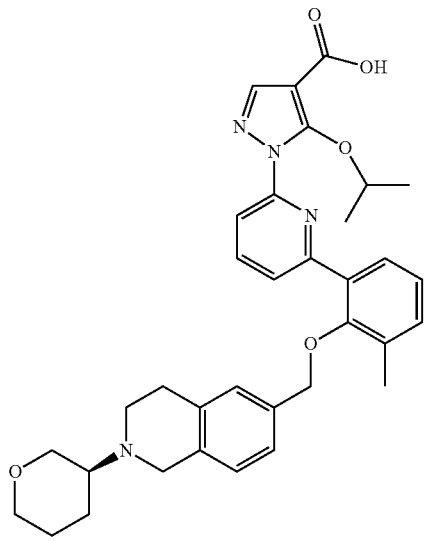 [SMILES: Cc1cccc(-c2cccc(-n3ncc(C(=O)O)c3OC(C)C)n2)c1OCc1ccc2c(c1)CCN([C@H]1CCCOC1)C2] |
-continued
| Cpd No. | Structure |
|---|---|
| 116 | 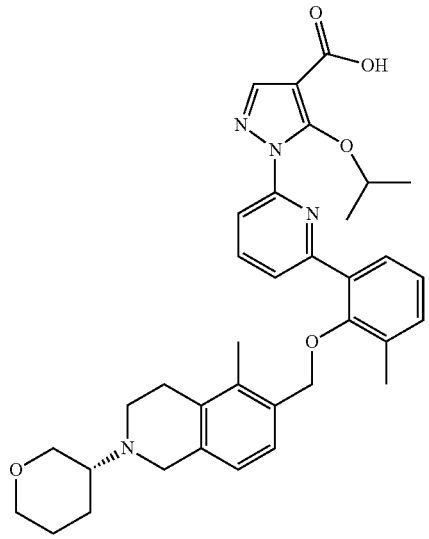 [SMILES: Cc1cccc(-c2cccc(-n3ncc(C(=O)O)c3OC(C)C)n2)c1OCc1ccc2c(c1C)CCN([C@@H]1CCCOC1)C2] |
| 117 | 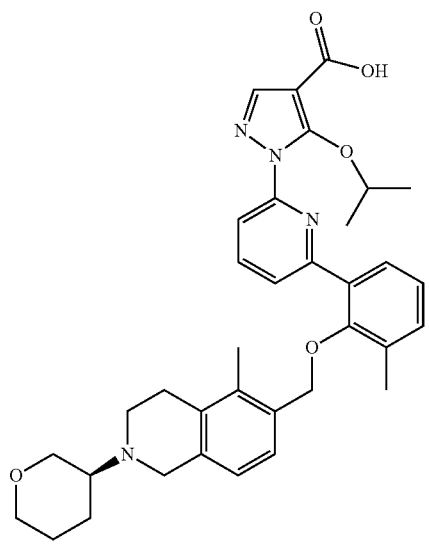 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 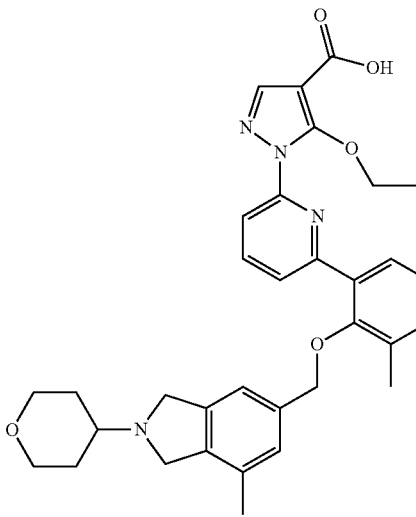 |

-continued
| Cpd No. | Structure |
|---|---|
| 119 | 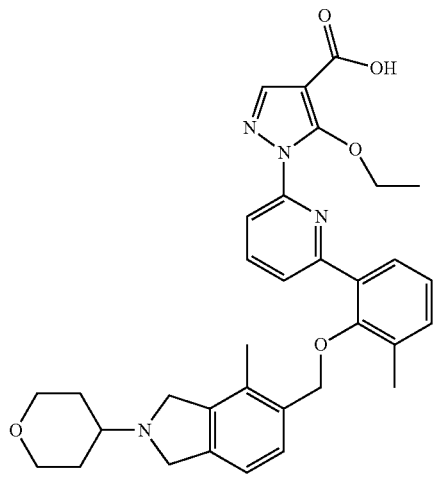 [SMILES: CCOc1c(C(=O)O)cnn1-c1cccc(-c2cccc(C)c2OCc2ccc3c(c2C)CN(C2CCOCC2)C3)n1] |
| 120 | 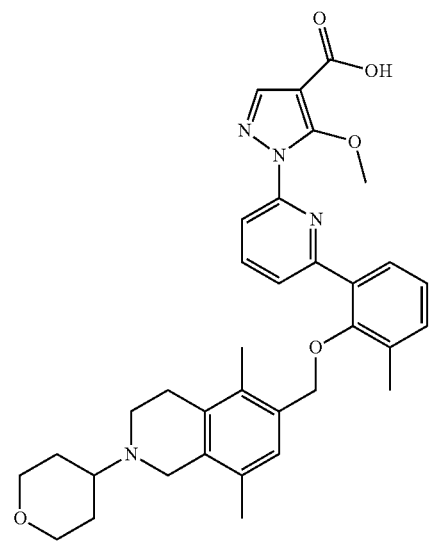 [SMILES: COc1c(C(=O)O)cnn1-c1cccc(-c2cccc(C)c2OCc2cc(C)c3c(c2C)CCN(C2CCOCC2)C3)n1] |
| 121 | 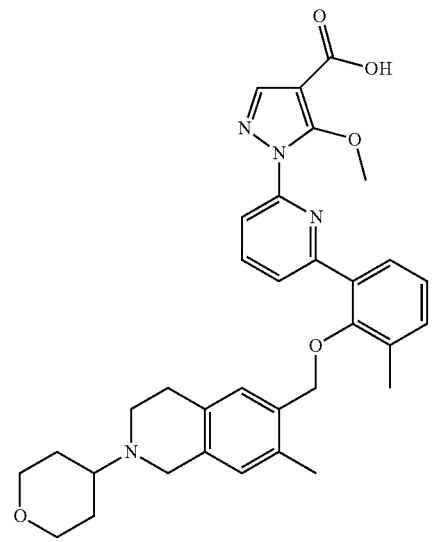 [SMILES: COc1c(C(=O)O)cnn1-c1cccc(-c2cccc(C)c2OCc2cc3c(cc2C)CN(C2CCOCC2)CC3)n1] |
-continued
| Cpd No. | Structure |
|---|---|
| 122 | 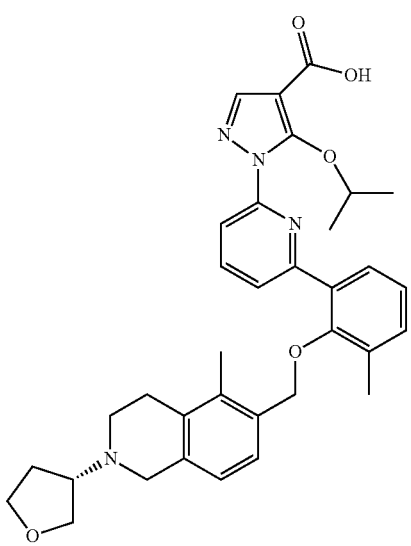 |
| 123 | 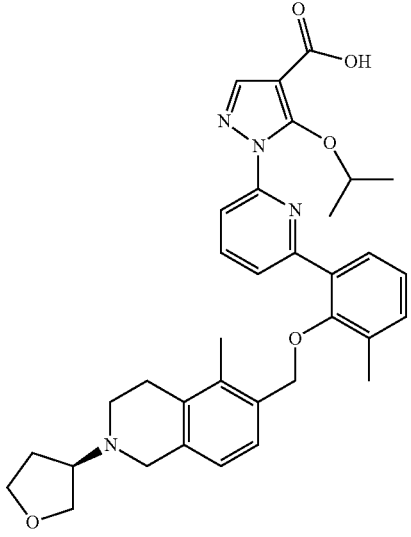 [SMILES: Cc1cccc(-c2cccc(-n3ncc(C(=O)O)c3OC(C)C)n2)c1OCc1ccc2c(c1C)CCN([C@@H]1CCOC1)C2] |

| Cpd No. | Structure |
|---|---|
| 124 | 5-methoxy-1-(6-(5-methyl-2-((5-methyl-2-(tetrahydro-2H-pyran-4-yl)-1,2,3,4-tetrahydroisoquinolin-6-yl)methoxy)phenyl)pyridin-2-yl)-1H-pyrazole-4-carboxylic acid |
| 125 | 5-ethoxy-1-(6-(2-((5-methyl-2-((S)-tetrahydrofuran-3-yl)-1,2,3,4-tetrahydroisoquinolin-6-yl)methoxy)-3-methylphenyl)pyrimidin-4-yl)-1H-pyrazole-4-carboxylic acid |
| 126 | 5-ethoxy-1-(6-(2-((5-methyl-2-((S)-tetrahydrofuran-3-yl)-1,2,3,4-tetrahydroisoquinolin-6-yl)methoxy)-3-methylphenyl)pyridin-2-yl)-1H-pyrazole-4-carboxylic acid |
| 127 | 1-(6-(2-((2-((1,4-dioxan-2-yl)methyl)-5-methyl-1,2,3,4-tetrahydroisoquinolin-6-yl)methoxy)-3-methylphenyl)pyridin-2-yl)-5-methoxy-1H-pyrazole-4-carboxylic acid |
| 128 | 5-ethoxy-1-(6-(2-((5-methyl-2-((S)-tetrahydro-2H-pyran-3-yl)-1,2,3,4-tetrahydroisoquinolin-6-yl)methoxy)-3-methylphenyl)pyridin-2-yl)-1H-pyrazole-4-carboxylic acid |

251
-continued
| Cpd No. | Structure |
|---|---|
| 129 | 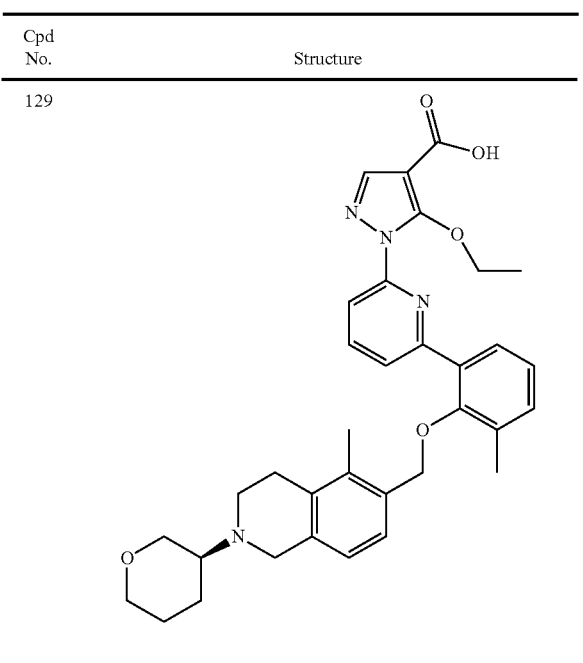 |
| 130 |  |
252
-continued
| Cpd No. | Structure |
|---|---|
| 131 | 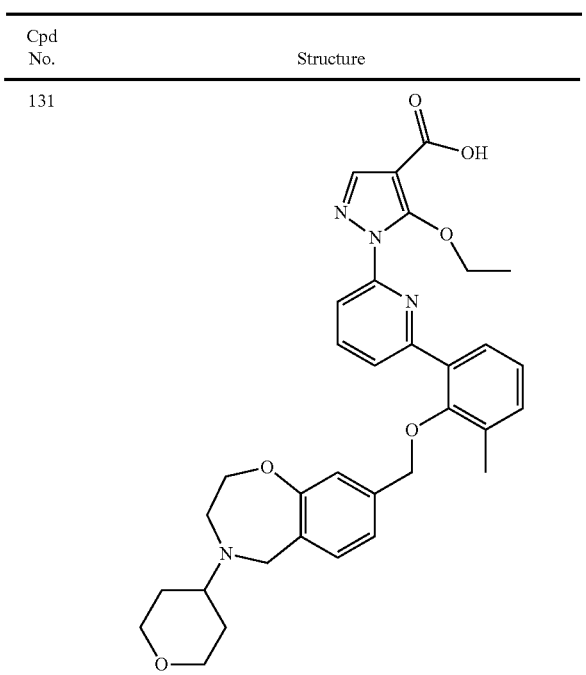 |
| 132 | 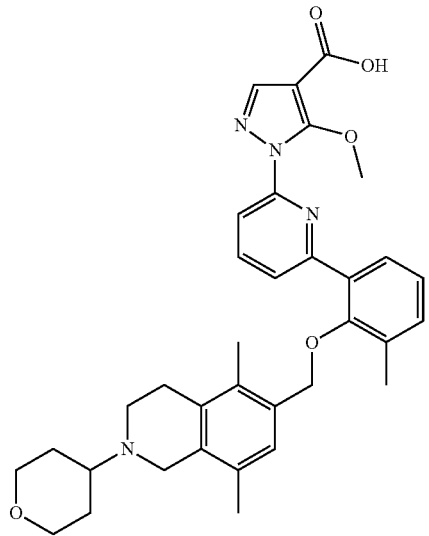 [SMILES: COc1c(C(=O)O)cnn1-c1cccc(-c2cccc(C)c2OCc2cc(C)c3c(c2C)CCN(C2CCOCC2)C3)n1] |

| Cpd No. | Structure |
|---|---|
| 133 | 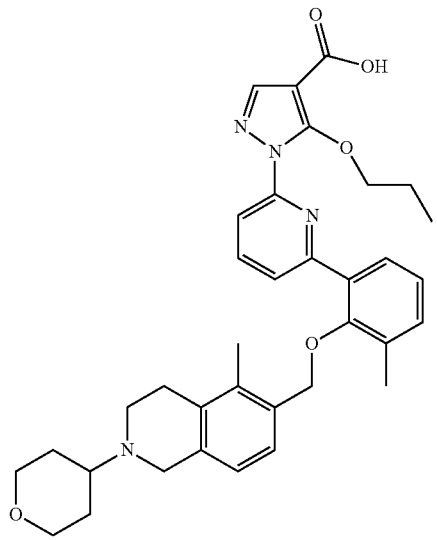 [SMILES: CCCOc1c(C(=O)O)cnn1-c1cccc(-c2cccc(C)c2OCc2ccc3c(c2C)CCN(C2CCOCC2)C3)n1] |
| 134 | 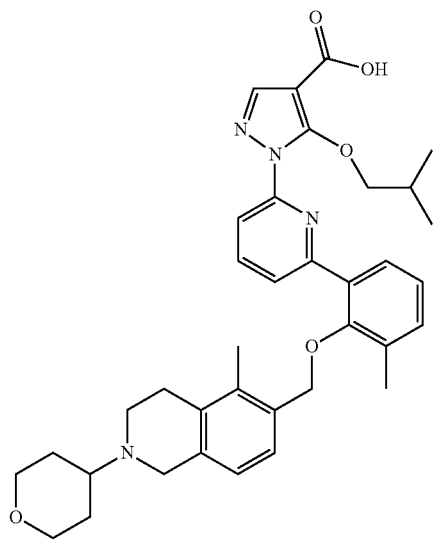 [SMILES: Cc1cccc(-c2cccc(-n3ncc(C(=O)O)c3OCC(C)C)n2)c1OCc1ccc2c(c1C)CCN(C1CCOCC1)C2] |
| Cpd No. | Structure |
|---|---|
| 135 | 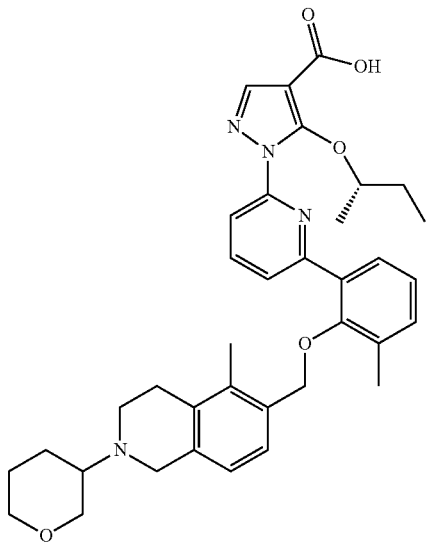 [SMILES: CC[C@H](C)Oc1c(C(=O)O)cnn1-c1cccc(-c2cccc(C)c2OCc2ccc3c(c2C)CCN(C2CCCOC2)C3)n1] |
| 136 | 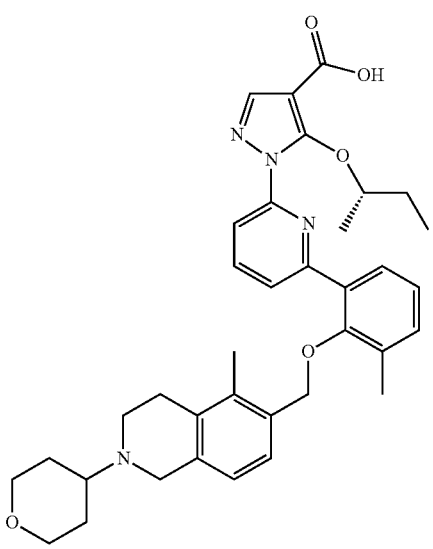 [SMILES: CC[C@H](C)Oc1c(C(=O)O)cnn1-c1cccc(-c2cccc(C)c2OCc2ccc3c(c2C)CCN(C2CCOCC2)C3)n1] |

US 8,906,904 B2
255
-continued
| Cpd No. | Structure |
|---|---|
| 137 | 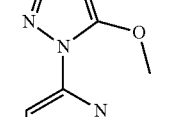 |
| 138 | 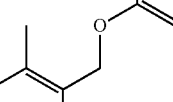 |
| 139 | 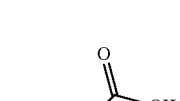 |
256
-continued
| Cpd No. | Structure |
|---|---|
| 140 | 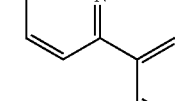 |
| 141 | 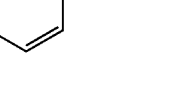 |
| 142 | 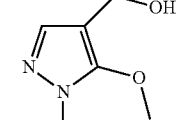 |

257
-continued
| Cpd No. | Structure |
|---|---|
| 143 | 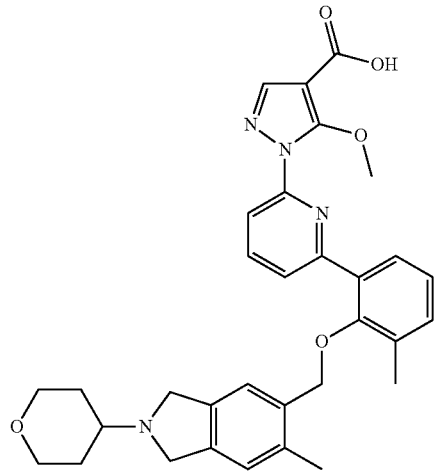 [SMILES: COc1c(C(=O)O)cnn1-c1cccc(-c2cccc(C)c2OCc2cc3c(cc2C)CN(C2CCOCC2)C3)n1] |
| 144 | 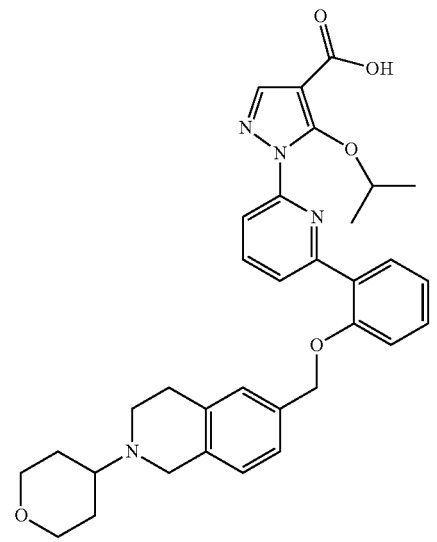 [SMILES: CC(C)Oc1c(C(=O)O)cnn1-c1cccc(-c2ccccc2OCc2ccc3c(c2)CCN(C2CCOCC2)C3)n1] |
| 145 | 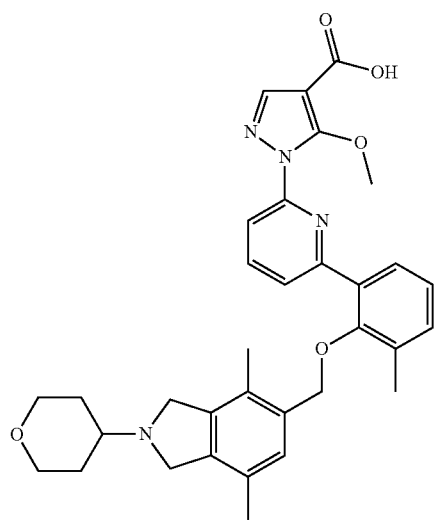 [SMILES: COc1c(C(=O)O)cnn1-c1cccc(-c2cccc(C)c2OCc2cc(C)c3c(c2C)CN(C2CCOCC2)C3)n1] |
258
-continued
| Cpd No. | Structure |
|---|---|
| 146 | 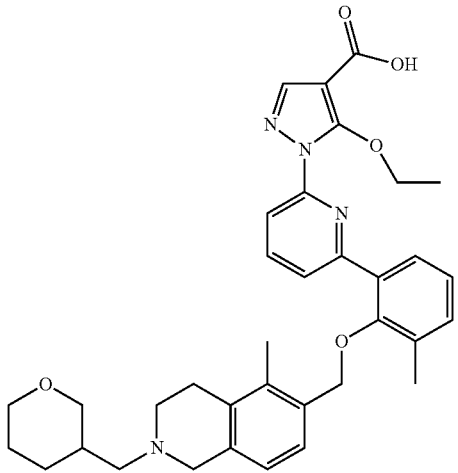 [SMILES: CCOc1c(C(=O)O)cnn1-c1cccc(-c2cccc(C)c2OCc2ccc3c(c2C)CCN(CC2CCCOC2)C3)n1] |
| 147 | 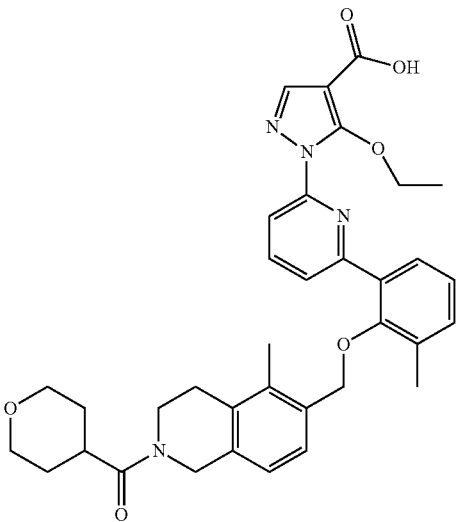 [SMILES: CCOc1c(C(=O)O)cnn1-c1cccc(-c2cccc(C)c2OCc2ccc3c(c2C)CCN(C(=O)C2CCOCC2)C3)n1] |
| 148 | 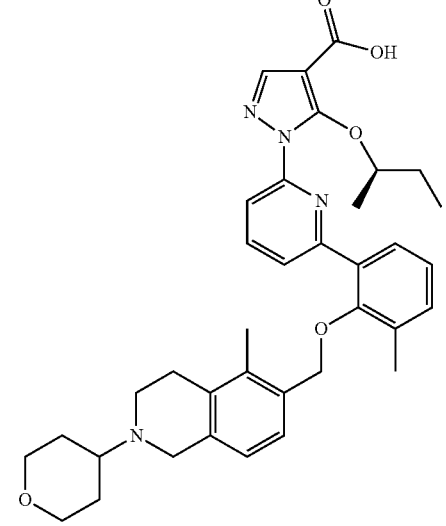 |

| Cpd No. | Structure |
|---|---|
| 149 | 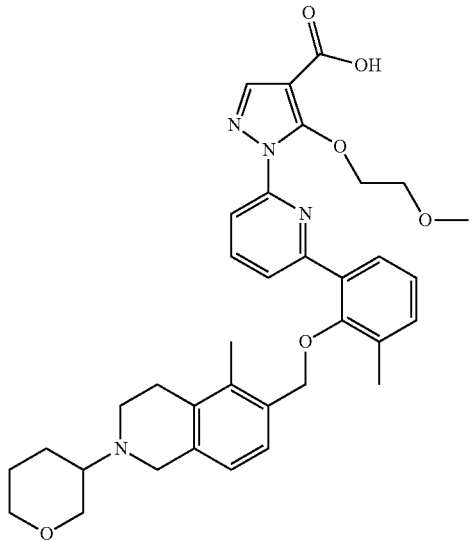 [SMILES: COCCOc1c(C(=O)O)cnn1-c1cccc(-c2cccc(C)c2OCc2ccc3c(c2C)CCN(C2CCCOC2)C3)n1] |
| 150 | 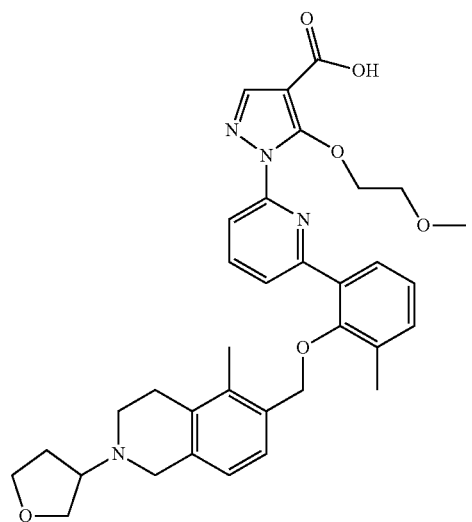 [SMILES: COCCOc1c(C(=O)O)cnn1-c1cccc(-c2cccc(C)c2OCc2ccc3c(c2C)CCN(C2CCOC2)C3)n1] |
| 151 | 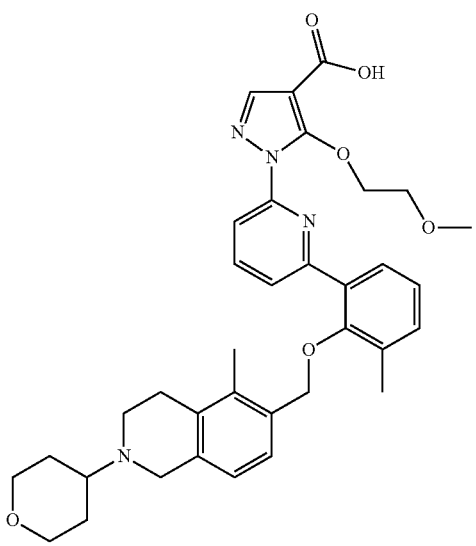 [SMILES: COCCOc1c(C(=O)O)cnn1-c1cccc(-c2cccc(C)c2OCc2ccc3c(c2C)CCN(C2CCOCC2)C3)n1] |
| 152 | 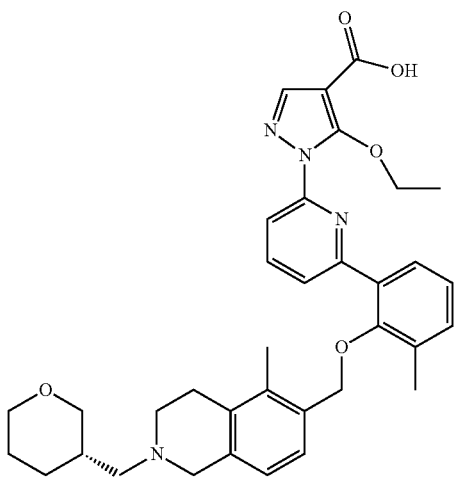 [SMILES: CCOc1c(C(=O)O)cnn1-c1cccc(-c2cccc(C)c2OCc2ccc3c(c2C)CCN(C[C@@H]2CCCOC2)C3)n1] |
| 153 | 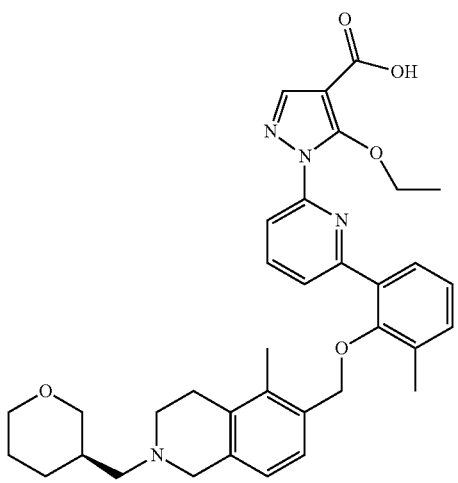 [SMILES: CCOc1c(C(=O)O)cnn1-c1cccc(-c2cccc(C)c2OCc2ccc3c(c2C)CCN(C[C@H]2CCCOC2)C3)n1] |
| 154 | 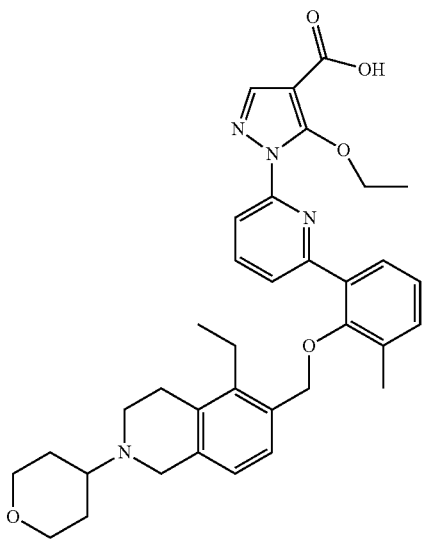 [SMILES: CCOc1c(C(=O)O)cnn1-c1cccc(-c2cccc(C)c2OCc2ccc3c(c2CC)CCN(C2CCOCC2)C3)n1] |

| Cpd No. | Structure |
|---|---|
| 155 | 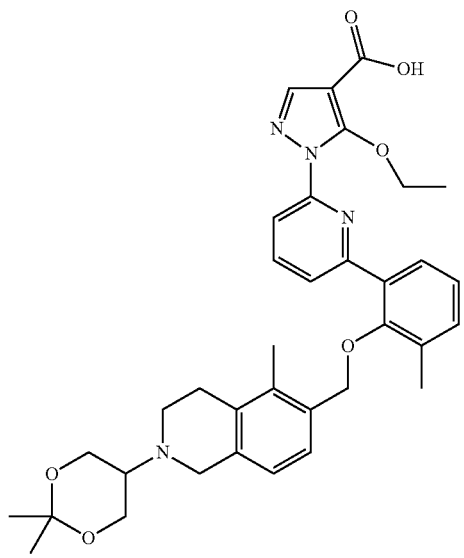 [SMILES: CCOc1c(C(=O)O)cnn1-c1cccc(-c2cccc(C)c2OCc2ccc3c(c2C)CCN(C2COC(C)(C)OC2)C3)n1] |
| 156 | 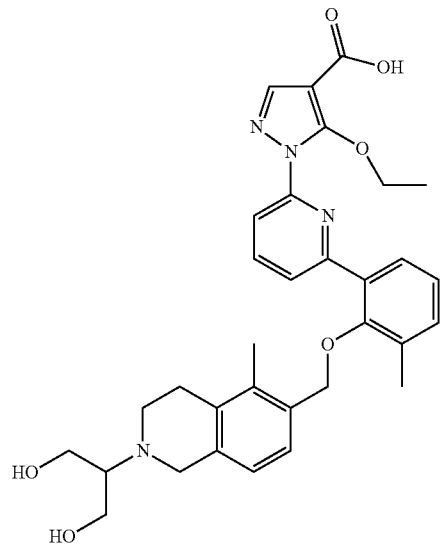 [SMILES: CCOc1c(C(=O)O)cnn1-c1cccc(-c2cccc(C)c2OCc2ccc3c(c2C)CCN(C(CO)CO)C3)n1] |
| Cpd No. | Structure |
|---|---|
| 157 | 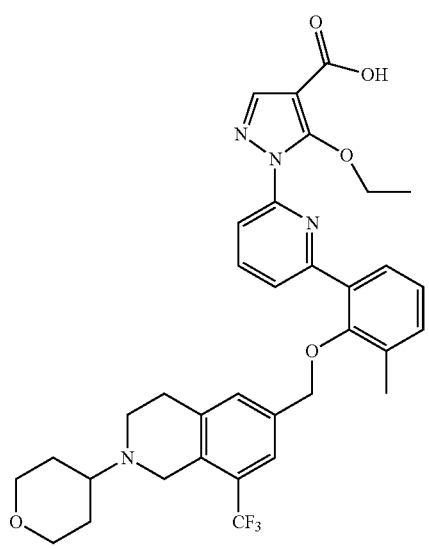 [SMILES: CCOc1c(C(=O)O)cnn1-c1cccc(-c2cccc(C)c2OCc2cc3c(c(C(F)(F)F)c2)CN(C2CCOCC2)CC3)n1] |
| 158 | 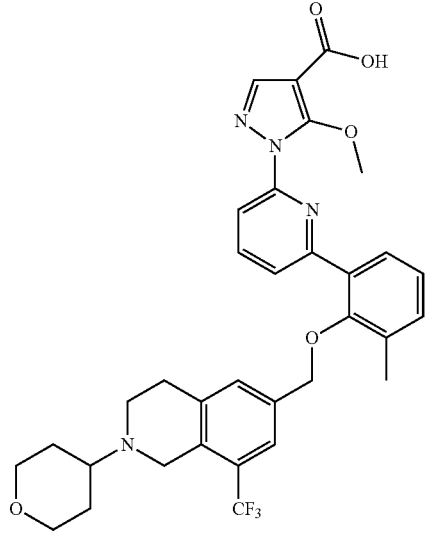 [SMILES: COc1c(C(=O)O)cnn1-c1cccc(-c2cccc(C)c2OCc2cc3c(c(C(F)(F)F)c2)CN(C2CCOCC2)CC3)n1] |

TABLE-continued
| Cpd No. | Structure |
|---|---|
| 159 | 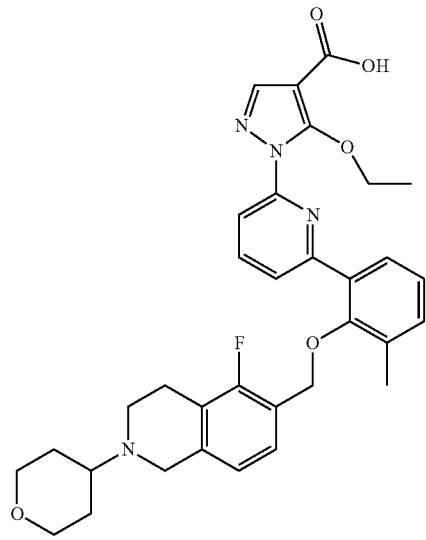 [SMILES: CCOc1c(C(=O)O)cnn1-c1cccc(-c2cccc(C)c2OCc2ccc3c(c2F)CCN(C2CCOCC2)C3)n1] |
| 160 | 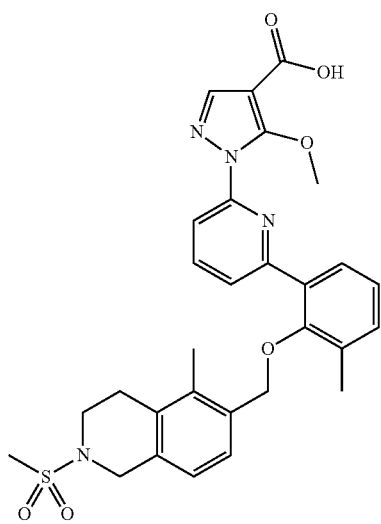 [SMILES: COc1c(C(=O)O)cnn1-c1cccc(-c2cccc(C)c2OCc2ccc3c(c2C)CCN(S(C)(=O)=O)C3)n1] |
| 161 | 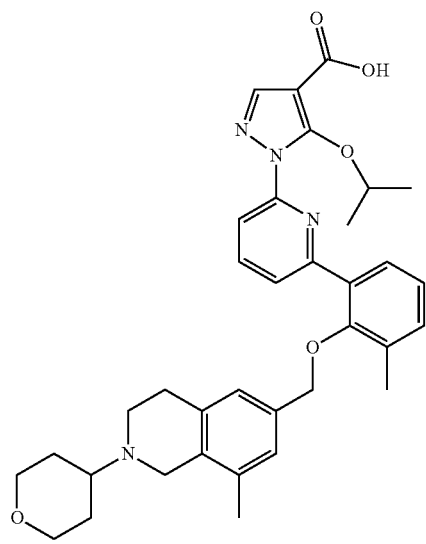 [SMILES: Cc1cc(COc2c(C)cccc2-c2cccc(-n3ncc(C(=O)O)c3OC(C)C)n2)cc2c1CN(C1CCOCC1)CC2] |
| Cpd No. | Structure |
|---|---|
| 162 | 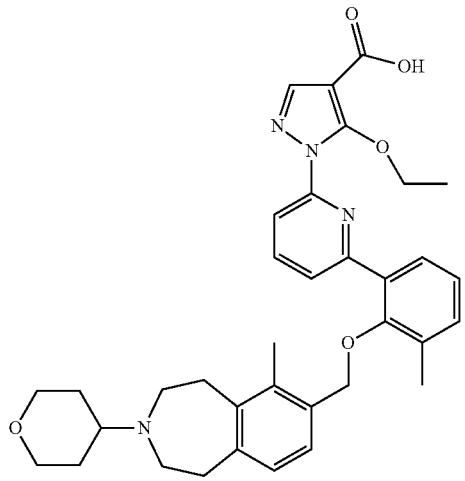 [SMILES: CCOc1c(C(=O)O)cnn1-c1cccc(-c2cccc(C)c2OCc2ccc3c(c2C)CCN(C2CCOCC2)CC3)n1] |
| 163 | 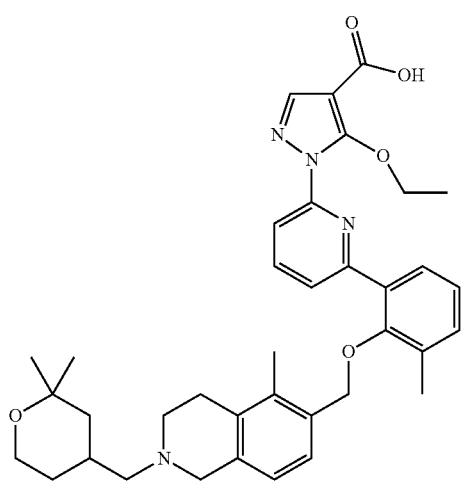 [SMILES: CCOc1c(C(=O)O)cnn1-c1cccc(-c2cccc(C)c2OCc2ccc3c(c2C)CCN(CC2CCOC(C)(C)C2)C3)n1] |
| 164 | 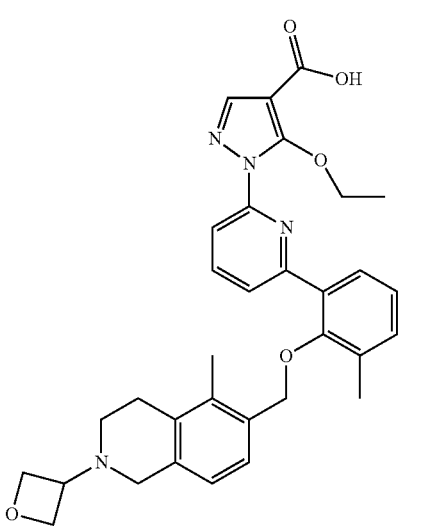 [SMILES: CCOc1c(C(=O)O)cnn1-c1cccc(-c2cccc(C)c2OCc2ccc3c(c2C)CCN(C2COC2)C3)n1] |

| Cpd No. | Structure |
|---|---|
| 165 | 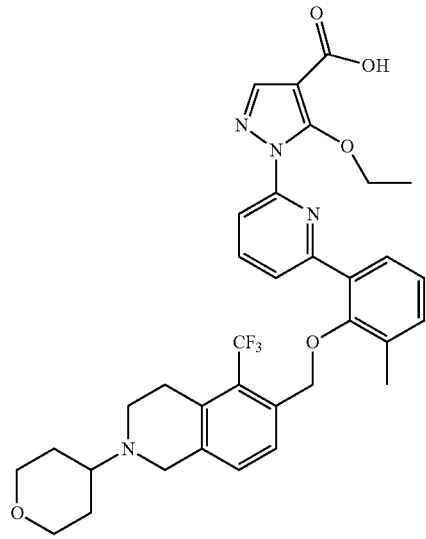 [SMILES: CCOc1c(C(=O)O)cnn1-c1cccc(-c2cccc(C)c2OCc2ccc3c(c2C(F)(F)F)CCN(C2CCOCC2)C3)n1] |
| 166 | 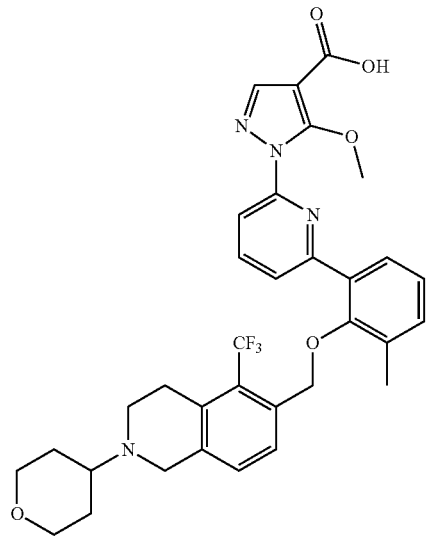 [SMILES: COc1c(C(=O)O)cnn1-c1cccc(-c2cccc(C)c2OCc2ccc3c(c2C(F)(F)F)CCN(C2CCOCC2)C3)n1] |
| Cpd No. | Structure |
|---|---|
| 167 | 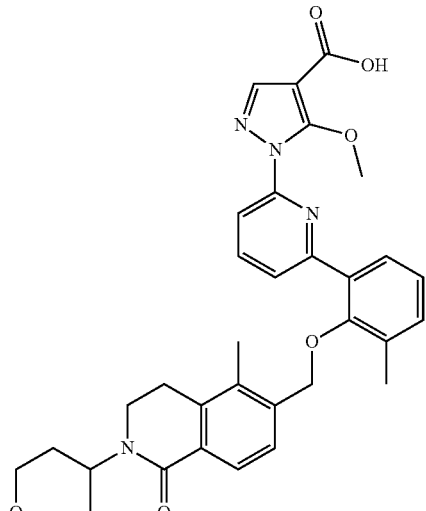 |
| 168 | |
| 169 | 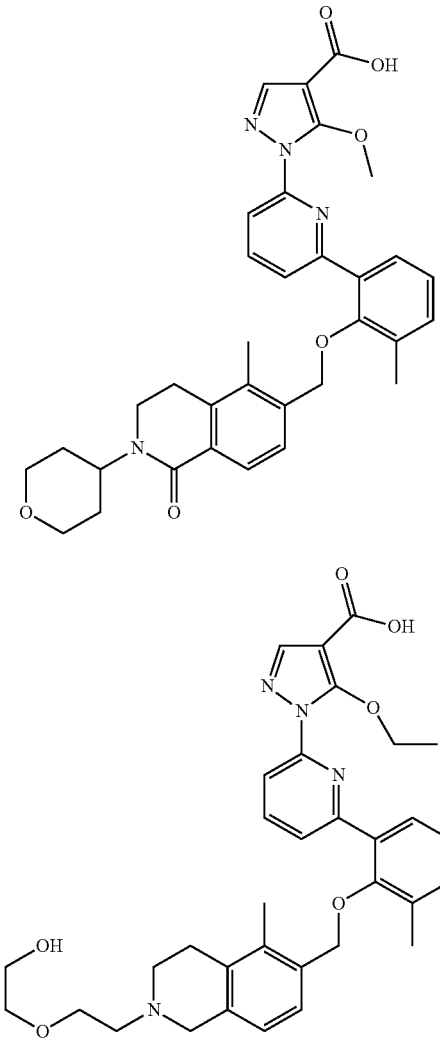 |

| Cpd No. | Structure |
|---|---|
| 170 | 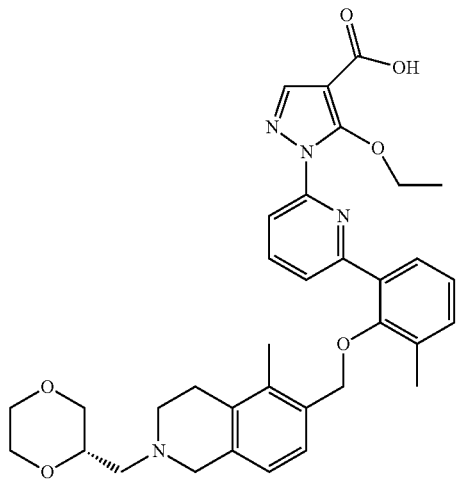 [SMILES: CCOc1c(C(=O)O)cnn1-c1cccc(-c2cccc(C)c2OCc2ccc3c(c2C)CCN(C[C@H]2COCCO2)C3)n1] |
| 171 | 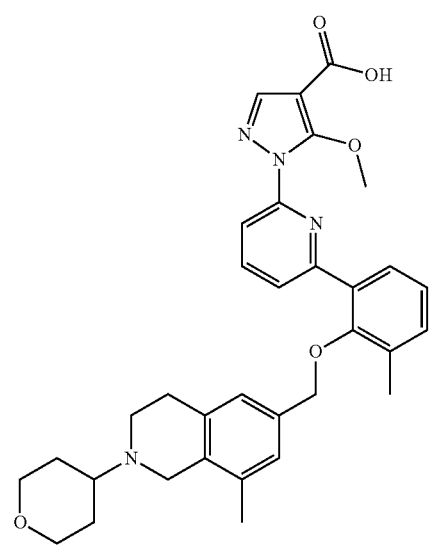 [SMILES: COc1c(C(=O)O)cnn1-c1cccc(-c2cccc(C)c2OCc2cc(C)c3c(c2)CCN(C2CCOCC2)C3)n1] |
| 172 | 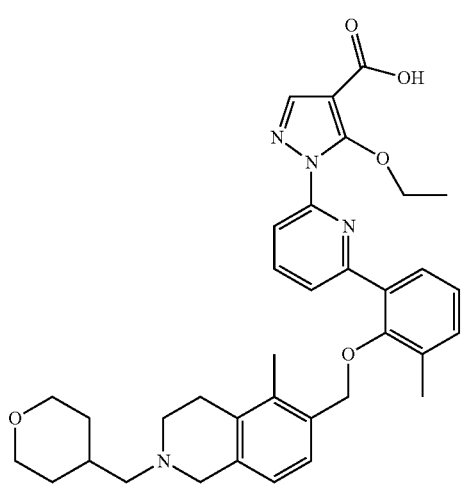 [SMILES: CCOc1c(C(=O)O)cnn1-c1cccc(-c2cccc(C)c2OCc2ccc3c(c2C)CCN(CC2CCOCC2)C3)n1] |
| Cpd No. | Structure |
|---|---|
| 173 | 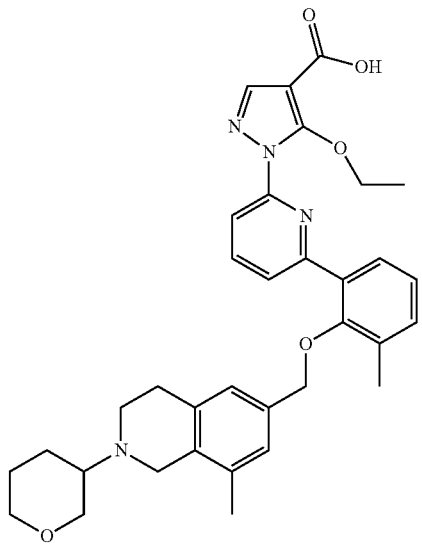 [SMILES: CCOc1c(C(=O)O)cnn1-c1cccc(-c2cccc(C)c2OCc2cc(C)c3c(c2)CCN(C2CCCOC2)C3)n1] |
| 174 | 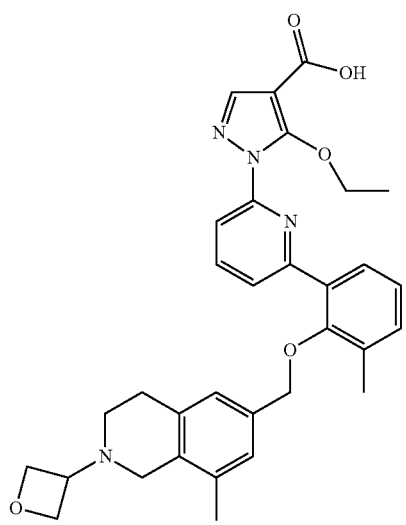 [SMILES: CCOc1c(C(=O)O)cnn1-c1cccc(-c2cccc(C)c2OCc2cc(C)c3c(c2)CCN(C2COC2)C3)n1] |
| 175 | 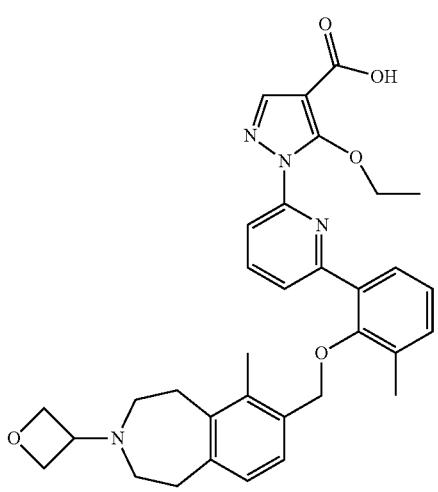 [SMILES: CCOc1c(C(=O)O)cnn1-c1cccc(-c2cccc(C)c2OCc2ccc3c(c2C)CCN(C2COC2)CC3)n1] |

-continued
| Cpd No. | Structure |
|---|---|
| 176 | 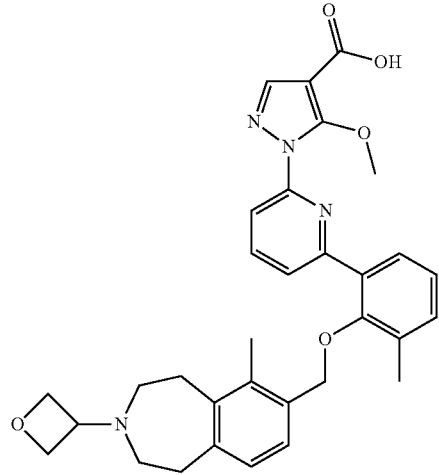 [SMILES: COc1c(C(=O)O)cnn1-c1cccc(-c2cccc(C)c2OCc2ccc3c(c2C)CCN(C2COC2)CC3)n1] |
| 177 | 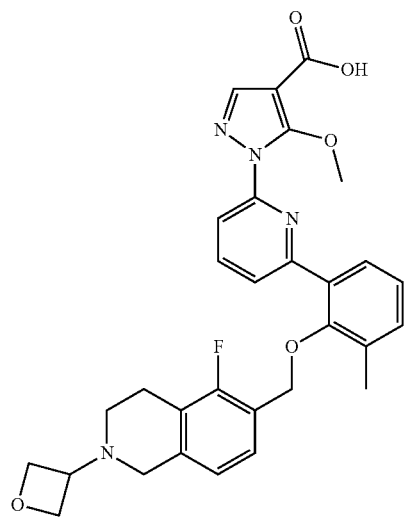 [SMILES: COc1c(C(=O)O)cnn1-c1cccc(-c2cccc(C)c2OCc2ccc3c(c2F)CCN(C2COC2)C3)n1] |
| 178 | 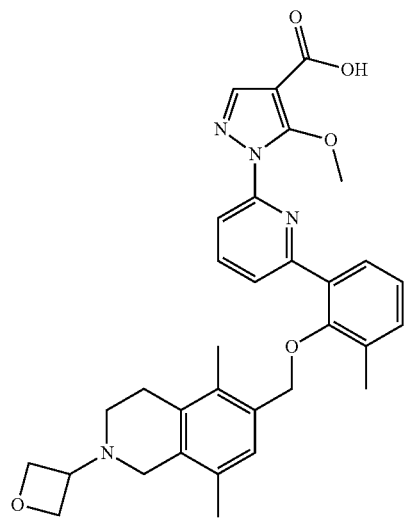 [SMILES: COc1c(C(=O)O)cnn1-c1cccc(-c2cccc(C)c2OCc2cc(C)c3c(c2C)CCN(C2COC2)C3)n1] |
-continued
| Cpd No. | Structure |
|---|---|
| 179 | 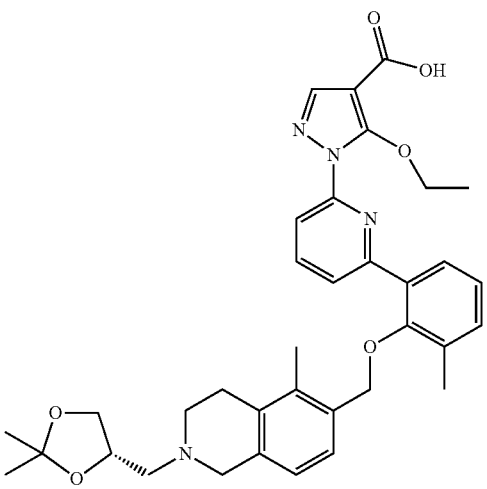 [SMILES: CCOc1c(C(=O)O)cnn1-c1cccc(-c2cccc(C)c2OCc2ccc3c(c2C)CCN(C[C@H]2COC(C)(C)O2)C3)n1] |
| 180 | 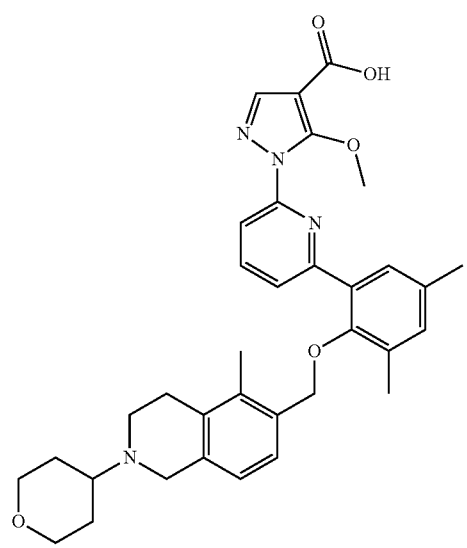 [SMILES: COc1c(C(=O)O)cnn1-c1cccc(-c2cc(C)cc(C)c2OCc2ccc3c(c2C)CCN(C2CCOCC2)C3)n1] |
| 181 | 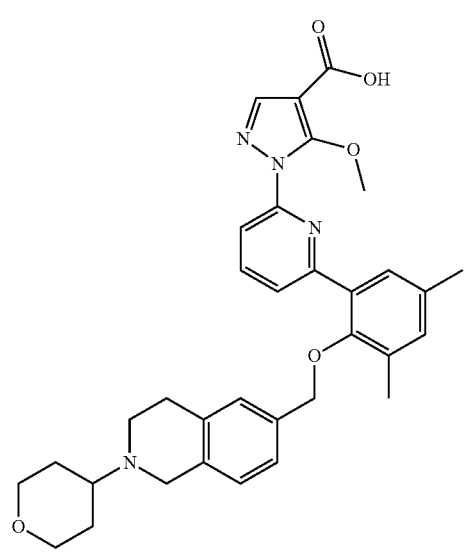 [SMILES: COc1c(C(=O)O)cnn1-c1cccc(-c2cc(C)cc(C)c2OCc2ccc3c(c2)CCN(C2CCOCC2)C3)n1] |

-continued
| Cpd No. | Structure |
|---|---|
| 182 | 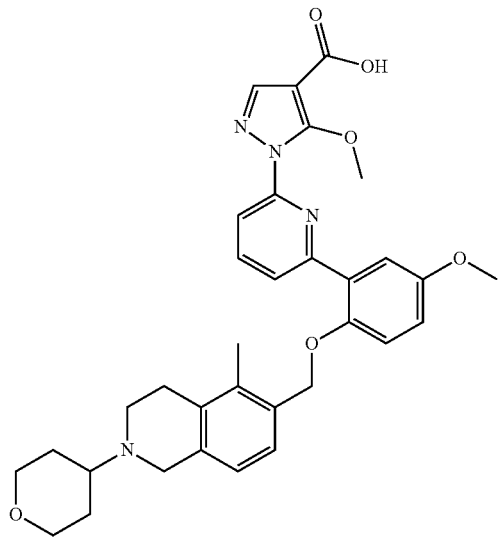 [SMILES: COc1ccc(OCc2ccc3c(c2C)CCN(C2CCOCC2)C3)c(-c2cccc(-n3ncc(C(=O)O)c3OC)n2)c1] |
| 183 | 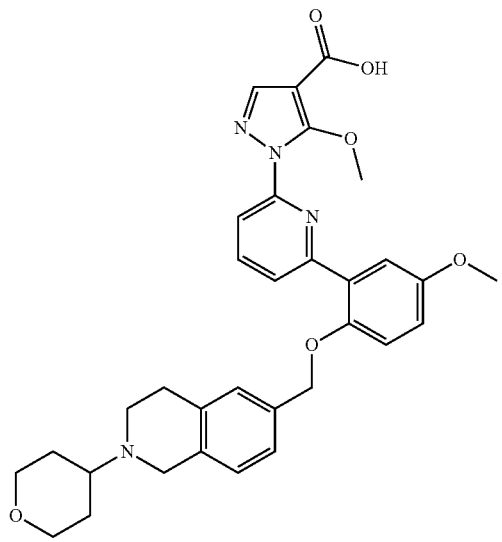 [SMILES: COc1ccc(OCc2ccc3c(c2)CCN(C2CCOCC2)C3)c(-c2cccc(-n3ncc(C(=O)O)c3OC)n2)c1] |
| 184 | 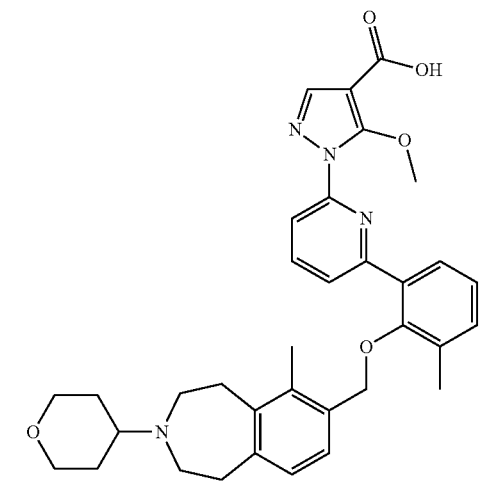 [SMILES: COc1c(C(=O)O)cnn1-c1cccc(-c2cccc(C)c2OCc2ccc3c(c2C)CCN(C2CCOCC2)CC3)n1] |
-continued
| Cpd No. | Structure |
|---|---|
| 185 | 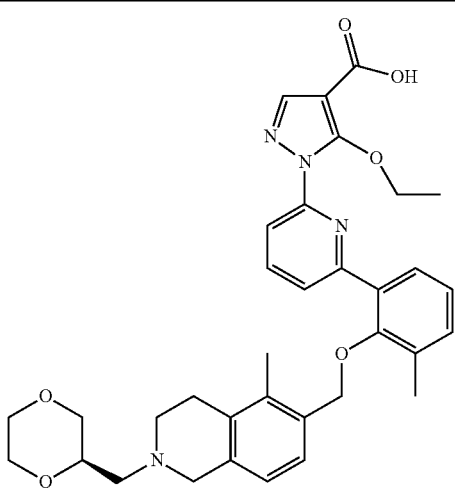 |
| 186 | 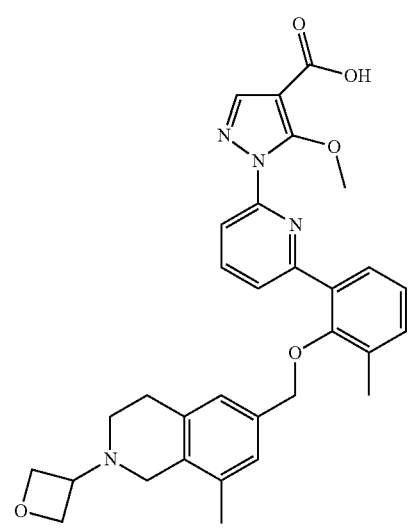 [SMILES: COc1c(C(=O)O)cnn1-c1cccc(-c2cccc(C)c2OCc2cc(C)c3c(c2)CCN(C2COC2)C3)n1] |
| 187 | 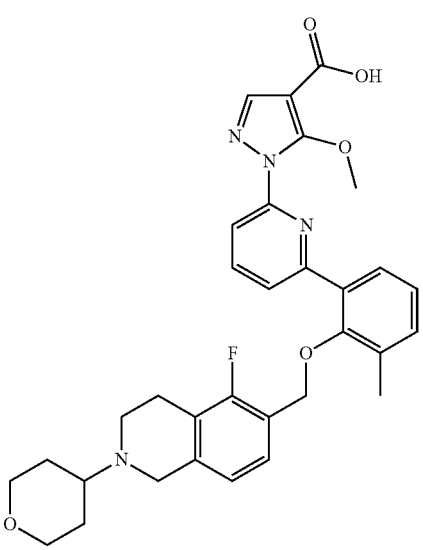 [SMILES: COc1c(C(=O)O)cnn1-c1cccc(-c2cccc(C)c2OCc2ccc3c(c2F)CCN(C2CCOCC2)C3)n1] |

| Cpd No. | Structure |
|---|---|
| 188 | 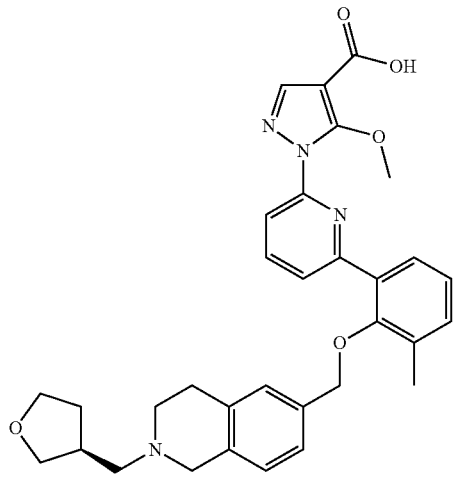 [SMILES: COc1c(C(=O)O)cnn1-c1cccc(-c2cccc(C)c2OCc2ccc3c(c2)CCN(C[C@@H]2CCOC2)C3)n1] |
| 189 | 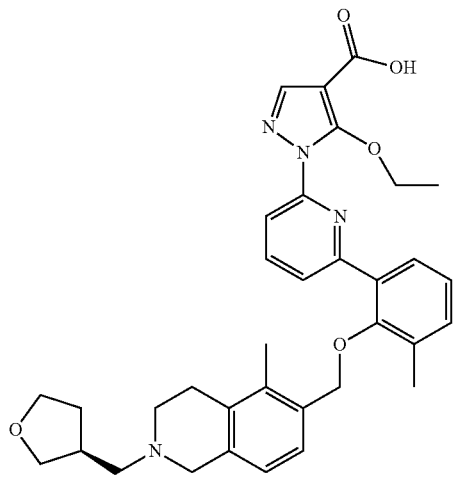 [SMILES: CCOc1c(C(=O)O)cnn1-c1cccc(-c2cccc(C)c2OCc2ccc3c(c2C)CCN(C[C@@H]2CCOC2)C3)n1] |
| 190 | 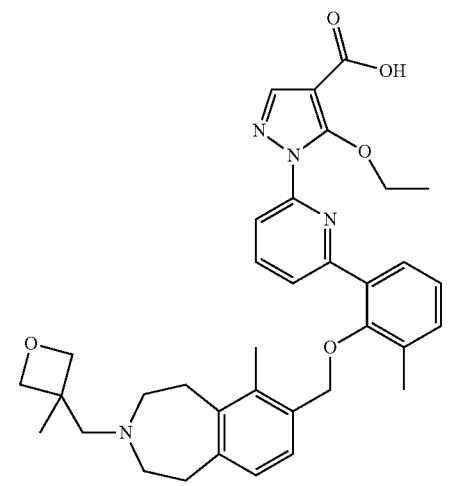 [SMILES: CCOc1c(C(=O)O)cnn1-c1cccc(-c2cccc(C)c2OCc2ccc3c(c2C)CCN(CC2(C)COC2)CC3)n1] |
| Cpd No. | Structure |
|---|---|
| 191 | 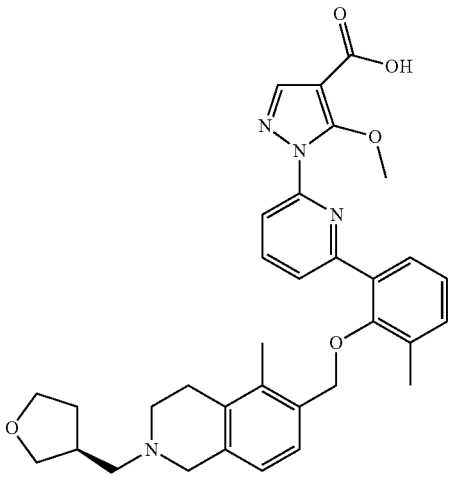 [SMILES: COc1c(C(=O)O)cnn1-c1cccc(-c2cccc(C)c2OCc2ccc3c(c2C)CCN(C[C@@H]2CCOC2)C3)n1] |
| 192 | 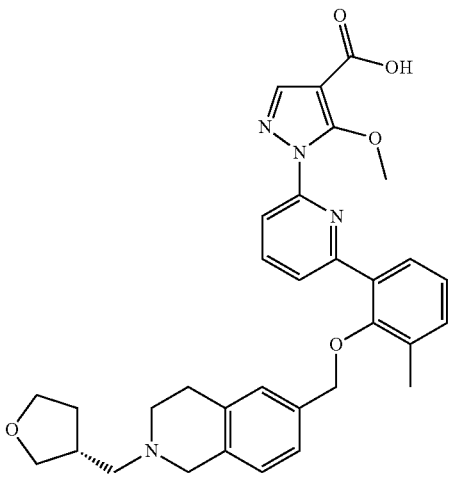 [SMILES: COc1c(C(=O)O)cnn1-c1cccc(-c2cccc(C)c2OCc2ccc3c(c2)CCN(C[C@H]2CCOC2)C3)n1] |
| 193 | 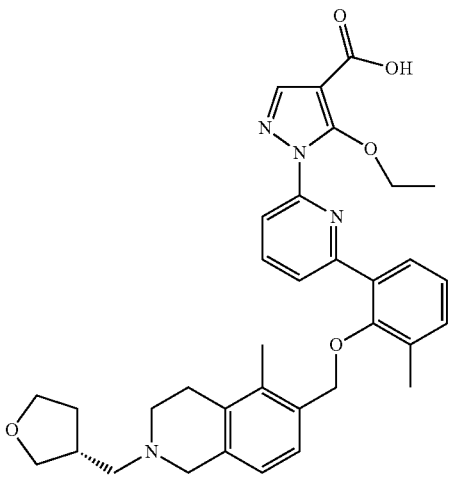 [SMILES: CCOc1c(C(=O)O)cnn1-c1cccc(-c2cccc(C)c2OCc2ccc3c(c2C)CCN(C[C@H]2CCOC2)C3)n1] |

275
-continued
| Cpd No. | Structure |
|---|---|
| 194 | 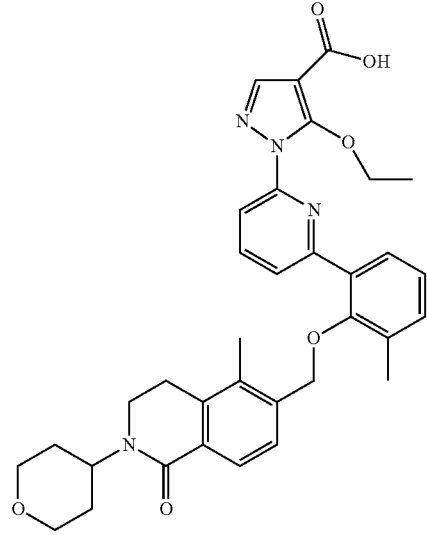 [SMILES: CCOc1c(C(=O)O)cnn1-c1cccc(-c2cccc(C)c2OCc2ccc3c(c2C)CCN(C2CCOCC2)C3=O)n1] |
| 195 | 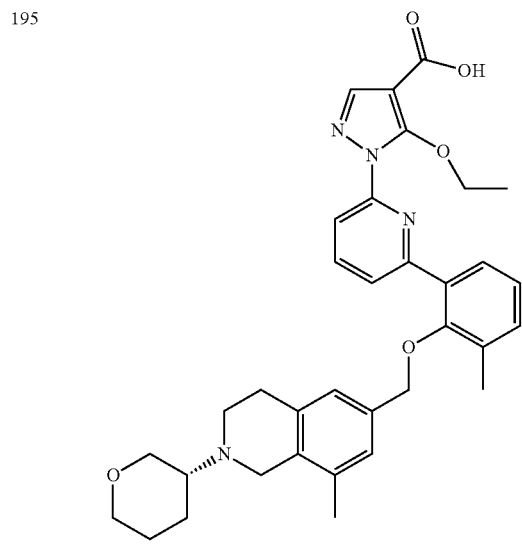 |
| 196 | 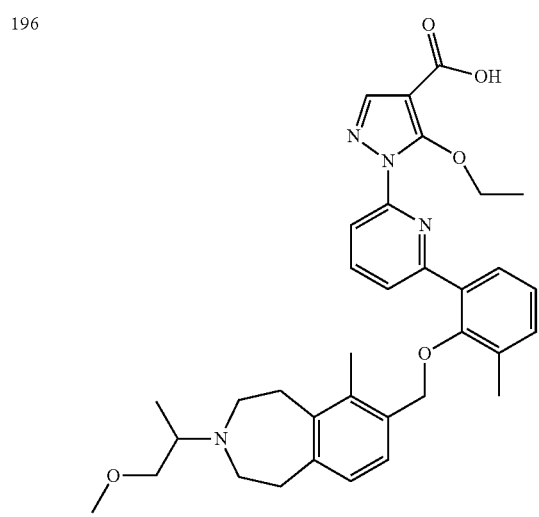 |
276
-continued
| Cpd No. | Structure |
|---|---|
| 197 | 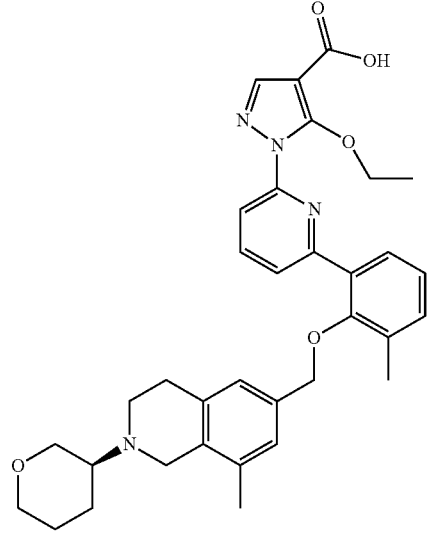 [SMILES: CCOc1c(C(=O)O)cnn1-c1cccc(-c2cccc(C)c2OCc2cc(C)c3c(c2)CCN([C@H]2CCCOC2)C3)n1] |
| 198 | 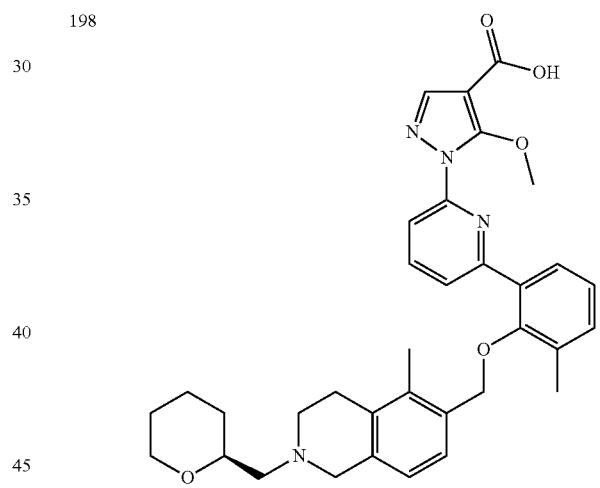 |
| 199 | 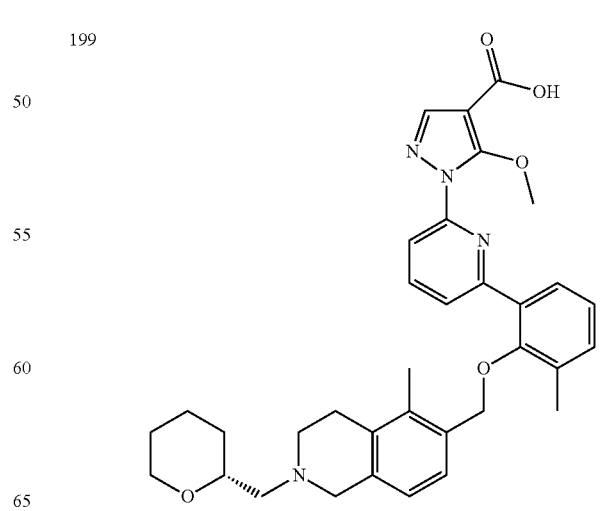 |

-continued

| Cpd No. | Structure |
|---|---|
| 200 | (structure) |
| 201 | (structure) |
| 202 | (structure) |

-continued

| Cpd No. | Structure |
|---|---|
| 203 | (structure) |
| 204 | (structure) |
| 205 | (structure) |

| Cpd No. | Structure |
|---|---|
| 206 | 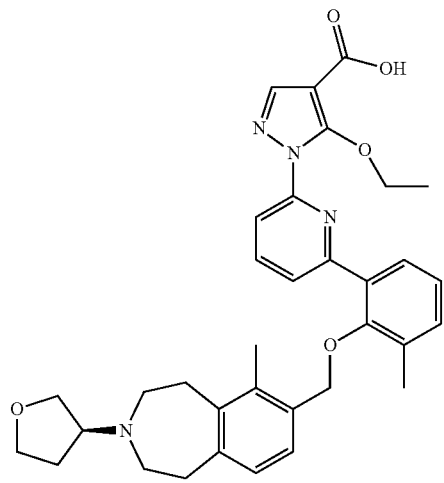 [SMILES: CCOc1c(C(=O)O)cnn1-c1cccc(-c2cccc(C)c2OCc2ccc3c(c2C)CCN([C@H]2CCOC2)CC3)n1] |
| 207 | 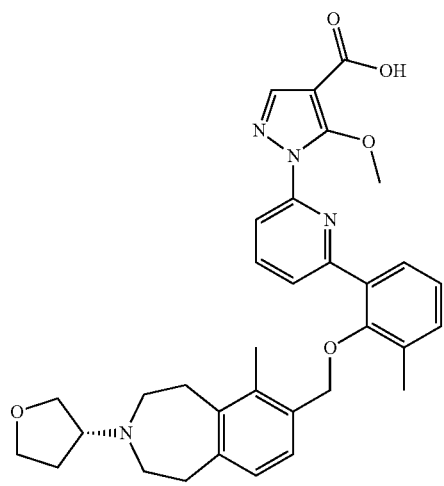 [SMILES: COc1c(C(=O)O)cnn1-c1cccc(-c2cccc(C)c2OCc2ccc3c(c2C)CCN([C@@H]2CCOC2)CC3)n1] |
| 208 | 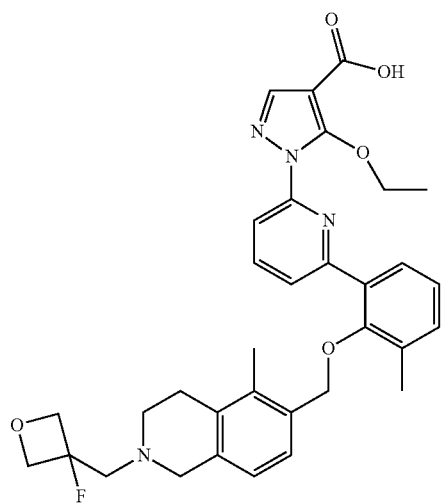 [SMILES: CCOc1c(C(=O)O)cnn1-c1cccc(-c2cccc(C)c2OCc2ccc3c(c2C)CCN(CC2(F)COC2)C3)n1] |
| Cpd No. | Structure |
|---|---|
| 209 | 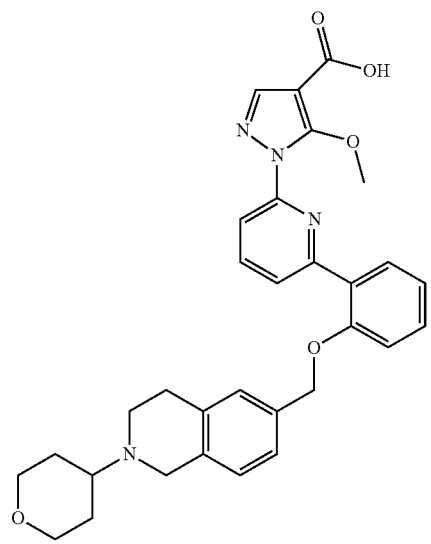 [SMILES: COc1c(C(=O)O)cnn1-c1cccc(-c2ccccc2OCc2ccc3c(c2)CCN(C2CCOCC2)C3)n1] |
| 210 | 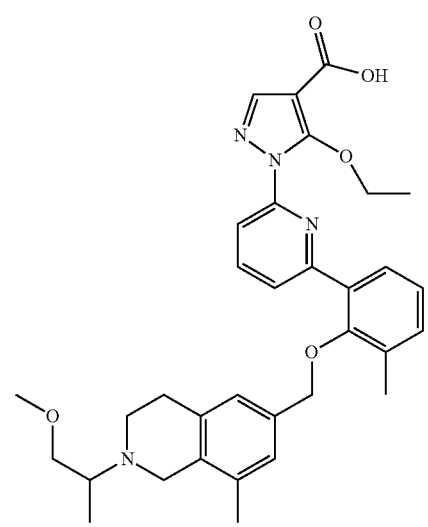 [SMILES: CCOc1c(C(=O)O)cnn1-c1cccc(-c2cccc(C)c2OCc2cc(C)c3c(c2)CCN(C(C)COC)C3)n1] |
| 211 | 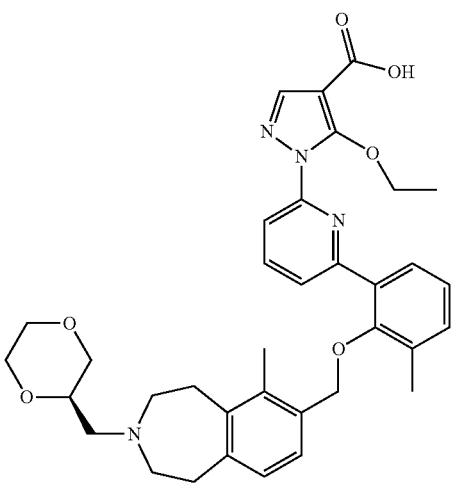 [SMILES: CCOc1c(C(=O)O)cnn1-c1cccc(-c2cccc(C)c2OCc2ccc3c(c2C)CCN(C[C@@H]2COCCO2)CC3)n1] |

| Cpd No. | Structure |
|---|---|
| 212 | 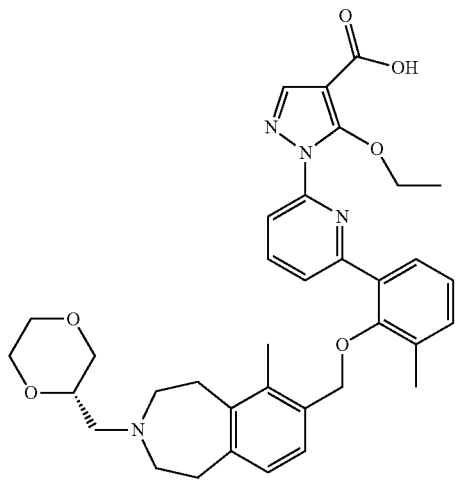 [SMILES: CCOc1c(C(=O)O)cnn1-c1cccc(-c2cccc(C)c2OCc2ccc3c(c2C)CCN(C[C@H]2COCCO2)CC3)n1] |
| 213 | 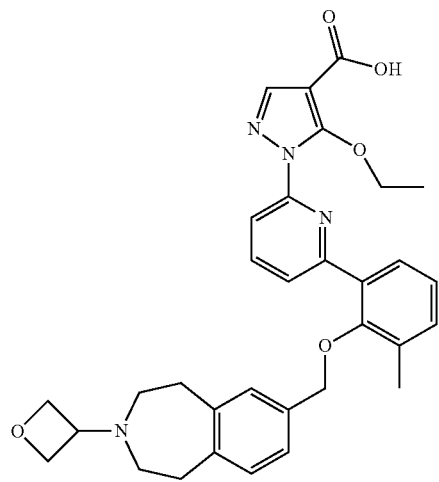 [SMILES: CCOc1c(C(=O)O)cnn1-c1cccc(-c2cccc(C)c2OCc2ccc3c(c2)CCN(C2COC2)CC3)n1] |
| 214 | 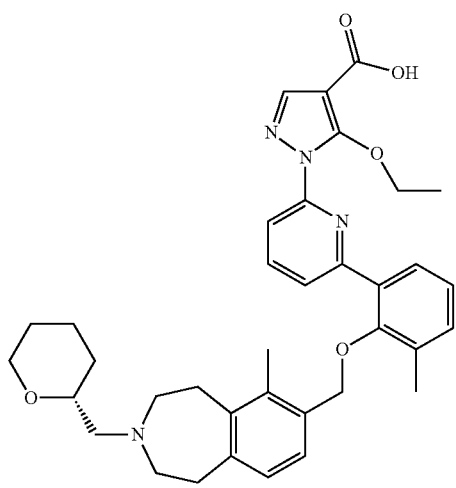 [SMILES: CCOc1c(C(=O)O)cnn1-c1cccc(-c2cccc(C)c2OCc2ccc3c(c2C)CCN(C[C@H]2CCCCO2)CC3)n1] |
| Cpd No. | Structure |
|---|---|
| 215 | 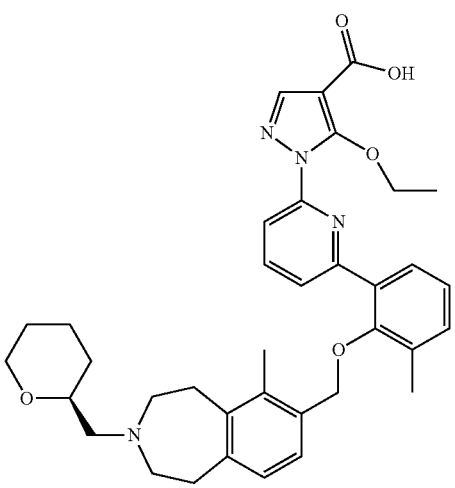 [SMILES: CCOc1c(C(=O)O)cnn1-c1cccc(-c2cccc(C)c2OCc2ccc3c(c2C)CCN(C[C@@H]2CCCCO2)CC3)n1] |
| 216 | 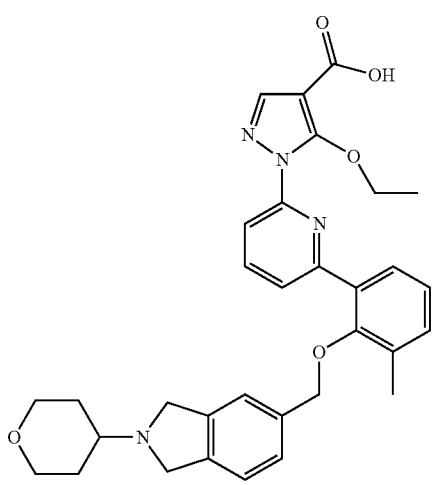 [SMILES: CCOc1c(C(=O)O)cnn1-c1cccc(-c2cccc(C)c2OCc2ccc3c(c2)CN(C2CCOCC2)C3)n1] |
| 217 | 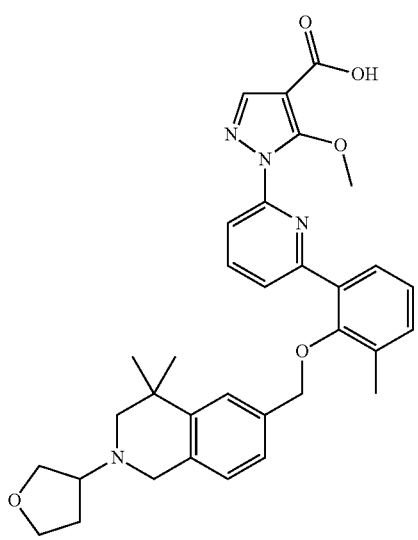 [SMILES: COc1c(C(=O)O)cnn1-c1cccc(-c2cccc(C)c2OCc2ccc3c(c2)C(C)(C)CN(C2CCOC2)C3)n1] |

| Cpd No. | Structure |
|---|---|
| 218 | 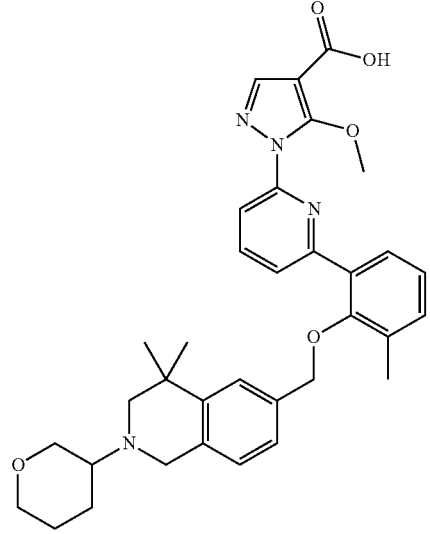 [SMILES: COc1c(C(=O)O)cnn1-c1cccc(-c2cccc(C)c2OCc2ccc3c(c2)C(C)(C)CN(C2CCCOC2)C3)n1] |
| 219 | 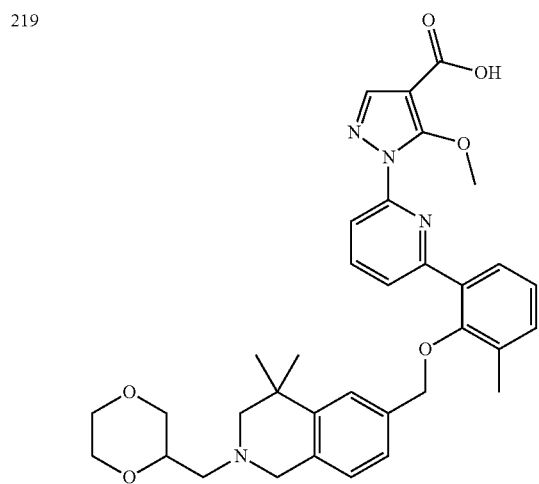 |
| 220 | 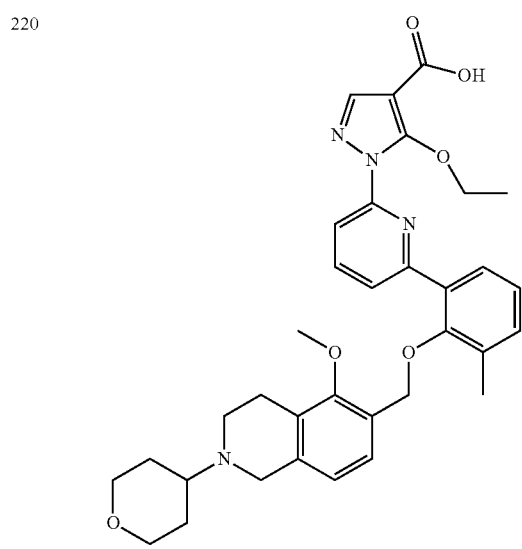 |//
| Cpd No. | Structure |
|---|---|
| 221 | 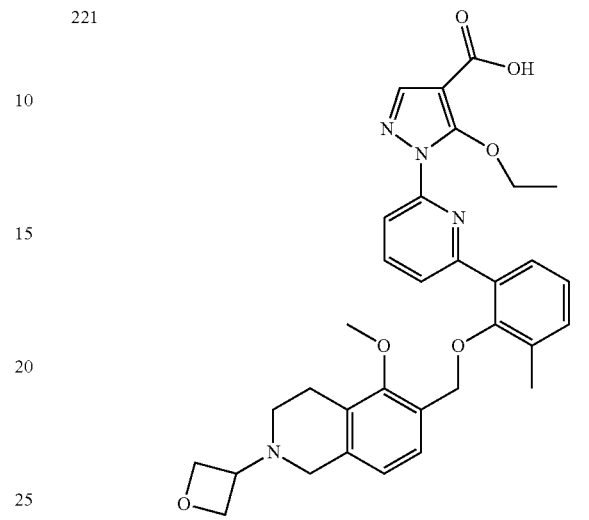 |
| 222 | 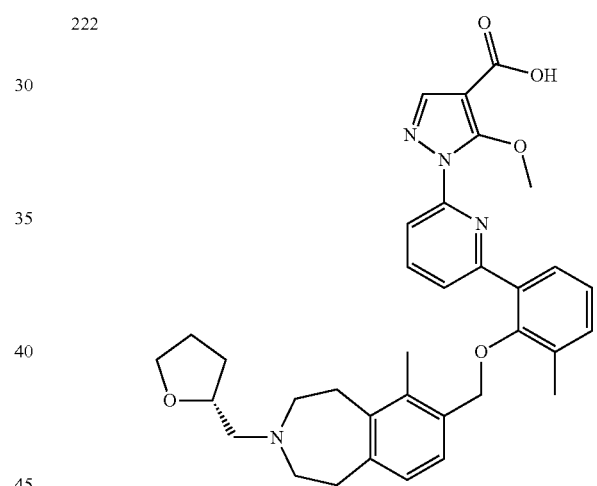 |
| 223 | 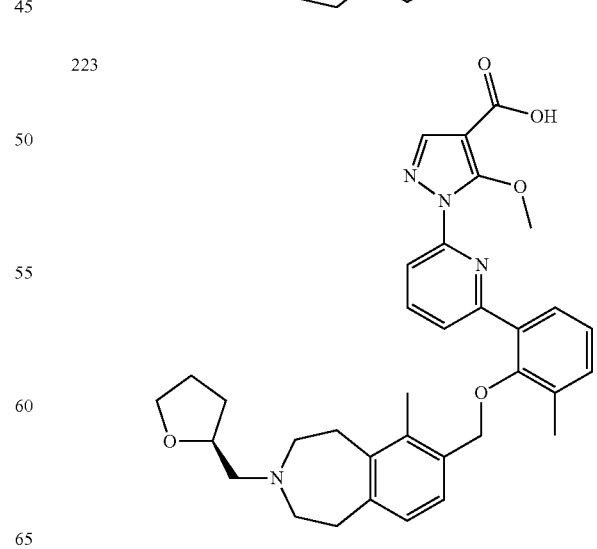 |

| Cpd No. | Structure |
|---|---|
| 224 | 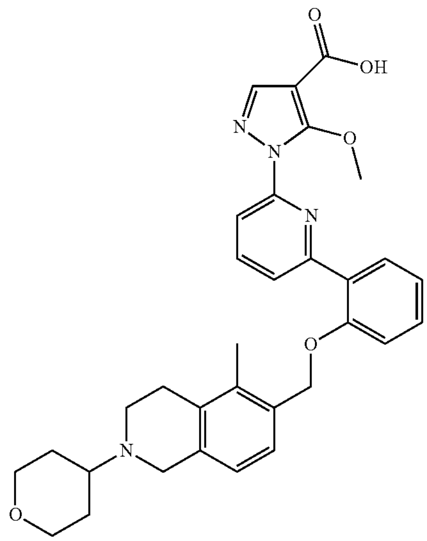 [SMILES: COc1c(C(=O)O)cnn1-c1cccc(-c2ccccc2OCc2ccc3c(c2C)CCN(C2CCOCC2)C3)n1] |
| 225 | 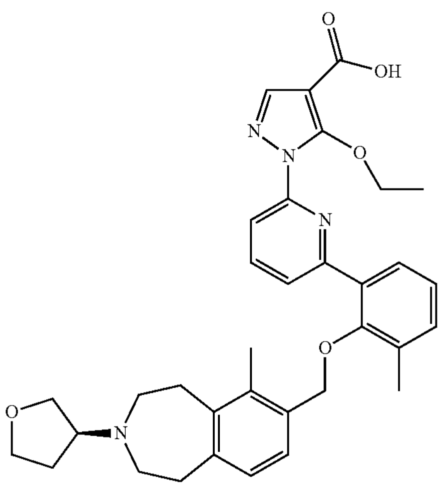 [SMILES: CCOc1c(C(=O)O)cnn1-c1cccc(-c2cccc(C)c2OCc2ccc3c(c2C)CCN([C@H]2CCOC2)CC3)n1] |
| 226 | 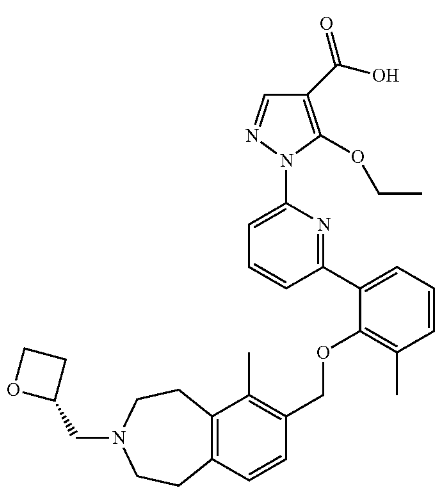 [SMILES: CCOc1c(C(=O)O)cnn1-c1cccc(-c2cccc(C)c2OCc2ccc3c(c2C)CCN(C[C@H]2CCO2)CC3)n1] |
| 227 | |
| 228 | |
| 229 | |

| Cpd No. | Structure |
|---|---|
| 230 | 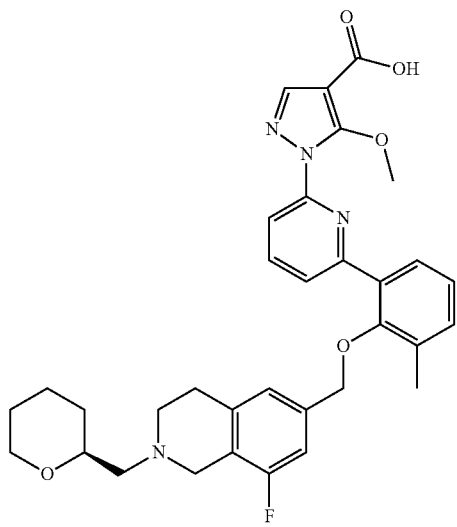 [SMILES: COc1c(C(=O)O)cnn1-c1cccc(-c2cccc(C)c2OCc2cc(F)c3c(c2)CCN(C[C@@H]2CCCCO2)C3)n1] |
| 231 | 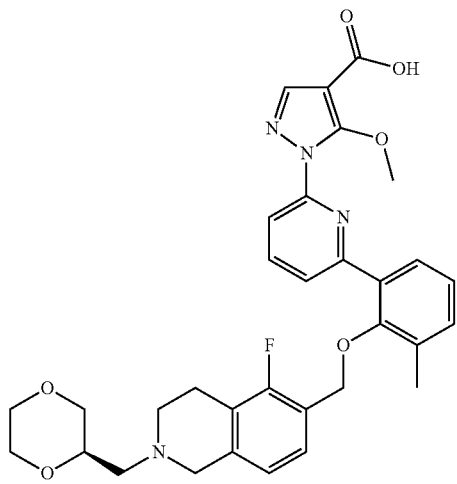 [SMILES: COc1c(C(=O)O)cnn1-c1cccc(-c2cccc(C)c2OCc2ccc3c(c2F)CCN(C[C@@H]2COCCO2)C3)n1] |
| 232 | 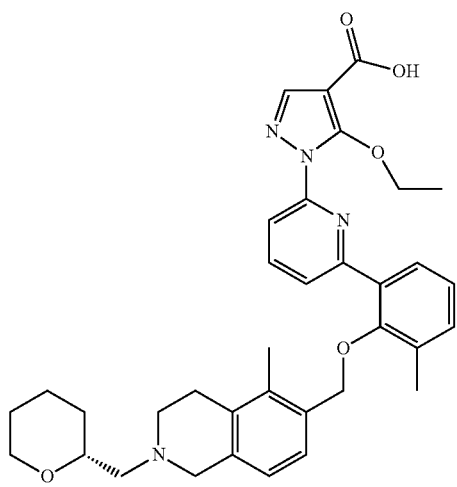 [SMILES: CCOc1c(C(=O)O)cnn1-c1cccc(-c2cccc(C)c2OCc2ccc3c(c2C)CCN(C[C@H]2CCCCO2)C3)n1] |
| Cpd No. | Structure |
|---|---|
| 233 | 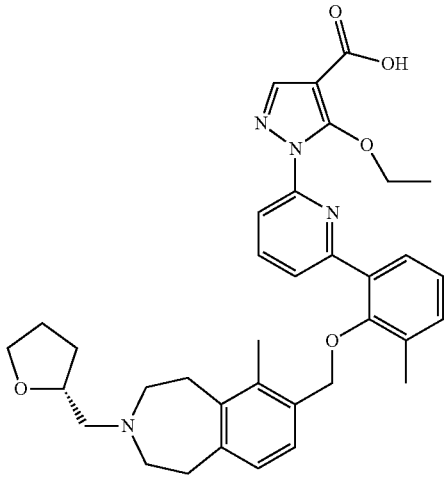 [SMILES: CCOc1c(C(=O)O)cnn1-c1cccc(-c2cccc(C)c2OCc2ccc3c(c2C)CCN(C[C@H]2CCCO2)CC3)n1] |
| 234 | 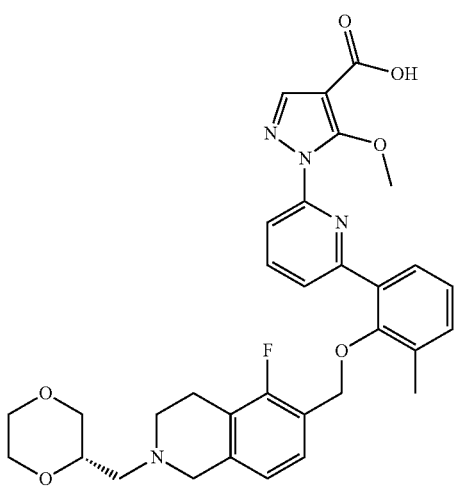 [SMILES: COc1c(C(=O)O)cnn1-c1cccc(-c2cccc(C)c2OCc2ccc3c(c2F)CCN(C[C@H]2COCCO2)C3)n1] |
| 235 | 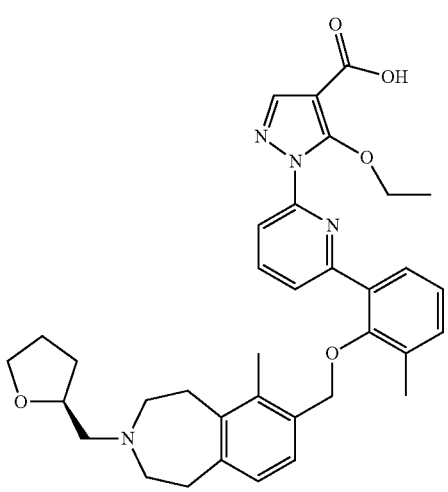 [SMILES: CCOc1c(C(=O)O)cnn1-c1cccc(-c2cccc(C)c2OCc2ccc3c(c2C)CCN(C[C@@H]2CCCO2)CC3)n1] |

| Cpd No. | Structure |
|---|---|
| 236 | 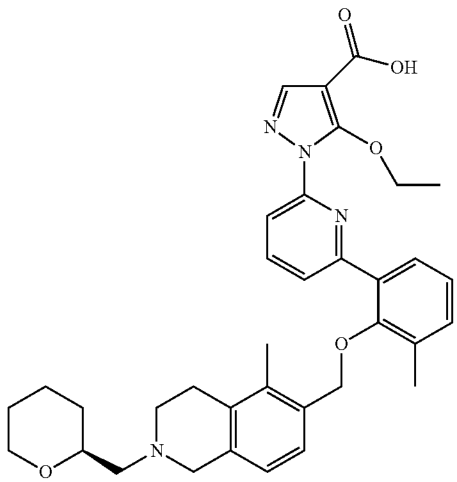 [SMILES: CCOc1c(C(=O)O)cnn1-c1cccc(-c2cccc(C)c2OCc2ccc3c(c2C)CCN(C[C@@H]2CCCCO2)C3)n1] |
| 237 | 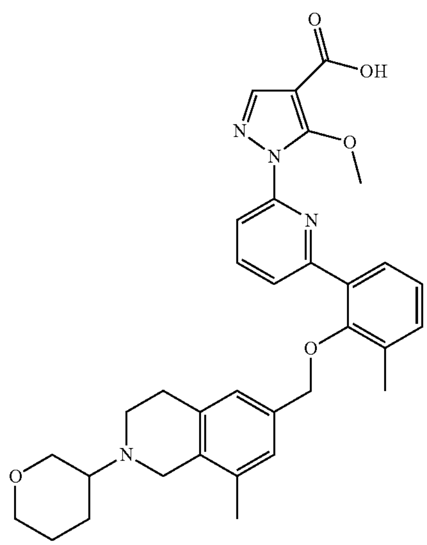 [SMILES: COc1c(C(=O)O)cnn1-c1cccc(-c2cccc(C)c2OCc2cc(C)c3c(c2)CCN(C2CCCOC2)C3)n1] |
| 238 | 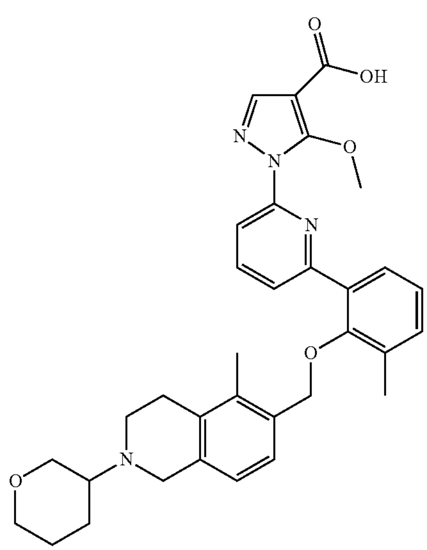 |
| 239 | |
| 240 | |
| 241 | |

| Cpd No. | Structure |
|---|---|
| 242 | 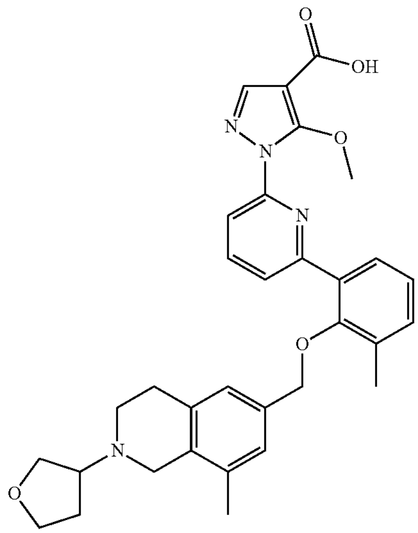 [SMILES: COc1c(C(=O)O)cnn1-c1cccc(-c2cccc(C)c2OCc2cc(C)c3c(c2)CCN(C2CCOC2)C3)n1] |
| 243 | 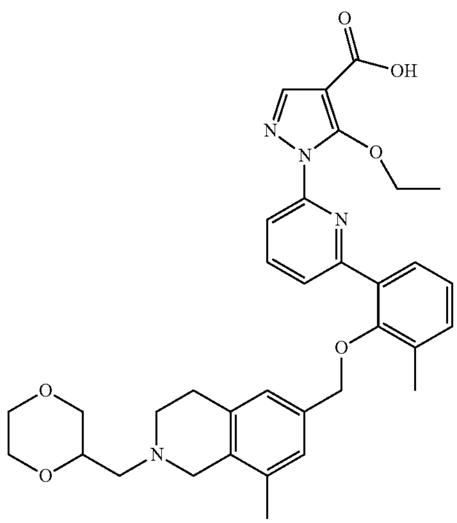 [SMILES: CCOc1c(C(=O)O)cnn1-c1cccc(-c2cccc(C)c2OCc2cc(C)c3c(c2)CCN(CC2COCCO2)C3)n1] |
| 244 | 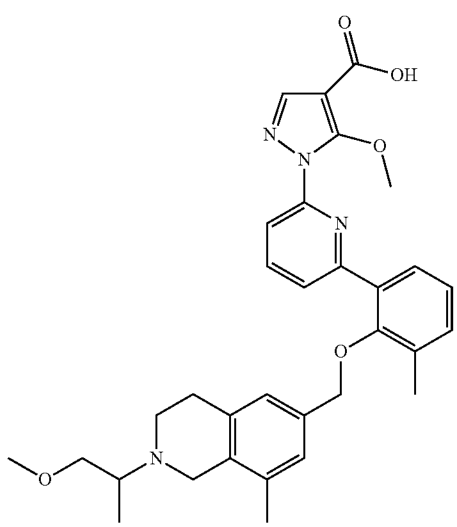 [SMILES: COCC(C)N1CCc2cc(COc3c(C)cccc3-c3cccc(-n4ncc(C(=O)O)c4OC)n3)cc(C)c2C1] |
| 245 | |
| 246 | |
| 247 | |

| Cpd No. | Structure |
|---|---|
| 248 | 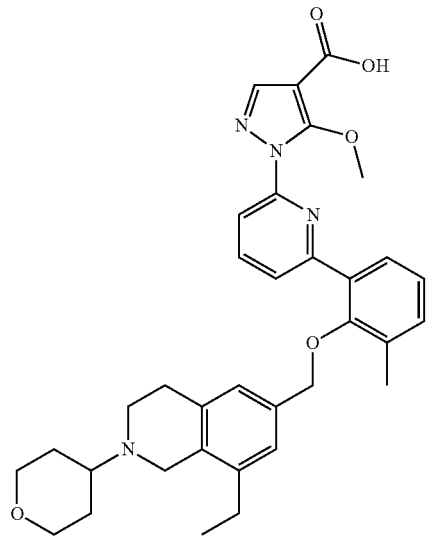 [SMILES: CCc1cc(COc2c(C)cccc2-c2cccc(-n3ncc(C(=O)O)c3OC)n2)cc2c1CN(C1CCOCC1)CC2] |
| 249 | 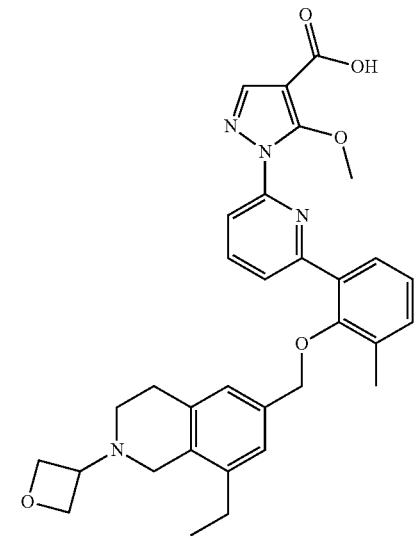 [SMILES: CCc1cc(COc2c(C)cccc2-c2cccc(-n3ncc(C(=O)O)c3OC)n2)cc2c1CN(C1COC1)CC2] |
| Cpd No. | Structure |
|---|---|
| 250 | 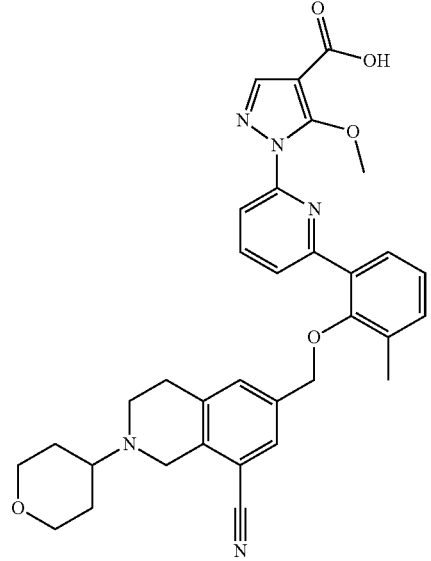 [SMILES: COc1c(C(=O)O)cnn1-c1cccc(-c2cccc(C)c2OCc2cc(C#N)c3c(c2)CCN(C2CCOCC2)C3)n1] |
| 251 | 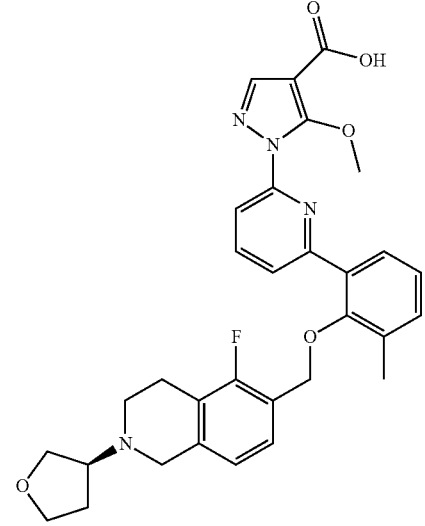 [SMILES: COc1c(C(=O)O)cnn1-c1cccc(-c2cccc(C)c2OCc2ccc3c(c2F)CCN([C@H]2CCOC2)C3)n1] |

| Cpd No. | Structure |
|---|---|
| 252 | 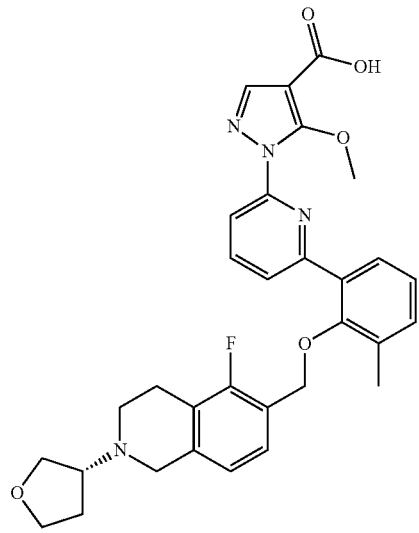 [SMILES: COc1c(C(=O)O)cnn1-c1cccc(-c2cccc(C)c2OCc2ccc3c(c2F)CCN([C@@H]2CCOC2)C3)n1] |
| 253 | 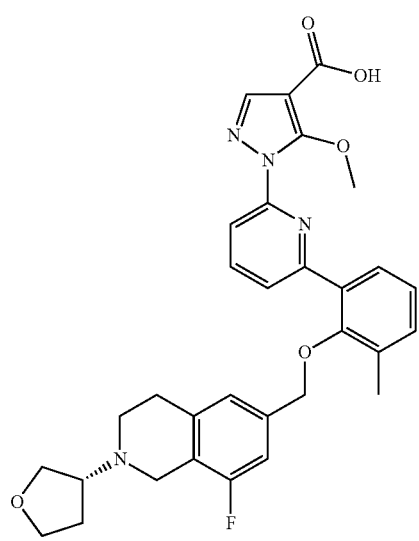 [SMILES: COc1c(C(=O)O)cnn1-c1cccc(-c2cccc(C)c2OCc2cc(F)c3c(c2)CCN([C@@H]2CCOC2)C3)n1] |
| 254 | 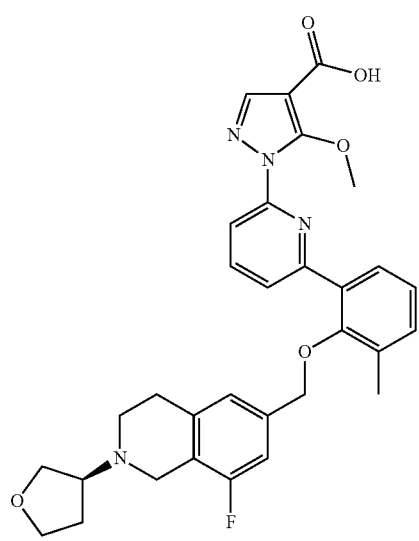 [SMILES: COc1c(C(=O)O)cnn1-c1cccc(-c2cccc(C)c2OCc2cc(F)c3c(c2)CCN([C@H]2CCOC2)C3)n1] |
| Cpd No. | Structure |
|---|---|
| 255 | 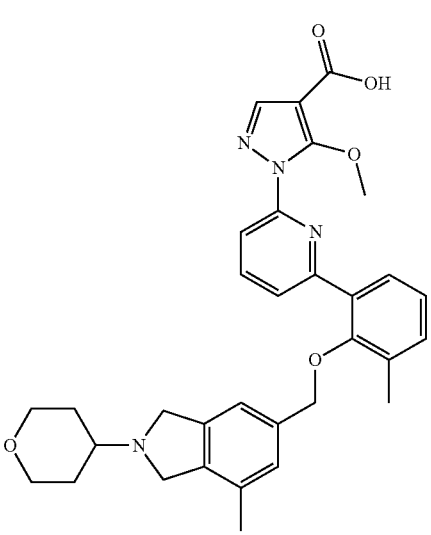 [SMILES: COc1c(C(=O)O)cnn1-c1cccc(-c2cccc(C)c2OCc2cc(C)c3c(c2)CN(C2CCOCC2)C3)n1] |
| 256 | 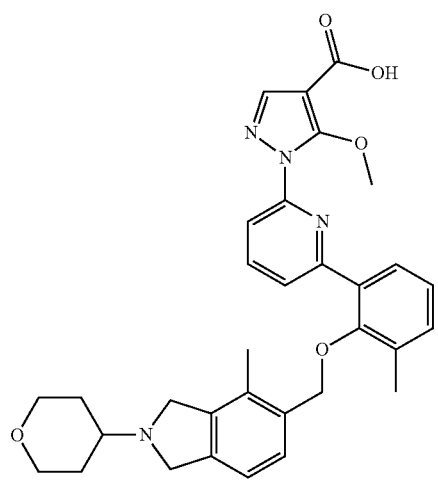 [SMILES: COc1c(C(=O)O)cnn1-c1cccc(-c2cccc(C)c2OCc2ccc3c(c2C)CN(C2CCOCC2)C3)n1] |
| 257 | 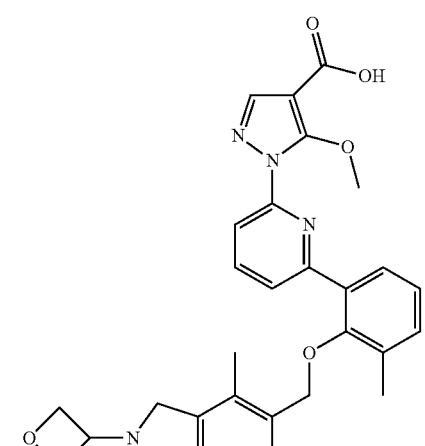 |

| Cpd No. | Structure |
|---|---|
| 258 | 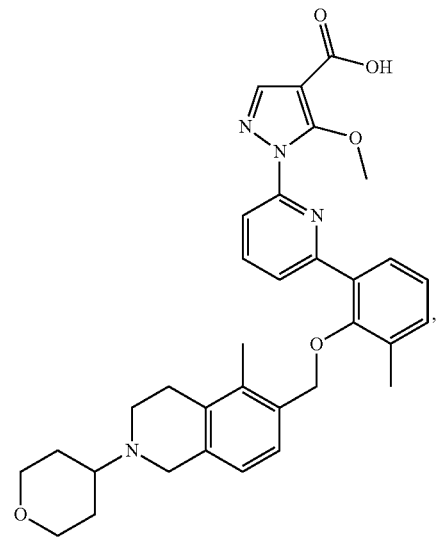 [SMILES: COc1c(C(=O)O)cnn1-c1cccc(-c2cccc(C)c2OCc2ccc3c(c2C)CCN(C2CCOCC2)C3)n1] | and the pharmaceutically acceptable salts thereof.

11. The compound according to claim 10 selected from the group consisting of compound numbers 1, 2, 3, 4, 5, 7, 8, 9, 12, 15, 16, 18, 21, 27, 28, 30, 31, 35, 36, 39, 41, 42, 44, 45, 46, 47, 48, 57, 59, 62, 68, 77, 78, 79, 80, 82, 83, 84, 85, 86, 88, 92, 93, and 94 and the pharmaceutically acceptable salts thereof.

12. The compound according to claim 10 selected from the group consisting of compound numbers 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 136, 137, 139, 140, 141, 142, 145, 146, 152, 153, 154, 155, 157, 158, 159, 161, 162, 163, 164, 165, 166, 167, 169, 170, 171, 172, 173, 174, 175, 176, 177, 178, 179, 180, 181, 184, 185, 186, 187, 188, 189, 191, 193, 194, 195, 196, 197, 198, 199, 201, 202, 203, 204, 205, 206, 207, 208, 210, 211, 212, 213, 214, 215, 216, 220, 222, 223, 224, 225, 227, 229, 230, 231, 232, 233, 234, 235, 236, 237, 238, 239, 240, 241, 242, 243, 244, 246, 247, 248, 249, 250, 251, 252, 253, 254, 255, 256, 257 and the pharmaceutically acceptable salts thereof.

13. A pharmaceutical composition comprising a compound according to claim 1 and a pharmaceutically acceptable excipient or carrier.

14. A method of treating a disease or disorder that can be alleviated by sGC activation or potentiation, wherein the disease or disorder is selected from hepatic fibrotic disorder, renal fibrotic disorder, pulmonary fibrotic disorder, cardiac fibrotic disorder, overactive bladder, benign prostatic hyperplasia, erectile dysfunction, Parkinson's disease, neuropathic pain and diabetic nephropathy, comprising administering a therapeutically effective amount of a compound according to claim 1 to patient in need thereof.

15. The method according to claim 14 wherein the disease is diabetic nephropathy.

16. A compound, wherein the compound is

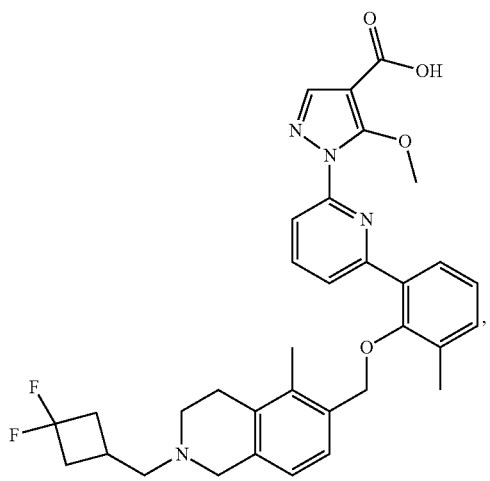 [SMILES: COc1c(C(=O)O)cnn1-c1cccc(-c2cccc(C)c2OCc2ccc3c(c2C)CCN(CC2CC(F)(F)C2)C3)n1]

or a pharmaceutically acceptable salt thereof.

17. A compound, wherein the compound is or a pharmaceutically acceptable salt thereof.

18. A compound, wherein the compound is
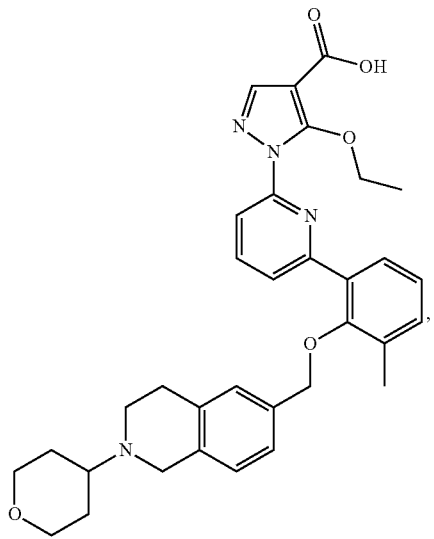 [SMILES: CCOc1c(C(=O)O)cnn1-c1cccc(-c2cccc(C)c2OCc2ccc3c(c2)CCN(C2CCOCC2)C3)n1]
or a pharmaceutically acceptable salt thereof.
19. A compound, wherein the compound is
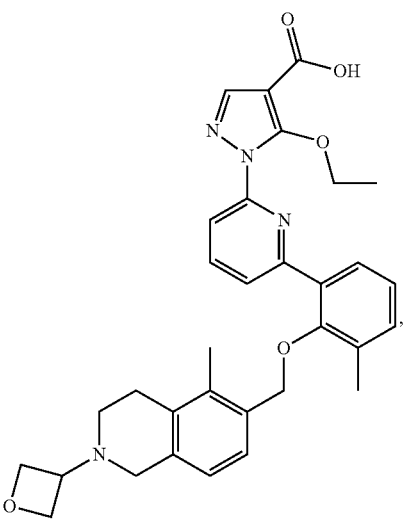 [SMILES: CCOc1c(C(=O)O)cnn1-c1cccc(-c2cccc(C)c2OCc2ccc3c(c2C)CCN(C2COC2)C3)n1]
or a pharmaceutically acceptable salt thereof.
20. A compound, wherein the compound is
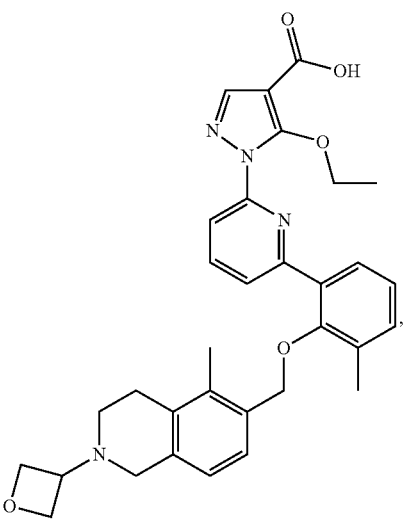 [SMILES: CCOc1c(C(=O)O)cnn1-c1cccc(-c2cccc(C)c2OCc2ccc3c(c2C)CCN(C2COC2)C3)n1]
or a pharmaceutically acceptable salt thereof.
21. A compound, wherein the compound is
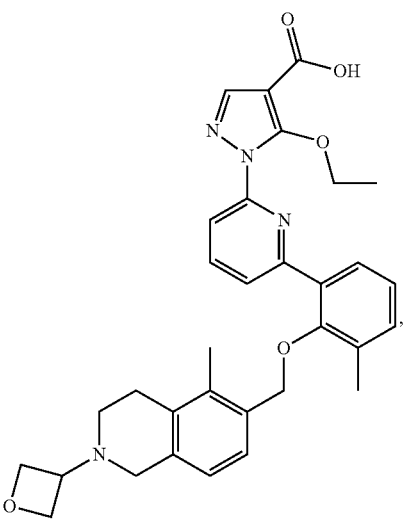 [SMILES: CCOc1c(C(=O)O)cnn1-c1cccc(-c2cccc(C)c2OCc2ccc3c(c2C)CCN(C2COC2)C3)n1]
or a pharmaceutically acceptable salt thereof.

22. A compound, wherein the compound is

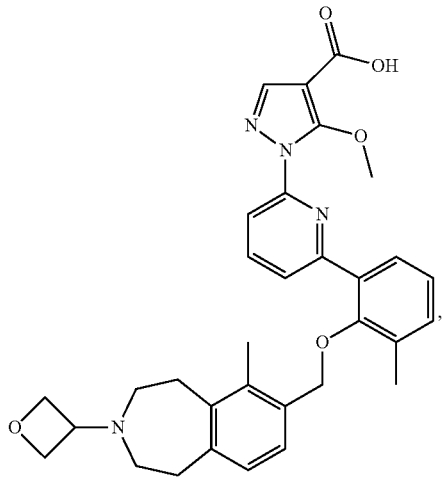 [SMILES: COc1c(C(=O)O)cnn1-c1cccc(-c2cccc(C)c2OCc2ccc3c(c2C)CCN(C2COC2)CC3)n1]

or a pharmaceutically acceptable salt thereof.

23. A compound, wherein the compound is

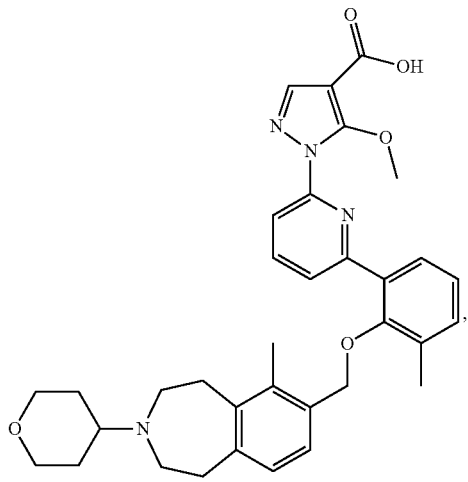 [SMILES: COc1c(C(=O)O)cnn1-c1cccc(-c2cccc(C)c2OCc2ccc3c(c2C)CCN(C2CCOCC2)CC3)n1]

or a pharmaceutically acceptable salt thereof.

24. A compound, wherein the compound is

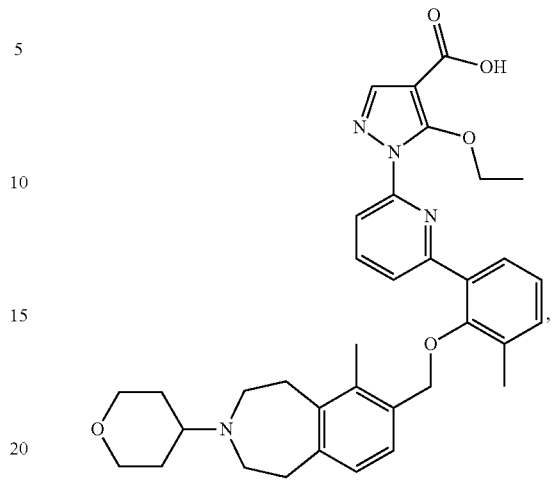

or a pharmaceutically acceptable salt thereof.

25. A compound, wherein the compound is

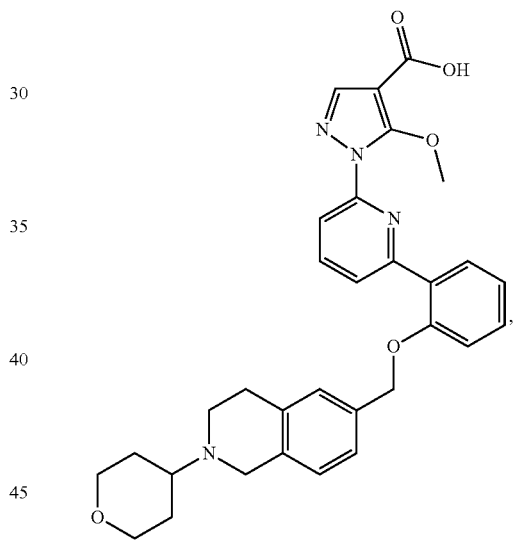

or a pharmaceutically acceptable salt thereof.

26. A pharmaceutical composition comprising a compound according to claim 16 and a pharmaceutically acceptable excipient or carrier.

27. A pharmaceutical composition comprising a compound according to claim 17 and a pharmaceutically acceptable excipient or carrier.

28. A pharmaceutical composition comprising a compound according to claim 18 and a pharmaceutically acceptable excipient or carrier.

29. A pharmaceutical composition comprising a compound according to claim 19 and a pharmaceutically acceptable excipient or carrier.

30. A pharmaceutical composition comprising a compound according to claim 20 and a pharmaceutically acceptable excipient or carrier.

31. A pharmaceutical composition comprising a compound according to claim 21 and a pharmaceutically acceptable excipient or carrier.

32. A pharmaceutical composition comprising a compound according to claim 22 and a pharmaceutically acceptable excipient or carrier.

33. A pharmaceutical composition comprising a compound according to claim 23 and a pharmaceutically acceptable excipient or carrier.

34. A pharmaceutical composition comprising a compound according to claim 24 and a pharmaceutically acceptable excipient or carrier.

35. A pharmaceutical composition comprising a compound according to claim 25 and a pharmaceutically acceptable excipient or carrier.

* * * * *